(12) United States Patent
Su et al.

(10) Patent No.: US 12,234,211 B2
(45) Date of Patent: *Feb. 25, 2025

(54) CYCLOOLEFIN SUBSTITUTED HETEROAROMATIC COMPOUNDS AND THEIR USE

(71) Applicant: HUTCHISON MEDIPHARMA LIMITED, Shanghai (CN)

(72) Inventors: Wei-Guo Su, Shanghai (CN); Guangxiu Dai, Shanghai (CN); Kun Xiao, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,925

(22) Filed: May 18, 2022

(65) Prior Publication Data

US 2022/0372005 A1 Nov. 24, 2022

Related U.S. Application Data

(63) Continuation of application No. 16/645,329, filed as application No. PCT/CN2018/104531 on Sep. 7, 2018, now Pat. No. 11,414,390.

(30) Foreign Application Priority Data

Sep. 7, 2017 (CN) .......................... 201710801364.3

(51) Int. Cl.
 C07D 251/48 (2006.01)
 C07D 401/12 (2006.01)
 C07D 403/04 (2006.01)
 C07D 403/12 (2006.01)
 C07D 405/12 (2006.01)
 C07D 417/12 (2006.01)
 C07D 471/04 (2006.01)
 C07F 5/02 (2006.01)

(52) U.S. Cl.
 CPC ......... *C07D 251/48* (2013.01); *C07D 401/12* (2013.01); *C07D 403/04* (2013.01); *C07D 403/12* (2013.01); *C07D 405/12* (2013.01); *C07D 417/12* (2013.01); *C07D 471/04* (2013.01); *C07F 5/025* (2013.01)

(58) Field of Classification Search
 CPC .. C07D 251/48; C07D 401/12; C07D 403/12; C07D 405/12; C07D 417/12; C07D 471/04
 See application file for complete search history.

(56) References Cited

U.S. PATENT DOCUMENTS

| | | | |
|---|---|---|---|
| 3,555,154 A | 1/1971 | Enkoji et al. | |
| 8,497,376 B2 | 7/2013 | Illig et al. | |
| 8,598,168 B2 | 12/2013 | Moradei et al. | |
| 9,763,937 B2 | 9/2017 | Bagdanoff et al. | |
| 10,632,125 B2 | 4/2020 | Scobie et al. | |
| 2006/0000420 A1 | 1/2006 | Davies et al. | |
| 2009/0137804 A1 | 5/2009 | Ding et al. | |
| 2009/0163545 A1 | 6/2009 | Goldfard et al. | |
| 2014/0179662 A1 | 6/2014 | Rühter et al. | |
| 2014/0235620 A1 | 8/2014 | Caferro et al. | |
| 2016/0159771 A1 | 6/2016 | Travins et al. | |
| 2019/0071452 A1 | 3/2019 | Ohashi et al. | |
| 2019/0144465 A1 | 5/2019 | Judd et al. | |
| 2020/0325153 A1 | 10/2020 | Judd et al. | |

FOREIGN PATENT DOCUMENTS

| | | |
|---|---|---|
| CL | 202000363 | 2/2020 |
| CL | 202000376 | 2/2020 |
| CL | 202002943 | 11/2020 |
| CN | 103044469 A | 4/2013 |
| CN | 105517996 A | 4/2016 |
| CN | 107382840 A | 11/2017 |
| EP | 0361489 A2 | 4/1990 |
| TW | 201321375 A | 6/2013 |
| WO | WO 2001/025220 A1 | 4/2001 |
| WO | WO 2006/000420 A1 | 1/2006 |
| WO | WO 2008/031556 A2 | 3/2008 |
| WO | WO 2008/122378 A1 | 10/2008 |
| WO | WO 2010/151791 A1 | 12/2010 |

(Continued)

OTHER PUBLICATIONS

Extended European Search Report for EP 18853366.5 dated Apr. 1, 2021.
International Search Report and Written Opinion mailed Dec. 11, 2018 in connection with International Application No. PCT/CN2018/104531.
RN 2151236-51-8 in Registry of STNEXT, 2017.
RN 2144351-79-9 in Registry of STNEXT, 2017.
RN 2140125-40-0 in Registry of STNEXT, 2017.
Baird et al., "A Simple Route to 3-(dihalomethylene)cycloalkenes," Tetrahedron Letters, vol. 23, No. 37, pp. 3795-3796, (1982), doi: 10.1016/S0040-4039(00)87709-6.
Balaha et al., "Synthesis, Evaluation and Docking Study of 1, 2, 5-Triazine Derivatives as Cytotoxic Agents against Lung Cancer," J. Appl Pharm Sci, vol. 6, No. 4, pp. 028-045, (2016).

(Continued)

*Primary Examiner* — Brian E McDowell
(74) *Attorney, Agent, or Firm* — Hoxie & Associates LLC

(57) ABSTRACT

Compounds of formula (I) or a pharmaceutically acceptable salt thereof, and/or solvates racemic mixtures, enantiomers, diasteromers, and tautomers thereof, wherein A, $R_1$, $R_2$, $R_3$, $R_3'$, $R_4$, $R_4'$, $R_5$, $R_6$, $R_7$, $R_8$, m, and n are as defined in the detailed description.

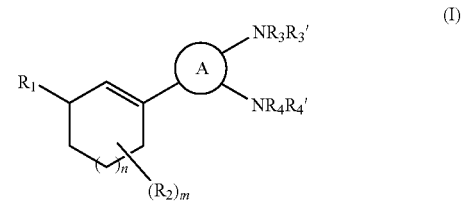

15 Claims, 2 Drawing Sheets

(56) References Cited

FOREIGN PATENT DOCUMENTS

| WO | WO 2011/078143 A1 | 6/2011 |
|---|---|---|
| WO | WO 2012/003283 A1 | 1/2012 |
| WO | WO 2012/117048 A1 | 9/2012 |
| WO | WO 2013/040044 A1 | 3/2013 |
| WO | WO 2013/040059 A1 | 3/2013 |
| WO | WO 2013/102431 A1 | 7/2013 |
| WO | WO 2014/064094 A1 | 5/2014 |
| WO | WO 2014/116594 A1 | 7/2014 |
| WO | WO 2015/003355 A2 | 1/2015 |
| WO | WO 2015/003360 A2 | 1/2015 |
| WO | WO 2015/003640 A1 | 1/2015 |
| WO | WO 2015/003641 A1 | 1/2015 |
| WO | WO 2015/006591 A1 | 1/2015 |
| WO | WO 2015/006592 A1 | 1/2015 |
| WO | WO 2015/017821 A2 | 2/2015 |
| WO | WO 2015/187088 A1 | 12/2015 |
| WO | WO 2017/016513 A1 | 2/2017 |
| WO | WO 2017/059280 A1 | 4/2017 |
| WO | WO 2017/096150 A1 | 6/2017 |
| WO | WO 2017/096309 A1 | 6/2017 |
| WO | WO 2017/096945 | 6/2017 |
| WO | WO 2017/181177 A1 | 10/2017 |

OTHER PUBLICATIONS

Bessiere-Chretieny et al., "Ene Synthesis in the S-triazine Series," J Heterocyclic Chemistry, vol. 11, No. 3, pp. 317-319, (1974).

Kumar et al., "Synthesis and Anticancer Activity of Some New S-triazine Derivatives," Med Chem Res, (2013).

Lack et al., "Targeting the Binding Function 3(BF3) Site of the Human Androgen Receptor through Virtual Screening," J Med Chem, vol. 54, pp. 8563-8573, (2011).

Martinez et al., "Fragmentation of Vinyl Triflates by Electron Impact. Mechanism of an Unusual Double Hydrogen Atom Transfer Reaction," Rapid Communications in Mass Spectrometry, vol. 8, No. 5, pp. 427-431, (1994), doi: 10.1002/rcm.1290080517.

Modest et al., "Communications to the Editor: Pyrimidine Derivatives. III. Novel Synthesis of 2,4diaminopyrimidines," JOC, vol. 27, No. 7, pp. 2708-2709, (1962).

Ratzon et al., "A Small Molecule Inhibitor of Bruton's Tyrosine Kinase Involved in B Cell Signaling," ACS Omega, vol. 2, No. 8, pp. 4398-4410, (2017).

Saczewski et al., "Synthesis, Structure and Anticancer Activity of Novel 2,4-diamino-1,3,5-triazine Derivatives," Eur J Med Chem, vol. 41, No. 2, pp. 219-225, (2006).

"FDA Approves New Treatment for Leukemia," Genetic Engineering & Biotechnology News, Aug. 2, 2017, Retrieved on: Sep. 27, 2024.

Magar, K. et al., "Ruthenium(II)-Catalyzed Protocol for Preparation of Diverse a, b- and b,b-Dihaloenones from Diazodicarbonyls," Adv. Synth. Catal., vol. 356, pp. 3422-3432, (2014).

Registry [STN online], entered Nov. 16, 1984, RN: 78137-68-5.

Registry [STN online], entered Nov. 22, 2013, RN: 1478625-47-6.

Second Patent Examination Report for New Zealand Application No. 762447 dated Apr. 26, 2023, 7 pages.

Yen, K. et al., "AG-221, a First-in-Class Therapy Targeting Acute Myeloid Leukemia Harboring Oncogenic IDH2 Mutations," Cancer Discovery, vol. 7, No. 5, pp. 478-493, (2017).

CYCLOOLEFIN SUBSTITUTED HETEROAROMATIC COMPOUNDS AND THEIR USE

CROSS REFERENCE TO RELATED APPLICATIONS

This application is a continuation application of U.S. patent application Ser. No. 16/645,329, filed on Mar. 6, 2020, which is a United States application under 35 U.S.C. 371 of International Application No. PCT/CN2018/104531, filed on Sep. 7, 2018, which claims benefit of Chinese Patent Application No. 201710801364.3, filed on Sep. 7, 2017, the contents of each of which are incorporated herein by reference.

FIELD OF THE INVENTION

The present invention relates to cycloolefin substituted heteroaromatic compounds and their use in the treatment of diseases induced by IDH mutations.

BACKGROUND OF THE INVENTION

The survival way of tumor cells is different from that of normal cells, so does the energy intake and utilization. The common metabolic pathway in aerobic organisms is tricarboxylic acid cycle, in which isocitrate dehydrogenase (IDH) catalyzing the conversion of isocitrate to α-ketoglutaric acid (α-KG) is a rate-limiting step. The known IDH family comprises three isozymes, IDH1, IDH2 and IDH3, which are located in different organelles and perform the same biological functions, i.e., catalyzing the formation of α-KG. Recent studies have shown that heterozygous IDH1/2 mutations were present in a certain proportion of a variety of tumors, such as glioma (60-80%), chondrosarcoma (55%), acute myeloid leukemia (15-25%), etc. The mutant IDH1 or IDH2 loses the capability of catalyzing the conversion of isocitrate to α-KG, whereas has the ability of catalyzing the reaction of α-KG to α-hydroxyglutaric acid (2-HG). As the structure of 2-HG is similar to the structure of α-KG, 2-HG can competitively inhibit the activity of many α-KG dependent enzymes (for example: histone demethylase and methylcytosine hydroxylase of the TET family, and the like) when it accumulates to a certain extent, and thus effects the demethylation of histones and DNA, interferes with normal cell differentiation, and results in the proliferation of immature cells.

Agios Pharmaceuticals published its research results in Science magazine in 2013: the mutant IDH1 enzyme inhibitor AGI-5198 (Science, 2013, 340, 626-630) and the mutant IDH2 enzyme inhibitor AGI-6780 (Science, 2013, 340, 622-626) developed by the company can effectively inhibit the generation of 2HG mediated by mutant IDH1/IDH2 in cells and can induce differentiation of abnormally proliferating cancer cells. Both the treatment of glioma cells harboring mutant IDH1 gene with AGI-5198 and the treatment of leukemia cells carrying mutant IDH2 gene with AG-6780 lead to increase of the expression of mature markers in cells.

The Phase I clinical trial of AG-120, a mutant IDH1 inhibitor developed by Agios Pharmaceuticals, showed that in patients with acute myeloid leukemia (AML) or myelodysplastic syndrome (MDS) having IDH1 mutations, it can be observed that 98% of the patients have decreased levels of α-hydroxyglutaric acid (2HG).

Acute myeloid leukemia (AML) is one of the most difficult diseases to be controlled in common hematological malignancies. Its recurrence rate is high. The development of new drug for the disease is slow resulting in the lack of effective drug therapy. Some studies have shown that about 15% of the patients with acute myeloid leukemia have IDH2 gene mutations. Enasidenib (former name AG-221), a mutant IDH2 inhibitor, developed by Agios Pharmaceuticals and Celgene, showed a significant effect on relapsed and refractory acute myelogenous leukemias with IDH2 gene mutations in clinical trial.

New IDH mutant inhibitors are needed to be developed to meet the need for treatment of patients with hematological tumors, especially acute myeloid leukemia, gliomas and other IDH mutation associated tumors. The present invention addresses these needs.

SUMMARY OF THE INVENTION

The present invention provides a compound of formula (I):

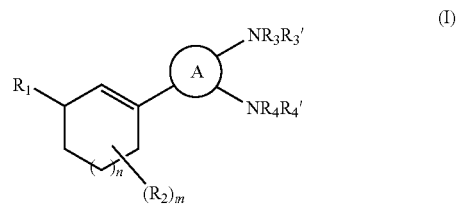

and/or a pharmaceutically acceptable salt thereof, and/or solvates, racemic mixtures, enantiomers, diasteromers, and tautomers thereof, wherein A, $R_1$, $R_2$, $R_3$, $R_{3'}$, $R_4$, $R_{4'}$, $R_5$, $R_6$, $R_7$, $R_8$, m, and n are as defined in the detailed description of the invention.

Also provided is a pharmaceutical composition, comprising at least one compound of formula (I) (e.g., any of the compounds described herein) and/or a pharmaceutically acceptable salt thereof, and optionally comprising at least one pharmaceutically acceptable excipient (e.g., a pharmaceutically acceptable carrier).

Also provided is a method of treating a disease induced by IDH mutation, comprising administering to the subject in need thereof an effective amount of at least one compound of formula (I) (e.g., any of the compounds described herein) and/or at least one pharmaceutically acceptable salt thereof.

Also provided is a use of at least one compound of formula (I) (e.g., any of the compounds described herein) and/or at least one pharmaceutically acceptable salt thereof for treating a disease induced by IDH mutation.

Also provided is a use of at least one compound of formula (I) (e.g., any of the compounds described herein) and/or at least one pharmaceutically acceptable salt thereof in the manufacture of a medicament for treating a disease induced by IDH mutation.

DETAILED DESCRIPTION OF THE INVENTION

Definitions

Figure 1:
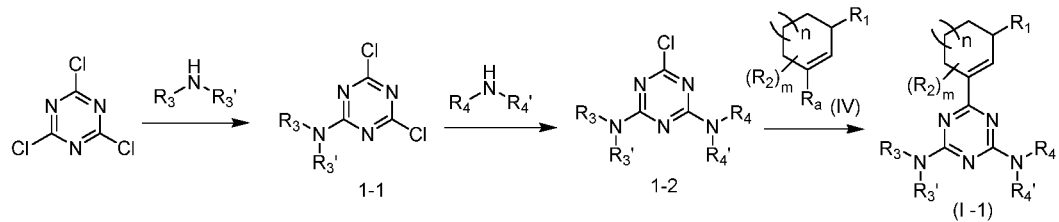
FIG. 1 shows the general synthetic route I for preparation of the compounds described herein.
Figure 2:
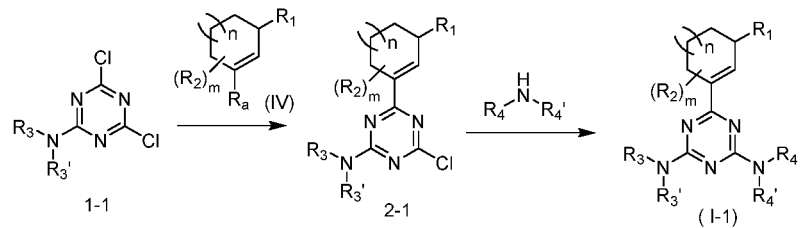
FIG. 2 shows the general synthetic route II for preparation of the compounds described herein.
Figure 3:
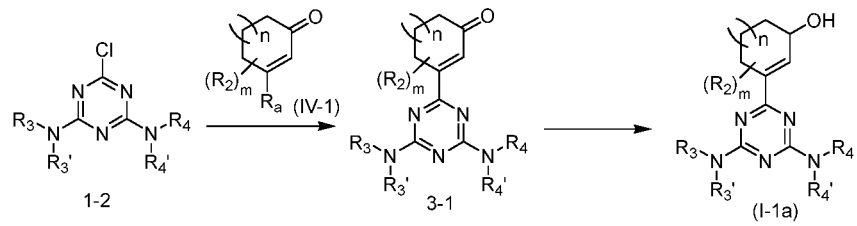
FIG. 3 shows the general synthetic route III for preparation of the compounds described herein.
Figure 4:
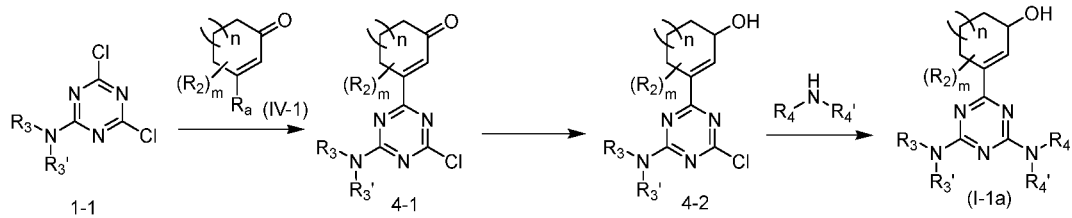
FIG. 4 shows the general synthetic route IV for preparation of the compounds described herein.
Figure 5:
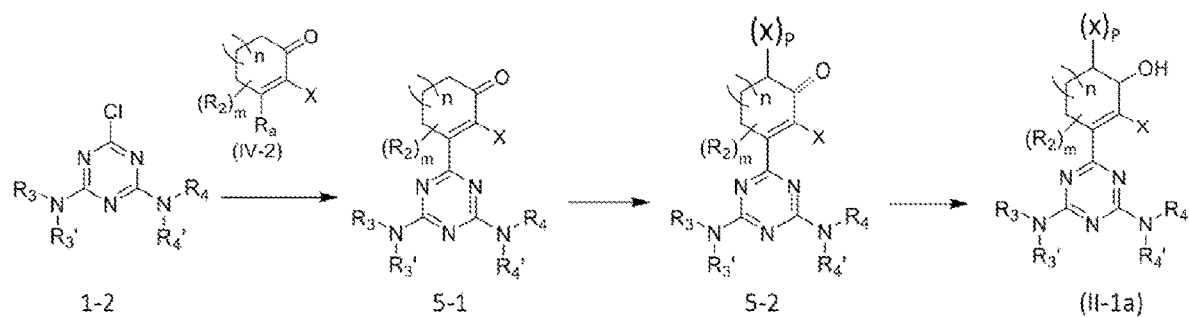
FIG. 5 shows the general synthetic route V for preparation of the compounds described herein.
Figure 6:
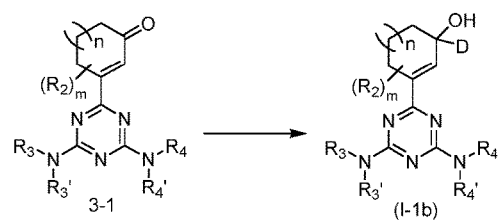
FIG. 6 shows the general synthetic route VI for preparation of the compounds described herein.

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —OR$_4$ is attached through the oxygen. However, when the point of attachment of a group is apparent to those skilled in the art, e.g., a halo substituent, the "-" sign may be omitted.

Unless clearly indicated otherwise, use of the terms "a", "an" and the like refer to one or more.

The term "alkyl" as used herein refers to a straight or branched saturated hydrocarbon radical containing 1-18 carbon atoms, preferably 1-10 carbon atoms, more preferably 1-6 carbon atoms, and even more preferably 1-4 carbon atoms. For example, "C$_{1-6}$ alkyl" refers to an alkyl containing 1-6 carbon atoms. Examples of alkyl groups include, but are not limited to, methyl ("Me"), ethyl ("Et"), n-propyl ("n-Pr"), i-propyl ("i-Pr"), n-butyl ("n-Bu"), i-butyl ("i-Bu"), s-butyl ("s-Bu") and t-butyl ("t-Bu").

The term "alkenyl" as used herein refers to a straight or branched hydrocarbon radical containing one or more, for example 1, 2, or 3 carbon-carbon double bonds (C=C) and 2-10 carbon atoms, preferably 2-6 carbon atoms, more preferably 2-4 carbon atoms. For example, "C$_{2-6}$ alkenyl" refers to an alkenyl containing 2-6 carbon atoms. Examples of alkenyl groups include, but are not limited to, vinyl, 2-propenyl, and 2-butenyl. The point of attachment for the alkenyl can be on or not on the double bonds.

The term "alkynyl" as used herein refers to a straight or branched hydrocarbon radical containing one or more, for example 1, 2, or 3, carbon-carbon triple bonds (C≡C) and 2-10 carbon atoms, preferably 2-6 carbon atoms, more preferably 2-4 carbon atoms. For example, "C$_{2-6}$ alkynyl" refers to an alkynyl containing 2-6 carbon atoms. Examples of alkynyl groups include, but are not limited to, ethynyl, 2-propynyl, and 2-butynyl. The point of attachment for the alkynyl can be on or not on the triple bonds.

The term "halogen" or "halo" as used herein means fluoro, chloro, bromo, and iodo, preferably fluoro, chloro and bromo, more preferably fluoro and chloro.

The term "haloalkyl" as used herein refers to an alkyl radical, as defined herein, in which one or more, for example 1, 2, 3, 4, or 5, hydrogen atoms are replaced with halogen atom, and when more than one hydrogen atoms are replaced with halogen atoms, the halogen atoms may be the same or different from each other. In certain an embodiment, the term "haloalkyl" as used herein refers to an alkyl radical, as defined herein, in which two or more, such as 2, 3, 4, or 5 hydrogen atoms are replaced with halogen atoms, wherein the halogen atoms are identical to each other. In another embodiment, the term "haloalkyl" as used herein refers to an alkyl radical, as defined herein, in which two or more hydrogen atoms, such as 2, 3, 4, or 5 hydrogen atoms are replaced with halogen atoms, wherein the halogen atoms are different from each other. Examples of haloalkyl groups include, but are not limited to, —CF$_3$, —CHF$_2$, —CH$_2$CF$_3$, and the like.

The term "alkoxy" as used herein refers to the group —O-alkyl, wherein the alkyl is as defined above. Examples of alkoxy groups include, but are not limited to, C$_{1-6}$ alkoxy, such as methoxy, ethoxy, n-propyloxy, i-propyloxy, n-butyloxy, i-butyloxy, t-butyloxy, pentyloxy, and hexyloxy, including their isomers.

The term "cycloalkyl" as used herein refers to saturated or partially unsaturated cyclic hydrocarbon radical having 3 to 12 ring carbon atoms, such as 3 to 8 ring carbon atoms, 5-7 ring carbon atoms, 4-7 ring carbon atoms or 3 to 6 ring carbon atoms, which may have one or more rings, such as 1, 2, or 3 rings, preferably 1 or 2 rings. For example, "C$_{3-12}$ cycloalkyl" refers to a cycloalkyl containing 3-12 carbon atoms in the ring. "Cycloalkyl" also includes a fused or bridged ring, or a spirocyclic ring. The rings of the cycle group may be saturated or has one or more, for example, one or two double bonds (i.e. partially unsaturated), but not fully conjugated, and not an aryl as defined herein. Examples of cycloalkyl groups include, but are not limited to, cyclopropyl, cyclobutyl, cyclopentyl, cyclohexyl, cycloheptyl, cyclooctyl, bicyclo[4.1.0]heptyl, bicyclo[3.1.1]heptyl, spiro[3.3]heptyl, spiro[2.2]pentyl, cyclopropenyl, cyclobutenyl, cyclopentenyl, cyclopentadienyl, cyclohexenyl, cycloheptenyl, cyclooctenyl, and bicyclo[3.1.1]hepta-2-ene.

The term "heterocycle", "heterocyclyl" or "heterocyclic" as used herein refers to monocyclic, bicyclic or tricyclic saturated or partially unsaturated cyclic radicals having 3-12 ring atoms, such as 3-8 ring atoms, 5-7 ring atoms, 4-7 ring atoms or 3-6 ring atoms, and containing one or more, for example 1, 2 or 3, preferably 1 or 2 heteroatoms independently chosen from N, O and S in the rings, with the remaining ring atoms being carbon. The heterocycle group also includes those wherein the N or S heteroatom are optionally oxidized to various oxidation states. The point of attachment of heterocyclyl can be on the N heteroatom or carbon. For example, "3-8 membered heterocycly" refers to a heterocyclyl containing 3-8 ring atoms and containing at least one heteroatom independently chosen from N, O and S.

The heterocycle group also includes a fused or bridged ring, or a spirocyclic ring, wherein, at least one ring contains at least one heteroatom chosen from O, S, and N and none of the other rings is aryl or heteroaryl as defined herein. The rings of the heterocycle group may be saturated or has one or more, for example, one or two double bonds (i.e. partially unsaturated), but not fully conjugated, and not a heteroaryl as defined herein. Examples of heterocycly groups include, but are not limited to, oxetanyl, azetidinyl, pyrrolidinyl, tetrahydrofuryl, dioxolaneyl, morpholinyl, thiomorpholinyl, piperidyl, piperazinyl, pyrazolidinyl, and oxaspiro[3.3]heptanyl.

The term "aryl" as used herein refers to carbocyclic hydrocarbon radical of 6 to 14 carbon atoms consisting of one ring or more fused rings, wherein at least one ring is an aromatic ring. Examples of aryl groups include, but are not limited to, phenyl, naphthalenyl, 1,2,3,4-tetrahydronaphthalenyl, indenyl, indanyl, azulenyl, preferably phenyl and naphthalenyl.

The term "heteroaryl" as used herein refers to:
monocyclic aromatic hydrocarbon radical having 5, 6 or 7 ring atoms, preferably having 6 ring atoms, and containing one or more, for example 1, 2 or 3, preferably 1 or 2 heteroatoms independently chosen from N, O, and S (preferably N) in the ring, with the remaining ring atoms being carbon; and bicyclic aromatic hydrocarbon radical having 8-12 ring atoms, preferably having 9 or 10 ring atoms, and containing one or more, for example, 1, 2, 3 or 4, preferably 2, 3 or 4 heteroatoms independently chosen from N, O, and S (preferably N) in the rings, with the remaining ring atoms being carbon, wherein at least one of the rings is aromatic. For example, the bicyclic heteroaryl includes a 5- to 6-membered heterocyclic aromatic ring fused to a 5- to 6-membered cycloalkyl ring.

When the total number of S and O atoms in the heteroaryl group exceeds 1, said S and O heteroatoms are not adjacent to one another.

The heteroaryl group also includes those wherein the N heteroatom occurs as N-oxide, such as pyridyl N-oxides.

Examples of the heteroaryl group include, but are not limited to, pyridyl, pyridyl N-oxide, pyrazinyl, pyrimidinyl, pyrazolyl, imidazolyl, oxazolyl, isoxazolyl, thiazolyl, isothiazolyl, thiadiazolyl, tetrazolyl, triazolyl, thienyl, furyl, pyranyl, pyrrolyl, pyridazinyl, benzodioxolyl, benzooxazolyl, benzoisoxazolyl, benzothienyl, benzothiazolyl, benzoisothiazolyl, imidazopyridyl (such as imidazo[1,2-a]pyridyl), pyrrolopyridyl, pyrrolopyrimidinyl, pyrazolopyridinyl (such as pyrazolo[1,5-a]pyridyl), pyrazolopyrimidinyl, triazolopyridinyl (such as [1,2,4]triazolo[1,5-a]pyridyl), tetrazolopyridinyl, tetrahydropyrazolopyridyl (such as 4,5,6,7-tetrahydropyrazolo[1,5-a]pyridyl, benzofuryl, benzoimidazolinyl, indolyl, indazolyl, purinyl, quinolinyl, and isoquinolinyl.

"Hydroxyl" as used herein refers to the —OH radical.
"Mercapto" as used herein refers to the —SH radical.
"Oxo" as used herein refers to the =O radical.

When a structure herein contains an asterisk "*", it means that the chiral center of the compound marked by "*" is in either R-configuration or S-configuration, and the content of the compound with single configuration marked by "*" is at least 90% (e.g., 90%, 91%, 92%, 93%, 94%, 95%, 96%, 97%, 98%, 99%, 99.5%, 99.9%, 100%, or any value between those enumerated values). The configuration of the compounds can be determined using a variety of analytical techniques, for example single crystal X-ray crystallography and/or optical polarimetry according to routine protocols by those of ordinary skill in the art.

When a structure herein contains "(RS)", it means that the chiral center of the compound marked by "(RS)" contains both R-configuration and S-configuration.

The term "optional" or "optionally" as used herein means that the subsequently described event or circumstance may or may not occur, and the description includes instances wherein the event or circumstance occur and instances in which it does not occur. For example, "optionally substituted alkyl" encompasses both "unsubstituted alkyl" and "substituted alkyl" as defined herein. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

The term "substituted" or "substituted with . . . ", as used herein, means that one or more hydrogens on the designated atom or group are replaced with one or more selections from the indicated group of substituents, provided that the designated atom's normal valence is not exceeded. When a substituent is oxo (i.e., =O), then 2 hydrogens on a single atom are replaced by the oxo. Combinations of substituents and/or variables are permissible only if such combinations result in a chemically correct and stable compound. A chemically correct and stable compound is meant to imply a compound that is sufficiently robust to survive sufficient isolation from a reaction mixture to be able to identify the chemical structure of the compound, and also sufficiently robust to allow subsequent formulation as an agent having at least one practical utility.

Unless otherwise specified, substituents are named into the core structure. For example, it is to be understood that when (cycloalkyl)alkyl is listed as a possible substituent, the point of attachment of this substituent to the core structure is in the alkyl portion.

The term "substituted with one or more substitutents" as used herein means that one or more hydrogens on the designated atom or group are independently replaced with one or more selections from the indicated group of substituents. In some embodiments, "substituted with one or more substitutents" means that the designated atom or group is substituted with 1, 2, 3, or 4 substitutents independently chosen from the indicated group of substituents.

It will be appreciated by the person of ordinary skill in the art ("POSITA") that some of the compounds of formula (I) may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the POSITA that the present invention includes all the individual stereoisomers (e.g. enantiomers), racemic mixtures or partially resolved mixtures of the compounds of formula (I) and, where appropriate, the individual tautomeric forms thereof.

In other words, in some embodiments, the present invention provides compounds of various stereoisomeric purities, i.e., diastereomeric or enantiomeric purity expressed as various "ee" or "de" Values. In some embodiments, the compound of formula (I) (e.g., as described herein) has an enantiomeric purity of at least 60% ee (e.g., 60%, 65%, 70%, 75%, 80%, 85%, 90%, 91%, 92%, 93%, 94%, 95%, 96%, 97%, 98%, 99%, 99.5%, 99.9% ee, or any value between those enumerated values). In some embodiments, the compound of formula (I) (e.g., as described herein) has an enantiomeric purity of greater than 99.9% ee, extending up to 100% ee. In some embodiments, the compound of formula (I) (e.g., as described herein) has a diastereomeric purity of at least 60% de (e.g., 60%, 65%, 70%, 75%, 80%, 85%, 90%, 91%, 92%, 93%, 94%, 95%, 96%, 97%, 98%, 99%, 99.5%, 99.9% de, or any value between those enumerated values). In some embodiments, the compound of formula (I) (e.g., as described herein) has a diastereomeric purity of greater than 99.9% de.

The term "enantiomeric excess" or "ee" designates how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as ([a]obs/[a]max)*100, where [a]obs is the optical rotation of the mixture of enantiomers and [a]max is the optical rotation of the pure enantiomer.

The term "diastereomeric excess" or "de" designates how much of one diastereomer is present compared to the other and is defined by analogy to enantiomeric excess. Thus, for a mixture of diastereomers, D1 and D2, the percent diastereomeric excess is defined as |D1−D2|*100, where D1 and D2 are the respective mole or weight fractions of diastereomers in a mixture such that D1+D2=1.

The determination of diastereomeric and/or enantiomeric excess can be accomplished using a variety of analytical techniques, including NMR spectroscopy, chiral column chromatography and/or optical polarimetry according to routine protocols familiar to to those skilled in the art.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent. Individual isomers can be prepared in chiral form from chiral precursors. Alternatively, individual isomers can be separated chemically from a mixture by forming diastereomeric salts with a chiral acid, such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of, for example, at least 91%, 92%, 93%, 94%, 95%, 96%, 97%, 98%, 99% or 99.5% by weight of the desired stereoisomer. Alternatively, the racemates can be covalently linked to a chiral compound (auxiliary) to produce diastereomers which can be separated by chromatography or by fractional crystallization after which time the chiral auxiliary is chemically removed to afford the pure enantiomers, as is known to the POSITA.

The term "tautomer" as used herein refers to constitutional isomers of compounds generated by rapid movement of an atom in two positions in a molecule. Tautomers readily interconvert into each other, e.g., enol form and ketone form are typical tautomers. For example, some compounds disclosed herein can exist in the forms of a, b, c, d, e, f, etc., as shown in the figure below, i.e., compounds in the forms of a, b, c, d, e, f are possible the tautomers of the compound of Formula (I). The single tautomer and the mixture of these tautomers in any ratio are all included in the compounds described herein.

A "pharmaceutically acceptable salt" is intended to mean a salt of a free acid or base of a compound of Formula (I) that is non-toxic, biologically tolerable, or otherwise biologically suitable for administration to the subject. For examples, see, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002.

In addition, if a compound described herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. The POSITA will recognize various synthetic methodologies that may be used without undue experimentation to prepare non-toxic pharmaceutically acceptable acid addition salts.

The term "solvates" means solvent addition forms that contain either stoichiometric or non-stoichiometric amounts of solvent. Some compounds have a tendency to trap a fixed molar ratio of solvent molecules in the solid state, thus forming a solvate. If the solvent is water, the solvate formed is a hydrate, when the solvent is alcohol, the solvate formed is an alcoholate. Hydrates are formed by the combination of one or more molecules of water with one molecule of the substances in which the water retains its molecular state as $H_2O$, such combination being able to form one or more hydrates, for example, hemihydrates, monohydrate, and dihydrate, as well as variable hydrates.

As used herein, the terms "group", "radical" and "moiety" are synonymous and are intended to indicate functional groups or fragments of molecules attachable to other fragments of molecules.

The term "active ingredient" is used to indicate a chemical substance which has biological activity. In some embodiments, an "active ingredient" is a chemical substance having pharmaceutical utility. In the United States, practical phar-

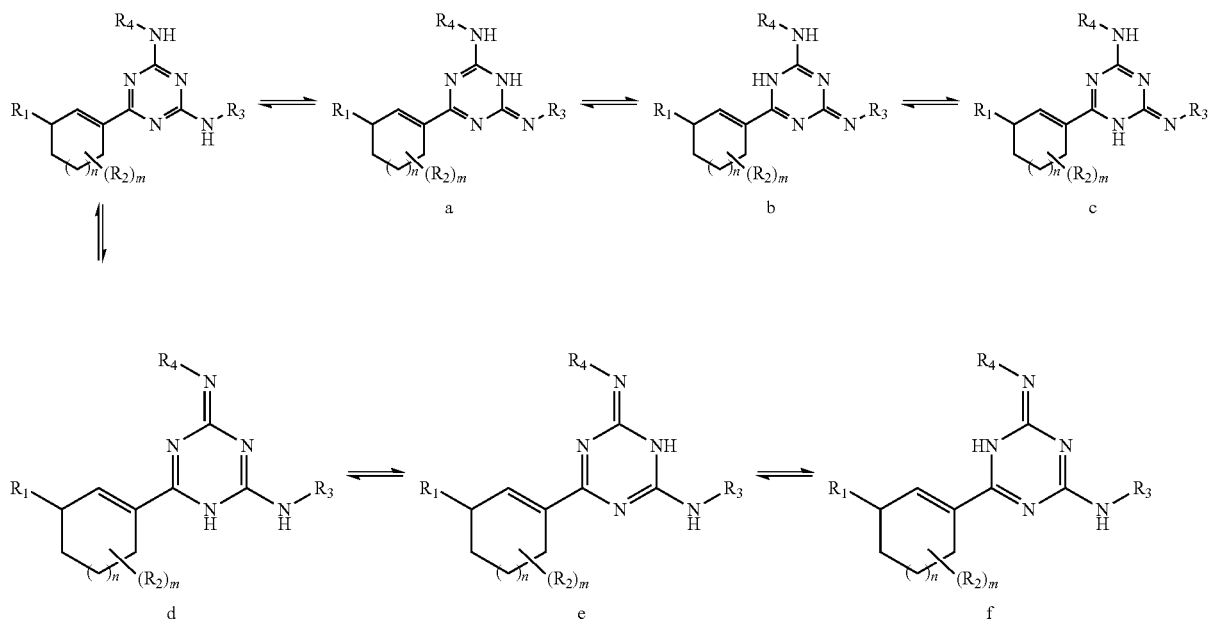

maceutical activity can be established by appropriate preclinical assays, whether in vitro or in vivo. Pharmaceutical activity sufficient to be accepted by a regulatory agency, such as FDA in the U.S., is a higher standard than the pre-clinical assay. Such a higher standard of pharmaceutical activity, the success of which cannot generally be reasonably expected from the pre-clinical results, can be established by appropriate and successful randomized, double blind, controlled clinical trials in humans.

The terms "treating", "treat," or "treatment" of a disease or disorder, in the context of achieving therapeutic benefit, refer to administering one or more pharmaceutical substances, especially a compound of formula (I) and/or a pharmaceutically acceptable salt thereof described herein to a subject that has the disease or disorder, or has a symptom of a disease or disorder, or has a predisposition toward a disease or disorder, with the purpose to cure, heal, alleviate, relieve, alter, remedy, ameliorate, improve, or affect the disease or disorder, the symptoms of the disease or disorder, or the predisposition toward the disease or disorder. In some embodiments, the disease or disorder is cancer.

The terms "treating", "contacting" and "reacting," in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount or dose of an IDH mutation inhibiting agent sufficient to generally bring about a therapeutic benefit in patients in need of treatment for a disease or disorder induced by IDH mutation. Effective amounts or doses of the active ingredient of the present disclosure may be ascertained by methods such as modeling, dose escalation studies or clinical trials, and by taking into consideration factors, e.g., the mode or route of administration or drug delivery, the pharmacokinetics of the agent, the severity and course of the disease or disorder, the subject's previous or ongoing therapy, the subject's health status and response to drugs, and the judgment of the attending physician. In the United States, the determination of effective doses is generally difficult to predict from preclinical trials. In fact, the dose is completely unpredictable and the dose will develop a new unpredictable dosing regimen after initial use in a randomized, double-blind, controlled clinical trials.

An exemplary dose is in the range of from about 0.0001 to about 200 mg of active agent per kg of subject's body weight per day, such as from about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease or disorder has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

In general, the term "about" is used herein to modify a numerical value above and below the stated value by a variance of 20%.

Technical and scientific terms used herein and not specifically defined have the meaning commonly understood by the POSITA to which the present disclosure pertains.

Provided is a compound of formula (I):

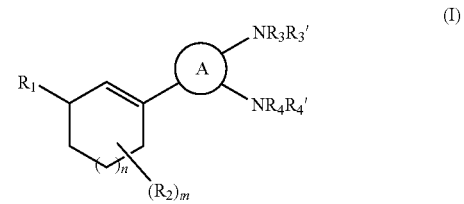

and/or a pharmaceutically acceptable salt thereof, and/or solvates, racemic mixtures, enantiomers, diasteromers, and tautomers thereof, wherein A is chosen from

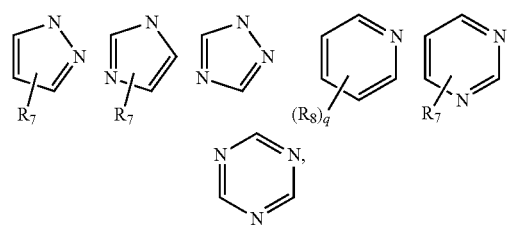

wherein, $R_7$ is chosen from H, halo, —CN, —OH, or —NH$_2$; $R_8$ is chosen from halo, —CN, —OH, or —NH$_2$; q is 1 or 2;

$R_1$ is chosen from H, —OH, halo, $C_{1-6}$ alkyl, $C_{1-6}$ alkoxyl, —NH$_2$, —NH($C_{1-4}$ alkyl), —N($C_{1-4}$ alkyl)$_2$, oxo, or $C_{3-8}$ cycloalkyl;

each of $R_2$ is independently chosen from H, deuterium, halo, —OH, —NH$_2$, —CN, —SH, $C_{1-6}$ alkyl, $C_{2-6}$ alkenyl, $C_{2-6}$ alkynyl, $C_{1-6}$ haloalkyl, $C_{3-8}$ cycloalkyl, oxo, —OR$_5$, —OCOR$_5$, —NHR$_5$, —N(R$_5$)(C$_{1-4}$ alkyl), —COR$_5$, —NHCOR$_5$, or 3-8 membered heterocyclyl; in which each of said $C_{1-6}$ alkyl, $C_{2-6}$ alkenyl, $C_{2-6}$ alkynyl, $C_{3-8}$ cycloalkyl or 3-8 membered heterocyclyl is optionally substituted with one or more groups chosen from deuterium, halo, —CN, —OH, —SH, —NH$_2$, —NH($C_{1-4}$ alkyl), —N($C_{1-4}$ alkyl)$_2$, or $C_{1-6}$ alkoxyl; or two $R_2$, which attach to the same carbon atom, together with the carbon atom they are attached to form a 3-5 membered cycloalkyl which is optionally substituted with one or more halo or deuterium;

$R_3$, $R_{3'}$, $R_4$ and $R_{4'}$ are independently chosen from H, $C_{1-6}$ alkyl, $C_{2-6}$ alkenyl, $C_{2-6}$ alkynyl, $C_{3-12}$ cycloalkyl, 3-12 membered heterocyclyl, phenyl, 5-12 membered heteroaryl, —C(O)R$_5$, —OR$_5$, or —NHR$_5$, in which each of said $C_{1-6}$ alkyl, $C_{2-6}$ alkenyl, $C_{2-6}$ alkynyl, $C_{3-12}$ cycloalkyl, 3-12 membered heterocyclyl, phenyl, or 5-12 membered heteroaryl is optionally substituted with one or more $R_6$; wherein $R_3$, $R_{3'}$, $R_4$ and $R_{4'}$ are not H simultaneously; provided that when one of $R_3$ and $R_4$ is optionally substituted phenyl or optionally substituted 5-6 membered heteroaryl, the other one is —$OR_5$ or —$NHR_5$;

or $R_3$ and $R_{3'}$ are independently chosen from H, $C_{1-6}$ alkyl, $C_{2-6}$ alkenyl, $C_{2-6}$ alkynyl, $C_{3-12}$ cycloalkyl, 3-12 membered heterocyclyl, phenyl, 5-12 membered heteroaryl, —$C(O)R_5$, —$OR_5$, or —$NHR_5$, in which each of said $C_{1-6}$ alkyl, $C_{2-6}$ alkenyl, $C_{2-6}$ alkynyl, $C_{3-12}$ cycloalkyl, 3-12 membered heterocyclyl, phenyl, or 5-12 membered heteroaryl is optionally substituted with one or more $R_6$; $R_4$ and $R_{4'}$ together with the N atom they are attached to form a 3-8 membered heterocyclic ring optionally substituted by one or more $R_6$;

$R_5$ is chosen from $C_{1-6}$ alkyl or $C_{3-8}$ cycloalkyl, each of which is optionally substituted with one or more groups independently chosen from halo, —CN, —OH, —SH, —$NH_2$, or $C_{1-6}$ alkoxyl;

each of $R_6$ is independently chosen from deuterium, halo, —CN, —OH, —SH, —$NH_2$, $C_{1-6}$ alkoxyl, $C_{1-6}$ alkyl, $C_{1-6}$ haloalkyl, $C_{3-8}$ cycloalkyl, 3-8 membered heterocyclyl, phenyl, or 5-6 membered heteroaryl, in which each of said $C_{1-6}$ alkoxyl, $C_{1-6}$ alkyl, $C_{3-8}$ cycloalkyl, 3-8 membered heterocyclyl, phenyl, or 5-6 membered heteroaryl is optionally substituted with one or more groups independently chosen from halo, —CN, —OH, —SH, —$NH_2$, $C_{1-6}$ alkoxyl, $C_{1-6}$ alkynyl, or $C_{1-6}$ alkyl;

m is 0, 1, 2, 3, 4, 5, or 6;

n is 0, 1, or 2.

In some embodiments of the compound of formula (I), $R_1$ is chosen from H, —OH or halo.

In some embodiments of the compound of formula (I), $R_1$ is chosen from —OH or halo.

In some embodiments of the compound of formula (I), $R_1$ is —OH.

In some embodiments of the compound of formula (I), $R_1$ is halo chosen from F, Cl, or Br. In some embodiments of the compound of formula (I), $R_1$ is F.

In some embodiments of the compound of formula (I), the two $R_2$, which attach to the same carbon atom, together with the carbon atom they are attached to form a 3-5 membered cycloalkyl optionally substituted by one or more F.

In some embodiments of the compound of formula (I), the two $R_2$, which attach to the same carbon atom, together with the carbon atom they are attached to form a cyclopropyl.

In some embodiments of the compound of formula (I), each of $R_2$ is independently chosen from H, deuterium, halo, —OH, —$NH_2$, —CN, —SH, $C_{1-6}$ alkyl, $C_{2-6}$ alkenyl, $C_{2-6}$ alkynyl, $C_{1-6}$ haloalkyl, $C_{3-8}$ cycloalkyl, oxo, —$OR_5$, —$OCOR_5$, —$NHR_5$, —$N(R_5)(C_{1-4}$ alkyl), —$NHCOR_5$, or 3-8 membered heterocyclyl.

In some embodiments of the compound of formula (I), each of $R_2$ is independently chosen from H, deuterium, halo, —OH, —$NH_2$, —CN, $C_{1-6}$ alkyl, $C_{1-6}$ haloalkyl, oxo, —$OR_5$, —$NHR_5$, or —$N(R_5)(C_{1-4}$ alkyl).

In some embodiments of the compound of formula (I), each of $R_2$ is independently chosen from H, deuterium, halo, $C_{1-6}$ alkyl, or $C_{1-6}$ haloalkyl.

In some embodiments of the compound of formula (I), each of $R_2$ is independently chosen from halo, such as F, Cl, or Br.

In some embodiments of the compound of formula (I), $R_2$ is F.

In some embodiments of the compound of formula (I), m is 0, 1, 2, 3, or 4.

In some embodiments of the compound of formula (I), m is 0, 1, or 2.

In some embodiments of the compound of formula (I), m is 1. In some embodiments of the compound of formula (I), m is 2. In some embodiments of the compound of formula (I), m is 3. In some embodiments of the compound of formula (I), m is 4.

In some embodiments of the compound of formula (I), $R_3$ and $R_4$ are independently chosen from $C_{1-6}$ alkyl, $C_{3-12}$ cycloalkyl, 3-12 membered heterocyclyl, phenyl, 5-12 membered heteroaryl, —$C(O)R_5$, —$OR_5$, or —$NHR_5$, in which each of said $C_{1-6}$ alkyl, $C_{3-12}$ cycloalkyl, 3-12 membered heterocyclyl, phenyl, or 5-12 membered heteroaryl is optionally substituted with one or more $R_6$; $R_{3'}$ and $R_{4'}$ are independently chosen from H or $C_{1-6}$ alkyl.

In some embodiments of the compound of formula (I), $R_{3'}$ and $R_{4'}$ are both H.

In some embodiments of the compound of formula (I), $R_3$ and $R_4$ are independently chosen from $C_{1-6}$ alkyl, $C_{3-12}$ cycloalkyl, or 3-12 membered heterocyclyl, each of which is optionally substituted with one or more $R_6$; $R_{3'}$ and $R_{4'}$ are both H.

In some embodiments of the compound of formula (I), $R_3$ and $R_4$ are independently chosen from $C_{1-6}$ alkyl substituted with one ore more halo, 5-12 membered heteroaryl substituted with $C_{1-6}$ haloalkyl, or —$OR_5$; $R_{3'}$ and $R_{4'}$ are both H.

In some embodiments of the compound of formula (I), $R_3$ and $R_4$ are independently chosen from $C_{1-6}$ alkyl optionally substituted with one or more halo; $R_{3'}$ and $R_{4'}$ are both H.

In some embodiments of the compound of formula (I), $R_3$ is 5-12 membered heteroaryl substituted with $C_{1-6}$ haloalkyl, $R_4$ is $C_{1-6}$ alkoxyl; $R_{3'}$ and $R_{4'}$ are both H.

In some embodiments of the compound of formula (I), $R_3$ is 5-7 heteroaryl substituted with $CF_3$, $R_4$ is $C_{1-6}$ alkoxyl; $R_{3'}$ and $R_{4'}$ are both H.

In some embodiments of the compound of formula (I), $R_3$ is chosen from H, $C_{1-6}$ alkyl optionally substituted by $C_{1-6}$ haloalkyl, or 5-12 membered heteroaryl optionally substituted by $C_{1-6}$ haloalkyl; $R_{3'}$ is H; $R_4$ and $R_{4'}$ together with the N atom they are attached to form a 3-8 membered heterocyclic ring optionally substituted by one or more groups chosen from halo, —OH, or $C_{1-6}$ haloalkyl.

In some embodiments of the compound of formula (I), $R_5$ is $C_{1-6}$ alkyl or $C_{3-8}$ cycloalkyl.

In some embodiments of the compound of formula (I), $R_5$ is $C_{1-6}$ alkyl optionally substituted with one or more halo.

In some embodiments of the compound of formula (I), each of $R_6$ is independently chosen from deuterium, halo, —CN, —OH, —$NH_2$, $C_{1-6}$ alkoxyl, $C_{1-6}$ alkyl, $C_{1-6}$ haloalkyl, $C_{3-8}$ cycloalkyl, 3-8 membered heterocyclyl, phenyl, or 5-6 membered heteroaryl, in which each of said $C_{1-6}$ alkoxyl, $C_{1-6}$ alkyl, $C_{3-8}$ cycloalkyl, 3-8 membered heterocyclyl, phenyl, or 5-6 membered heteroaryl is optionally substituted with one or more halo.

In some embodiments of the compound of formula (I), each of $R_6$ is independently chosen from deuterium, halo, —OH, $C_{1-6}$ alkoxyl, $C_{1-6}$ alkyl, $C_{1-6}$ haloalkyl, $C_{3-8}$ cycloalkyl, 3-8 membered heterocyclyl, phenyl, or 5-6 membered heteroaryl.

In some embodiments of the compound of formula (I), each of $R_6$ is independently chosen from deuterium, halo, —CN, —OH, —$NH_2$, $C_{1-6}$ alkoxyl, $C_{1-6}$ alkyl, $C_{1-6}$ haloalkyl, or $C_{3-8}$ cycloalkyl.

In some embodiments of the compound of formula (I), each of $R_6$ is independently chosen from deuterium, halo, or $C_{1-6}$ haloalkyl.

In some embodiments of the compound of formula (I), n is 1.

In some embodiments of the compound of formula (I), $R_7$ and $R_8$ are independently chosen from halo or —CN.

In some embodiments of the compound of formula (I), $R_7$ and $R_8$ are independently chosen from F or —CN.

In some embodiments of the compound of formula (I), the compound of formula (I) is chosen from

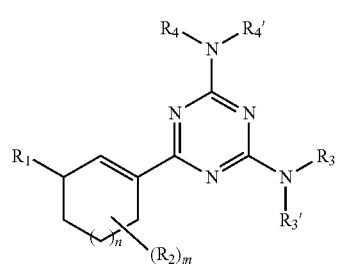

(I-1)

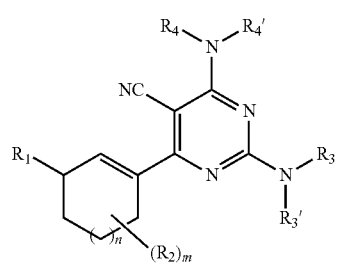

(I-2)

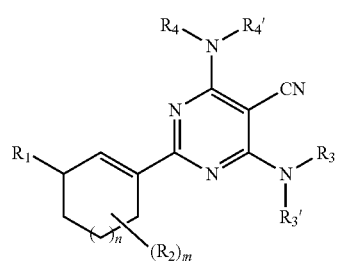

(I-3)

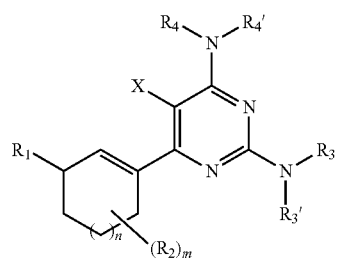

(I-4)

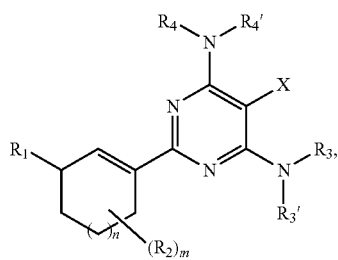

(I-5)

wherein X is halo; $R_1$, $R_2$, $R_3$, $R_{3'}$, $R_4$, $R_{4'}$, m and n are as defined in the compound of formula (I).

In some embodiments of the compound of formula (I), formula (I) is formula (I-1), wherein $R_1$, $R_2$, $R_3$, $R_{3'}$, $R_4$, $R_{4'}$, m and n are as defined in the compound of formula (I),

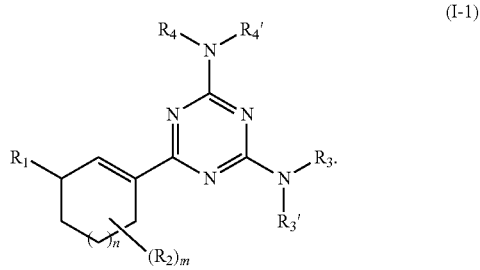

(I-1)

In some embodiments of the compound of formula (I), formula (I) is formula (I-1a), wherein $R_2$, $R_3$, $R_{3'}$, $R_4$, $R_{4'}$, m and n are as defined in the compound of formula (I),

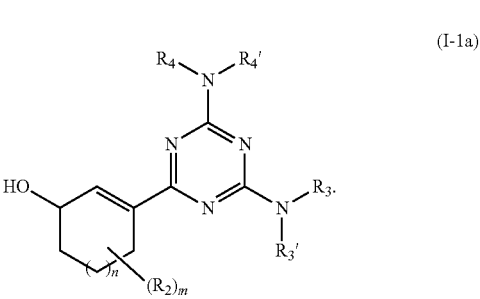

(I-1a)

In some embodiments of the compound of formula (I), formula (I) is formula (I-1b), wherein $R_2$, $R_3$, $R_{3'}$, $R_4$, $R_{4'}$, m and n are as defined in the compound of formula (I),

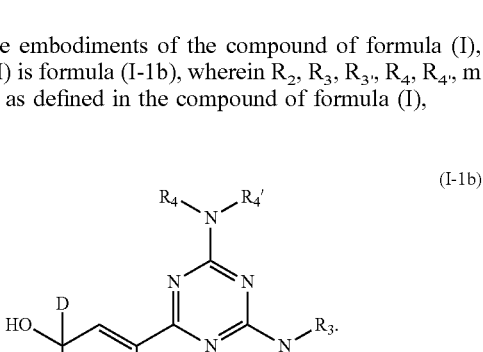

(I-1b)

In some embodiments of the compound of formula (I), formula (I) is formula (II), wherein $R_1$, $R_2$, $R_3$, $R_{3'}$, $R_4$, $R_{4'}$, n and A are as defined in the compound of formula (I); X is halo; p is 0, 1, or 2; m is 0, 1, or 2,

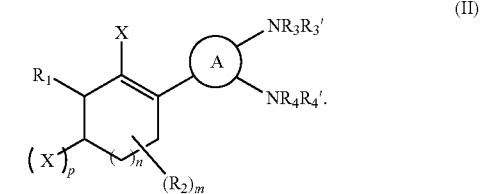

(II)

In some embodiments of the compound of formula (II), X is F.

In some embodiments of the compound of formula (II), $R_1$ is F.

In some embodiments of the compound of formula (II), $R_1$ is —OH.

In some embodiments of the compound of formula (II), p is 0.

In some embodiments of the compound of formula (II), p is 1.

In some embodiments of the compound of formula (II), p is 2.

In some embodiments of the compound of formula (I), formula (II) is chosen from

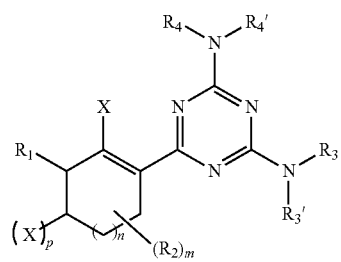
(II-1)

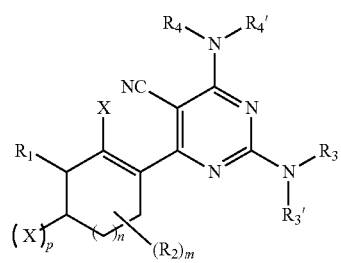
(II-2)

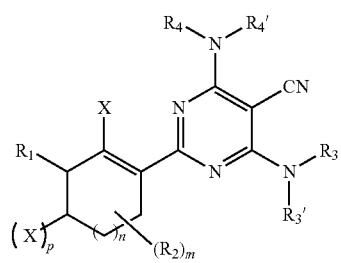
(II-3)

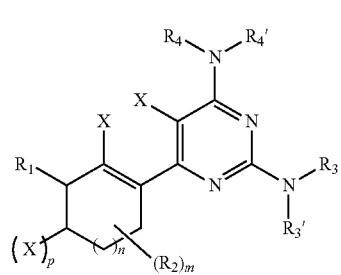
(II-4)

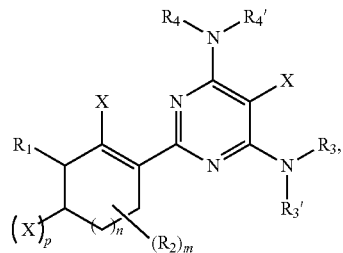
(II-5)

wherein $R_1$, $R_2$, $R_3$, $R_{3'}$, $R_4$, $R_{4'}$, m and n are as defined in the compound of formula (I); X is halo; p is 0, 1, or 2; m is 0, 1, or 2.

In some embodiments of the compound of formula (I), formula (II) is formula (II-1), wherein $R_1$, $R_2$, $R_3$, $R_{3'}$, $R_4$, $R_{4'}$, m and n are as defined in the compound of formula (I); X is halo; p is 0, 1, or 2; m is 0, 1, or 2,

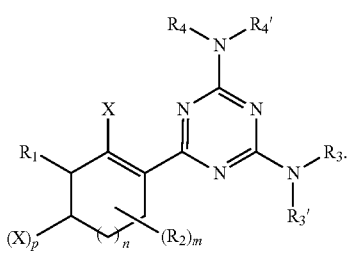
(II-1)

In some embodiments of the compound of formula (I), formula (II) is formula (II-1a), wherein $R_2$, $R_3$, $R_{3'}$, $R_4$, $R_{4'}$, m and n are as defined in the compound of formula (I); X is halo; p is 0, 1, or 2; m is 0, 1, or 2,

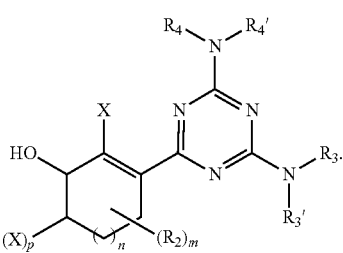
(II-1a)

In some embodiments of the compound of formula (I), formula (II) is formula (II-1b), wherein $R_2$, $R_3$, $R_{3'}$, $R_4$, $R_{4'}$, m and n are as defined in the compound of formula (I); X is halo; p is 0, 1, or 2; m is 0, 1, or 2,

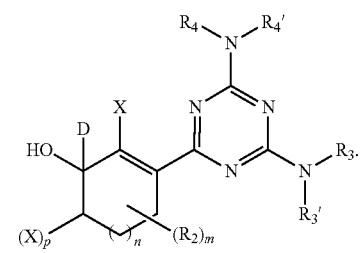

In some embodiments of the compound of formula (II-1)-formula (II-5), X is F.

In some embodiments of the compound of formula (II-1)-formula (II-5), $R_1$ is F.

In some embodiments of the compound of formula (II-1)-formula (II-5), $R_1$ is —OH.

In some embodiments of the compound of formula (II-1)-formula (II-5), p is 0.

In some embodiments of the compound of formula (II-1)-formula (II-5), p is 1.

In some embodiments of the compound of formula (II-1)-formula (II-5), p is 2.

In some embodiments of the compound of formula (I), formula (I) is formula (III), wherein $R_1$, $R_2$, $R_3$, $R_{3'}$, $R_4$, $R_{4'}$, n and A are as defined in the compound of formula (I); X is halo; p is 0, 1, or 2; m is 0, 1, or 2; v is 0, 1, or 2,

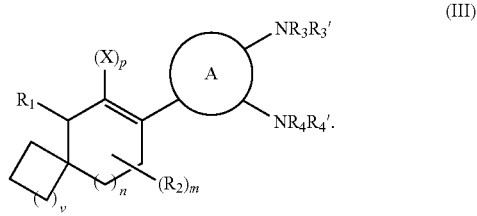
(III)

In some embodiments of the compound of formula (III), X is F.

In some embodiments of the compound of formula (III), $R_1$ is F.

In some embodiments of the compound of formula (III), $R_1$ is —OH.

In some embodiments of the compound of formula (III), p is 0.

In some embodiments of the compound of formula (III), p is 1.

In some embodiments of the compound of formula (III), p is 2.

In some embodiments of the compound of formula (III), v is 0.

In some embodiments of the compound of formula (III), v is 1.

In some embodiments of the compound of formula (III), v is 2.

In some embodiments of the compound of formula (I), formula (III) is chosen from

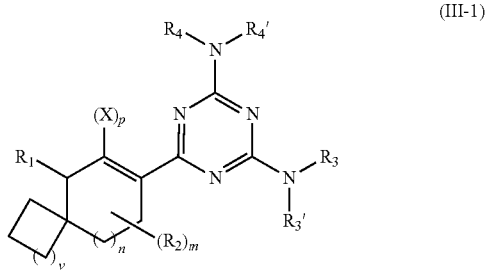
(III-1)

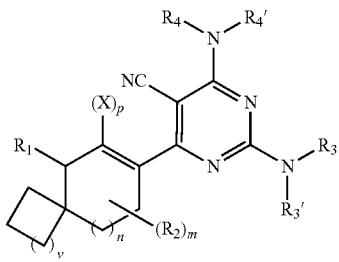
(II-2)

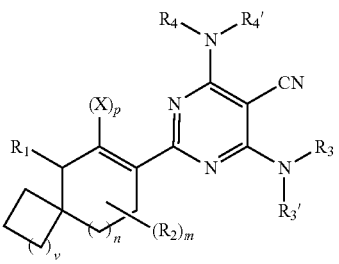
(III-3)

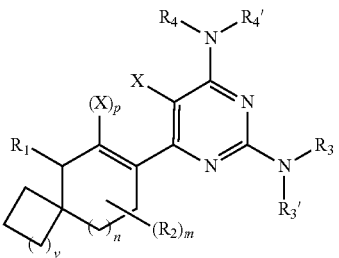
(III-4)

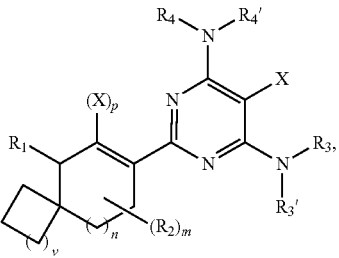
(III-5)

wherein $R_1$, $R_2$, $R_3$, $R_{3'}$, $R_4$, $R_{4'}$, m and n are as defined in the compound of formula (I); X is halo; p is 0, 1, or 2; m is 0, 1, or 2; v is 0, 1, or 2.

In some embodiments of the compound of formula (I), formula (III) is formula (III-1), wherein $R_1$, $R_2$, $R_3$, $R_{3'}$, $R_4$, $R_{4'}$, m and n are as defined in the compound of formula (I); X is halo; p is 0, 1, or 2; m is 0, 1, or 2; v is 0, 1, or 2,

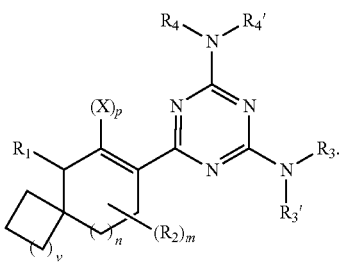
(III-1)

In some embodiments of the compound of formula (III-1)-formula (III-5), X is F.

In some embodiments of the compound of formula (III-1)-formula (III-5), $R_1$ is F.

In some embodiments of the compound of formula (III-1)-formula (III-5), $R_1$ is —OH.

In some embodiments of the compound of formula (III-1)-formula (III-5), p is 0.

In some embodiments of the compound of formula (III-1)-formula (III-5), p is 1.

In some embodiments of the compound of formula (III-1)-formula (III-5), p is 2.

In some embodiments of the compound of formula (III-1)-formula (III-5), v is 0.

In some embodiments of the compound of formula (III-1)-formula (III-5), v is 1.

In some embodiments of the compound of formula (III-1)-formula (III-5), v is 2.

Also provided is a compound chosen from Compounds 1-87, 89-184, 186-301, as numbered in the experimental section, and/or a pharmaceutically acceptable salt thereof.

In another aspect, provided is a pharmaceutical composition, comprising a compound of formula (I) (e.g., any of the compounds described herein) and/or a pharmaceutically acceptable salt thereof, and optionally comprising at least one pharmaceutically acceptable excipient (e.g., a pharmaceutically acceptable carrier).

In another aspect, provided is a method of treating a disease induced by IDH mutation in a subject, comprising administering to the subject in need thereof an amount of a compound of formula (I) (e.g., any of the compounds described herein) and/or a pharmaceutically acceptable salt thereof effective to inhibit the increase of α-hydroxyglutaric acid (2HG) induced by IDH mutation in said subject.

In another aspect, provided is a method of treating a disease induced by IDH mutation in a subject, comprising administering to the subject in need thereof an amount of a pharmaceutical composition comprising a compound of formula (I) (e.g., any of the compounds described herein) and/or a pharmaceutically acceptable salt thereof and at least one pharmaceutically acceptable excipient (e.g., a pharmaceutically acceptable carrier) effective to inhibit the increase of α-hydroxyglutaric acid (2HG) induced by IDH mutation in said subject.

In another aspect, provided is a use of a compound of formula (I) (e.g., any of the compounds described herein) and/or a pharmaceutically acceptable salt thereof described herein for treating a disease induced by IDH mutation by inhibiting the increase of α-hydroxyglutaric acid (2HG) induced by IDH mutation in a subject.

In another aspect, provided is a use of a compound of formula (I) (e.g., any of the compounds described herein) and/or a pharmaceutically acceptable salt thereof described herein in the manufacture of a medicament for treating a disease induced by IDH mutation.

In some embodiments, the IDH mutation is IDH1 gene mutation.

In some embodiments, the IDH mutation is IDH2 gene mutation.

In some embodiments, the IDH mutation is IDH1-R132H or IDH2-R140Q gene mutation.

In some embodiments, the disease induced by IDH mutation is cancer.

In some embodiments, the cancer is chosen from solid cancer, neurogliocytoma, or hematological malignant tumor, such as leukemia, lymphoma, or myeloma.

In some embodiments, the cancer is chosen from acute myeloid leukemia (AML), acute promyelocytic leukemia (APL), glioblastoma (GBM), myelodysplastic syndrome (MDS), myeloproliferative neoplasms (MPN), cholangiocarcinoma, such as intrahepatic cholangiocarcinoma (IHCC), chondrosarcoma, giant cell tumor, intestinal cancer, melanoma, lung cancer, or non-Hodgkin's lymphoma (NHL).

In another aspect, provided is a compound of formula (IV) and/or a salt thereof, and/or racemic mixtures or enantiomers thereof, which can be used in the manufacture of compounds of formula (I) (e.g., any of the compounds described herein),

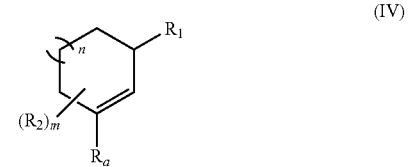

(IV)

wherein, $R_1$, $R_2$, m and n are as defined in the compound of formula (I); $R_a$ is chosen from halo, —OS(O)$_2$CF$_3$, —B(OH)$_2$, —B(OC$_{1-6}$ alkyl)$_2$,

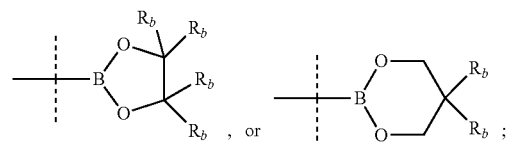

$R_b$ is H or C$_{1-6}$ alkyl.

In some embodiments of the compound of formula (IV), $R_a$ is chosen from —B(OH)$_2$, —B(OC$_{1-6}$ alkyl)$_2$,

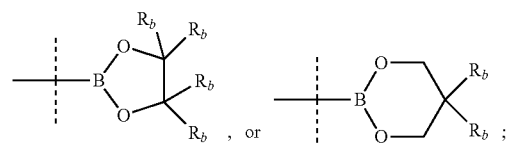

$R_b$ is H or C$_{1-6}$ alkyl.

In some embodiments of the compound of formula (IV), $R_a$ is chosen from —B(OH)$_2$, —B(OCH$_3$)$_2$, —B[OCH(CH$_3$)$_2$]$_2$,

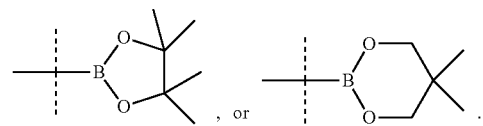

In some embodiments of the compound of formula (IV), formula (IV) is formula (IV-1), wherein m is 0, 1, or 2;

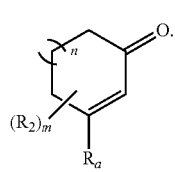
(IV-1)

In some embodiments of the compound of formula (IV), formula (IV) is formula (IV-2), wherein X is halo; m is 0, 1, or 2;

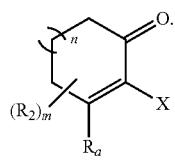
(IV-2)

In some embodiments of the compound of formula (IV), formula (IV) is formula (IV-3), wherein X is halo; p is 0, 1, or 2; m is 0, 1, or 2;

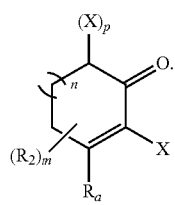
(IV-3)

In some embodiments of the compound of formula (IV), $R_1$ is —OH or oxo.

In some embodiments of the compound of formula (IV), X is F.

In some embodiments of the compound of formula (IV), p is 0.

In some embodiments of the compound of formula (IV), p is 1.

In some embodiments of the compound of formula (IV), p is 2.

In some embodiments of the compound of formula (IV), the compound of formula (IV) is chosen from

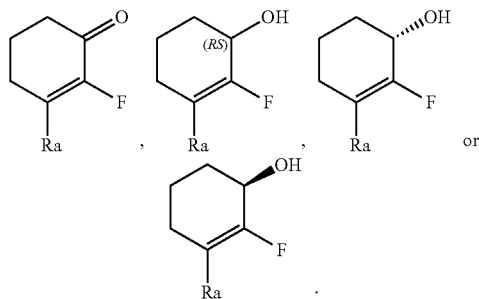

In some embodiments of the compound of formula (IV), the compound of formula (IV) is chosen from

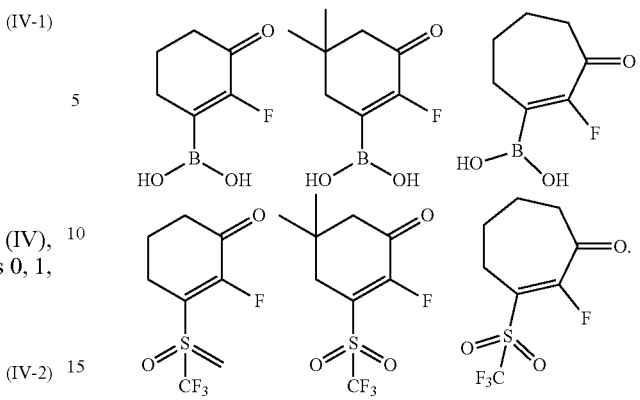

General Synthetic Methods for Disclosed Embodiments

The compound of formula (I) and/or a pharmaceutically acceptable salt thereof described herein can be synthesized from commercially available starting material by methods well known in the art, taken together with the disclosure in this patent application. The drawings 1-6 illustrate general methods for preparation of the compounds described herein.

As shown in FIG. 1, substitution reaction of 2,4,6-trichloro-1,3,5-triazine with an amine substituted with $R_3$ and $R_{3'}$ provides compound of formula 1-1. Substitution reaction of the compound of formula 1-1 with an amine substituted with $R_4$ and $R_{4'}$ provides compound of formula 1-2. Suzuki coupling reaction of compound of formula 1-2 with an intermediate represented by formula (IV) under the catalysis of a suitable palladium reagent gives a compound of formula (I-1) as described herein, wherein $R_1$, $R_2$, $R_3$, $R_{3'}$, $R_4$, $R_{4'}$, Ra, m, and n are as defined herein. The Pd-catalyzed C—C coupling reaction can be carried out under suitable conditions, and the solvent used can be selected from polar solvents such as 1,4-dioxane, DMF, THF, a mixture of 1,4-dioxane and water and the like, the base used can be selected from $Cs_2CO_3$, $Na_2CO_3$, $K_3PO_4$ and the like, and the catalyst used can be selected from $Pd(dppf)Cl_2CH_2Cl_2$, $Pd(PPh_3)_4$, $Pd(OAc)_2$ and the like.

As shown in Scheme 2, Suzuki coupling reaction of compound of formula 1-1 with an intermediate represented by formula (IV) under the catalysis of a suitable palladium reagent affords compound of formula 2-1. Substitution reaction of compound of formula 2-1 with an amine substituted with $R_4$ and $R_{4'}$ gives a compound of formula (I-1) as described herein, wherein $R_1$, $R_2$, $R_3$, $R_{3'}$, $R_4$, $R_{4'}$, Ra, m, and n are as defined herein.

As shown in Scheme 3, Suzuki coupling reaction of compound of formula 1-2 with an intermediate represented by formula (IV-1) under the catalysis of a suitable palladium reagent provides compound of formula 3-1. The Pd-catalyzed C—C coupling reaction can be carried out under suitable conditions, and the solvent used can be selected from polar solvents such as 1,4-dioxane, DMF, THF, a mixture of 1,4-dioxane and water and the like, the base used can be selected from $Cs_2CO_3$, $Na_2CO_3$, $K_3PO_4$ and the like, and the catalyst used can be selected from $Pd(dppf)Cl_2CH_2Cl_2$, $Pd(PPh_3)_4$, $Pd(OAc)_2$ and the like. Reduction of compound of formula 3-1 provides compound of formula (I-1a) as described herein.

As shown in Scheme 4, Suzuki coupling reaction of compound of formula 1-1 with an intermediate represented by formula (IV-1) under the catalysis of a suitable palladium reagent affords compound of formula 4-1. Reduction of Compound of formula 4-1 provides compound of formula 4-2. Substitution reaction of compound of formula 4-2 with an amine substituted with $R_4$ and $R_{4'}$ gives a compound of formula (I-1a) as described herein.

As shown in Scheme 5, Suzuki coupling reaction of compound of formula 1-2 with an intermediate represented by formula (IV-2) under the catalysis of a suitable palladium reagent provides compound of formula 5-1. Halogenation of compound of formula 5-1 using a halogenating reagent such as NFSI and the like, in presence of a base such as LiHMDS, KHMDS, LDA and the like, and in suitable polar solvents such as THF, DCM and the like, results in compound of formula 5-2. Reduction of compound of formula 5-2 provides compound of formula (II-1a) as described herein.

As shown in Scheme 6, compound of formula 3-1 reacts with a deuterating reagent such as $NaBD_4$, deuterated borane and the like gives a compound of formula (I-1b) as described herein.

The substituents of the compounds thus obtained can be further modified to provide other desired compounds. Synthetic chemistry transformations are described, for example, in R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

Before use, the compound of formula (I) and/or a pharmaceutically acceptable salt thereof described herein can be purified by column chromatography, high performance liquid chromatography, crystallization or other suitable methods.

Pharmaceutical Compositions and Practical Utility

The compound of formula (I) (e.g., any of those described herein) and/or a pharmaceutically acceptable salt thereof described herein is used, alone or in combination with one or more additional active ingredients, to formulate pharmaceutical compositions. A pharmaceutical composition comprises: (a) an effective amount of a compound of formula (I) and/or a pharmaceutically acceptable salt thereof described herein; and (b) a pharmaceutically acceptable excipient (e.g., a pharmaceutically acceptable carrier).

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compound of formula (I) and/or a pharmaceutically acceptable salt thereof described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in Remington's Pharmaceutical Sciences, A. Osol, a standard reference text in the art.

A pharmaceutical composition comprising a compound of formula (I) (e.g., any of those described herein) and/or a pharmaceutically acceptable salt thereof described herein can be administered in various known manners, such as orally, topically, rectally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A pharmaceutical composition described herein can be prepared in the form of tablet, capsule, sachet, dragee, powder, granule, lozenge, powder for reconstitution, liquid preparation, or suppository. In some embodiments, a pharmaceutical composition comprising a compound of formula (I) and/or a pharmaceutically acceptable salt thereof is formulated for intravenous infusion, topical administration, or oral administration.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In some embodiments, the compound of formula (I) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a tablet. In some embodiments, the compound of formula (I) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a capsule.

A sterile injectable composition (e.g., aqueous or oleaginous suspension) can be formulated according to techniques known in the art using suitable dispersing or wetting agents (such as, for example, Tween 80) and suspending agents. The sterile injectable Intermediate can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the Intermediate of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

Suitable in vitro assays can be used to evaluate the practical utility of the compound of formula (I) and/or a pharmaceutically acceptable salt thereof described herein, in inhibiting the IDH mutation. The compound of formula (I) and/or a pharmaceutically acceptable salt thereof described herein can further be examined for additional practical utility in treating cancer by in vivo assays. For example, the compound of formula (I) and/or a pharmaceutically acceptable salt thereof described herein can be administered to an animal (e.g., a mouse model) having cancer and its therapeutic effects can be accessed. If the pre-clinical results are successful, the dosage range and administration route for animals, such as humans, can be projected.

The compound of formula (I) and/or a pharmaceutically acceptable salt thereof described herein can be shown to have sufficient pre-clinical practical utility to merit clinical trials hoped to demonstrate a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic malignancies. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's lymphoma; non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), refractory anemia with excess blasts (RAEB), and RAEB in transformation (RAEB-T); and myeloproliferative syndromes.

In some embodiment, exemplary hematologic malignancies include leukemia, such as acute lymphocytic leukemia (ALL), acute myeloid leukemia (AML), chronic lymphocytic leukemia (CLL), and chronic myelogenous leukemia (CML); multiple myeloma (MM); and lymphoma, such as Hodgkin's lymphoma, non-Hodgkin's lymphoma (NHL), mantle cell lymphoma (MCL), follicular lymphoma, B-cell lymphoma, T-cell lymphoma, and diffuse large B-cell lymphoma (DLBCL).

The compound of formula (I) and/or a pharmaceutically acceptable salt described herein can be used to achieve a beneficial therapeutic or prophylactic effect, for example, in subjects with cancer.

In addition, the compound of formula (I) (e.g., any of those described herein) and/or a pharmaceutically acceptable salt thereof described herein may be used in combination with additional active ingredients in the treatment of cancer. The additional active ingredients may be coadministered separately with the compound of formula (I) and/or a pharmaceutically acceptable salt thereof described herein or included with such an ingredient in a pharmaceutical composition according to the disclosure, such as a fixed-dose combination drug product. In an exemplary embodiment, additional active ingredients are those that are known or discovered to be effective in the treatment of diseases induced by IDH mutation, such as another mutant IDH inhibitor or a compound active against another target associated with the particular disease. The combination may serve to increase efficacy (e.g., by including in the combination a compound potentiating the potency or effectiveness of the compound of formula (I) and/or a pharmaceutically acceptable salt thereof described herein), decrease one or more side effects, or decrease the required dose of the compound of formula (I) and/or a pharmaceutically acceptable salt thereof described herein.

In some embodiments, the compound of formula (I) (e.g., any of those described herein) and/or a pharmaceutically acceptable salt thereof described herein is administered in conjunction with an anti-neoplastic agent. As used herein, the term "anti-neoplastic agent" refers to any agent that is administered to a subject with cancer for purposes of treating the cancer. Nonlimiting examples anti-neoplastic agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, azacitidine (VIDAZA®); mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

EXAMPLES

The examples below are intended to be exemplary and should not be considered to be limiting in any way. Efforts have been made to ensure accuracy with respect to numbers used (for example, amounts, temperature, etc.) but some experimental errors and deviations should be accounted for. Unless indicated otherwise, parts are parts by weight, temperature is in degrees Centigrade, and pressure is at or near atmospheric. All MS data was determined by agilent 6120 or agilent 1100. All NMR data were generated using a Varian 400-MR machine. All reagents, except intermediates, used in this invention are commercially available. All compound names except the reagents were generated by Chemdraw 12.0.

If there is any atom with empty valence(s) in any one of the structures disclosed herein, the empty valence(s) is(are) the hydrogen atom(s) which is(are) omitted for convenience purpose.

In the present application, in the case of inconsistency of the structure and name of a compound, when the two of which are both given for the compound, it is subject to the structure of the compound, unless the context shows that the structure of the compound is incorrect and the name is correct.

In the following examples, the abbreviations below are used:

AcOK potassium acetate
BAST bis(2-methoxyethyl)aminosulfur trifluoride
BINAP (±)-2,2'-bis(diphenylphosphino)-1,1'-binaphthalene
t-BuONa sodium tert-butoxide
(n-Bu$_3$Sn)$_2$ 1,1,1,2,2,2-hexabutyldistannane
(S)—CBS (S)-3,3-diphenyl-1-methylpyrrolidino[1,2-c]-1,3,2-oxazaborole
CD$_3$OD methanol-d$_4$
DAST diethylaminosulphur trifluoride
DCM dichloromethane
DIEA N,N-diisopropylethylamine
DMF N,N-dimethylformamide
DMSO-d$_6$ dimethyl sulfoxide-d$_6$
EA/EtOAc ethyl acetate
Et$_3$N triethylamine
EtOH ethanol
Et$_2$Zn diethyl zinc
G gram
HC(OMe)$_3$ trimethyl orthoformate
L litre
LiHMDS lithium bis(trimethylsilyl)amide
M mol/L
MeOH methanol
MeCN acetonitrile
Mg milligram
mL millilitre
Mmol millimole
Mol mole
NaBH(OAc)$_3$ sodium triacetoxyborohydride
NaOMe sodium methoxide
NaOEt sodium ethoxide
NCS N-chlorosuccinimide
NFSI N-fluorobenzenesulfonimide
PdCl$_2$(PPh$_3$)$_2$ bis(triphenylphosphine)palladium(II) dichloride
Pd$_2$(dba)$_3$ tris(dibenzylideneacetone)dipalladium(0)
Pd(dppf)Cl$_2$ [1,1'-bis(diphenylphosphino)ferrocene]dichloropalladium(II)
Pd(dppf)Cl$_2$·CH$_2$Cl$_2$ [1,1'-bis(diphenylphosphino)ferrocene]dichloropalladium(II) dichloromethane complex
Pd(PPh$_3$)$_4$ tetrakis(triphenylphosphine)palladium(0)
PE petroleum ether
Selectfluor® 1-chloromethyl-4-fluoro-1,4-diazoniabicyclo[2.2.2]octane bis(tetrafluoroborate),
TBAF tetrabutylammonium fluoride
TBSOTf tert-butyldimethylsilyltrifluoromethanesulfonate
TFA trifluoroacetic acid
Tf$_2$O trifluoromethanesulfonic anhydride
THF tetrahydrofuran
TsOH·H$_2$O 4-methylbenzenesulfonic acid monohydrate Example 1

Preparation of Intermediates

Intermediate I-1

3-(4-Chloro-6-(((R)-1,1,1-trifluoropropan-2-yl)amino)-1,3,5-triazin-2-yl)-2-fluorocyclohex-2-en-1-ol and Intermediate I-61

(*)3-(4-Chloro-6-(((R)-1,1,1-trifluoropropan-2-yl)amino)-1,3,5-triazin-2-yl)-2-fluoro-cyclohex-2-en-1-ol

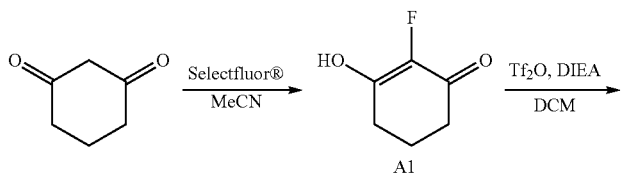

A1

-continued

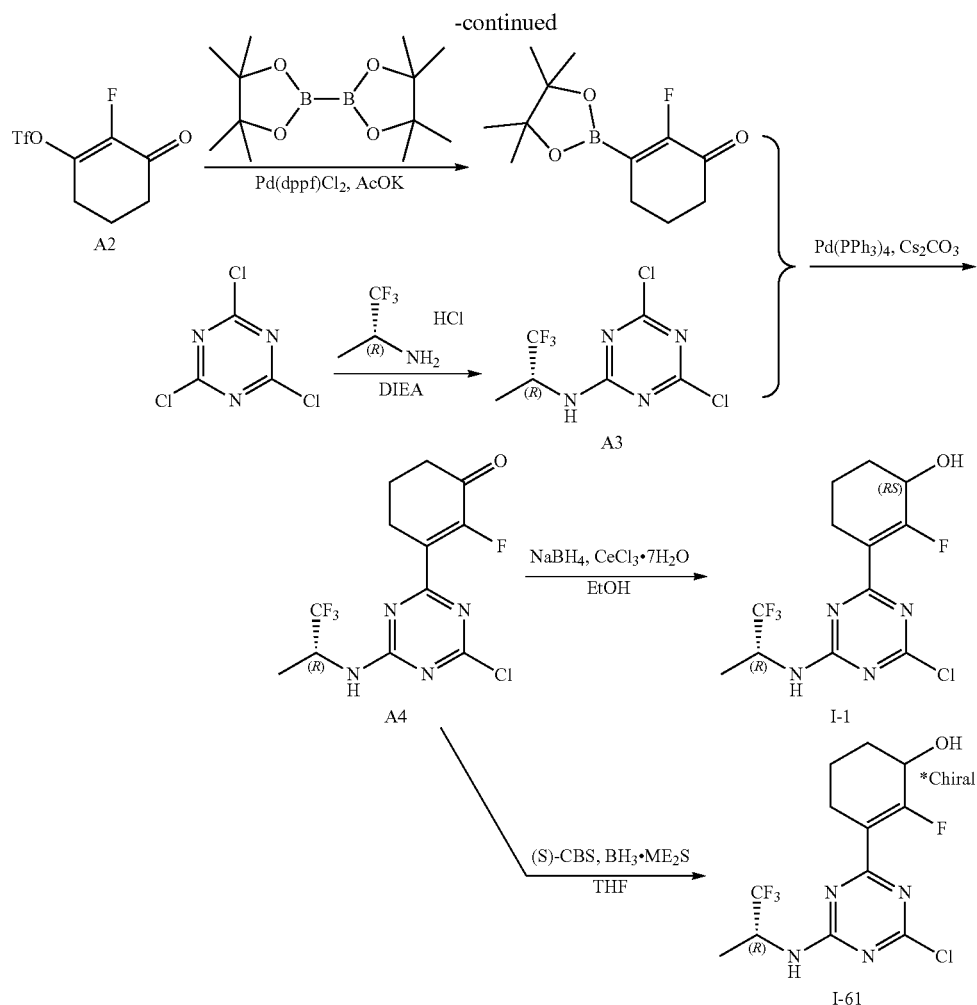

(A) 2-Fluoro-3-hydroxycyclohex-2-en-1-one (A1)

A mixture of cyclohexane-1,3-dione (30 g, 268 mmol) and Selectfluor® (94.8 g, 268 mmol) in MeCN (1.2 L) was stirred at 70° C. for 96 hours under nitrogen atmosphere. Then, the mixture was concentrated in vacuo. The residue was dissolved in DCM (1.2 L) and filtered. The filtrate was concentrated in vacuo and purified by flash column chromatography (eluting with gradient PE/EA=100:0-0:100) to give compound A1 as white solid (7.7 g, yield: 22%). MS (m/z): 131.1 [M+H]$^+$ (B) 2-Fluoro-3-oxocyclohex-1-en-1-yl trifluoromethanesulfonate (A2)

Under nitrogen atmosphere, compound A1 (208 mg, 1.6 mmol) was dissolved in DCM and cooled to 0° C. Then, DIEA (415 mg, 3.2 mmol) and Tf$_2$O (540 mg, 1.92 mmol) were added at 0° C. and the mixture was stirred for 2 hours at 0° C. under nitrogen atmosphere. After the reaction was completed, it was quenched by the addition of water and extracted with DCM. The organic layer was collected, condensed and purified by flash column chromatography (eluting with PE/EA) to give compound A2 as yellow oil (220 mg, yield: 52.5%). MS (m/z): 263.0 [M+H]$^+$ (C) (R)-4,6-dichloro-N-(1,1,1-trifluoropropan-2-yl)-1,3,5-triazin-2-amine (A3)

A solution of 2,4,6-trichloro-1,3,5-triazine (9.1 g, 49.3 mmol) in dry THF was cooled to 0° C. and (R)-1,1,1-trifluoropropan-2-amine hydrochloride (7.37 g, 49.3 mmol) was added. The reaction mixture was stirred at room temperature for 16 hours. After reaction was completed, the mixture was adjusted to pH=7 by the addition of saturated NaHCO$_3$ aqueous solution and extracted with EtOAc. The organic layer was collected, condensed and purified by flash column chromatography (eluting with gradient PE/EA=100: 0-0:100) to give compound A3 as colorless oil (7.8 g, yield: 60.6%). MS (m/z): 260.9[M+H]$^+$ (D) (R)-3-(4-chloro-6-((1,1,1-trifluoropropan-2-yl) amino)-1,3,5-triazin-2-yl)-2-fluoro-cyclohex-2-en-1-one (A4)

Under nitrogen atmosphere, a mixture of compound A2 (4.0 g, 15.3 mmol), 4,4,4',4',5,5,5',5'-octamethyl-2,2'-bi(1,3,2-dioxaborolane) (4.3 g, 16.8 mmol), AcOK (3.8 g, 38.3 mmol), Pd(dppf)Cl$_2$ (0.63 g, 0.77 mmol) in 1,4-dioxane (40 mL) was stirred at reflux for 2 hours. Then, the reaction mixture was cooled to room temperature, then was added compound A3 (4.0 g, 15.3 mmol), Cs$_2$CO$_3$ (14.4 g, 38.3 mmol), Pd(PPh$_3$)$_4$ (0.89 g, 0.77 mmol) and water (8 mL) in sequence. The reaction was stirred at 80° C. for another 2 hours. After the reaction was completed, the mixture was cooled to room temperature, condensed and purified by flash column chromatography (eluting with gradient PE/EA=100:0-0:100) to give compound A4 as white solid (0.8 g, yield: 15.4%). MS (m/z): 339.0[M+H]⁺

(E) 3-(4-Chloro-6-(((R)-1,1,1-trifluoropropan-2-yl)amino)-1,3,5-triazin-2-yl)-2-fluoro-cyclohex-2-en-1-ol (I-1

To a flask were added compound A4 (1150 mg, 3.41 mmol), CeCl$_3$·7H$_2$O (1269 mg, 3.41 mmol) and EtOH (20 mL). The mixture was cooled to 0° C., NaBH$_4$ (130 mg, 3.41 mmol) was added and the mixture was stirred at 0° C. for 2 hours. After the reaction was completed, the mixture was quenched by the addition of saturated NH$_4$Cl aqueous solution (10 mL) and water (50 mL) and extracted with EtOAc. The organic layer was collected, condensed and purified by flash column chromatography (eluting with gradient PE/EA=100:0-0:100) to give I-1 as white solid (800 mg, yield: 68.9%). MS (m/z): 341.2 [M+H]⁺

(F) (*)3-(4-Chloro-6-(((R)-1,1,1-trifluoropropan-2-yl)amino)-1,3,5-triazin-2-yl)-2-fluoro-cyclohex-2-en-1-ol (I-61

Under nitrogen atmosphere, to dry THF (5 mL) was added 1 mol/L (S)—CBS/THF solution (2.4 mL, 2.4 mmol) under ice bath cooling ° C., then 2 mol/L BH$_3$·Me$_2$S/THF solution (2.4 mL, 4.8 mmol) was added in one-portion. After stirred for 2 minutes, to the above solution was added compound A4 (800 mg, 2.4 mmol) in THF (3 mL) dropwise. After stirring under ice bath cooling ° C. for 1 hour, to the reaction mixture was added MeOH (0.5 mL), EtOAc (10 mL) and water (20 mL). The organic layer was collected. The aqueous phase was extracted with EtOAc (10 mL). The organic layers were combined, dried over Na$_2$SO$_4$, filtered. The filtrate was condensed and purified by flash column chromatography (eluting with gradient PE/EA=100:0-0:100) to give Intermediate I-61 as white solid (360 mg). MS (m/z): 341.2 [M+H]⁺

The compounds in the below table were prepared according to the procedure of Intermediate I-1 using the corresponding intermediates and reagents under appropriate conditions that will be recognized by the POSITA:

| Intermediate | Structure | MS (M + H)⁺ |
|---|---|---|
| I-22 | | 314.0 |
| I-23 | 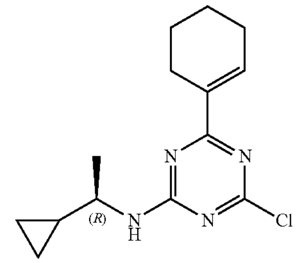 | 279.1 |
| I-24 | 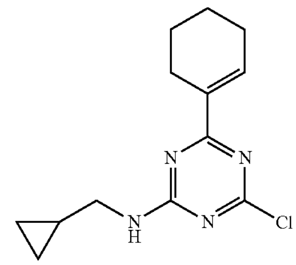 [SMILES: Clc1nc(NCC2CC2)nc(C2=CCCCC2)n1] | 265.1 |
| I-25 | 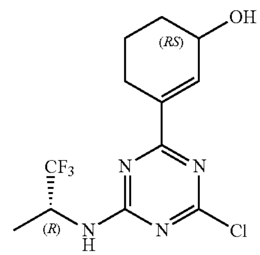 | 323.0 |
| I-80 | 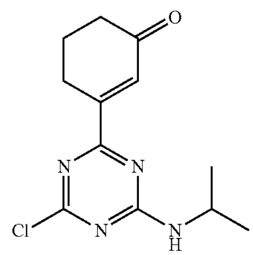 [SMILES: CC(C)Nc1nc(Cl)nc(C2=CC(=O)CCC2)n1] | 285.0 |

Intermediate I-2

(R)-6-Chloro-N²-isopropyl-N⁴-(1,1,1-trifluoropropan-2-yl)-1,3,5-triazine-2,4-diamine

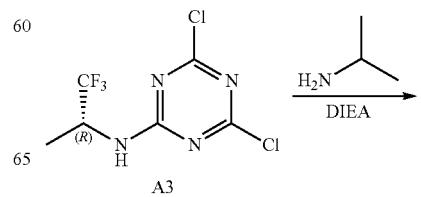

-continued

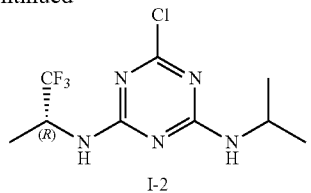
I-2

To a sealed tube was added compound A3 (3.5 g, 13.4 mmol), propan-2-amine (872 mg, 14.7 mmol), DIEA (3.5 g, 26.8 mmol) and THF (20 mL) in sequence, and the mixture was stirred at 50° C. overnight. After the reaction was completed, the mixture was cooled to room temperature, condensed and purified by flash column chromatography (eluting with PE/EA) to give Intermediate I-2 as white solid (3.8 g, yield: 100%). MS (m/z): 284.0 [M+H]$^+$ The compounds in the below table were prepared according to the procedure of Intermediate I-2 using the corresponding intermediates and reagents under appropriate conditions that will be recognized by POSITA:

| Intermediate | Structure | MS (M + H)$^+$ |
|---|---|---|
| I-7 | 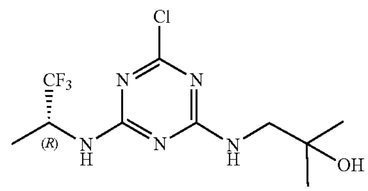 | 314.0 |
| I-8 | 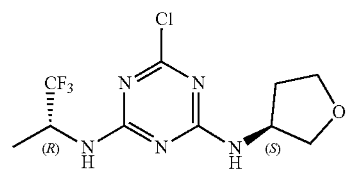 | 312.0 |
| I-9 | 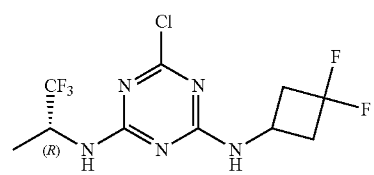 | 332.0 |
| I-11 | 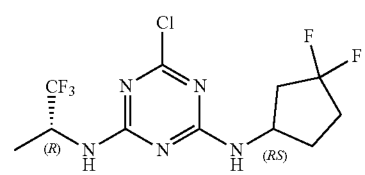 | 346.0 |
| I-12 | 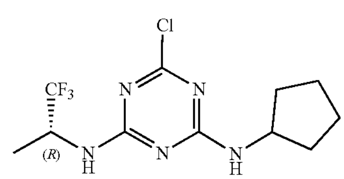 | 310.0 |
| I-13 | 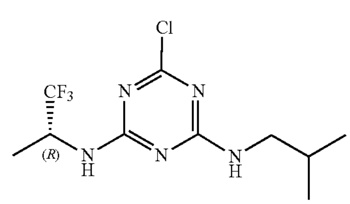 | 298.1 |

-continued
| Intermediate | Structure | MS (M + H)+ |
|---|---|---|
| I-14 | 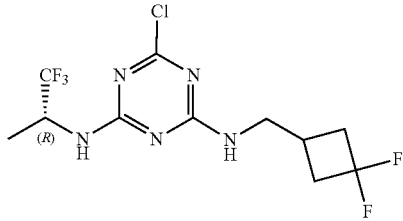 | 346.0 |
| I-15 | 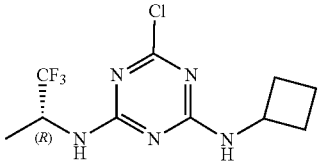 | 296.0 |
| I-16 | 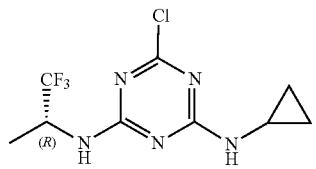 | 282.0 |
| I-17 | 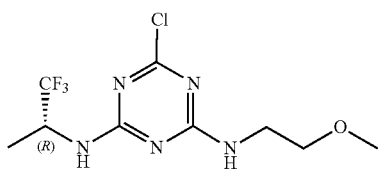 | 300.0 |
| I-18 | 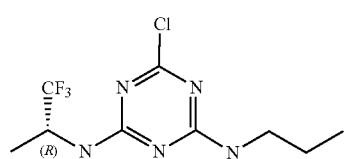 | 284.0 |
| I-19 | 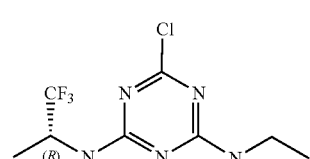 | 270.0 |
| I-20 | 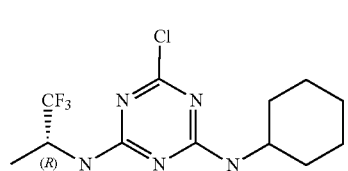 | 324.1 |
| I-21 | 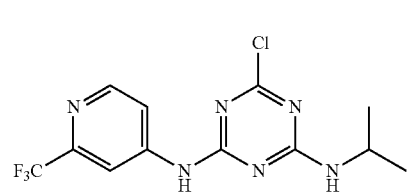 [SMILES: CC(C)Nc1nc(Cl)nc(Nc2ccnc(C(F)(F)F)c2)n1] | 333.0 |

-continued

| Intermediate | Structure | MS (M + H)+ |
|---|---|---|
| I-30 | 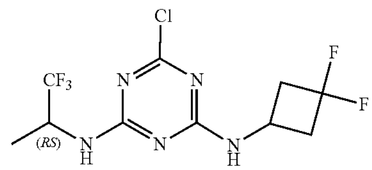 | 332.0 |
| I-31 | 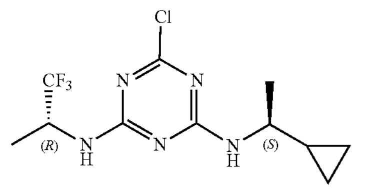 | 310.0 |
| I-33 | 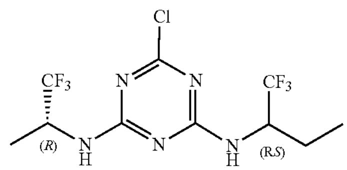 | 352.2 |
| I-35 | 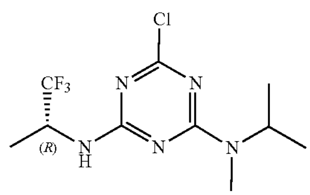 | 298.1 |
| I-36 | 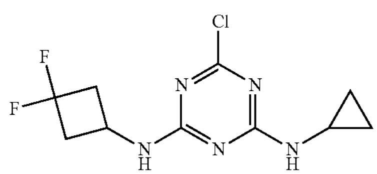 [SMILES: FC1(F)CC(Nc2nc(Cl)nc(NC3CC3)n2)C1] | 276.0 |
| I-37 | 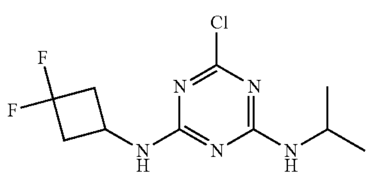 [SMILES: CC(C)Nc1nc(Cl)nc(NC2CC(F)(F)C2)n1] | 278.0 |
| I-38 | 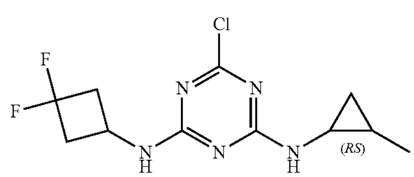 [SMILES: CC1CC1Nc1nc(Cl)nc(NC2CC(F)(F)C2)n1] | 290.0 |
| I-39 | 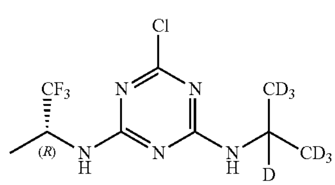 | 291.1 |

-continued

| Intermediate | Structure | MS (M + H)+ |
|---|---|---|
| I-40 | 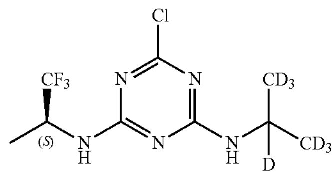 | 291.1 |
| I-42 | 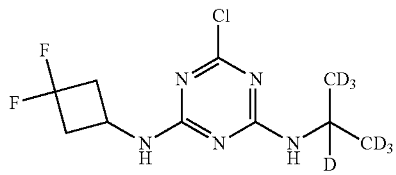 [SMILES: [2H]C([2H])([2H])C([2H])(Nc1nc(Cl)nc(NC2CC(F)(F)C2)n1)C([2H])([2H])[2H]] | 285.1 |
| I-49 | 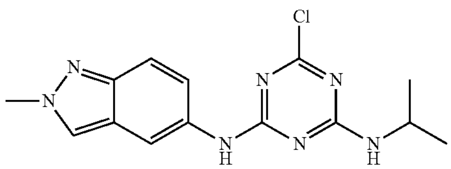 [SMILES: CC(C)Nc1nc(Cl)nc(Nc2ccc3nn(C)cc3c2)n1] | 318.0 |
| I-50 | 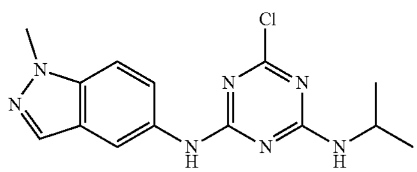 | 318.0 |
| I-51 | 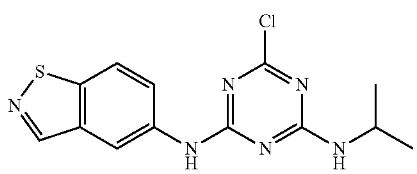 [SMILES: CC(C)Nc1nc(Cl)nc(Nc2ccc3sncc3c2)n1] | 321.0 |
| I-54 | 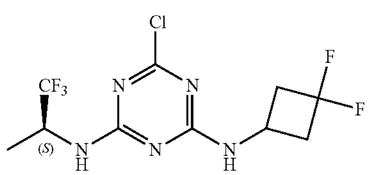 | 332.0 |
| I-55 | 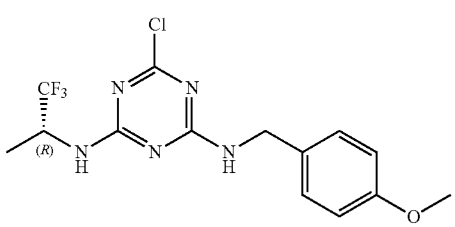 | 362.1 |
| I-71 | 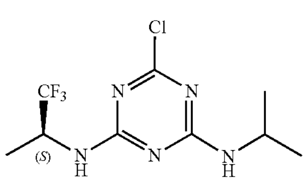 | 284.0 |

-continued

| Intermediate | Structure | MS (M + H)+ |
|---|---|---|
| I-72 | 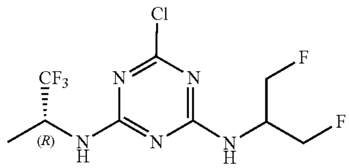 | 320.4 |
| I-73 | 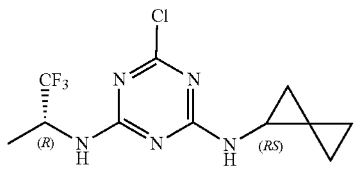 | 308.1 |
| I-74 | 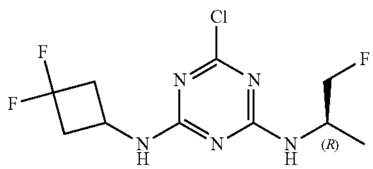 | 296.1 |
| I-75 | 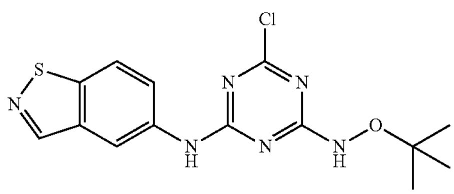 [SMILES: CC(C)(C)ONc1nc(Cl)nc(Nc2ccc3sncc3c2)n1] | 350.9 |
| I-76 | 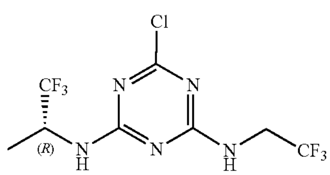 | 323.9 |
| I-77 | 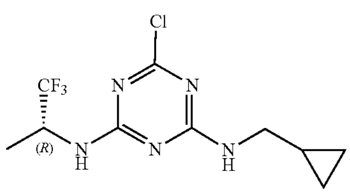 | 296.0 |
| I-78 | 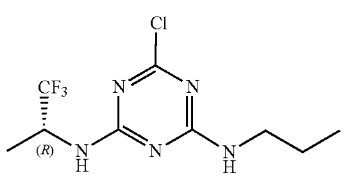 | 284.0 |
| I-79 | 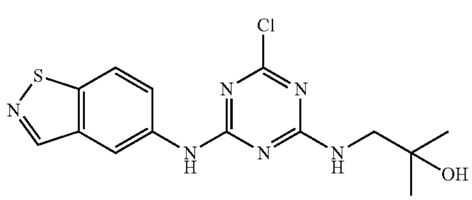 [SMILES: CC(C)(O)CNc1nc(Cl)nc(Nc2ccc3sncc3c2)n1] | 351.0 |

-continued

| Intermediate | Structure | MS (M + H)+ |
|---|---|---|
| I-81 | 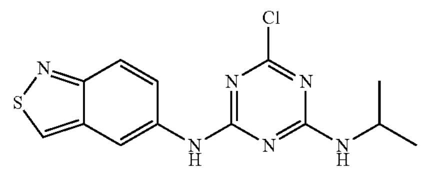 [SMILES: CC(C)Nc1nc(Cl)nc(Nc2ccc3nscc3c2)n1] | 321.0 |
| I-82 | 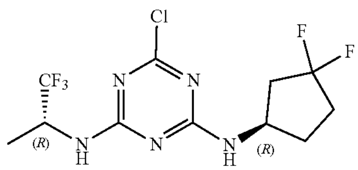 | 346.0 |
| I-83 | 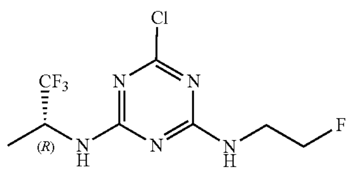 | 288.0 |
| I-84 | 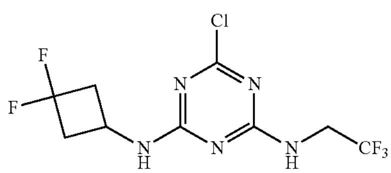 [SMILES: FC(F)(F)CNc1nc(Cl)nc(NC2CC(F)(F)C2)n1] | 318.0 |
| I-85 | 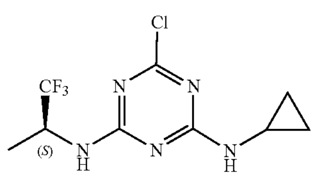 | 282.2 |
| I-86 | 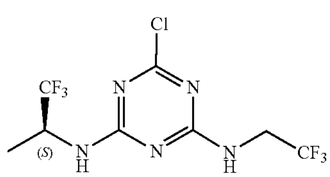 | 324.0 |
| I-87 | 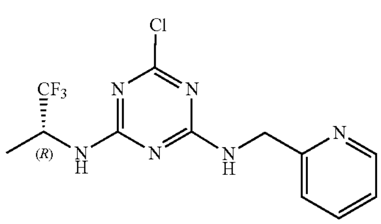 | 333.0 |
| I-89 | 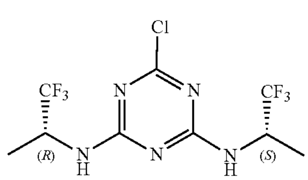 | 338.0 |

| Intermediate | Structure | MS (M + H)⁺ |
|---|---|---|
| I-90 | 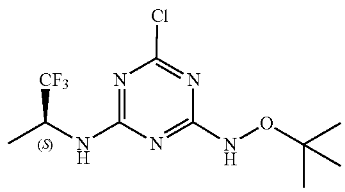 | 314.1 |
| I-91 | 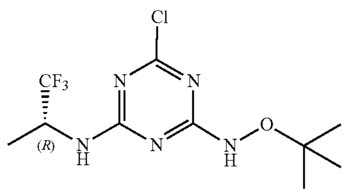 | 314.1 |
| I-101 | 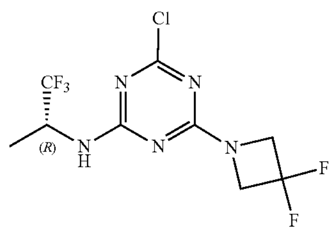 | 318.0 |
| I-102 | 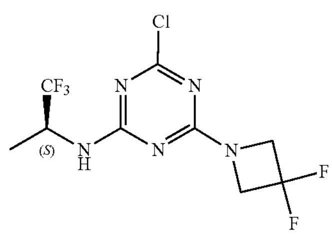 | 318.1 |

Intermediate I-3

6-Chloro-N²,N⁴-bis((R)-1,1,1-trifluoropropan-2-yl)-1,3,5-triazine-2,4-diamine CF₃

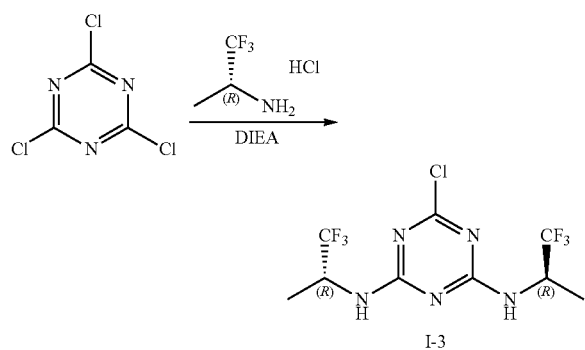

At 0° C., to a flask were added 1,4-dioxane (50 mL), 2,4,6-trichloro-1,3,5-triazine (1.84 g, 10 mmol), (R)-1,1,1-trifluoropropan-2-amine hydrochloride (2.99 g, 20 mmol) and DIEA (5.17 g, 40 mmol). The reaction was heated to 60° C. and stirred for 4 hours. After the reaction was completed, the mixture was condensed and purified by flash column chromatography (eluting with gradient water/MeOH=100:0-0:100) to give Intermediate I-3 as yellow solid (2.50 g, yield: 74%). MS (m/z): 338.0 [M+H]⁺

The compounds in the below table were prepared according to the procedure of Intermediate I-3 using the corresponding intermediates and reagents under appropriate conditions that will be recognized by POSITA:

| Intermediate | Structure | MS (M + H)+ |
|---|---|---|
| I-6 | 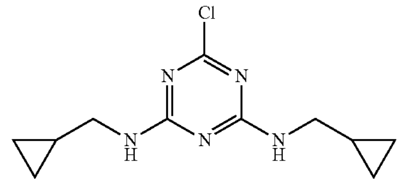 [SMILES: Clc1nc(NCC2CC2)nc(NCC2CC2)n1] | 254.1 |
| I-10 | 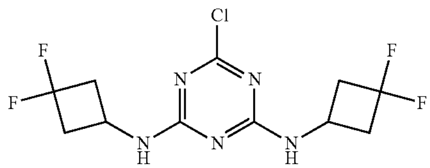 [SMILES: FC1(F)CC(Nc2nc(Cl)nc(NC3CC(F)(F)C3)n2)C1] | 326.0 |
| I-32 | 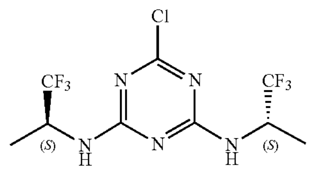 | 338.0 |
| I-34 | 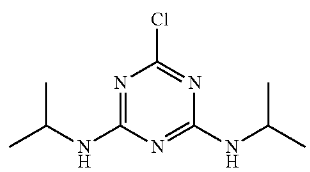 | 230.1 |
| I-106 | 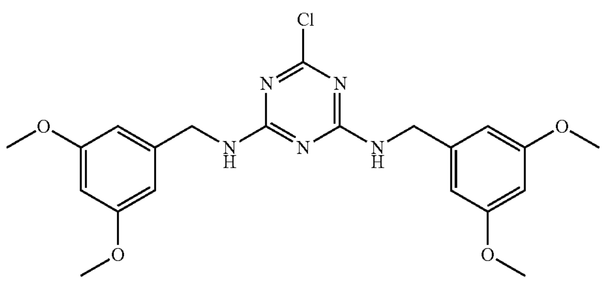 | 446.0 |

Intermediate I-4

(R)—N-(4-Chloro-6-((1,1,1-trifluoropropan-2-yl)amino)-1,3,5-triazin-2-yl)isobutyramide

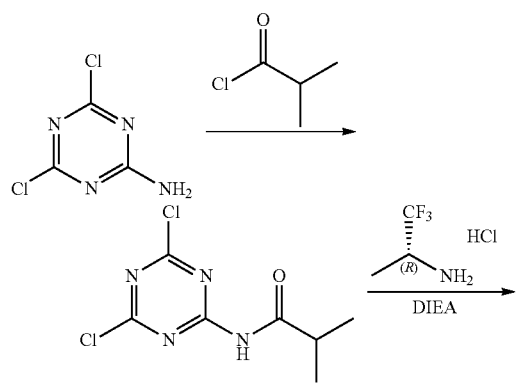

-continued

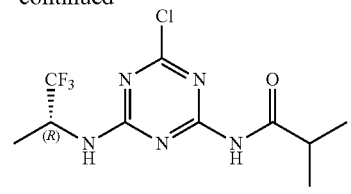

I-4

A mixture of 4,6-dichloro-1,3,5-triazin-2-amine (1 g, 6.06 mmol) in isobutyryl chloride (5 mL) was stirred at 100° C. for 2 hours. After the reaction was completed, the mixture was cooled to room temperature and concentrated to dryness in vacuo to afford N-(4,6-dichloro-1,3,5-triazin-2-yl)isobutyramide as yellow solid. Then, to 1,4-dioxane (10 mL) was added N-(4,6-dichloro-1,3,5-triazin-2-yl)isobutyramide obtained above, (R)-1,1,1-trifluoropropan-2-amine hydrochloride (900 mg, 6.06 mmol) and DIEA (2.34 g, 18.18 mmol). The mixture was heated to reflux and stirred for 2 hours. After the reaction was completed, the mixture was quenched by the addition of water, extracted with EtOAc (20 mL). The organic layer was collected, concentrated under reduced pressure and purified by flash column chromatography (eluting with PE/EA) to give Intermediate I-4 (80 mg). MS (m/z): 312.1 [M+H]$^+$ Intermediates I-26 and I-27

3-(4-Chloro-6-(((R)-1,1,1-trifluoropropan-2-yl)amino)-1,3,5-triazin-2-yl)cyclohex-2-en-1-ol optically pure diastereoisomers

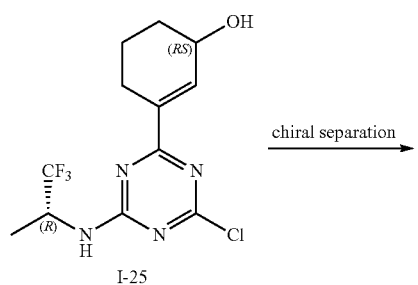

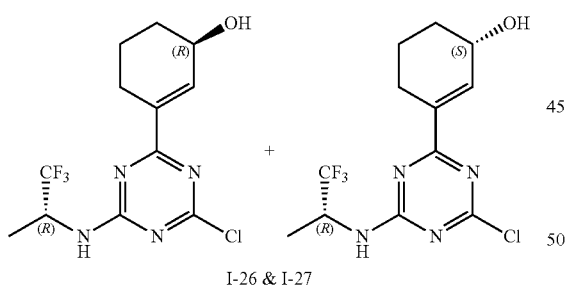

Intermediates I-26 and I-27 were obtained by resolution of Intermediate I-25 using chiral HPLC (chiral HMPL conditions: column: AS-H; mobile phase: n-heptane/isopropanol=80:20; flow rate: 0.5 mL/min; detection wavelength: UV 254 nm). The isomer obtained from the first eluent (RT=1.703 min) was named as I-26, de %=100%, MS (m/z): 400.1 [M+H]$^+$. The isomer obtained from the second eluent (RT=2.067 min) was named as I-27, de %=99.4%, MS (m/z): 400.1 [M+H]$^+$).

Intermediate I-41

6-Chloro-$N^2$-(propan-2-yl-d$_7$)-$N^4$-(2-(trifluoromethyl)pyridin-4-yl)-1,3,5-triazine-2,4-diamine

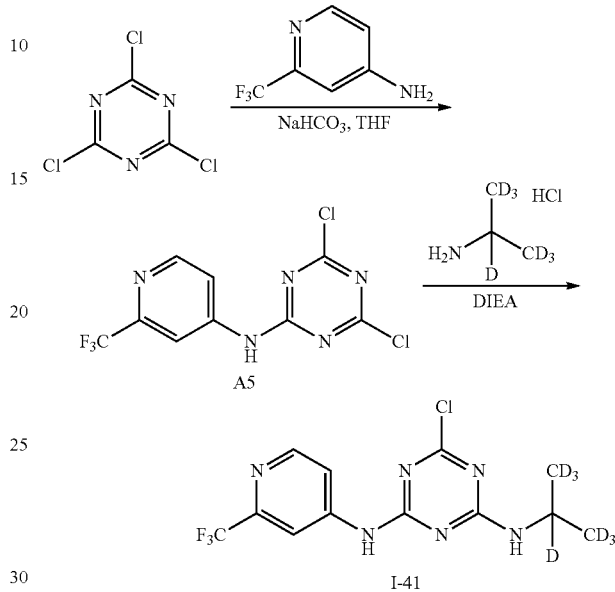

(A) 4,6-Dichloro-N-(2-(trifluoromethyl)pyridin-4-yl)-1,3,5-triazin-2-amine (A5)

To a solution of 2,4,6-trichloro-1,3,5-triazine (1.84 g, 10 mmol) and 2-(trifluoromethyl)pyridin-4-amine (1.62 g, 10 mmol) in dry THF (20 mL) was added NaHCO$_3$ (1.68 g, 20 mmol) at 0° C. The mixture was stirred at room temperature for 16 hours. After reaction was completed, the mixture was filtered. The filtrate was condensed and purified by flash column chromatography (eluting with gradient PE/EA=100:0-0:100) to give compound A5 as white solid (2.68 g, yield: 86%). MS (m/z): 309.9 [M+H]$^+$ (B) 6-Chloro-$N^2$-(propan-2-yl-d$_7$)-$N^4$-(2-(trifluoromethyl)pyridin-4-yl)-1,3,5-triazine-2,4-diamine To a sealed tube were added compound A5 (465 mg, 1.5 mmol), propan-d$_7$-2-amine hydrochloride (154 mg, 1.5 mmol), DIEA (388 mg, 3.0 mmol) and 1,4-dioxane (20 mL) in sequence. The mixture was heated to 60° C. and stirred for 5 hours. After reaction was completed, the mixture was cooled to room temperature, condensed and purified by flash column chromatography (eluting with gradient PE/EA=100:0-0:100) to give Intermediate I-41 as white solid (485 mg, yield: 95%). MS (m/z): 340.0 [M+H]$^+$ The compounds in the below table were prepared according to the procedure of Intermediate I-41 using the corresponding intermediates and reagents under appropriate conditions that will be recognized by POSITA:

| Intermediate | Structure | MS (M + H)+ |
|---|---|---|
| I-43 | 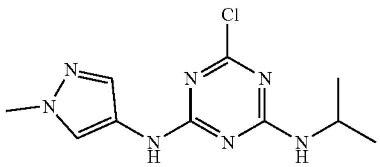 [SMILES: CC(C)Nc1nc(Cl)nc(Nc2cnn(C)c2)n1] | 268.0 |
| I-44 | 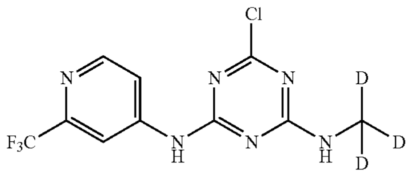 [SMILES: [2H]C([2H])([2H])Nc1nc(Cl)nc(Nc2ccnc(C(F)(F)F)c2)n1] | 308.0 |
| I-45 | 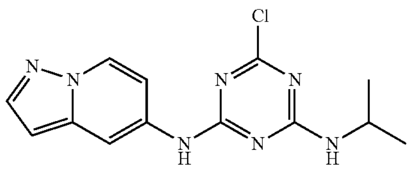 [SMILES: CC(C)Nc1nc(Cl)nc(Nc2ccn3nccc3c2)n1] | 304.0 |
| I-53 | 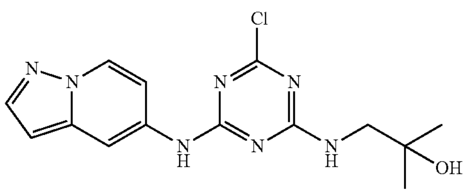 [SMILES: CC(C)(O)CNc1nc(Cl)nc(Nc2ccn3nccc3c2)n1] | 334.0 |
| I-59 | 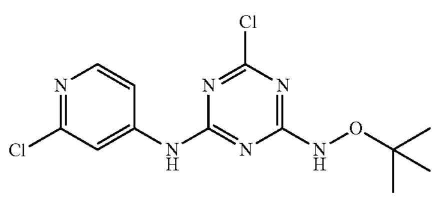 [SMILES: CC(C)(C)ONc1nc(Cl)nc(Nc2ccnc(Cl)c2)n1] | 329.0 |
| I-63 | 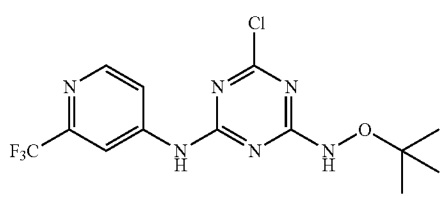 [SMILES: CC(C)(C)ONc1nc(Cl)nc(Nc2ccnc(C(F)(F)F)c2)n1] | 363.0 |
| I-66 | 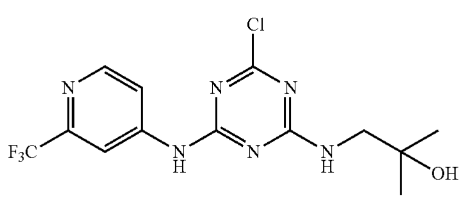 [SMILES: CC(C)(O)CNc1nc(Cl)nc(Nc2ccnc(C(F)(F)F)c2)n1] | 363.0 |
| I-68 | 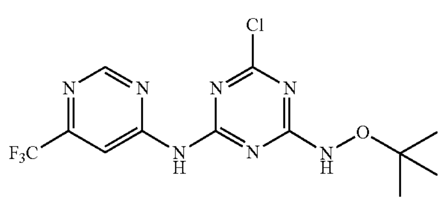 [SMILES: CC(C)(C)ONc1nc(Cl)nc(Nc2cc(C(F)(F)F)ncn2)n1] | 364.0 |

-continued
| Intermediate | Structure | MS (M + H)+ |
|---|---|---|
| I-92 | 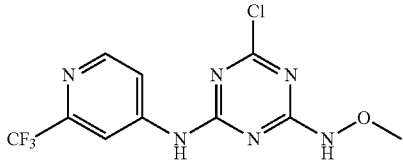 [SMILES: CONc1nc(Cl)nc(Nc2ccnc(C(F)(F)F)c2)n1] | 321.1 |
| I-93 | 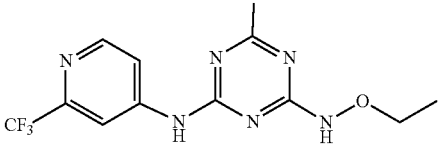 | 335.1 |
| I-94 | 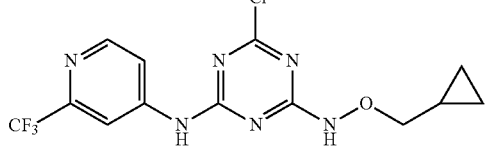 | 361.1 |
| I-96 | 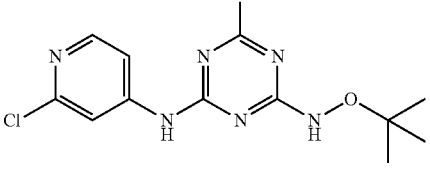 | 329.0 |
| I-97 | 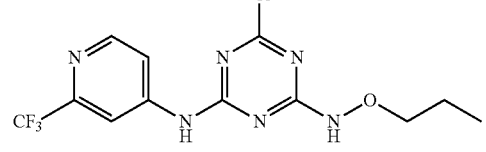 | 349.1 |
| I-98 | 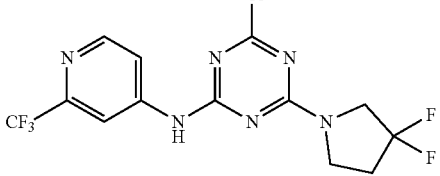 | 381.1 |
| I-99 | 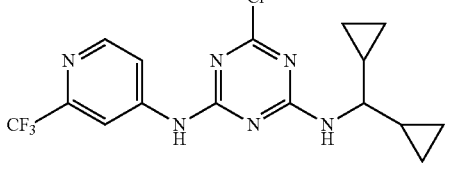 | 385.0 |
| I-100 | 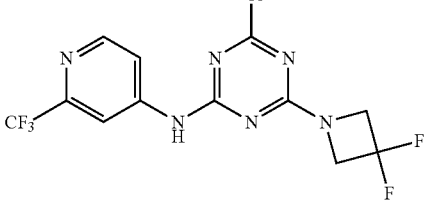 | 366.9 |

| Intermediate | Structure | MS (M + H)+ |
|---|---|---|
| I-101 | 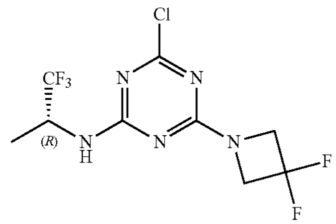 | 318.0 |
| I-103 | 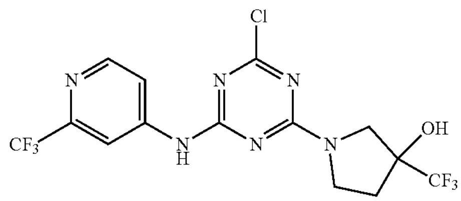 [SMILES: OC1(C(F)(F)F)CCN(c2nc(Cl)nc(Nc3ccnc(C(F)(F)F)c3)n2)C1] | 428.9 |
| I-104 | 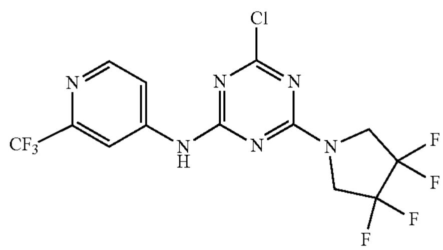 [SMILES: FC(F)(F)c1cc(Nc2nc(Cl)nc(N3CC(F)(F)C(F)(F)C3)n2)ccn1] | 416.9 |
| I-105 | 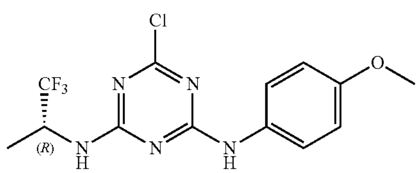 | 362.1 |

Intermediate I-46

2-((4-(Tert-butoxyamino)-6-chloro-1,3,5-triazin-2-yl)amino)isonicotinonitrile

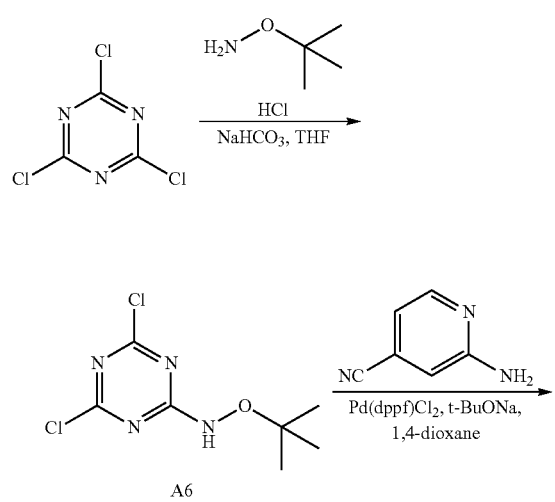

(A) O-(Tert-butyl)-N-(4,6-dichloro-1,3,5-triazin-2-yl)hydroxylamine (A6)

To a solution of 2,4,6-trichloro-1,3,5-triazine (0.92 g, 5 mmol) and O-(tert-butyl)hydroxylamine hydrochloride (0.63 g, 5 mmol) in dry THF (50 mL) was added NaHCO₃ (1.26 g, 15 mmol) at 0° C. The mixture was stirred at 0° C. for 2 hours. After the reaction was completed, the mixture was filtered. The filtrate was condensed and purified by flash column chromatography (eluting with gradient PE/EA=100:0-0:100) to give compound A6 as colorless oil (0.83 g, yield: 80%). MS (m/z): 237.0 [M+H]⁺

(B) 2-((4-(Tert-butoxyamino)-6-chloro-1,3,5-triazin-2-yl)amino)isonicotinonitrile To a sealed tube were sequentially added compound A6 (0.83 g, 4.0 mmol), 2-aminoisonicotinonitrile (0.48 g, 4.0 mmol), Pd(dppf)Cl$_2$ (0.15 g, 0.2 mmol), t-BuONa (0.77 g, 8.0 mmol) and 1,4-dioxane (10 mL). The mixture was heated to 90° C. and stirred for 3 hours. After reaction was completed, the mixture was cooled to room temperature, condensed and purified by flash column chromatography (eluting with gradient PE/EA=100:0-0:100) to give Intermediate I-46 as yellow solid (109 mg, yield: 8%). MS (m/z): 320.0 [M+H]$^+$ The compounds in the below table were prepared according to the procedure of Intermediate I-46 using the corresponding intermediates and reagents under appropriate conditions that will be recognized by POSITA:

| Intermediate | Structure | MS (M + H)$^+$ |
|---|---|---|
| I-47 | 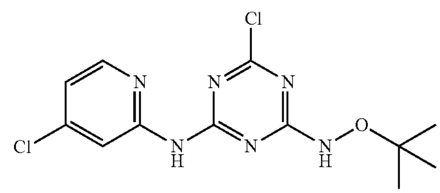 [SMILES: CC(C)(C)ONc1nc(Cl)nc(Nc2cc(Cl)ccn2)n1] | 329.0 |
| I-48 | 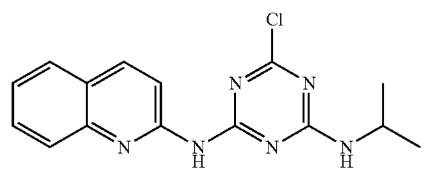 [SMILES: CC(C)Nc1nc(Cl)nc(Nc2ccc3ccccc3n2)n1] | 315.0 |
| I-52 | 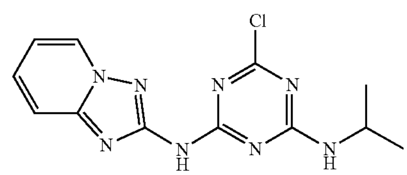 [SMILES: CC(C)Nc1nc(Cl)nc(Nc2nc3ccccn3n2)n1] | 305.0 |
| I-56 | 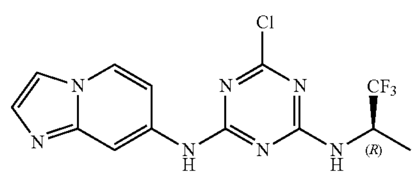 | 358.0 |
| I-57 | 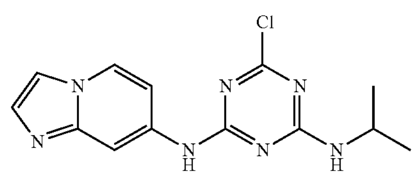 [SMILES: CC(C)Nc1nc(Cl)nc(Nc2ccn3ccnc3c2)n1] | 304.1 |
| I-58 | 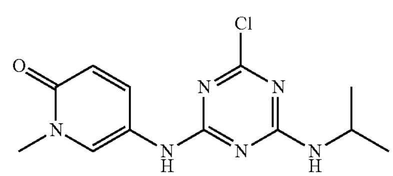 [SMILES: CC(C)Nc1nc(Cl)nc(Nc2ccc(=O)n(C)c2)n1] | 295.0 |
| I-60 | 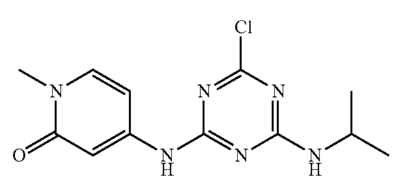 [SMILES: CC(C)Nc1nc(Cl)nc(Nc2ccn(C)c(=O)c2)n1] | 295.1 |

-continued

| Intermediate | Structure | MS (M + H)+ |
|---|---|---|
| I-62 | 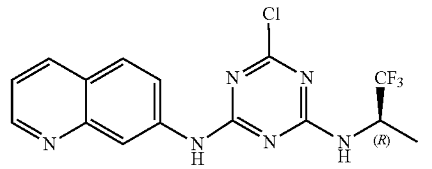 | 369.0 |
| I-64 | 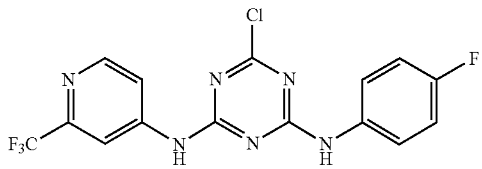 [SMILES: Fc1ccc(Nc2nc(Cl)nc(Nc3ccnc(C(F)(F)F)c3)n2)cc1] | 385.0 |
| I-65 | 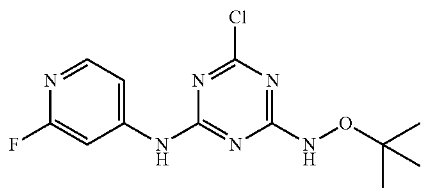 [SMILES: CC(C)(C)ONc1nc(Cl)nc(Nc2ccnc(F)c2)n1] | 313.0 |
| I-67 | 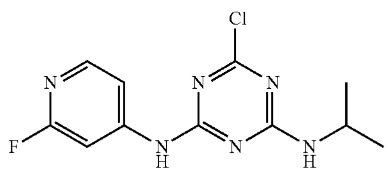 [SMILES: CC(C)Nc1nc(Cl)nc(Nc2ccnc(F)c2)n1] | 283.0 |
| I-69 | 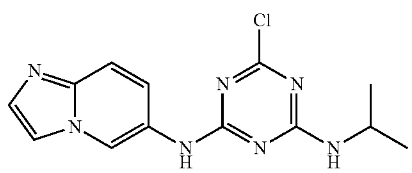 [SMILES: CC(C)Nc1nc(Cl)nc(Nc2ccc3nccn3c2)n1] | 304.0 |
| I-70 | 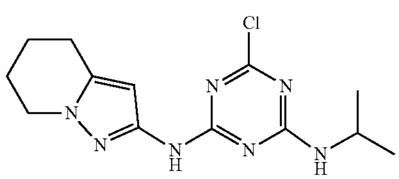 [SMILES: CC(C)Nc1nc(Cl)nc(Nc2cc3n(n2)CCCC3)n1] | 308.0 |
| I-5 | 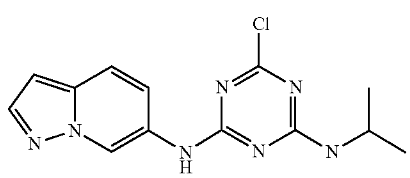 | 304.0 |
| I-28 | 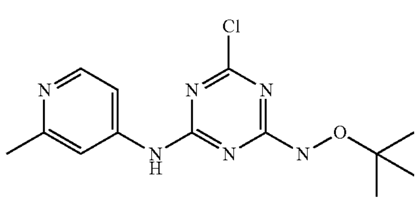 | 309.0 |

| Intermediate | Structure | MS (M + H)+ |
|---|---|---|
| I-29 | 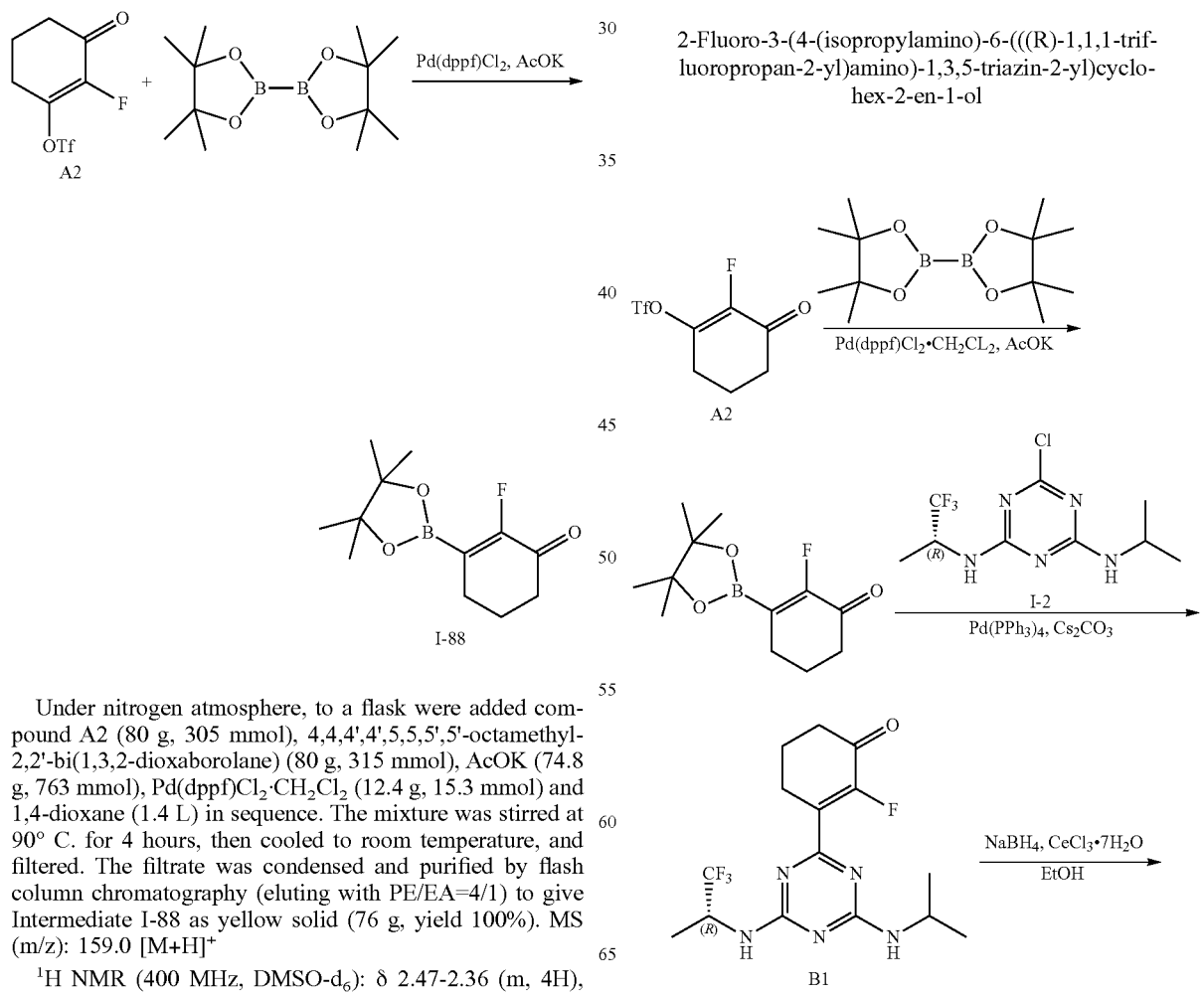 | 310.0 |
| I-95 | 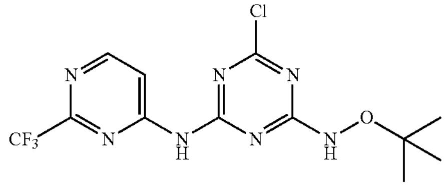 [SMILES: CC(C)(C)ONc1nc(Cl)nc(Nc2ccnc(C(F)(F)F)n2)n1] | 363.9 |

Intermediate I-88

2-Fluoro-3-(4,4,5,5-tetramethyl-1,3,2-dioxaborolan-2-yl)cyclohex-2-en-1-one

Under nitrogen atmosphere, to a flask were added compound A2 (80 g, 305 mmol), 4,4,4',4',5,5,5',5'-octamethyl-2,2'-bi(1,3,2-dioxaborolane) (80 g, 315 mmol), AcOK (74.8 g, 763 mmol), Pd(dppf)Cl$_2$·CH$_2$Cl$_2$ (12.4 g, 15.3 mmol) and 1,4-dioxane (1.4 L) in sequence. The mixture was stirred at 90° C. for 4 hours, then cooled to room temperature, and filtered. The filtrate was condensed and purified by flash column chromatography (eluting with PE/EA=4/1) to give Intermediate I-88 as yellow solid (76 g, yield 100%). MS (m/z): 159.0 [M+H]$^+$ $^1$H NMR (400 MHz, DMSO-d$_6$): δ 2.47-2.36 (m, 4H), 1.91-1.82 (m, 2H), 1.22 (s, 12H).

Example 2

Synthesis of Compounds 1-87, 89-184, 186-301

Compound 1

2-Fluoro-3-(4-(isopropylamino)-6-(((R)-1,1,1-trifluoropropan-2-yl)amino)-1,3,5-triazin-2-yl)cyclohex-2-en-1-ol

(A) (R)-2-fluoro-3-(4-(isopropylamino)-6-((1,1,1-trifluoropropan-2-yl)amino)-1,3,5-triazin-2-yl)cyclohex-2-en-1-one (B1)

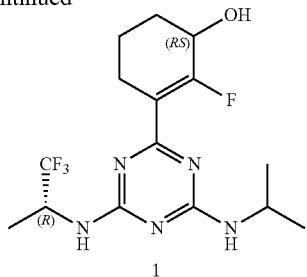

Under nitrogen atmosphere, to a flask were added compound A2 (220 mg, 0.84 mmol), 4,4,4',4',5,5,5',5'-octamethyl-2,2'-bi(1,3,2-dioxaborolane) (234 mg, 0.92 mmol), AcOK (206 mg, 2.10 mmol), Pd(dppf)Cl$_2$·CH$_2$Cl$_2$ (32 mg, 0.04 mmol) and 1,4-dioxane (20 mL) in sequence and stirred at reflux for 16 hours. Then, the mixture was cooled to room temperature, and was added Intermediate I-2 (238 mg, 0.84 mmol), Cs$_2$CO$_3$ (682 mg, 2.1 mmol), Pd(PPh$_3$)$_4$ (46.2 mg, 0.04 mmol) and water (4 mL) in sequence, and stirred at 80° C. for 2 hours. After the reaction was completed, the mixture was cooled to room temperature, condensed and purified by flash column chromatography (eluting with gradient PE/EA=100:0-0:100) to give compound B1 as white solid (160 mg, yield: 52.8%). MS (m/z): 362.1 [M+H]$^+$

(B) 2-Fluoro-3-(4-(isopropylamino)-6-(((R)-1,1,1-trifluoropropan-2-yl)amino)-1,3,5-triazin-2-yl)cyclohex-2-en-1-ol To a flask were added compound B1 (80 mg, 0.22 mmol), CeCl$_3$·7H$_2$O (107 mg, 0.29 mmol) and EtOH (5 mL). The mixture was cooled to 0° C. Then, NaBH$_4$ (11 mg, 0.29 mmol) was added and the mixture was stirred at 0° C. for 2 hours. After the reaction was completed, the mixture was quenched by the addition of saturated NH$_4$Cl aqueous solution (2 mL) and water (20 mL), and extracted with EtOAc. The organic layer was collected, condensed and purified by flash column chromatography (eluting with gradient PE/EA=100:0-0:100) to give Compound 1 as a white solid (61 mg, yield: 76.3%). MS (m/z): 364.1 [M+H]$^+$ $^1$H NMR (400 MHz, CD$_3$OD): δ 4.99-4.87 (m, 1H), 4.33-4.23 (m, 1H), 4.19-4.07 (m, 1H), 2.61-2.47 (m, 1H), 2.40-2.24 (m, 1H), 1.89-1.73 (m, 3H), 1.70-1.61 (m, 1H), 1.38-1.31 (m, 3H), 1.22-1.16 (m, 6H).

The compounds in the below table were prepared according to the procedure of Compound 1 using the corresponding intermediates and reagents under appropriate conditions that will be recognized by POSITA:

| Comp. | Structure | MS (M + H)$^+$ | $^1$H NMR | Intermediate |
|---|---|---|---|---|
| 2 | 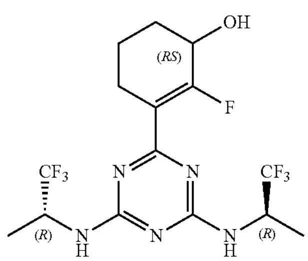 | 418.1 | $^1$H NMR (400 MHz, CD$_3$OD): δ 5.01-4.88 (m, 2H), 4.36-4.24 (m, 1H), 2.66-2.50 (m, 1H), 2.41-2.31 (m, 1H), 1.97-1.60 (m, 4H), 1.38-1.30 (m, 6H). | I-3 |
| 3 | 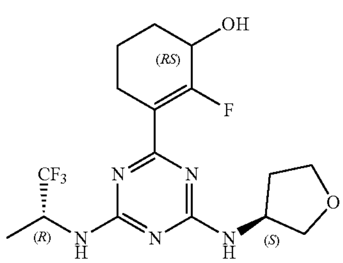 | 392.1 | $^1$H NMR (400 MHz, CD$_3$OD): δ 5.06-4.90 (m, 1H), 4.61-4.46 (m, 1H), 4.37-4.21 (m, 1H), 4.04-3.87 (m, 2H), 3.85-3.76 (m, 1H), 3.73-3.60 (m, 1H), 2.66-2.49 (m, 1H), 2.44-2.14 (m, 2H), 2.01-1.60 (m, 5H), 1.45-1.30 (m, 3H). | I-8 |
| 4 | 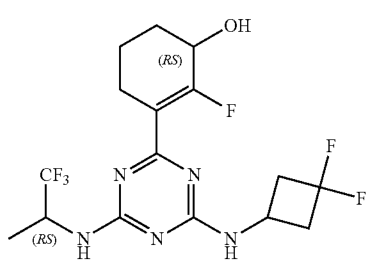 | 412.1 | $^1$H NMR (400 MHz, CD$_3$OD): δ 5.01-4.87 (m, 1H), 4.37-4.15 (m, 2H), 3.05-2.84 (m, 2H), 2.77-2.49 (m, 3H), 2.42-2.24 (m, 1H), 1.96-1.56 (m, 4H), 1.44-1.31 (m, 3H). | I-30 |

-continued

| Comp. | Structure | MS (M + H)+ | 1H NMR | Intermediate |
|---|---|---|---|---|
| 5 | 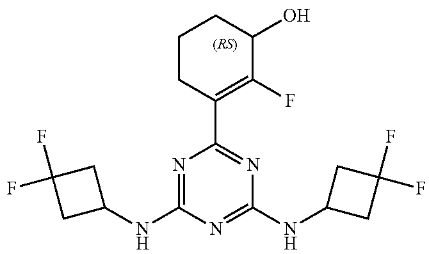 [SMILES: OC1CCCC(c2nc(NC3CC(F)(F)C3)nc(NC3CC(F)(F)C3)n2)=C1F] | 406.1 | 1H NMR (400 MHz, CD3OD): δ 4.37-4.22 (m, 3H), 3.02-2.86 (m, 4H), 2.73-2.50 (m, 5H), 2.41-2.25 (m, 1H), 1.91-1.72 (m, 3H), 1.72-1.62 (m, 1H). | I-10 |
| 6 | 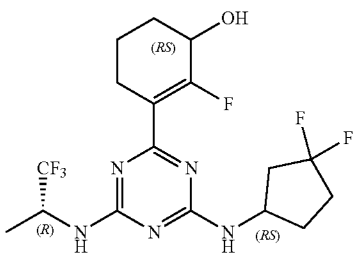 | 426.1 | 1H NMR (400 MHz, CD3OD): δ 5.00-4.90 (m, 1H), 4.51-4.41 (m, 1H), 4.34-4.25 (m, 1H), 2.62-2.47 (m, 2H), 2.38-2.17 (m, 3H), 2.14-1.96 (m, 2H), 1.90-1.75 (m, 4H), 1.70-1.61 (m, 1H), 1.40-1.31 (m, 3H). | I-11 |
| 7 | 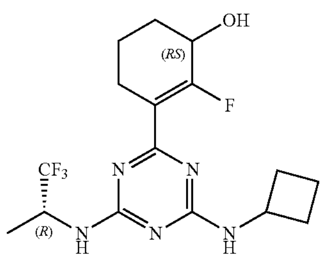 | 376.1 | 1H NMR (400 MHz, CD3OD): δ 5.02-4.89 (m, 1H), 4.33-4.24 (m, 1H), 4.19-4.06 (m, 1H), 2.63-2.47 (m, 1H), 2.40-2.25 (m, 1H), 1.92-1.60 (m, 4H), 1.40-1.30 (m, 3H), 1.23-1.15 (m, 6H). | I-15 |
| 8 | 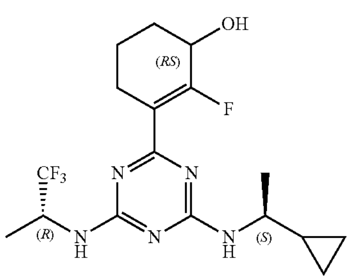 | 390.1 | 1H NMR (400 MHz, CD3OD): δ 4.99-4.87 (m, 1H), 4.36-4.22 (m, 1H), 3.60-3.40 (m, 1H), 2.66-2.47 (m, 1H), 2.40-2.26 (m, 1H), 1.91-1.62 (m, 4H), 1.37-1.31 (m, 3H), 1.27-1.21 (m, 3H), 1.01-0.85 (m, 1H), 0.55-0.15 (m, 4H). | I-31 |
| 9 | 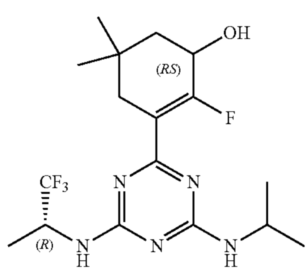 | 392.3 | 1H NMR (400 MHz, CD3OD): δ 4.99-4.88 (m, 1H), 4.42-4.34 (m, 1H), 4.18-4.07 (m, 1H), 2.40-2.17 (m, 2H), 1.91-1.80 (m, 1H), 1.62-1.53 (m, 1H), 1.38-1.31 (m, 3H), 1.22-1.15 (m, 6H), 1.06 (s, 3H), 1.00 (s, 3H). | I-2 |
| 10 | 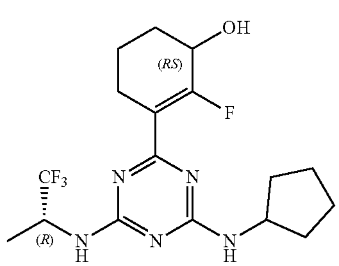 | 390.1 | 1H NMR (400 MHz, CD3OD): δ 5.03-4.89 (m, 1H), 4.37-4.16 (m, 2H), 2.64-2.47 (m, 1H), 2.40-2.24 (m, 1H), 2.04-1.44 (m, 12H), 1.39-1.31 (m, 3H). | I-12 |

-continued

| Comp. | Structure | MS (M + H)+ | 1H NMR | Intermediate |
|---|---|---|---|---|
| 11 | 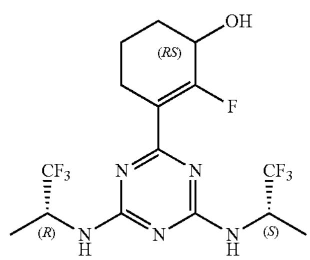 | 418.1 | 1H NMR (400 MHz, CD3OD): δ 5.04-4.90 (m, 2H), 4.35-4.24 (m, 1H), 2.66-2.52 (m, 1H), 2.43-2.27 (m, 1H), 1.95-1.60 (m, 4H), 1.43-1.31 (m, 6H). | I-3 |
| 12 | 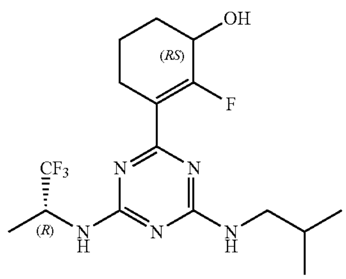 | 378.1 | 1H NMR (400 MHz, CD3OD): δ 5.00-4.89 (m, 1H), 4.35-4.23 (m, 1H), 3.26-3.05 (m, 2H), 2.66-2.48 (m, 1H), 2.42-2.25 (m, 1H), 1.97-1.59 (m, 5H), 1.41-1.30 (m, 3H), 0.96-0.88 (m, 6H). | I-13 |
| 13 | 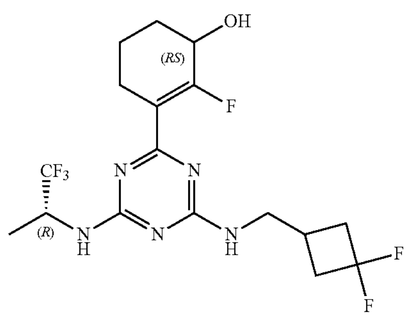 | 426.1 | 1H NMR (400 MHz, CD3OD): δ 5.02-4.89 (m, 1H), 4.35-4.23 (m, 1H), 3.63-3.40 (m, 2H), 2.65-2.51 (m, 3H), 2.47-2.21 (m, 4H), 1.89-1.61 (m, 4H), 1.39-1.31 (m, 3H). | I-14 |
| 14 | 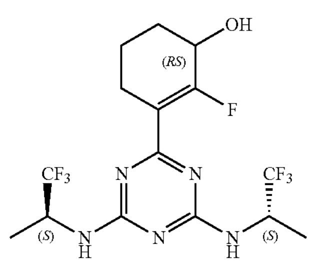 | 418.1 | 1H NMR (400 MHz, CD3OD): δ 5.03-4.90 (m, 2H), 4.36-4.23 (m, 1H), 2.67-2.49 (m, 1H), 2.42-2.26 (m, 1H), 1.94-1.61 (m, 4H), 1.40-1.31 (m, 6H). | I-32 |
| 15 | 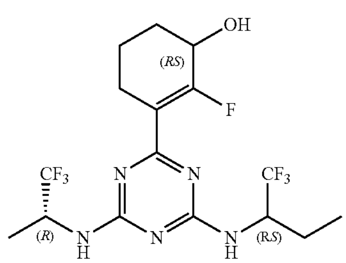 | 432.3 | 1H NMR (400 MHz, CD3OD): δ 5.04-4.93 (m, 1H), 4.82-4.70 (m, 1H), 4.34-4.23 (m, 1H), 2.65-2.51 (m, 1H), 2.43-2.28 (m, 1H), 1.91-1.74 (m, 4H), 1.71-1.61 (br, 2H), 1.40-1.31 (m, 3H), 1.04-0.93 (m, 3H). | I-33 |

-continued

| Comp. | Structure | MS (M + H)+ | 1H NMR | Intermediate |
|---|---|---|---|---|
| 16 | 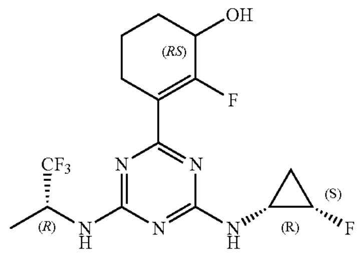 | 380.1 | 1H NMR (400 MHz, CD3OD): δ 5.12-4.92 (m, 1H), 4.80-4.53 (m, 1H), 4.37-4.26 (m, 1H), 2.87-2.77 (m, 1H), 2.68-2.51 (m, 1H), 2.46-2.27 (m, 1H), 1.97-1.60 (m, 4H), 1.43-1.31 (m, 3H), 1.2-1.06 (m, 1H), 1.02-0.87 (m, 1H). | I-1 |
| 17 | 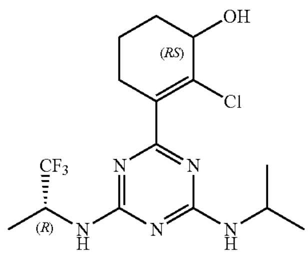 | 380.4 | 1H NMR (400 MHz, CD3OD): δ 5.00-4.92 (m, 1H), 4.22-4.07 (m, 2H), 2.50-2.27 (m, 2H), 1.95-1.81 (m, 3H), 1.76-1.66 (m, 1H), 1.41-1.32 (m, 3H), 1.23-1.18 (m, 6H). | I-2 |
| 18 | 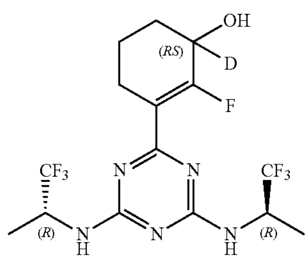 | 419.1 | 1H NMR (400 MHz, CD3OD): δ 5.02-4.87 (m, 2H), 2.68-2.51 (m, 1H), 2.44-2.28 (m, 1H), 1.92-1.63 (m, 4H), 1.42-1.30 (m, 6H). | I-3 |
| 19 | 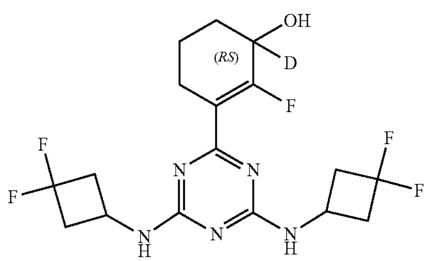 [SMILES: [2H]C1(O)CCCC(c2nc(NC3CC(F)(F)C3)nc(NC3CC(F)(F)C3)n2)=C1F] | 407.1 | 1H NMR (400 MHz, CD3OD): δ 4.38-4.15 (m, 2H), 3.05-2.85 (m, 4H), 2.72-2.48 (m, 5H), 2.40-2.26 (m, 1H), 1.90-1.61 (m, 4H). | I-10 |
| 20 | 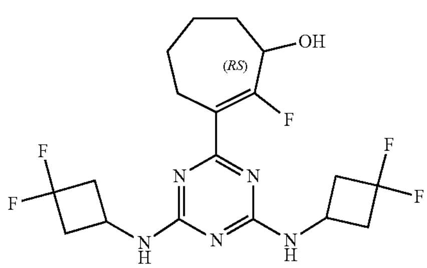 [SMILES: OC1CCCCC(c2nc(NC3CC(F)(F)C3)nc(NC3CC(F)(F)C3)n2)=C1F] | 420.2 | 1H NMR (400 MHz, CD3OD): δ 4.52-4.38 (m, 1H), 4.33-4.17 (m, 2H), 2.99-2.84 (m, 4H), 2.71-2.48 (m, 5H), 2.37-2.23 (m, 1H), 2.01-1.82 (m, 3H), 1.74-1.60 (m, 3H). | I-10 |
| 21 | 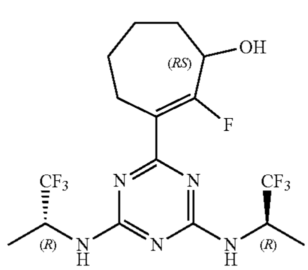 | 432.3 | 1H NMR (400 MHz, CD3OD): δ 5.02-4.89 (m, 2H), 4.53-4.41 (m, 1H), 2.77-2.62 (m, 1H), 2.40-2.27 (m, 1H), 2.02-1.83 (m, 3H), 1.74-1.61 (m, 3H), 1.39-1.32 (m, 6H). | I-3 |

-continued

| Comp. | Structure | MS (M + H)+ | 1H NMR | Intermediate |
|---|---|---|---|---|
| 22 | 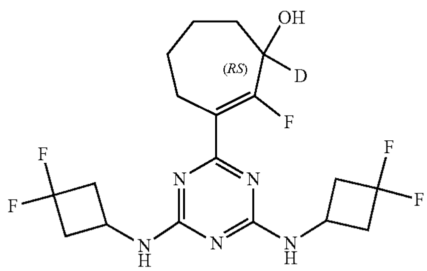 [SMILES: [2H]C1(O)CCCCC(c2nc(NC3CC(F)(F)C3)nc(NC3CC(F)(F)C3)n2)=C1F] | 421.1 | 1H NMR (400 MHz, CD3OD): δ 4.36-4.16 (m, 2H), 3.00-2.84 (m, 4H), 2.73-2.50 (m, 5H), 2.39-2.21 (m, 1H), 2.01-1.82 (m, 3H), 1.75-1.59 (m, 3H). | I-10 |
| 23 | 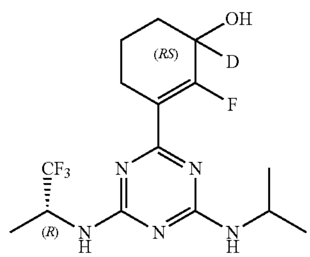 | 365.2 | 1H NMR (400 MHz, CD3OD): δ 4.99-4.86 (m, 1H), 4.20-4.07 (m, 1H), 2.61-2.47 (m, 1H), 2.37-2.25 (m, 1H), 1.88-1.62 (m, 4H), 1.37-1.29 (m, 3H), 1.20-1.17 (m, 6H). | I-2 |
| 24 | 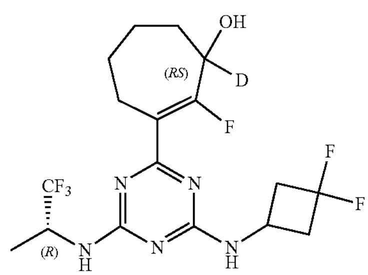 | 427.1 | 1H NMR (400 MHz, CD3OD): δ 4.99-4.86 (m, 1H), 4.34-4.15 (m, 1H), 2.97-2.83 (m, 2H), 2.73-2.51 (m, 3H), 2.37-2.25 (m, 1H), 2.01-1.82 (m, 3H), 1.72-1.60 (m, 3H), 1.39-1.13 (m, 3H). | I-9 |
| 25 | 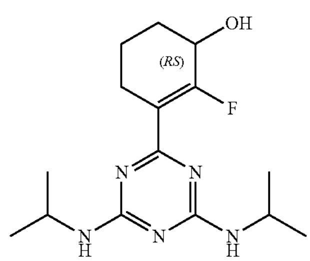 [SMILES: CC(C)Nc1nc(NC(C)C)nc(C2=C(F)C(O)CCC2)n1] | 310.1 | 1H NMR (400 MHz, CD3OD): δ 4.36-4.24 (m, 1H), 4.24-4.00 (m, 2H), 2.62-2.43 (m, 1H), 2.39-2.22 (m, 1H), 1.91-1.82 (m, 2H), 1.82-1.72 (m, 1H), 1.70-1.60 (m, 1H), 1.19 (s, 12H). | I-34 |
| 26 | 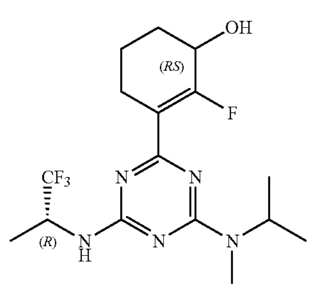 | 378.1 | 1H NMR (400 MHz, CD3OD): δ 5.19-4.88 (m, 2H), 4.38-4.22 (m, 1H), 2.96 (s, 3H), 2.68-2.49 (m, 1H), 2.43-2.28 (m, 1H), 1.91-1.83 (m, 2H), 1.83-1.70 (m, 1H), 1.70-1.59 (m, 1H), 1.35 (d, J = 5.3 Hz, 3H), 1.16 (d, J = 6.5 Hz, 6H). | I-35 |

-continued

| Comp. | Structure | MS (M + H)+ | 1H NMR | Intermediate |
|---|---|---|---|---|
| 27 | 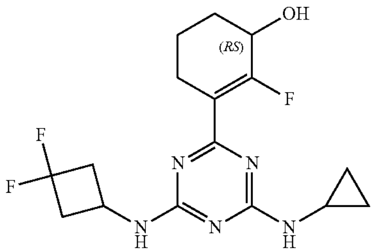 [SMILES: OC1CCCC(c2nc(NC3CC3)nc(NC3CC(F)(F)C3)n2)=C1F] | 356.1 | 1H NMR (400 MHz, CD3OD): δ 4.42-4.13 (m, 2H), 3.02-2.86 (m, 2H), 2.83-2.46 (m, 4H), 2.44-2.21 (m, 1H), 1.92-1.83 (m, 2H), 1.83-1.60 (m, 2H), 0.82-0.67 (m, 2H), 0.60-0.45 (m, 2H). | I-36 |
| 28 | 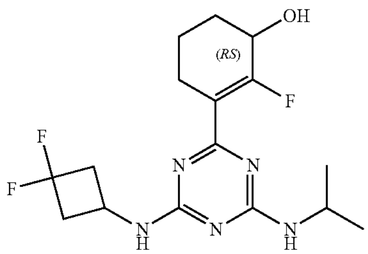 [SMILES: CC(C)Nc1nc(NC2CC(F)(F)C2)nc(C2=C(F)C(O)CCC2)n1] | 358.1 | 1H NMR (400 MHz, CD3OD): δ 4.36-4.20 (m, 2H), 4.20-4.04 (m, 1H), 3.01-2.84 (m, 2H), 2.71-2.45 (m, 3H), 2.40-2.23 (m, 1H), 1.90-1.83 (m, 2H), 1.83-1.60 (m, 2H), 1.20 (s, 6H). | I-37 |
| 29 | 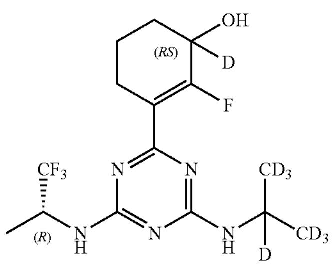 | 372.1 | 1H NMR (400 MHz, CD3OD): δ 4.98-4.88 (m, 1H), 2.65-2.43 (m, 1H), 2.41-2.23 (m, 1H), 1.92-1.70 (m, 3H), 1.70-1.59 (m, 1H), 1.37-1.29 (m, 3H). | I-39 |
| 30 | 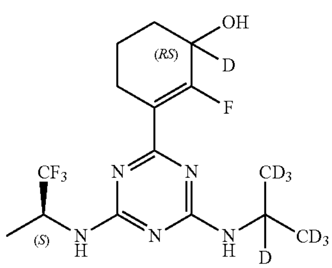 | 372.1 | 1H NMR (400 MHz, CD3OD): δ 4.97-4.89 (m, 1H), 2.70-2.42 (m, 1H), 2.41-2.21 (m, 1H), 1.90-1.72 (m, 3H), 1.69-1.59 (m, 1H), 1.37-1.29 (m, 3H). | I-40 |
| 31 | 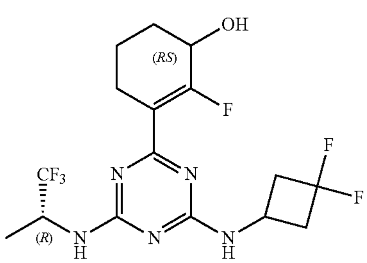 | 412.1 | 1H NMR (400 MHz, CD3OD): δ 5.02-4.89 (m, 1H), 4.38-4.14 (m, 2H), 3.03-2.86 (m, 2H), 2.80-2.49 (m, 3H), 2.44-2.26 (m, 1H), 1.95-1.59 (m, 4H), 1.41-1.31 (m, 3H). | I-9 |
| 32 | 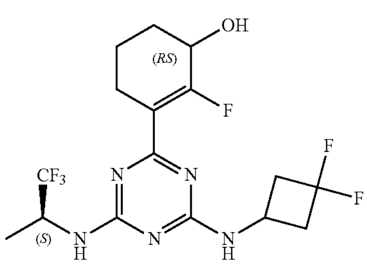 | 412.1 | 1H NMR (400 MHz, CD3OD): δ 5.03-4.90 (m, 1H), 4.38-4.16 (m, 2H), 3.02-2.86 (m, 2H), 2.82-2.50 (m, 3H), 2.43-2.25 (m, 1H), 1.94-1.60 (m, 4H), 1.42-1.32 (m, 3H). | I-54 |

| Comp. | Structure | MS (M + H)+ | 1H NMR | Intermediate |
|---|---|---|---|---|
| 33 | 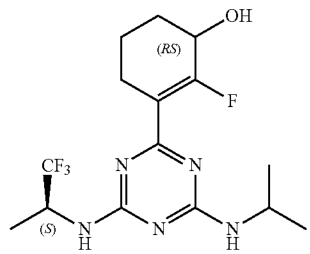 | 364.1 | 1H NMR (400 MHz, CD3OD): δ 5.02-4.90 (m, 1H), 4.38-4.22 (m, 1H), 4.18-4.04 (m, 1H), 2.66-2.49 (m, 1H), 2.39-2.20 (m, 1H), 2.03-1.58 (m, 4H), 1.42-1.29 (m, 3H), 1.23-1.10 (m, 6H). | I-71 |
| 34 | 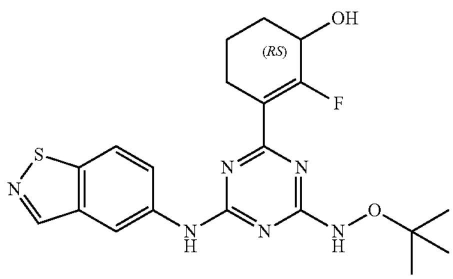 | 431.0 | 1H NMR (400 MHz, CD3OD) δ 8.93-8.75 (m, 2H), 7.98-7.93 (m, 1H), 7.83-8.77 (m, 1H), 4.37-4.29 (m, 1H), 2.72-2.60 (m, 1H), 2.47-2.35 (m, 341H), 1.92-1.85 (m, 2H), 1.84-1.75 (m, 1H), 1.73-1.65 (m, 1H), 1.32 (s, 9H). | I-75 |
| 200 | 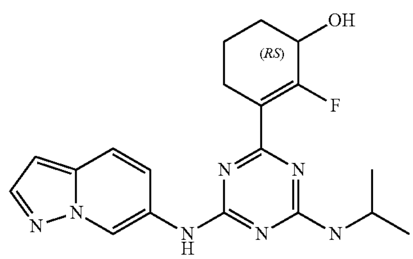 | 384.1 | 1H NMR (400 MHz, CD3OD): δ 9.55 (s, 1H), 7.91-7.78 (m, 1H), 7.64-7.48 (m, 1H), 7.33-7.13 (m, 1H), 6.62-6.47 (m, 1H), 4.41-4.14 (m, 2H), 2.72-2.32 (m, 2H), 1.91-1.63 (m, 4H), 1.29-1.20 (m, 6H). | I-5 |
| 205 | 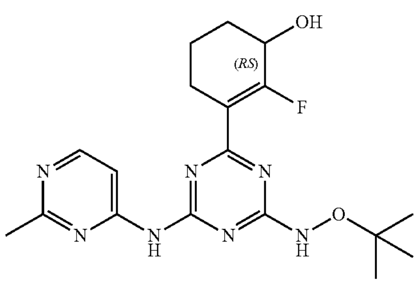 [SMILES: Cc1nccc(Nc2nc(NOC(C)(C)C)nc(C3=C(F)C(O)CCC3)n2)n1] | 390.1 | 1H NMR (400 MHz, CD3OD): δ 8.59-8.34 (m, 2H), 4.39-4.28 (m, 1H), 2.74-2.61 (m, 1H), 2.55 (s, 3H), 2.51-2.37 (m, 1H), 1.98-1.66 (m, 4H), 1.31 (s, 9H). | I-29 |
| 219 | 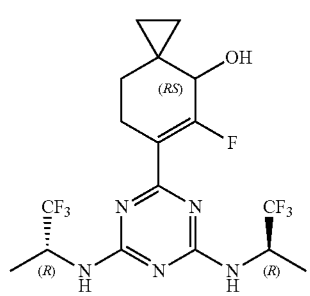 | 444.2 | 1H NMR (400 MHz, CD3OD): δ 5.05-4.86 (m, 2H), 3.49-3.39 (m, 1H), 2.73-2.58 (m, 1H), 2.53-2.38 (m, 1H), 2.22-2.09 (m, 1H), 1.39-1.32 (m, 6H), 1.03-0.94 (m, 1H), 0.78-0.68 (m, 1H), 0.51-0.40 (m, 3H). | I-3 |

| Comp. | Structure | MS (M + H)+ | 1H NMR | Intermediate |
|---|---|---|---|---|
| 229 | 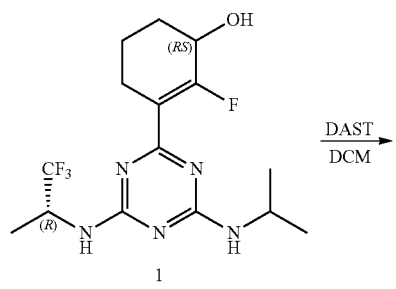 | 401.0 | 1H NMR (400 MHz, CD3OD): δ 9.34-9.19 (m, 1H), 8.60-8.36 (m, 1H), 7.73-7.54 (m, 2H), 4.39-4.30 (m, 1H), 4.26-4.15 (m, 1H), 2.72-2.56 (m, 1H), 2.48-2.33 (m, 1H), 1.93-1.63 (m, 4H), 1.29-1.21 (m, 6H). | I-81 |

Compound 35

6-(2,3-Difluorocyclohex-1-en-1-yl)-$N^2$-isopropyl-$N^4$-((R)-1,1,1-trifluoropropan-2-yl)-1,3,5-triazine-2,4-diamine

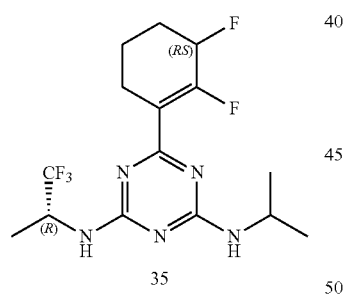

At 0° C., Compound 1 (20 mg, 0.06 mmol) was dissolved in DCM (3 mL), and DAST (17 mg, 0.12 mmol) was added. The mixture was stirred at 0° C. for 2.5 hours. After the reaction was completed, the mixture was quenched by the addition of saturated NH4Cl aqueous solution (5 mL) and water (5 mL), and extracted with EtOAc. The organic layer was collected, condensed and purified by flash column chromatography (eluting with gradient PE/EA=100:0-0:100) to give the title compound as a white solid (14 mg, yield: 70%). MS (m/z): 366.2 [M+H]+

1H NMR (400 MHz, CD3OD): δ 5.15-4.86 (m, 2H), 4.21-4.08 (m, 1H), 2.70-2.51 (m, 1H), 2.42-2.26 (m, 1H), 2.20-2.08 (m, 1H), 1.92-1.67 (m, 3H), 1.37-1.31 (m, 3H), 1.21-1.16 (m, 6H).

The compounds in the below table were prepared according to the procedure of Compound 35 using the corresponding intermediates and reagents under appropriate conditions that will be recognized by POSITA:

| Comp. | Structure | MS (M + H)+ | 1H NMR | Intermediate |
|---|---|---|---|---|
| 36 | 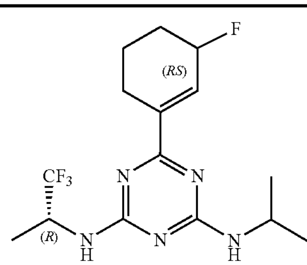 | 348.0 | 1H NMR (400 MHz, CD3OD): δ 7.16-6.94 (m, 1H), 5.25-5.06 (m, 1H), 5.05-4.89 (m, 1H), 4.27-4.06 (m, 1H), 2.63-2.26 (m, 2H), 1.95-1.63 (m, 4H), 1.39-1.30 (d, J = 5.2 Hz, 3H), 1.24-1.16 (m, 6H). | Comp. 124 |

| Comp. | Structure | MS (M + H)+ | 1H NMR | Intermediate |
|---|---|---|---|---|
| 37 | (structure: 6-(6-fluorocyclohex-1-en-1-yl)-N2-((R)-1,1,1-trifluoropropan-2-yl)-N4-isopropyl-1,3,5-triazine-2,4-diamine, (RS)) | 348.3 | 1H NMR (400 MHz, CD3OD): δ 7.26-7.00 (m, 1H), 5.08-4.85 (m, 2H), 4.26-4.07 (m, 1H), 2.87-2.70 (m, 1H), 2.68-2.53 (m, 1H), 2.44-2.26 (m, 2H), 1.95-1.80 (m, 2H), 1.36-1.30 (m, 3H), 1.20-1.16 (m, 6H). | Comp. 144 |
| 38 | (structure: 6-(4-fluorocyclohex-1-en-1-yl)-N2-((R)-1,1,1-trifluoropropan-2-yl)-N4-isopropyl-1,3,5-triazine-2,4-diamine, (RS)) | 348.3 | 1H NMR (400 MHz, CD3OD): δ 7.13-6.85 (m, 1H), 5.03-4.85 (m, 2H), 4.24-4.07 (m, 1H), 2.63-2.35 (m, 4H), 2.01-1.82 (m, 2H), 1.36-1.31 (m, 3H), 1.20-1.16 (m, 6H). | Com. 145 |

Compound 39

(*)3-(4,6-Bis((3,3-difluorocyclobutyl)amino)-1,3,5-triazin-2-yl)-2-fluorocyclohept-2-en-1-ol

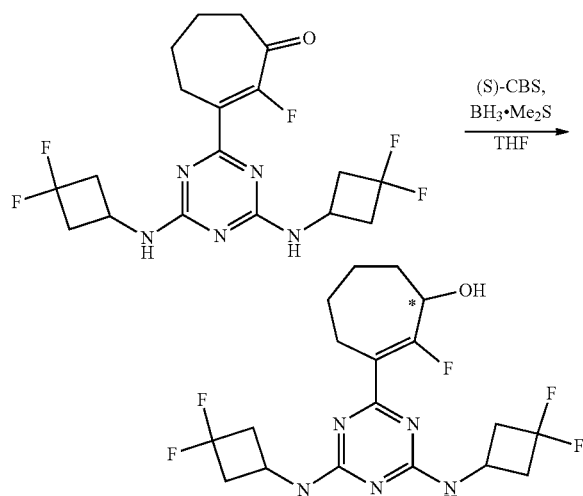

Under nitrogen atmosphere, 1 mol/L (S)—CBS/THF solution (1.4 mL, 1.4 mmol) was added to dry THF (5 mL) under ice bath cooling ° C., then to the solution was added 2 mol/L BH3·Me2S/THF solution (1.4 mL, 2.8 mmol) in one-portion. After stirred for 2 minutes, 3-(4,6-bis((3,3-difluorocyclobutyl)amino)-1,3,5-triazin-2-yl)-2-fluoro cyclohept-2-en-1-one (prepared according to the procedure of Compound 1 using Intermediate I-10, 600 mg, 1.4 mmol) in THF (3 mL) was added dropwise and the mixture was stirred in ice-bath for 1 hour. Then, MeOH (0.5 mL), EtOAc (10 mL) and water (20 mL) were added to the reaction mixture. The organic layer was collected. The aqueous was extracted with EtOAc (10 mL). The organic layers were combined, dried over Na2SO4 and filtered. The filtrate was condensed and purified by flash column chromatography (eluting with gradient PE/EA=100:0-0:100) to give the title compound as white solid (60 mg, yield: 10%). MS (m/z): 420.1 [M+H]+

1H NMR (400 MHz, CD3OD): δ 4.52-4.38 (m, 1H), 4.33-4.17 (m, 2H), 2.99-2.84 (m, 4H), 2.71-2.48 (m, 5H), 2.37-2.23 (m, 1H), 2.01-1.82 (m, 3H), 1.74-1.60 (m, 3H).

The compounds in the below table were prepared according to the procedure of Compound 39 using the corresponding intermediates and reagents under appropriate conditions that will be recognized by POSITA:

| Comp. | Structure | MS (M + H)+ | 1H NMR | Intermediate |
|---|---|---|---|---|
| 40 | 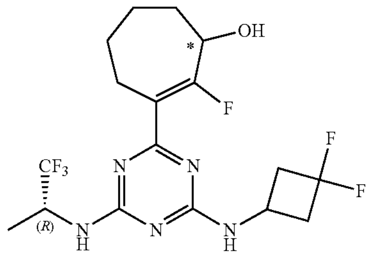 | 426.1 | 1H NMR (400 MHz, CD3OD): δ 4.98-4.87 (m, 1H), 4.51-4.41 (m, 1H), 4.31-4.16 (m, 1H), 2.97-2.84 (m, 2H), 2.73-2.49 (m, 3H), 2.37-2.23 (m, 1H), 2.00-1.81 (m, 3H), 1.72-1.58 (m, 3H), 1.39-1.30 (m, 3H). | I-9 |
| 41 | 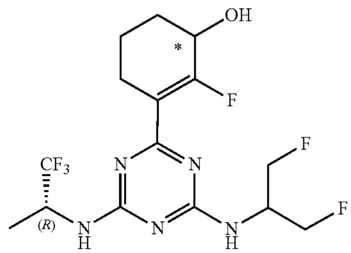 | 400.1 | 1H NMR (400 MHz, CD3OD): δ 5.00-4.89 (m, 1H), 4.69-4.44 (m, 5H), 4.34-4.22 (m, 1H), 2.65-2.50 (m, 1H), 2.40-2.25 (m, 1H), 1.89-1.57 (m, 4H), 1.38-1.29 (m, 3H). | I-72 |
| 42 | 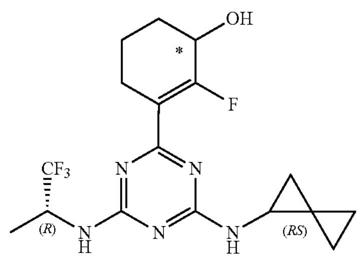 | 388.2 | 1H NMR (400 MHz, CD3OD): δ 5.00-4.89 (m, 1H), 4.33-4.21 (m, 1H), 3.13-2.99 (m, 1H), 2.62-2.47 (m, 1H), 2.37-2.18 (m, 1H), 1.87-1.61 (m, 4H), 1.37-1.30 (m, 3H), 1.25-1.19 (m, 1H), 1.00-0.71 (m, 5H). | I-73 |
| 43 | 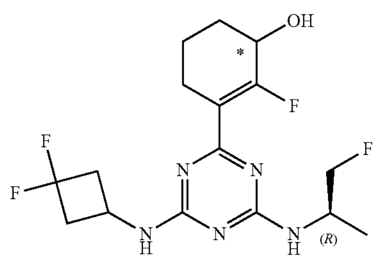 | 376.1 | 1H NMR (400 MHz, CD3OD): δ 4.51-4.18 (m, 5H), 3.01-2.82 (m, 2H), 2.71-2.45 (m, 3H), 2.38-2.20 (m, 1H), 1.87-1.59 (m, 4H), 1.27-1.19 (m, 3H). | I-74 |
| 44 | 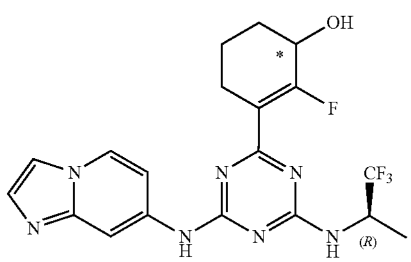 | 438.1 | 1H NMR (400 MHz, CD3OD): δ 8.47-8.11 (m, 2H), 7.66 (s, 1H), 7.49-7.37 (m, 1H), 7.18-7.05 (m, 1H), 5.08-4.94 (m, 1H), 4.40-4.27 (m, 1H), 2.75-2.61 (m, 1H), 2.51-2.37 (m, 1H), 1.92-1.66 (m, 4H), 1.43-1.37 (m, 3H). | I-56 |
| 45 | 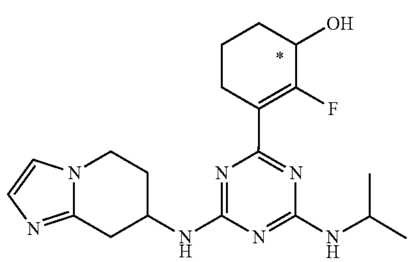 [SMILES: CC(C)Nc1nc(NC2CCn3ccnc3C2)nc(C2=C(F)C(O)CCC2)n1] | 384.1 | 1H NMR (400 MHz, CD3OD): δ 8.37-8.29 (br, 1H), 8.29-8.16 (m, 1H), 7.65 (s, 1H), 7.47-7.38 (m, 1H), 7.15-6.99 (m, 1H), 4.37-4.18 (m, 2H), 2.74-2.56 (m, 1H), 2.51-2.34 (m, 1H), 1.90-1.64 (m, 4H), 1.29-1.22 (m, 6H). | I-57 |

-continued

| Comp. | Structure | MS (M + H)+ | 1H NMR | Intermediate |
|---|---|---|---|---|
| 46 | 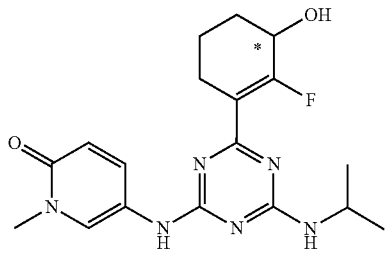 [SMILES: CC(C)Nc1nc(Nc2ccc(=O)n(C)c2)nc(C2=C(F)C(O)CCC2)n1] | 375.1 | 1H NMR (400 MHz, CD3OD): δ 8.63-8.10 (m, 1H), 7.69-7.53 (m, 1H), 6.52 (d, J = 9.6 Hz, 1H), 4.36-4.24 (m, 1H), 4.22-4.04 (m, 1H), 3.57 (s, 3H), 2.68-2.50 (m, 1H), 2.43-2.28 (m, 1H), 1.89-1.61 (m, 4H), 1.23-1.16 (m, 6H). | I-58 |
| 47 | 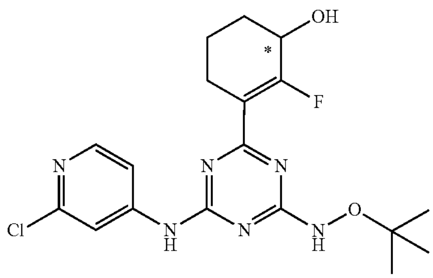 [SMILES: CC(C)(C)ONc1nc(Nc2ccnc(Cl)c2)nc(C2=C(F)C(O)CCC2)n1] | 409.2 | 1H NMR (400 MHz, CD3OD): δ 8.48-8.19 (m, 1H), 8.14-8.04 (m, 1H), 7.65-7.46 (m, 1H), 4.38-4.26 (m, 1H), 2.73-2.58 (m, 1H), 2.49-2.34 (m, 1H), 1.91-1.64 (m, 4H), 1.32 (s, 9H). | I-59 |
| 48 | 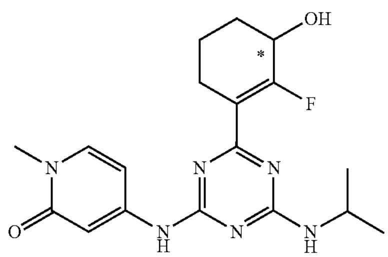 [SMILES: CC(C)Nc1nc(Nc2ccn(C)c(=O)c2)nc(C2=C(F)C(O)CCC2)n1] | 375.2 | 1H NMR (400 MHz, CD3OD): δ 7.50-7.42 (m, 1H), 7.26-7.20 (m, 1H), 6.81-6.68 (m, 1H), 4.36-4.13 (m, 2H), 3.48 (s, 3H), 2.74-2.55 (m, 1H), 2.46-2.32 (m, 1H), 1.89-1.62 (m, 4H), 1.27-1.17 (m, 6H). | I-60 |
| 49 | 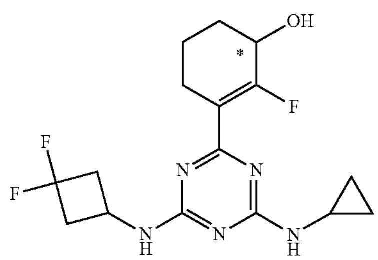 [SMILES: OC1CCCC(c2nc(NC3CC3)nc(NC3CC(F)(F)C3)n2)=C1F] | 356.1 | 1H NMR (400 MHz, CD3OD): δ 4.39-4.18 (m, 2H), 2.99-2.86 (m, 2H), 2.80-2.46 (m, 4H), 2.39-2.23 (m, 1H), 1.89-1.82 (m, 2H), 1.81-1.62 (m, 2H), 0.79-0.67 (m, 2H), 0.55-0.48 (m, 2H). | I-36 |
| 50 | 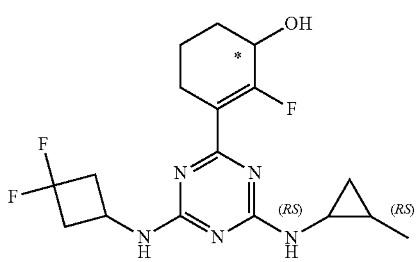 [SMILES: CC1CC1Nc1nc(NC2CC(F)(F)C2)nc(C2=C(F)C(O)CCC2)n1] | 370.1 | 1H NMR (400 MHz, CD3OD): δ 4.45-4.14 (m, 2H), 3.05-2.82 (m, 2H), 2.79-2.23 (m, 5H), 1.91-1.61 (m, 4H), 1.18-0.45 (m, 6H). | I-38 |
| 51 | 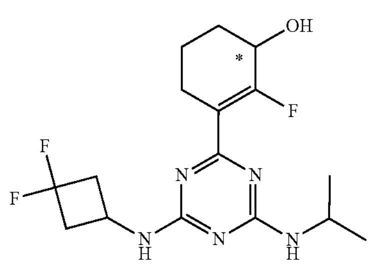 [SMILES: CC(C)Nc1nc(NC2CC(F)(F)C2)nc(C2=C(F)C(O)CCC2)n1] | 358.1 | 1H NMR (400 MHz, CD3OD): δ 4.35-4.20 (m, 2H), 4.20-4.06 (m, 1H), 2.98-2.86 (m, 2H), 2.70-2.45 (m, 3H), 2.38-2.23 (m, 1H), 1.89-1.82 (m, 2H), 1.81-1.60 (m, 2H), 1.19 (s, 6H). | I-37 |

-continued

| Comp. | Structure | MS (M + H)⁺ | ¹H NMR | Intermediate |
|---|---|---|---|---|
| 52 | 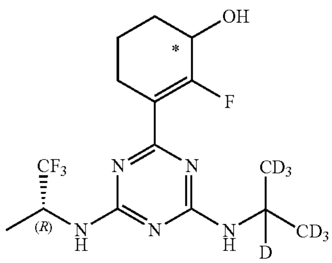 | 371.1 | ¹H NMR (400 MHz, CD₃OD): δ 4.99-4.87 (m, 1H), 4.33-4.23 (m, 1H), 2.64-2.45 (m, 1H), 2.40-2.21 (m, 1H), 1.89-1.71 (m, 3H), 1.70-1.58 (m, 1H), 1.36-1.30 (m, 3H). | I-39 |
| 53 | 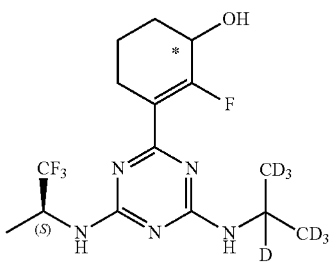 | 371.1 | ¹H NMR (400 MHz, CD₃OD): δ 4.98-4.88 (m, 1H), 4.35-4.19 (m, 1H), 2.63-2.44 (m, 1H), 2.44-2.21 (m, 1H), 1.93-1.70 (m, 3H), 1.70-1.53 (m, 1H), 1.39-1.29 (m, 3H). | I-40 |
| 54 | 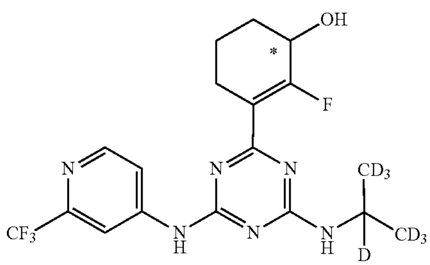 [SMILES: [2H]C([2H])([2H])C([2H])(Nc1nc(Nc2ccnc(C(F)(F)F)c2)nc(C2=C(F)C(O)CCC2)n1)C([2H])([2H])[2H]] | 420.1 | ¹H NMR (400 MHz, CD₃OD): δ 8.60-8.22 (m, 2H), 8.09-7.74 (m, 1H), 4.38-4.27 (m, 1H), 2.75-2.58 (m, 1H), 2.48-2.33 (m, 1H), 1.91-1.75 (m, 3H), 1.73-1.64 (m, 1H). | I-41 |
| 55 | 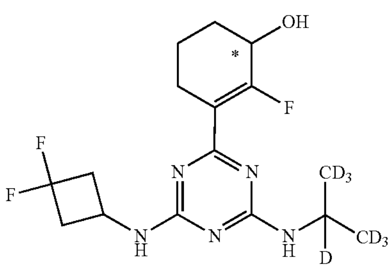 [SMILES: [2H]C([2H])([2H])C([2H])(Nc1nc(NC2CC(F)(F)C2)nc(C2=C(F)C(O)CCC2)n1)C([2H])([2H])[2H]] | 365.1 | ¹H NMR (400 MHz, CD₃OD): δ 4.36-4.15 (m, 2H), 3.02-2.81 (m, 2H), 2.73-2.41 (m, 3H), 2.40-2.19 (m, 1H), 1.89-1.71 (m, 3H), 1.70-1.59 (m, 1H). | I-42 |
| 56 | 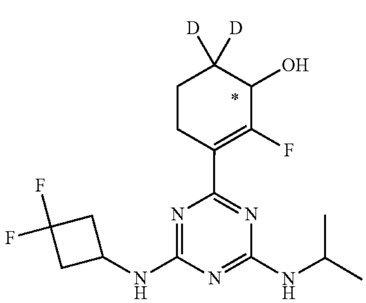 [SMILES: [2H]C1([2H])CCC(c2nc(NC(C)C)nc(NC3CC(F)(F)C3)n2)=C(F)C1O] | 360.1 | ¹H NMR (400 MHz, CD₃OD): δ 4.32-4.19 (m, 2H), 4.19-4.04 (m, 1H), 2.98-2.83 (m, 2H), 2.72-2.43 (m, 3H), 2.39-2.21 (m, 1H), 1.80-1.70 (m, 1H), 1.68-1.58 (m, 1H), 1.25-1.11 (br, 6H). | I-37 |

| Comp. | Structure | MS (M + H)+ | 1H NMR | Intermediate |
|---|---|---|---|---|
| 57 | 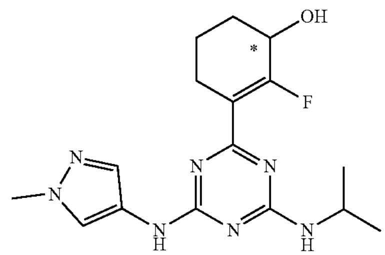 [SMILES: CC(C)Nc1nc(Nc2cnn(C)c2)nc(C2=C(F)C(O)CCC2)n1] | 348.1 | 1H NMR (400 MHz, CD3OD): δ 8.16-7.44 (m, 2H), 4.38-4.24 (m, 1H), 4.24-4.10 (m, 1H), 3.84 (s, 3H), 2.69-2.49 (m, 1H), 2.47-2.27 (m, 1H), 1.91-1.74 (m, 3H), 1.72-1.61 (m, 1H), 1.29-1.18 (m, 6H). | I-43 |
| 58 | 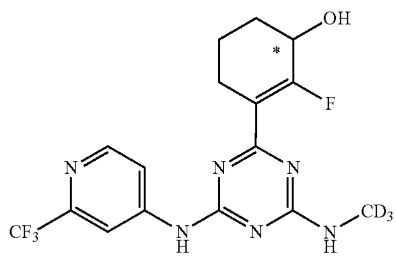 [SMILES: [2H]C([2H])([2H])Nc1nc(Nc2ccnc(C(F)(F)F)c2)nc(C2=C(F)C(O)CCC2)n1] | 388.0 | 1H NMR (400 MHz, CD3OD): δ 8.61-8.24 (m, 2H), 8.04-7.81 (m, 1H), 4.39-4.27 (m, 1H), 2.75-2.58 (m, 1H), 2.51-2.31 (m, 1H), 1.92-1.75 (m, 3H), 1.73-1.64 (m, 1H). | I-44 |
| 59 | 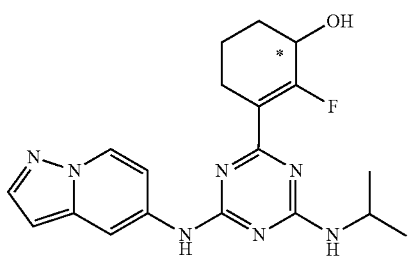 [SMILES: CC(C)Nc1nc(Nc2ccn3nccc3c2)nc(C2=C(F)C(O)CCC2)n1] | 348.1 | 1H NMR (400 MHz, CD3OD): δ 8.39-8.25 (m, 2H), 7.86-7.79 (m, 1H), 7.13-7.02 (m, 1H), 6.42-6.36 (m, 1H), 4.37-4.28 (m, 1H), 4.26-4.15 (m, 1H), 2.72-2.55 (m, 1H), 2.47-2.34 (m, 1H), 1.91-1.85 (m, 2H), 1.85-1.74 (m, 1H), 1.73-1.64 (m, 1H), 1.28-1.21 (m, 6H). | I-45 |
| 60 | 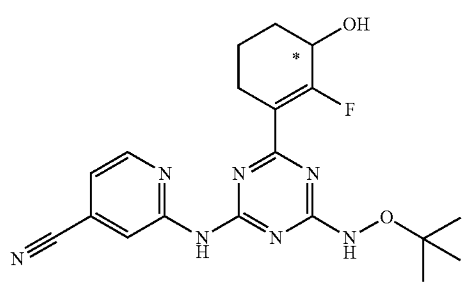 [SMILES: CC(C)(C)ONc1nc(Nc2cc(C#N)ccn2)nc(C2=C(F)C(O)CCC2)n1] | 400.1 | 1H NMR (400 MHz, CD3OD): δ 9.07-8.95 (m, 1H), 8.49-8.43 (m, 1H), 7.68-7.57 (m, 2H), 7.57-7.52 (m, 1H), 7.30-7.25 (m, 1H), 4.39-4.28 (m, 1H), 2.75-2.59 (m, 1H), 2.48-2.35 (m, 1H), 1.92-1.84 (m, 2H), 1.84-1.76 (m, 1H), 1.74-1.65 (m, 1H), 1.33 (s, 9H). | I-46 |
| 61 | 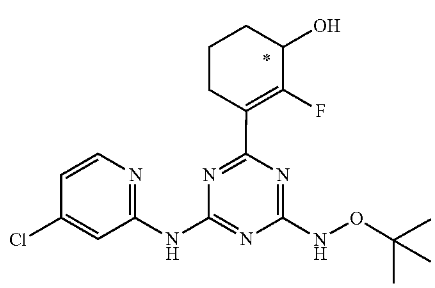 [SMILES: CC(C)(C)ONc1nc(Nc2cc(Cl)ccn2)nc(C2=C(F)C(O)CCC2)n1] | 409.1 | 1H NMR (400 MHz, CD3OD): δ 8.91-8.64 (m, 1H), 8.27-8.16 (m, 1H), 7.11-6.99 (m, 1H), 4.38-4.28 (m, 1H), 2.74-2.56 (m, 1H), 2.48-2.33 (m, 1H), 1.92-1.84 (m, 2H), 1.84-1.76 (m, 1H), 1.73-1.64 (m, 1H), 1.33 (s, 9H). | I-47 |

| Comp. | Structure | MS (M + H)⁺ | ¹H NMR | Intermediate |
|---|---|---|---|---|
| 62 | 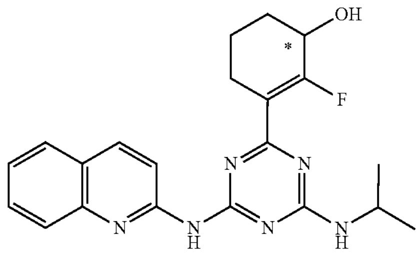 [SMILES: CC(C)Nc1nc(Nc2ccc3ccccc3n2)nc(C2=C(F)C(O)CCC2)n1] | 395.1 | ¹H NMR (400 MHz, CD₃OD): δ 8.75-8.53 (m, 1H), 8.25-8.15 (m, 1H), 7.83-7.73 (m, 2H), 7.66-7.59 (m, 1H), 7.45-7.36 (m, 1H), 4.39-4.28 (m, 1H), 4.26-4.15 (m, 1H), 2.73-2.56 (m, 1H), 2.48-2.33 (m, 1H), 1.92-1.85 (m, 2H), 1.85-1.75 (m, 1H), 1.72-1.63 (m, 1H), 1.27-1.20 (m, 6H). | I-48 |
| 63 | 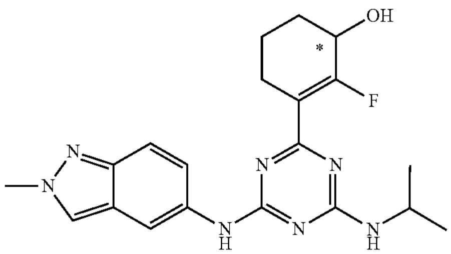 [SMILES: CC(C)Nc1nc(Nc2ccc3nn(C)cc3c2)nc(C2=C(F)C(O)CCC2)n1] | 398.1 | ¹H NMR (400 MHz, CD₃OD): δ 8.18-8.11 (m, 1H), 8.09-8.01 (m, 1H), 7.52-7.46 (m, 1H), 7.46-7.32 (m, 1H), 4.35-4.26 (m, 1H), 4.22-4.16 (m, 1H), 4.15 (s, 3H), 2.70-2.29 (m, 2H), 1.90-1.84 (m, 2H), 1.84-1.74 (m, 1H), 1.71-1.63 (m, 1H), 1.25-1.18 (m, 6H). | I-49 |
| 64 | 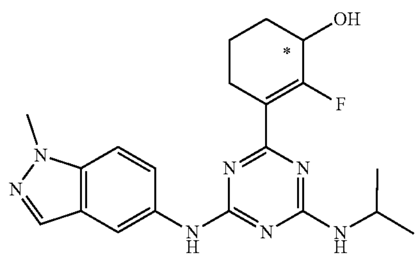 [SMILES: CC(C)Nc1nc(Nc2ccc3c(cnn3C)c2)nc(C2=C(F)C(O)CCC2)n1] | 398.1 | ¹H NMR (400 MHz, CD₃OD): δ 8.25-8.10 (m, 1H), 7.94-7.86 (m, 1H), 7.66-7.39 (m, 2H), 4.35-4.25 (br, 1H), 4.23-4.11 (m, 1H), 4.02 (s, 3H), 2.70-2.51 (m, 1H), 2.45-4.28 (m, 1H), 1.91-1.83 (m, 2H), 1.83-1.74 (m, 1H), 1.71-1.62 (m, 1H), 1.26-1.17 (m, 6H). | I-50 |
| 65 | 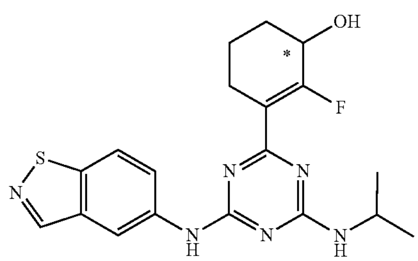 [SMILES: CC(C)Nc1nc(Nc2ccc3sncc3c2)nc(C2=C(F)C(O)CCC2)n1] | 401.1 | ¹H NMR (400 MHz, CD₃OD): δ 8.89-8.84 (m, 1H), 8.83-8.66 (m, 1H), 7.98-7.91 (m, 1H), 7.82-7.70 (m, 1H), 4.36-4.28 (m, 1H), 4.25-4.18 (m, 1H), 2.71-2.56 (m, 1H), 2.47-2.34 (m, 1H), 1.91-1.85 m, 2H), 1.85-1.77 (m, 1H), 1.72-1.64 (m, 1H), 1.28-1.22 (m, 6H). | I-51 |
| 66 | 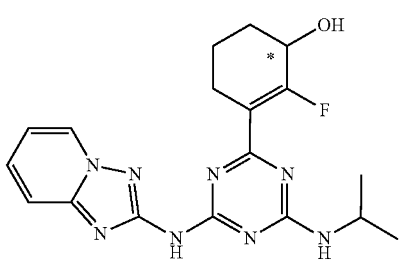 [SMILES: CC(C)Nc1nc(Nc2nc3ccccn3n2)nc(C2=C(F)C(O)CCC2)n1] | 385.1 | ¹H NMR (400 MHz, CD₃OD/CDCl3 = 2/1): δ 8.63-8.54 (m, 1H), 7.62-7.57 (m, 2H), 7.13-7.04 (m, 1H), 4.38-4.12 (m, 2H), 2.70-2.32 (m, 2H), 1.91-1.84 (m, 2H), 1.84-1.74 (m, 1H), 1.73-1.63 (m, 1H), 1.25-1.20 (m, 6H). | I-52 |
| 67 | 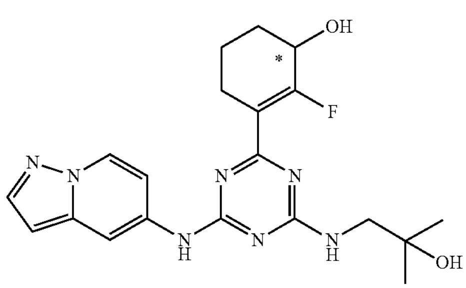 [SMILES: CC(C)(O)CNc1nc(Nc2ccn3nccc3c2)nc(C2=C(F)C(O)CCC2)n1] | 414.1 | ¹H NMR (400 MHz, CD₃OD): δ 8.38-8.22 (m, 2H), 7.89-7.76 (m, 1H), 7.12-7.01 (m, 1H), 6.45-6.34 (m, 1H), 4.38-4.27 (m, 1H), 3.51-3.42 (m, 2H), 2.70-2.56 (m, 1H), 2.46-2.34 (m, 1H), 1.91-1.84 (m, 2H), 1.83-1.74 (m, 1H), 1.72-1.64 (m, 1H), 1.26-1.18 (m, 6H). | I-53 |

-continued

| Comp. | Structure | MS (M + H)+ | 1H NMR | Intermediate |
|---|---|---|---|---|
| 68 | 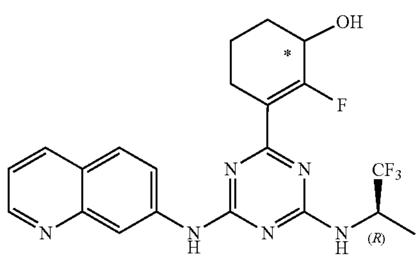 | 449.1 | 1H NMR (400 MHz, CD3OD): δ 8.86-7.07 (m, 6H), 5.19-4.97 (m, 1H), 4.41-4.27 (m, 1H), 2.78-2.60 (m, 1H), 2.53-2.37 (m, 1H), 1.94-1.78 (m, 3H), 1.76-1.65 (m, 1H), 1.45-1.36 (m, 3H). | I-62 |
| 69 | 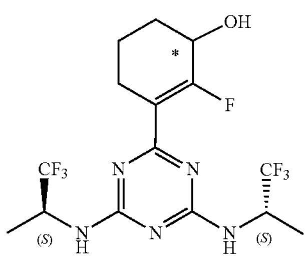 | 418.1 | 1H NMR (400 MHz, CD3OD): δ 5.00-4.87 (m, 2H), 4.36-4.22 (m, 1H), 2.65-2.51 (m, 1H), 2.43-2.29 (m, 1H), 1.89-1.60 (m, 4H), 1.38-1.29 (m, 6H). | I-32 |
| 70 | 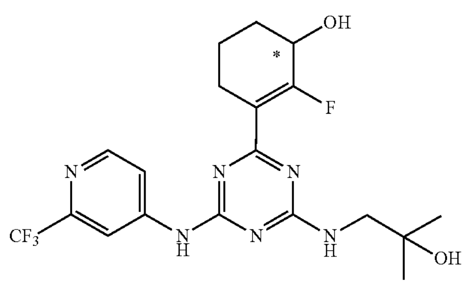 [SMILES: CC(C)(O)CNc1nc(Nc2ccnc(C(F)(F)F)c2)nc(C2=C(F)C(O)CCC2)n1] | 443.1 | 1H NMR (400 MHz, CD3OD): δ 8.64-7.73 (m, 3H), 4.43-4.27 (m, 1H), 3.53-3.43 (m, 2H), 2.79-2.61 (m, 1H), 2.52-2.36 (m, 1H), 1.92-1.67 (m, 4H), 1.24-1.16 (m, 6H). | I-66 |
| 71 | 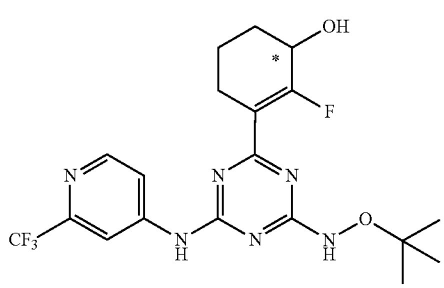 [SMILES: CC(C)(C)ONc1nc(Nc2ccnc(C(F)(F)F)c2)nc(C2=C(F)C(O)CCC2)n1] | 443.1 | 1H NMR (400 MHz, CD3OD): δ 8.55-8.36 (m, 2H). 8.01-7.90 (m, 1H), 4.41-4.30 (m, 1H), 2.77-2.62 (m, 1H), 2.52-2.32 (m, 1H), 1.96-1.64 (m, 4H), 1.31 (s, 9H). | I-63 |
| 72 | 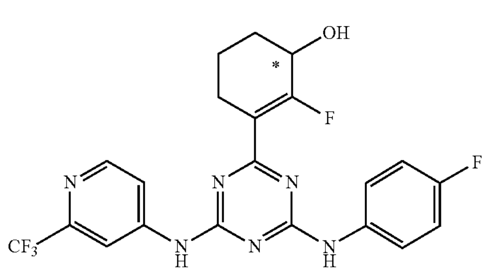 [SMILES: OC1CCCC(c2nc(Nc3ccc(F)cc3)nc(Nc3ccnc(C(F)(F)F)c3)n2)=C1F] | 465.0 | 1H NMR (400 MHz, CD3OD): δ 8.58-7.52 (m, 5H), 7.14-6.94 (m, 2H), 4.42-4.27 (m, 1H), 2.80-2.65 (m, 1H), 2.56-2.37 (m, 1H), 1.94-1.66 (m, 4H). | I-64 |

| Comp. | Structure | MS (M + H)⁺ | ¹H NMR | Intermediate |
|---|---|---|---|---|
| 73 | 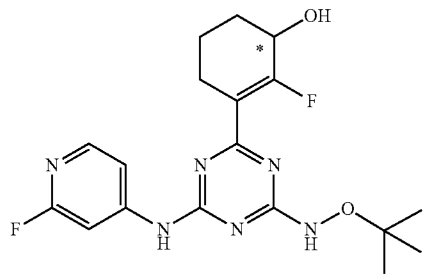 [SMILES: CC(C)(C)ONc1nc(Nc2ccnc(F)c2)nc(C2=C(F)C(O)CCC2)n1] | 393.1 | ¹H NMR (400 MHz, CD₃OD): δ 8.09-7.85 (m, 2H), 7.51-7.39 (m, 1H), 4.41-4.26 (m, 1H), 2.74-2.57 (m, 1H), 2.49-2.32 (m, 1H), 1.96-1.64 (m, 4H), 1.32-1.29 (m, 9H). | I-65 |
| 74 | 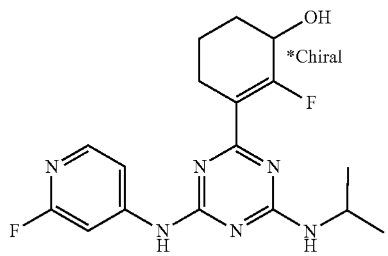 [SMILES: CC(C)Nc1nc(Nc2ccnc(F)c2)nc(C2=C(F)C(O)CCC2)n1] | 363.1 | ¹H NMR (400 MHz, CD₃OD): δ 8.02-7.88 (m, 1H), 7.85-7.72 (m, 1H), 7.52-7.39 (m, 1H), 4.39-4.29 (m, 1H), 4.26-4.12 (m, 1H), 2.76-2.56 (m, 1H), 2.49-2.32 (m, 1H), 1.99-1.61 (m, 4H), 1.28-1.20 (m, 6H). | I-67 |
| 75 | 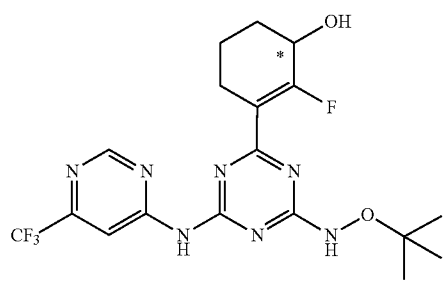 [SMILES: CC(C)(C)ONc1nc(Nc2cc(C(F)(F)F)ncn2)nc(C2=C(F)C(O)CCC2)n1] | 444.1 | ¹H NMR (400 MHz, CD₃OD): δ 9.18-8.77 (m, 2H), 4.45-4.24 (m, 1H), 2.81-2.64 (m, 1H), 2.53-2.34 (m, 1H), 2.00-1.66 (m, 4H), 1.37-1.26 (m, 9H). | I-68 |
| 76 | 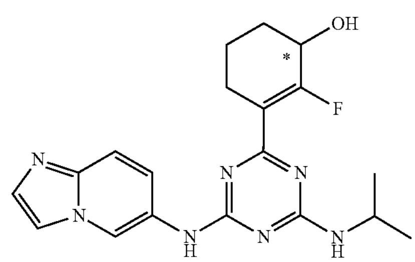 [SMILES: CC(C)Nc1nc(Nc2ccc3nccn3c2)nc(C2=C(F)C(O)CCC2)n1] | 384.1 | ¹H NMR (400 MHz, CD₃OD): δ 9.63-9.01 (m, 1H), 7.74 (s, 1H), 7.54-7.48 (m, 1H), 7.47-7.40 (m, 1H), 7.38-7.22 (m, 1H), 4.39-4.29 (m, 1H), 4.25-4.12 (m, 1H), 2.73-2.55 (m, 1H), 2.50-2.31 (m, 1H), 1.96-1.63 (m, 4H), 1.29-1.18 (m, 6H). | I-69 |
| 77 | 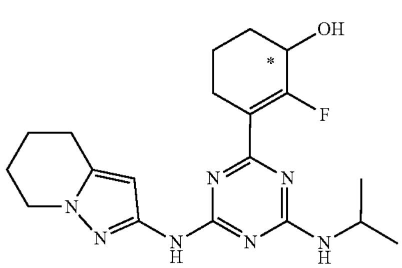 [SMILES: CC(C)Nc1nc(Nc2cc3n(n2)CCCC3)nc(C2=C(F)C(O)CCC2)n1] | 388.1 | ¹H NMR (400 MHz, CD₃OD): δ 6.59-6.32 (m, 1H), 4.36-4.27 (m, 1H), 4.23-4.10 (m, 1H), 4.03-3.90 (m, 2H), 2.82-2.72 (m, 2H), 2.65-2.51 (m, 1H), 2.46-2.29 (m, 1H), 2.09-1.97 (m, 2H), 1.90-1.63 (m, 6H), 1.25-1.16 (m, 6H). | I-70 |

-continued

| Comp. | Structure | MS (M + H)+ | 1H NMR | Intermediate |
|---|---|---|---|---|
| 78 | 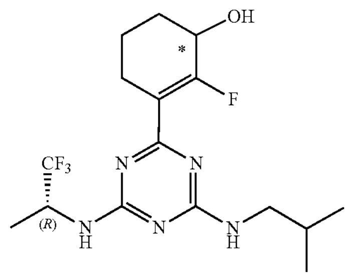 | 378.2 | 1H NMR (400 MHz, CD3OD): δ 5.04-4.89 (m, 1H), 4.34-4.24 (m, 1H), 3.25-3.07 (m, 2H), 2.65-2.48 (m, 1H), 2.40-2.20 (m, 1H), 1.96-1.59 (m, 5H), 1.38-1.30 (m, 3H), 0.95-0.87 (m, 6H). | I-13 |
| 79 | 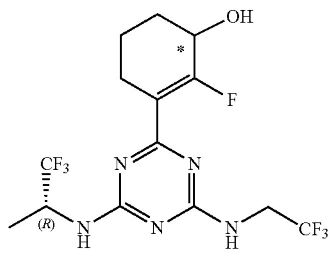 | 404.1 | 1H NMR (400 MHz, CD3OD): δ 5.03-4.90 (m, 1H), 4.35-4.26 (m, 1H), 4.21-4.00 (m, 2H), 2.65-2.49 (m, 1H), 2.43-2.24 (m, 1H), 1.93-1.59 (m, 4H), 1.42-1.30 (m, 3H). | I-76 |
| 80 | 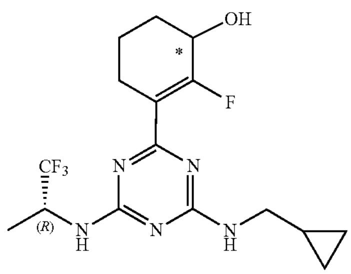 | 376.1 | 1H NMR (400 MHz, CD3OD): δ 5.50-4.87 (m, 1H), 4.34-4.23 (m, 1H), 3.26-3.14 (m, 2H), 2.62-2.47 (m, 1H), 2.39-2.22 (m, 1H), 1.89-1.82 (m, 2H), 1.82-1.73 (m, 1H), 1.71-1.63 (br, 1H), 1.37-1.31 (m, 3H), 1.14-0.99 (m, 1H), 0.51-0.42 (m, 2H), 0.26-0.19 (m, 2H). | I-77 |
| 81 | 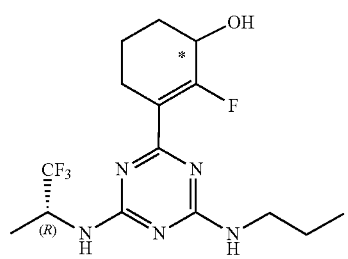 | 364.1 | 1H NMR (400 MHz, CD3OD): δ 5.01-4.87 (m, 1H), 4.34-4.22 (m, 1H), 3.37-3.30 (m, 1H), 3.28-3.23 (m, 1H), 2.62-2.48 (m, 1H), 2.38-2.22 (m, 1H), 1.88-1.82 (m, 2H), 1.82-1.72 (m, 1H), 1.69-1.62 (m, 1H), 1.62-1.53 (m, 2H), 1.37-1.30 (m, 3H), 0.96-0.89 (m, 3H). | I-78 |
| 199 | 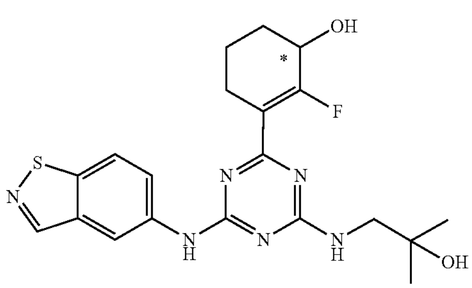 [SMILES: CC(C)(O)CNc1nc(Nc2ccc3sncc3c2)nc(C2=C(F)C(O)CCC2)n1] | 431.0 | 1H NMR (400 MHz, CD3OD): δ 8.91-8.85 (m, 1H), 8.80-8.66 (m, 1H), 7.99-7.91 (m, 1H), 7.82-7.72 (m, 1H), 4.38-4.28 (m, 1H), 3.53-3.40 (m, 2H), 2.72-2.58 (m, 1H), 2.48-4.34 (m, 1H), 1.93-1.85 (m, 2H), 1.84-1.76 (m, 1H), 1.73-1.65 (m, 1H), 1.25-1.19 (m, 6H). | I-79 |

-continued

| Comp. | Structure | MS (M + H)+ | 1H NMR | Intermediate |
|---|---|---|---|---|
| 204 | 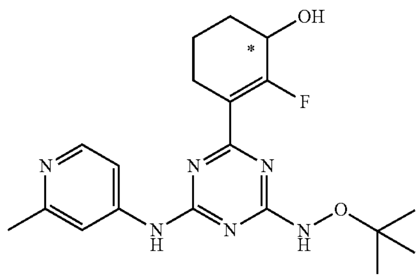 [SMILES: Cc1cc(Nc2nc(NOC(C)(C)C)nc(C3=C(F)C(O)CCC3)n2)ccn1] | 389.1 | 1H NMR (400 MHz, CD3OD): δ 8.30-8.09 (m, 1H), 7.93-7.58 (m, 2H), 4.40-4.28 (m, 1H), 2.75-2.60 (m, 1H), 2.52-2.36 (m, 4H), 1.95-1.65 (m, 4H), 1.32 (s, 9H). | I-28 |
| 224 | 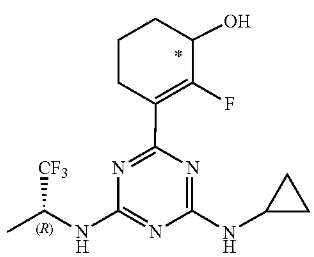 | 362.0 | 1H NMR (400 MHz, CD3OD): δ 5.12-4.89 (m, 1H), 4.36-4.21 (m, 1H), 2.81-2.66 (m, 1H), 2.65-2.46 (m, 1H), 2.41-2.21 (m, 1H), 1.90-1.82 (m, 2H), 1.82-1.72 (m, 1H), 1.70-1.59 (m, 1H), 1.39-1.29 (m, 3H), 0.77-0.68 (m, 2H), 0.55-0.47 (m, 2H). | I-16 |
| 240 | 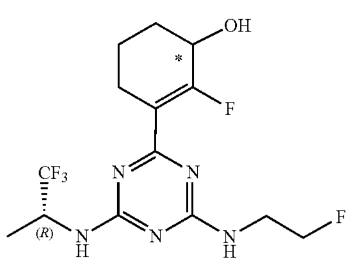 | 368.0 | 1H NMR (400 MHz, CD3OD): δ 4.98-4.90 (m, 1H), 4.60-4.52 (m, 1H), 4.49-4.40 (m, 1H), 4.35-4.20 (m, 1H), 3.74-3.54 (m, 2H), 2.68-2.45 (m, 1H), 2.43-2.22 (m, 1H), 1.91-1.81 (m, 2H), 1.81-1.72 (m, 1H), 1.70-1.60 (m, 1H), 1.34 (s, 3H). | I-83 |
| 241 | 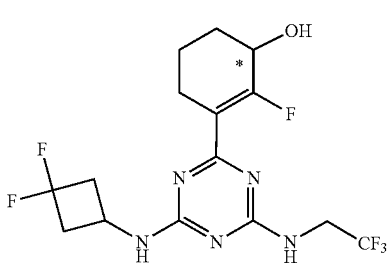 [SMILES: OC1CCCC(c2nc(NCC(F)(F)F)nc(NC3CC(F)(F)C3)n2)=C1F] | 398.0 | 1H NMR (400 MHz, CD3OD): δ 4.35-4.17 (m, 2H), 4.16-4.04 (m, 2H), 3.00-2.84 (m, 2H), 2.71-2.48 (m, 3H), 2.42-2.26 (m, 1H), 1.91-1.82 (m, 2H), 1.82-1.73 (m, 1H), 1.70-1.60 (m, 1H). | I-84 |

Compounds 82 and 83

(*)3-(4,6-Bis(((R)-1,1,1-trifluoropropan-2-yl)amino)-1,3,5-triazin-2-yl)-2-fluorocyclohex-2-en-6,6-D$_2$-1-ol and 3-(4,6-bis(((R)-1,1,1-trifluoropropan-2-yl)amino)-1,3,5-triazin-2-yl)-2-fluorocyclohex-2-en-1,6,6-D$_3$-1-ol

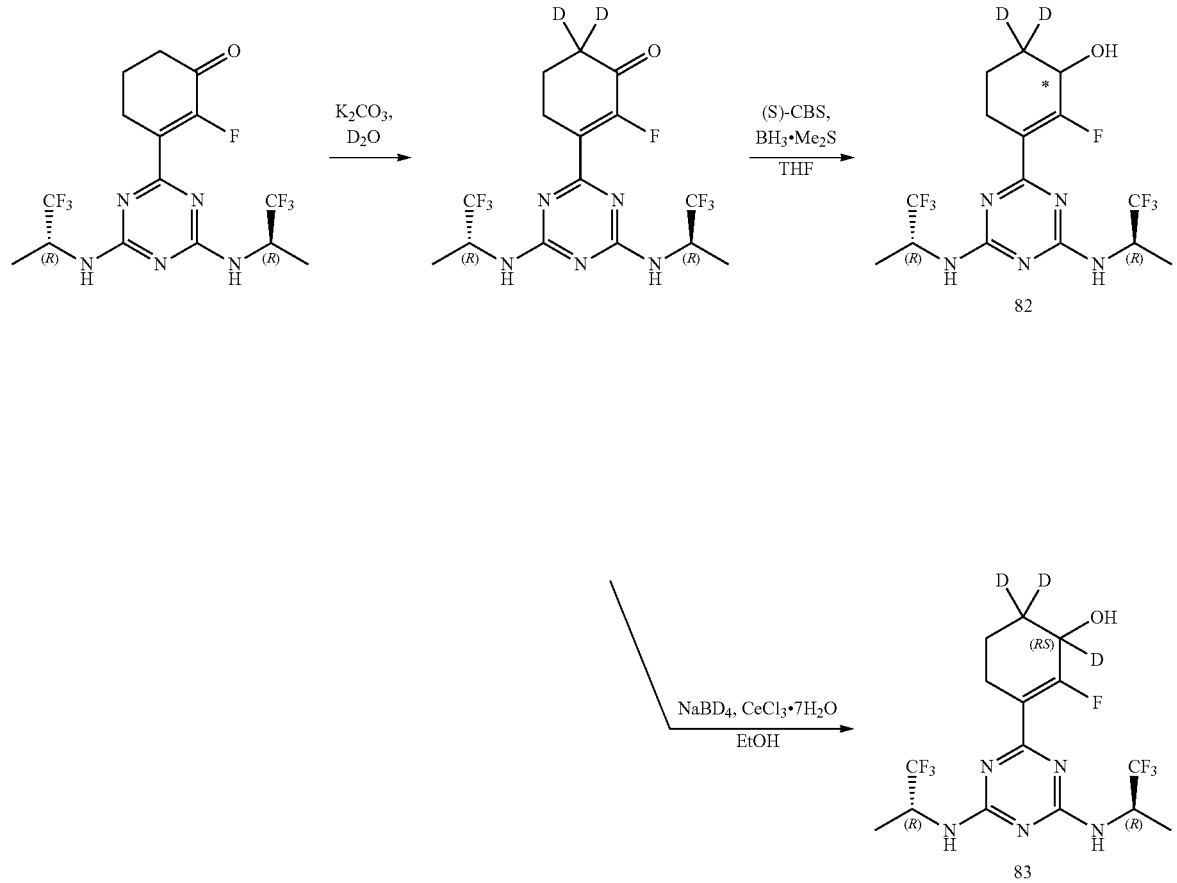

(A) 3-(4,6-Bis(((R)-1,1,1-trifluoropropan-2-yl)amino)-1,3,5-triazin-2-yl)-2-fluorocyclohex-2-en-1-one-6,6-D$_2$ To a solution of 3-(4,6-bis(((R)-1,1,1-trifluoropropan-2-yl)amino)-1,3,5-triazin-2-yl)-2-fluorocyclohex-2-en-1-one (prepared according to the procedure of Compound 1 using Intermediate I-3, 114 mg, 0.27 mmol) in 1,4-dioxane (6 mL) was added D$_2$O (2 mL) and K$_2$CO$_3$ (75 mg, 0.54 mmol). The mixture was stirred at 80° C. for 4.5 hours. Then, the solvent was removed in vacuo and the residue was purified by flash column chromatography (eluting with gradient PE/EA=100:0-0:100) to afford the title compound as yellow oil (64 mg, yield: 56%). MS (m/z): 418.0 [M+H]$^+$ (B) (*)3-(4,6-Bis(((R)-1,1,1-trifluoropropan-2-yl)amino)-1,3,5-triazin-2-yl)-2-fluoro-cyclohex-2-en-6,6-D$_2$-1-ol Compound 82 was prepared according to the procedure of Compound 39. MS (m/z): 420.1 [M+H]$^+$ $^1$H NMR (400 MHz, CD$_3$OD): δ 5.00-4.87 (m, 2H), 4.32-4.23 (m, 1H), 2.63-2.53 (m, 1H), 2.37-2.26 (m, 1H), 1.81-1.69 (m, 1H), 1.67-1.60 (m, 1H), 1.37-1.31 (m, 6H).

(C) 3-(4,6-Bis(((R)-1,1,1-trifluoropropan-2-yl)amino)-1,3,5-triazin-2-yl)-2-fluorocyclohex-2-en-1,6,6-D$_3$-1-ol Compound 83 was prepared according to the procedure of Compound 1 step (B), using NaBD$_4$. MS (m/z): 421.1 [M+H]$^+$ $^1$H NMR (400 MHz, CD$_3$OD): δ 5.00-4.87 (m, 2H), 2.63-2.53 (m, 1H), 2.37-2.26 (m, 1H), 1.81-1.69 (m, 1H), 1.67-1.60 (m, 1H), 1.37-1.31 (m, 6H).

The compounds in the below table were prepared according to the procedure of Compound 82 using the corresponding intermediates and reagents under appropriate conditions that will be recognized by POSITA:

| Comp. | Structure | MS (M + H)+ | 1H NMR | Intermediate |
|---|---|---|---|---|
| 84 | 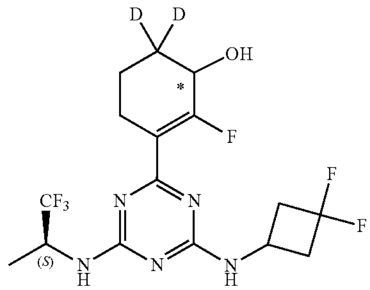 | 414.1 | 1H NMR (400 MHz, CD3OD): δ 4.98-4.89 (m, 1H), 4.35-4.13 (m, 2H), 3.02-2.81 (m, 2H), 2.75-2.46 (m, 3H), 2.44-2.24 (m, 1H), 1.82-1.71 (m, 1H), 1.69-1.58 (m, 1H), 1.38-1.28 (m, 3H). | I-54 |
| 85 | 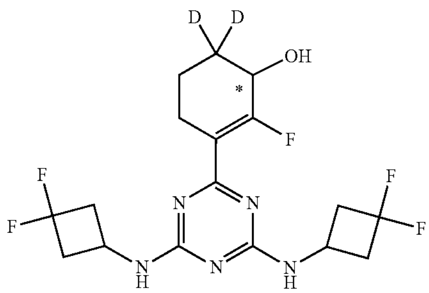 [SMILES: [2H]C1([2H])CCC(c2nc(NC3CC(F)(F)C3)nc(NC3CC(F)(F)C3)n2)=C(F)C1O] | 408.1 | 1H NMR (400 MHz, CD3OD): δ 4.36-4.14 (m, 3H), 2.98-2.85 (m, 4H), 2.67-2.46 (m, 5H), 2.39-2.22 (m, 1H), 1.82-1.71 (m, 1H), 1.68-1.57 (m, 1H). | I-10 |
| 86 | 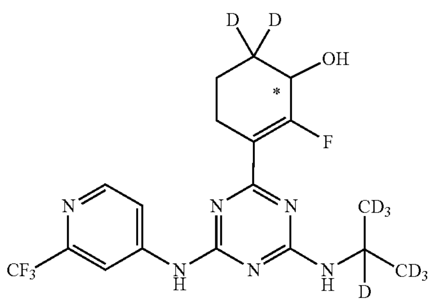 [SMILES: [2H]C1([2H])CCC(c2nc(Nc3ccnc(C(F)(F)F)c3)nc(NC([2H])(C([2H])([2H])[2H])C([2H])([2H])[2H])n2)=C(F)C1O] | 422.1 | 1H NMR (400 MHz, CD3OD): δ 8.60-8.23 (m, 2H), 8.10-7.75 (m, 1H), 4.36-4.28 (m, 1H), 2.72-2.56 (m, 1H), 2.48-2.33 (m, 1H), 1.83-1.73 (m, 1H), 1.71-1.63 (m, 1H). | I-41 |
| 87 | 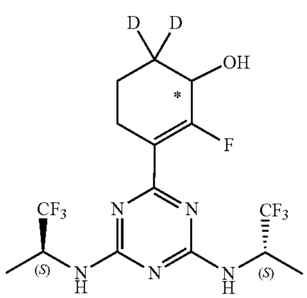 | 420.0 | 1H NMR (400 MHz, CD3OD): δ 5.02-4.88 (m, 2H), 4.34-4.24 (m, 1H), 2.60-2.48 (m, 1H), 2.42-2.30 (m, 1H), 1.88-1.72 (m, 1H), 1.70-1.58 (m, 1H), 1.36-1.31 (m, 6H). | I-32 |
| 89 | 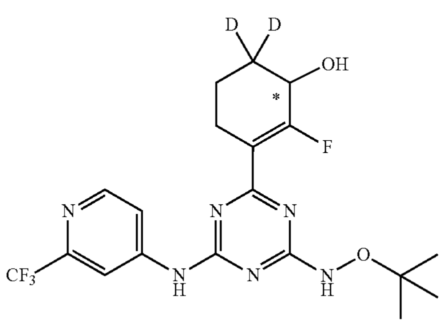 [SMILES: [2H]C1([2H])CCC(c2nc(NOC(C)(C)C)nc(Nc3ccnc(C(F)(F)F)c3)n2)=C(F)C1O] | 445.1 | 1H NMR (400 MHz, CD3OD): δ 8.54-8.35 (m, 2H), 8.03-7.83 (m, 1H), 4.40-4.24 (m, 1H), 2.74-2.60 (m, 1H), 2.48-2.32 (m, 1H), 1.85-1.74 (m, 1H), 1.71-1.60 (m, 1H), 1.31 (s, 9H). | I-63 |

The compounds in the below table were prepared according to the procedure of Compound 83 using the corresponding intermediates and reagents under appropriate conditions that will be recognized by POSITA:

| Comp. | Structure | MS (M + H)+ | ¹H NMR | Intermediate |
|---|---|---|---|---|
| 90 | 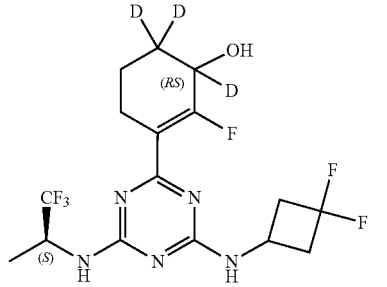 | 415.1 | ¹H NMR (400 MHz, CD$_3$OD): δ 4.98-4.89 (m, 1H), 4.35-4.13 (m, 1H), 3.02-2.81 (m, 2H), 2.75-2.46 (m, 3H), 2.44-2.24 (m, 1H), 1.82-1.71 (m, 1H), 1.69-1.58 (m, 1H), 1.38-1.28 (m, 3H). | I-54 |
| 91 | 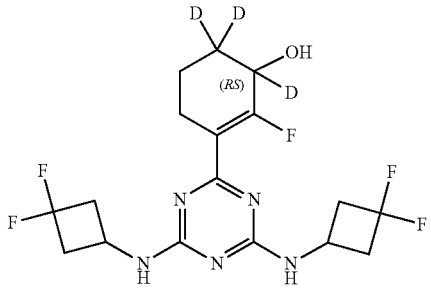 | 409.1 | ¹H NMR (400 MHz, CD$_3$OD): δ 4.36-4.14 (m, 2H), 2.98-2.85 (m, 4H), 2.67-2.46 (m, 5H), 2.39-2.22 (m, 1H), 1.82-1.71 (m, 1H), 1.68-1.57 (m, 1H). | I-10 |
| 92 | 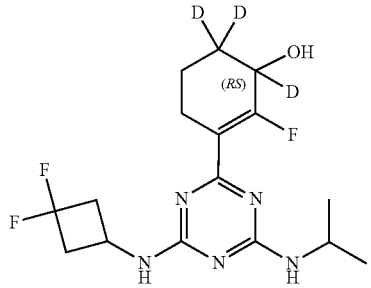 | 361.1 | ¹H NMR (400 MHz, CD$_3$OD): δ 4.34-4.18 (m, 1H), 4.18-4.00 (m, 1H), 3.01-2.81 (m, 2H), 2.72-2.41 (m, 3H), 2.41-2.18 (m, 1H), 1.80-1.70 (m, 1H), 1.69-1.58 (m, 1H), 1.25-1.11 (br, 6H). | I-37 |

Compound 93

(*)3-(4-Amino-6-(((R)-1,1,1-trifluoropropan-2-yl)amino)-1,3,5-triazin-2-yl)-2-fluoro-cyclohex-2-en-1-ol

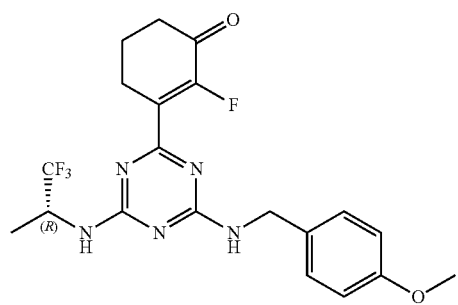

B2

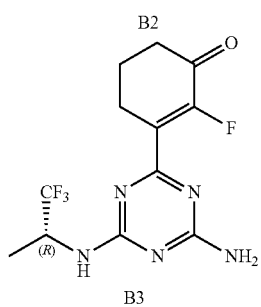

B3

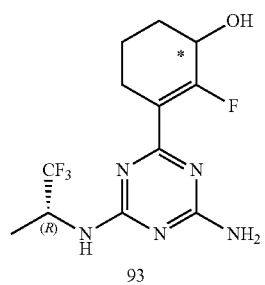

93

(A) (R)-2-fluoro-3-(4-((4-methoxybenzyl)amino)-6-((1,1,1-trifluoropropan-2-yl)amino)-1,3,5-triazin-2-yl)cyclohex-2-en-1-one (B2)

The title Compound B2 was prepared according to the procedure of Compound 1, using Intermediate I-55. MS (m/z): 440.1 [M+H]$^+$

(B) (R)-3-(4-amino-6-((1,1,1-trifluoropropan-2-yl)amino)-1,3,5-triazin-2-yl)-2-fluoro-cyclohex-2-en-1-one (B3)

A solution of Compound B2 (1.1 g, 2.5 mmol) in TFA (10 mL) was stirred at reflux for 4 hours. The solvent was removed. The residue was washed with saturated NaHCO$_3$ aqueous solution and purified by flash column chromatography (eluting with gradient PE/EA=100:0-0:100) to give Compound B3 as pale yellow solid. MS (m/z): 320.0[M+H]$^+$

(C) (*)3-(4-Amino-6-(((R)-1,1,1-trifluoropropan-2-yl)amino)-1,3,5-triazin-2-yl)-2-fluoro-cyclohex-2-en-1-ol Compound 93 was prepared according to the procedure of Compound 39. MS (m/z): 322.0 [M+H]$^+$ $^1$H NMR (400 MHz, CD$_3$OD): δ 5.01-4.89 (m, 1H), 4.38-4.19 (m, 1H), 2.62-2.47 (m, 1H), 2.38-2.24 (m, 1H), 1.89-1.61 (m, 4H), 1.36-1.29 (m, 3H).

Compounds 95 and 96

2,6-Difluoro-3-(4-(isopropylamino)-6-(((R)-1,1,1-trifluoropropan-2-yl)amino)-1,3,5-triazin-2-yl)cyclohex-2-en-1-ol, optically pure diastereoisomers

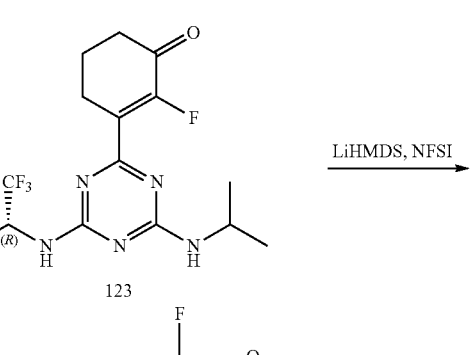

123

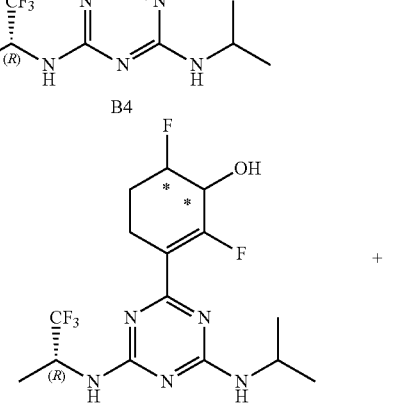

B4

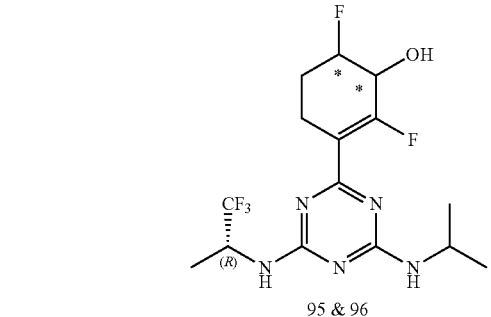

95 & 96

(A) 2,6-difluoro-3-(4-(isopropylamino)-6-(((R)-1,1,1-trifluoropropan-2-yl)amino)-1,3,5-triazin-2-yl)cyclohex-2-en-1-one (B4)

Under nitrogen atmosphere, to 1 mol/L of LiHMDS/THF solution (14.85 mL, 14.85 mmoL) was added dropwise a solution of Compound 123 (1.2 g, 3.30 mmol) in THF (20 mL) at −78° C. The mixture was stirred at 0° C. for 2 hours. A solution of NFSI (3.12 g, 9.90 mmol) in THF added drop-wise slowly, then the mixture was warmed to room temperature and stirred for 3 hours. After the reaction was completed, the mixture was quenched by the addition of saturated $NH_4Cl$ aqueous solution (30 mL). The organic layer was collected and the aqueous was extracted with EtOAc. The organic layers were combined, dried over anhydrous $Na_2SO_4$ and filtered. The filtrate was condensed in vacuo and purified by flash column chromatography (eluting with gradient PE/EA=100:0-0:100) to give Compound B4 as white solid (190 mg, yield: 15.2%). MS (m/z): 380.2 $[M+H]^+$

(B) 2,6-Difluoro-3-(4-(isopropylamino)-6-(((R)-1,1,1-trifluoropropan-2-yl)amino)-1,3,5-triazin-2-yl)cyclohex-2-en-1-ol Compounds 95 and 96 were prepared according to the procedure of Compound 39, and purified by preparative TLC (eluting with PE/EA=2/1).

Compound 95, Rf≈0.55, MS (m/z): 382.1 $[M+H]^+$; $^1H$ NMR (400 MHz, $CD_3OD$): δ 4.97-4.90 (m, 1H), 4.72-4.55 (m, 1H), 4.38-4.03 (m, 2H), 2.63-2.46 (m, 2H), 2.06-1.90 (m, 2H), 1.38-1.31 (m, 3H), 1.23-1.13 (s, 6H).

Compound 96, Rf≈0.50, MS (m/z): 382.2 $[M+H]^+$; $^1H$ NMR (400 MHz, $CD_3OD$): δ 4.97-4.90 (m, 1H), 4.71-4.55 (m, 1H), 4.51-4.40 (m, 1H), 4.20-4.05 (m, 1H), 2.76-2.58 (m, 1H), 2.48-2.31 (m, 1H), 2.15-2.01 (m, 1H), 1.98-1.81 (m, 1H), 1.40-1.30 (m, 3H), 1.22-1.12 (m, 6H).

The compounds in the below table were prepared according to the procedure of Compounds 95 and 96 using the corresponding intermediates and reagents under appropriate conditions that will be recognized by POSITA:

| Comp. | Structure | MS (M + H)+ | $^1H$ NMR | Intermediate |
|---|---|---|---|---|
| 97 | 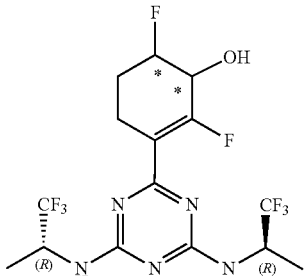 Rf ≈ 0.55 | 436.2 | $^1H$ NMR (400 MHz, $CD_3OD$): δ 4.98-4.88 (m, 2H), 4.82-4.63 (m, 1H), 4.35-4.18 (m, 1H), 2.64-2.49 (m, 2H), 2.06-1.90 (m, 2H), 1.37-1.31 (m, 6H). | I-3 |
| 98 | 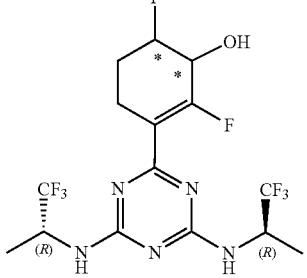 Rf ≈ 0.50 | 436.1 | $^1H$ NMR (400 MHz, $CD_3OD$): δ 5.03-4.89 (m, 2H), 4.80-4.65 (m, 1H), 4.55-4.38 (m, 1H), 2.80-2.62 (m, 1H), 2.52-2.34 (m, 1H), 2.17-2.02 (m, 1H), 1.98-1.84 (m, 1H), 1.40-1.29 (m, 6H). | I-3 |
| 201 | 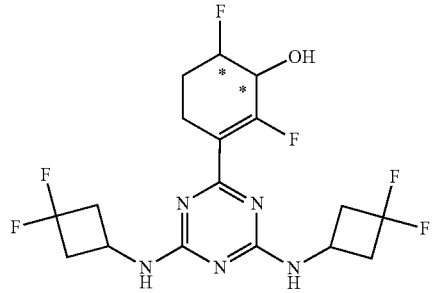 Rf ≈ 0.55 | 424.2 | $^1H$ NMR (400 MHz, $CD_3OD$): δ 4.79-4.64 (m, 1H), 4.37-4.15 (m, 3H), 2.99-2.83 (m, 4H), 2.70-2.47 (m, 6H), 2.06-1.88 (m, 2H). | I-10 |

| Comp. | Structure | MS (M + H)+ | 1H NMR | Intermediate |
|---|---|---|---|---|
| 202 | 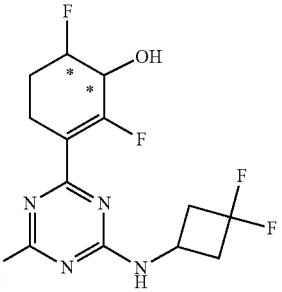 Rf ≈ 0.50 | 424.2 | 1H NMR (400 MHz, CD3OD): δ 4.81-4.64 (m, 1H), 4.52-4.38 (m, 1H), 4.34-4.17 (m, 2H), 2.99-2.83 (m, 4H), 2.70-2.32 (m, 6H), 2.13-2.01 (m, 1H), 1.96-1.81 (m, 1H). | I-10 |
| 225 | 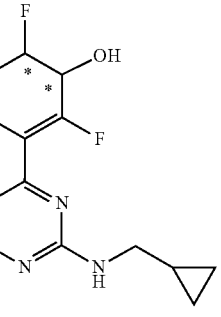 Rf ≈ 0.55 | 394.2 | 1H NMR (400 MHz, CD3OD): δ 5.01-4.90 (m, 1H), 4.79-4.62 (m, 1H), 4.35-4.19 (m, 1H), 3.27-3.11 (m, 2H), 2.65-2.43 (m, 2H), 2.07-1.87 (m, 2H), 1.40-1.29 (m, 3H), 1.13-1.00 (m, 1H), 0.55-0.40 (m, 2H), 0.31-0.15 (m, 2H). | I-77 |
| 226 | 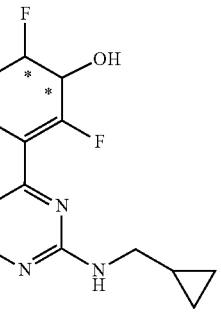 Rf ≈ 0.50 | 394.2 | 1H NMR (400 MHz, CD3OD): δ 5.00-4.89 (m, 1H), 4.80-4.64 (m, 1H), 4.51-4.37 (m, 1H), 3.27-3.09 (m, 2H), 2.78-2.57 (m, 1H), 2.52-2.30 (m, 1H), 2.15-2.01 (m, 1H), 1.97-1.80 (m, 1H), 1.40-1.27 (m, 3H), 1.13-0.98 (m, 1H), 0.55-0.40 (m, 2H), 0.30-0.14 (m, 2H). | I-77 |
| 227 | 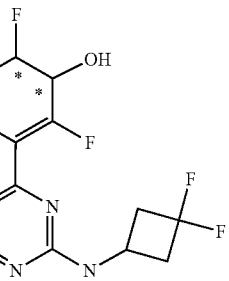 Rf ≈ 0.55 | 430.0 | 1H NMR (400 MHz, CD3OD): δ 5.01-4.90 (m, 1H), 4.80-4.63 (m, 1H), 4.35-4.11 (m, 2H), 3.01-2.86 (m, 2H), 2.55 (s, 4H), 2.09-1.92 (m, 2H), 1.42-1.31 (m, 3H). | I-9 |

-continued
| Comp. | Structure | MS (M + H)+ | 1H NMR | Intermediate |
|---|---|---|---|---|
| 228 | 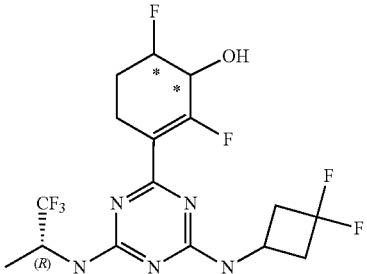 Rf ≈ 0.50 | 430.0 | 1H NMR (400 MHz, CD3OD): δ 5.05-4.88 (m, 1H), 4.82-4.64 (m, 1H), 4.54-4.40 (m, 1H), 4.36-4.17 (m, 1H), 3.00-2.84 (m, 2H), 2.77-2.34 (m, 4H), 2.16-2.02 (m, 1H), 1.96-1.83 (m, 1H), 1.41-1.30 (m, 3H). | I-9 |
| 230 & 231 | 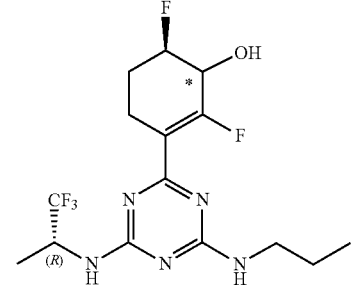 | 382.1 382.0 | 1H NMR (400 MHz, DMSO-d6): δ 7.89-7.69 (m, 1H), 7.54-7.36 (m, 1H), 5.82-5.56 (m, 1H), 4.93-4.59 (m, 2H), 4.39-4.28 (m, 1H), 3.22-3.10 (m, 2H), 2.56-2.39 (m, 1H), 2.38-2.20 (m, 1H), 1.98-1.88 (m, 1H), 1.86-1.73 (m, 1H), 1.50-1.41 (m, 2H), 1.29-1.23 (m, 3H), 0.86-0.79 (m, 3H). | I-18 I-18 |
|  | 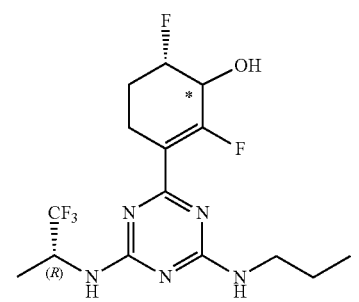 |  | 1H NMR (400 MHz, DMSO-d6): δ 7.92-7.69 (m, 1H), 7.60-7.34 (m, 1H), 6.11-5.82 (m, 1H), 4.96-4.59 (m, 2H), 4.24-4.08 (m, 1H), 3.22-3.09 (m, 2H), 2.45-2.29 (m, 2H), 1.97-1.89 (m, 2H), 1.52-1.40 (m, 2H), 1.29-1.22 (m, 3H), 0.86-0.78 (m, 3H). |  |
| 232 | 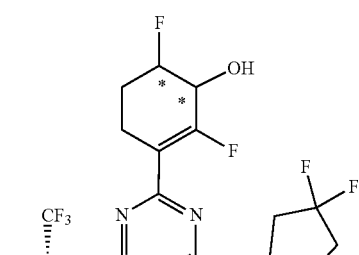 Rf ≈ 0.55 | 444.2 | 1H NMR (400 MHz, CD3OD): δ 5.00-4.89 (m, 1H), 4.81-4.63 (m, 1H), 4.52-4.37 (m, 1H), 4.36-4.19 (m, 1H), 2.65-2.46 (m, 3H), 2.28-2.14 (m, 2H), 2.13-1.91 (m, 4H), 1.85-1.70 (m, 1H), 1.39-1.29 (m, 3H). | I-82 |

| Comp. | Structure | MS (M + H)+ | 1H NMR | Intermediate |
|---|---|---|---|---|
| 233 | 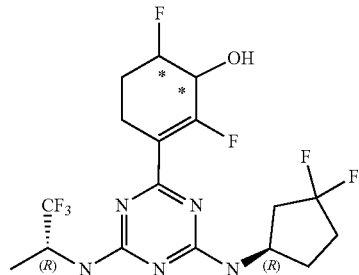<br>Rf ≈ 0.50 | 444.2 | 1H NMR (400 MHz, CD3OD): δ 5.01-4.89 (m, 1H), 4.80-4.62 (m, 1H), 4.57-4.29 (m, 2H), 2.74-2.34 (m, 3H), 2.29-1.71 (m, 7H), 1.41-1.27 (m, 3H). | I-82 |

Note:
Compounds 230 and 231 were obtained via flash column chromatography (eluting with gradient H2O/MeOH = 100:0-0:100). The compound obtained from the first elution was named as Compound 230 and the compound obtained from the second elution was named as Compound 231.

Compounds 242, 266-269

3-(4,6-Bis(((R)-1,1,1-trifluoropropan-2-yl)amino)-1,3,5-triazin-2-yl)-2,6-difluorocyclohex-2-en-1-D-1-ol, optically pure diastereoisomers

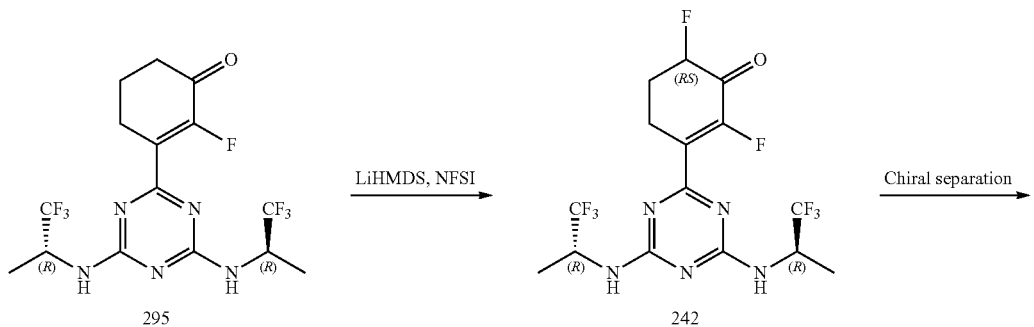

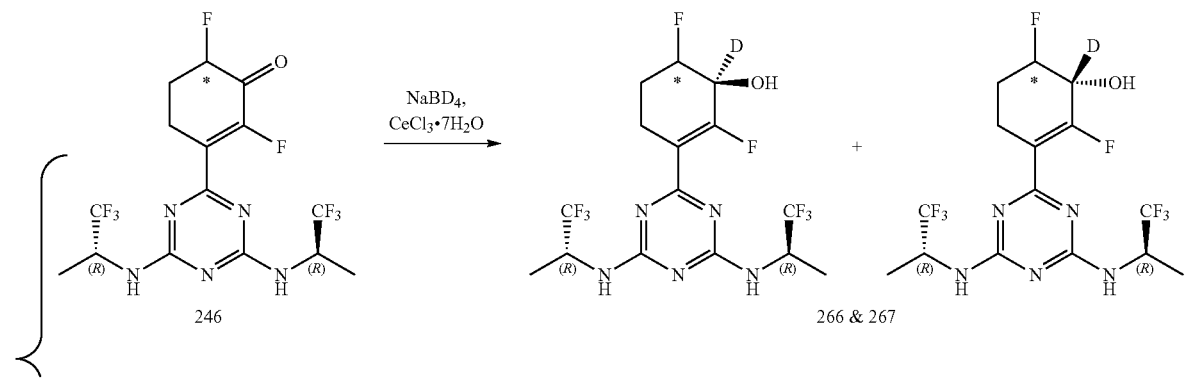

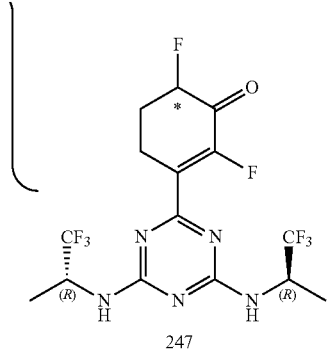
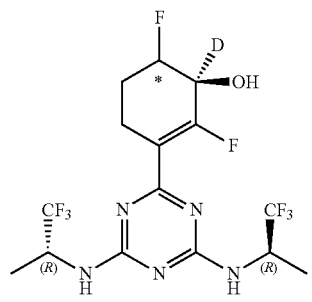

(A) 3-(4,6-Bis(((R)-1,1,1-trifluoropropan-2-yl)amino)-1,3,5-triazin-2-yl)-2,6-difluoro-cyclohex-2-en-1-one Compound 242 was prepared according to the procedure of Step A of Compounds 95 and 96, using Compound 295 and corresponding reagents. MS (m/z): 434.0 [M+H]+;
$^1$H NMR (400 MHz, CD$_3$OD): δ 5.31-5.06 (m, 1H), 5.03-4.90 (m, 2H), 3.09-3.00 (br, 1H), 2.90-2.74 (m, 1H), 2.57-2.42 (m, 1H), 2.31-2.12 (m, 1H), 1.39-1.31 (m, 6H).

(B) 3-(4,6-Bis(((R)-1,1,1-trifluoropropan-2-yl)amino)-1,3,5-triazin-2-yl)-2,6-difluoro-cyclohex-2-en-1-one, optically pure diastereoisomers Compound 242 was separated by chiral HPLC to give a pair of optically pure diastereoisomers, Compounds 246 and 247 (Chiral HMPL conditions: Column: AD-H (0.46 cm I.D.×15 cm L); mobile phase: n-heptane/isopropanol=80/20; flow rate: 0.5 mL/min; detection wavelength: UV 254 nm). The first elution (Compound 246: RT=2.025 min, de %=100%, MS (m/z): 434.0 [M+H]$^+$). The second elution (Compound 247: RT=2.083 min, de %=100%, MS (m/z): 434.0 [M+H]$^+$).

(C) 3-(4,6-Bis(((R)-1,1,1-trifluoropropan-2-yl)amino)-1,3,5-triazin-2-yl)-2,6-difluoro-cyclohex-2-en-1-D-1-ol, optically pure diastereoisomers Compounds 266 and 267 were prepared according to the procedure of Compound 1, using Compound 246 and NaBD$_4$, purified by flash column chromatography (eluting with PE/EA).

Compound 266: Rf≈0.55, MS (m/z): 437.2 [M+H]$^+$; $^1$H NMR (400 MHz, CD$_3$OD): δ 4.93-4.80 (m, 2H), 4.71-4.55 (m, 1H), 2.54-2.40 (m, 2H), 1.97-1.83 (m, 2H), 1.30-1.22 (m, 6H).

Compound 267: Rf≈0.50, MS (m/z): 437.2 [M+H]$^+$; $^1$H NMR (400 MHz, CD$_3$OD): δ 4.95-4.79 (m, 2H), 4.75-4.57 (m, 1H), 2.68-2.52 (m, 1H), 2.45-2.27 (m, 1H), 2.07-1.92 (m, 1H), 1.90-1.75 (m, 1H), 1.31-1.21 (m, 6H).

Compounds 268 and 269 were prepared according to the procedure of Compound 1, using Compound 247 and NaBD$_4$, purified by flash column chromatography (eluting with PE/EA).

Compound 268: Rf≈0.55, MS (m/z): 437.2 [M+H]$^+$; $^1$H NMR (400 MHz, CD$_3$OD): δ 4.93-4.80 (m, 2H), 4.71-4.55 (m, 1H), 2.54-2.40 (m, 2H), 1.97-1.83 (m, 2H), 1.30-1.22 (m, 6H).

Compound 269: Rf≈0.50, MS (m/z): 437.2 [M+H]$^+$; $^1$H NMR (400 MHz, CD$_3$OD): δ 4.95-4.79 (m, 2H), 4.75-4.57 (m, 1H), 2.68-2.52 (m, 1H), 2.45-2.27 (m, 1H), 2.07-1.92 (m, 1H), 1.90-1.75 (m, 1H), 1.31-1.21 (m, 6H).

Compound 94

2,6,6-Trifluoro-3-(4-(isopropylamino)-6-(((R)-1,1,1-trifluoropropan-2-yl)amino)-1,3,5-triazin-2-yl)cyclohex-2-en-1-ol

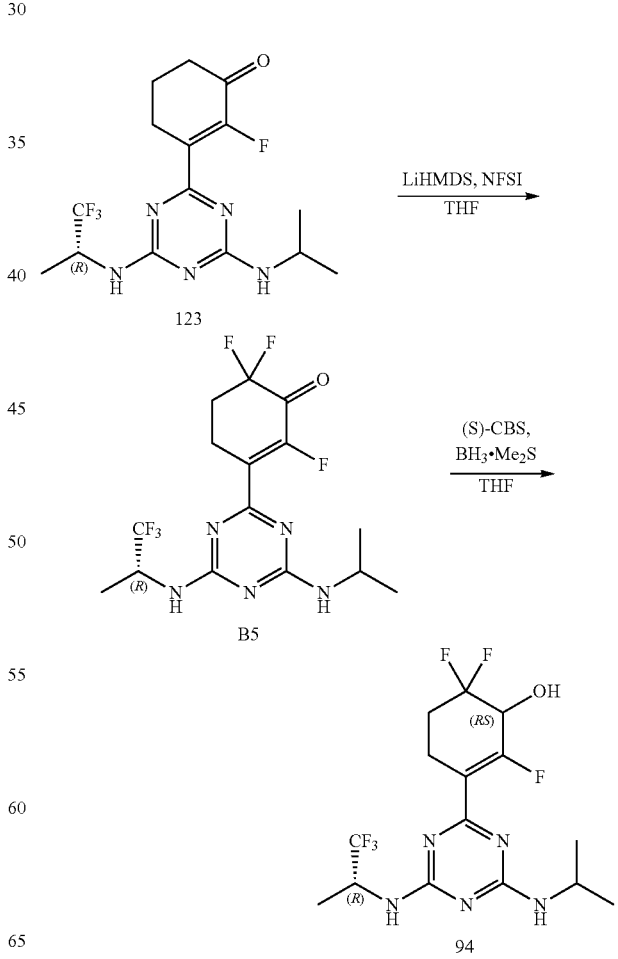

(A) (R)-2,6,6-trifluoro-3-(4-(isopropylamino)-6-((1,1,1-trifluoropropan-2-yl)amino)-1,3,5-triazin-2-yl)cyclohex-2-en-1-one (B5)

Under nitrogen atmosphere, to a solution of 1 mol/L LiHMDS in THF (14.85 mL, 14.85 mmoL) was added a solution of Compound 123 (1.2 g, 3.30 mmol) in THF (20 mL) dropwise at −78° C. The mixture was stirred at 0° C. for 2 hours. Then, to the mixture was added a solution of NFSI (3.12 g, 9.90 mmol) in THF drop-wise, then the reaction was warmed to room temperature slowly and stirred for another 3 hours. After the reaction was completed, the mixture was quenched by the addition of saturated NH$_4$Cl aqueous solution (30 mL). The organic layer was collected and the aqueous layer was extracted with EtOAc. The organic layers were combined, dried over Na$_2$SO$_4$ and filtered. The filtrate was condensed in vacuo and purified by flash column chromatography (eluting with gradient PE/EA=100:0-0:100) to give compound B5 as a white solid (25 mg, yield: 1.9%). MS (m/z): 398.1 [M+H]$^+$

(B) 2,6,6-Trifluoro-3-(4-(isopropylamino)-6-(((R)-1,1,1-trifluoropropan-2-yl)amino)-1,3,5-triazin-2-yl)cyclohex-2-en-1-ol Compound 94 was prepared according to the procedure of Compound 39, using compound B5 and corresponding reagents. MS (m/z): 400.2 [M+H]$^+$ $^1$H NMR (400 MHz, CD$_3$OD): δ 4.97-4.88 (m, 1H), 4.33-4.19 (m, 1H), 4.19-4.07 (m, 1H), 2.78-2.61 (m, 1H), 2.59-2.40 (m, 1H), 2.21-2.00 (m, 2H), 1.37-1.30 (m, 3H), 1.21-1.12 (m, 6H).

The compounds in the below table were prepared according to the procedure of Compound 94 using the corresponding intermediates and reagents under appropriate conditions that will be recognized by POSITA:

| Comp. | Structure | MS (M + H)$^+$ | $^1$H NMR | Intermediate |
|---|---|---|---|---|
| 196 | 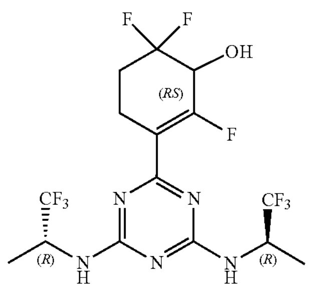 | 454.1 | $^1$H NMR (400 MHz, CD$_3$OD): δ 5.00-4.86 (m, 2H), 4.36-4.17 (m, 1H), 2.80-2.65 (m, 1H), 2.58-2.42 (m, 1H), 2.25-2.05 (m, 2H), 1.37-1.31 (m, 6H). | I-3 |
| 203 | 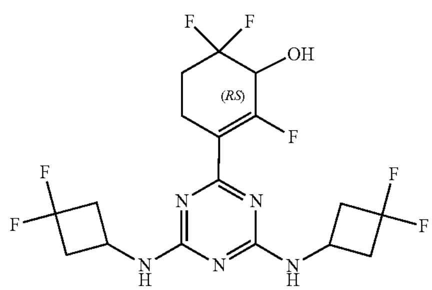 [SMILES: OC1C(F)=C(c2nc(NC3CC(F)(F)C3)nc(NC3CC(F)(F)C3)n2)CCC1(F)F] | 442.2 | $^1$H NMR (400 MHz, CD$_3$OD): δ 4.37-4.14 (m, 3H), 3.00-2.85 (m, 4H), 2.74-2.44 (m, 6H), 2.24-2.02 (m, 2H). | I-10 |
| 208 | 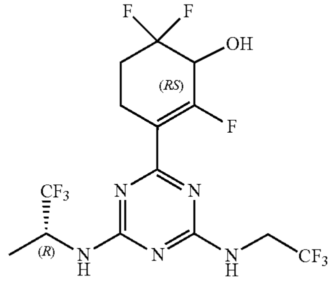 | 440.0 | $^1$H NMR (400 MHz, CD$_3$OD): δ 5.01-4.92 (m, 1H), 4.35-4.01 (m, 3H), 2.77-2.67 (br, 1H), 2.63-2.46 (m, 1H), 2.33-2.01 (m, 2H), 1.41-1.32 (m, 3H). | I-76 |

| Comp. | Structure | MS (M + H)+ | 1H NMR | Intermediate |
|---|---|---|---|---|
| 209 | 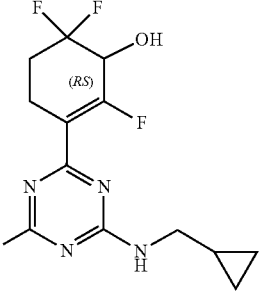 | 412.2 | 1H NMR (400 MHz, CD3OD): δ 4.99-4.90 (m, 1H), 4.31-4.20 (m, 1H), 3.25-3.16 (m, 2H), 2.79-2.63 (m, 1H), 2.59-2.44 (m, 1H), 2.23-2.03 (m, 2H), 1.37-1.31 (m, 3H), 1.13-0.99 (m, 1H), 0.53-0.41 (m, 2H), 0.28-0.17 (m, 2H). | I-78 |
| 210 | 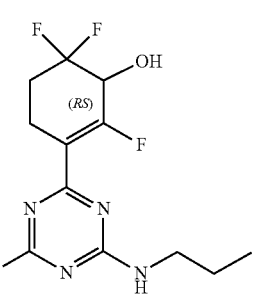 | 400.0 | 1H NMR (400 MHz, CD3OD): δ 5.03-4.89 (m, 1H), 4.55-4.37 (m, 1H), 4.02-3.77 (m, 2H), 2.81-2.61 (m, 1H), 2.58-2.37 (m, 1H), 2.17-2.05 (m, 1H), 2.04-1.84 (m, 1H), 1.81-1.51 (m, 2H), 1.43-1.31 (m, 3H), 1.05-0.90 (m, 3H). | I-18 |
| 239 | 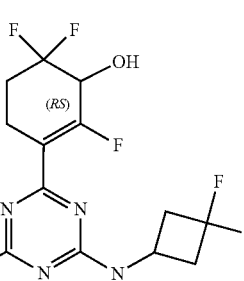 | 448.0 | 1H NMR (400 MHz, CD3OD): δ 5.02-4.89 (m, 1H), 4.38-4.14 (m, 2H), 3.03-2.86 (m, 2H), 2.78-2.44 (m, 4H), 2.30-2.01 (m, 2H), 1.42-1.30 (m, 3H). | I-54 |
| 245 | 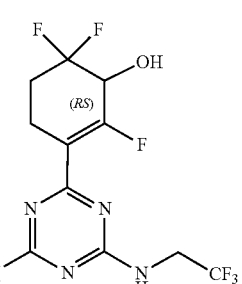 | 440.0 | 1H NMR (400 MHz, CD3OD): δ 5.01-4.92 (m, 1H), 4.35-4.01 (m, 3H), 2.77-2.67 (br, 1H), 2.63-2.46 (m, 1H), 2.33-2.01 (m, 2H), 1.41-1.32 (m, 3H). | I-76 |

121

Compound 234

3-(4-((Cyclopropylmethyl)amino)-6-(((R)-1,1,1-trifluoropropan-2-yl)amino)-1,3,5-triazin-2-yl)-2,6,6-trifluorocyclohex-2-en-1-ol

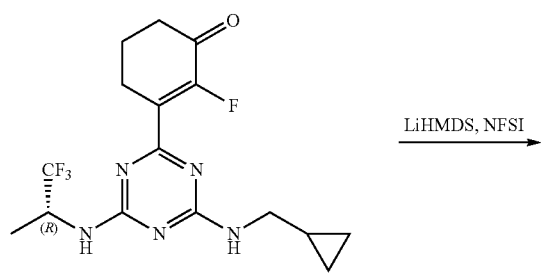

B6

LiHMDS, NFSI →

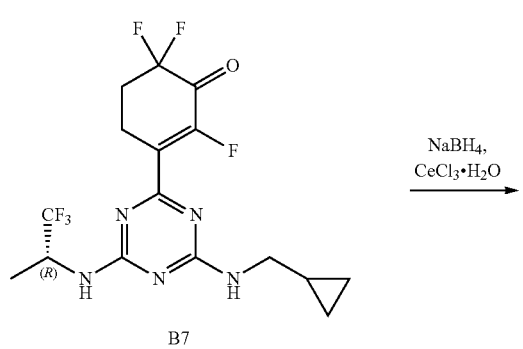

B7

NaBH₄, CeCl₃·H₂O →

122

-continued

[Structure of compound 234]

234

(A) (R)-3-(4-((cyclopropylmethyl)amino)-6-((1,1,1-trifluoropropan-2-yl)amino)-1,3,5-triazin-2-yl)-2,6,6-trifluorocyclohex-2-en-1-one (B7)

The title compound B7 was prepared according to the procedure of Step A of Compound 94 using compound B6 (prepared according to the procedure of Compound 1 using Intermediate I-77) and corresponding reagents.

(B) 3-(4-((Cyclopropylmethyl)amino)-6-(((R)-1,1,1-trifluoropropan-2-yl)amino)-1,3,5-triazin-2-yl)-2,6,6-trifluorocyclohex-2-en-1-ol Compound 234 was prepared according to the procedure of Compound 1, using compound B7 and corresponding reagents. MS (m/z): 412.2 [M+H]⁺

¹H NMR (400 MHz, CD₃OD): δ 4.99-4.90 (m, 1H), 4.31-4.20 (m, 1H), 3.25-3.16 (m, 2H), 2.79-2.63 (m, 1H), 2.59-2.44 (m, 1H), 2.23-2.03 (m, 2H), 1.37-1.31 (m, 3H), 1.13-0.99 (m, 1H), 0.53-0.41 (m, 2H), 0.28-0.17 (m, 2H).

The compounds in the below table were prepared according to the procedure of Compound 234 using the corresponding intermediates and reagents under appropriate conditions that will be recognized by POSITA:

| Comp. | Structure | MS (M + H)⁺ | ¹H NMR | Intermediate |
|---|---|---|---|---|
| 211 | [Structure] | 455.1 | ¹H NMR (400 MHz, CD₃OD): δ 5.03-4.87 (m, 2H), 2.82-2.66 (m, 1H), 2.62-2.45 (m, 1H), 2.27-2.02 (m, 2H), 1.40-1.29 (m, 6H). | I-3 |
| 235 | [Structure] | 462.2 | ¹H NMR (400 MHz, CD₃OD): δ 5.02-4.88 (m, 1H), 4.54-4.39 (m, 1H), 4.33-4.17 (m, 1H), 2.79-2.64 (m, 1H), 2.61-2.44 (m, 2H), 2.29-2.00 (m, 6H), 1.90-1.67 (m, 1H), 1.39-1.31 (m, 3H). | I-82 |

| Comp. | Structure | MS (M + H)+ | 1H NMR | Intermediate |
|---|---|---|---|---|
| 238 | 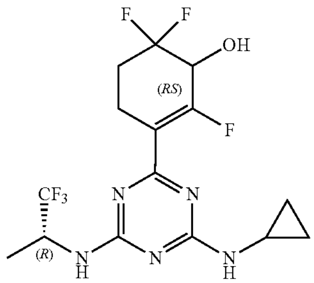 | 398.0 | 1H NMR (400 MHz, CD3OD): δ 5.05-4.91 (m, 1H), 4.31-4.20 (m, 1H), 2.86-2.60 (m, 2H), 2.59-2.43 (m, 1H), 2.24-2.04 (m, 2H), 1.38-1.31 (m, 3H), 0.78-0.66 (m, 2H), 0.57-0.44 (m, 2H). | I-16 |
| 248 | 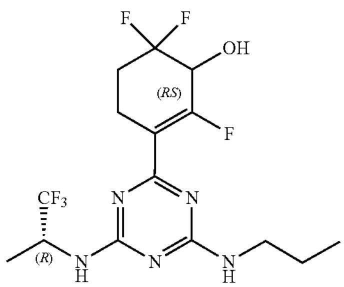 | 400.0 | 1H NMR (400 MHz, CD3OD): δ 4.98-4.90 (m, 1H), 4.32-4.19 (m, 1H), 3.38-3.23 (m, 2H), 2.80-2.61 (m, 1H), 2.60-2.41 (m, 1H), 2.28-2.02 (m, 2H), 1.64-1.52 (m, 2H), 1.38-1.30 (m, 3H), 0.99-0.87 (m, 3H). | I-18 |
Compound 259
3-(4-((3,3-Difluorocyclobutyl)amino)-6-(((R)-1,1,1-trifluoropropan-2-yl)amino)-1,3,5-triazin-2-yl)-2,6,6-trifluorocyclohex-2-en-1-ol
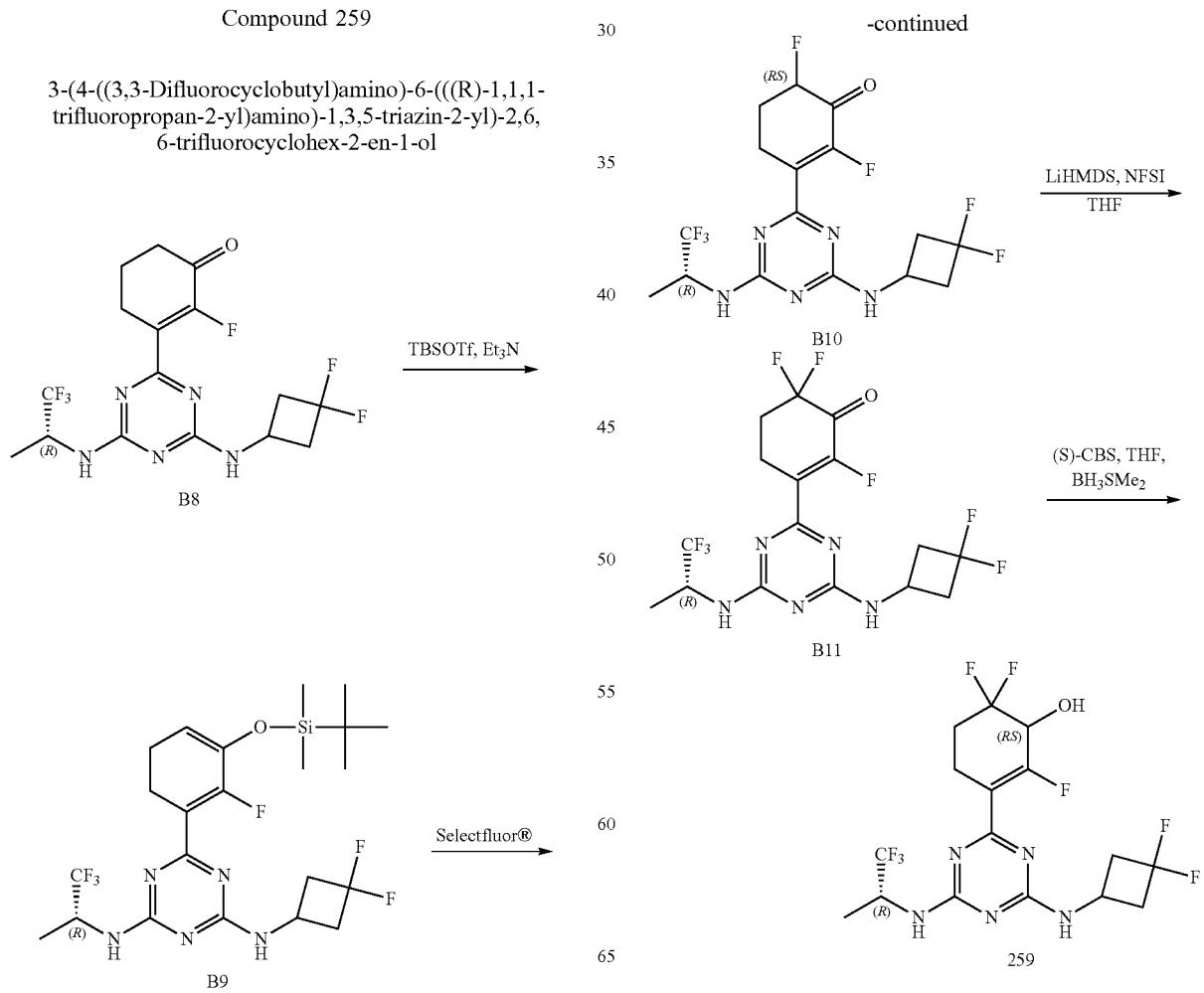

(A) (R)-6-(3-((tert-butyldimethylsilyl)oxy)-2-fluoro-cyclohexa-1,3-dien-1-yl)-$N^2$-(3,3-difluorocyclobutyl)-$N^4$-(1,1,1-trifluoropropan-2-yl)-1,3,5-triazine-2,4-diamine (B9)

Under $N_2$, to a mixture of compound B8 (prepared according to Compound 39 using Intermediate I-9: 750 mg, 1.83 mmol) and $Et_3N$ (371 mg, 3.66 mmol) in dry DCM (15 mL) was added a solution of TBSOTf (726 mg, 2.75 mmol) in DCM (5 mL) at 0-5° C. The mixture was stirred for 30 minutes. Then, it was poured into water and extracted with DCM. The organic layer was collected, dried over anhydrous $Na_2SO_4$ condensed under reduced pressuer and purified by flash column chromatography (eluting with PE/EA) to give compound B9 as a yellow oil (958 mg, yield: 100%). MS (m/z): 524.1 $[M+H]^+$

(B) 3-(4-((3,3-Difluorocyclobutyl)amino)-6-(((R)-1,1,1-trifluoropropan-2-yl)amino)-1,3,5-triazin-2-yl)-2,6-difluorocyclohex-2-en-1-one (B10)

Under $N_2$, a solution of compound B9 (958 mg, 1.83 mmol) in dry MeCN (20 mL) was added to the suspension of Selectfluor® (778 mg, 2.20 mmol) in dry acetonitrile (20 mL) dropwise at 0-5° C. and stirred for 2 hours. The reaction mixture was poured into water and extracted with EtOAc. The organic layer was collected, condensed under reduce pressure and purified by flash column chromatography (eluting with PE/EA) to give compound B10 as white solid (512 mg, yield: 66%). MS (m/z): 428.0 $[M+H]^+$.

(C) (R)-3-(4-((3,3-difluorocyclobutyl)amino)-6-((1,1,1-trifluoropropan-2-yl)amino)-1,3,5-triazin-2-yl)-2,6,6-trifluorocyclohex-2-en-1-one (B11)

Under $N_2$, to a solution of compound B10 (512 mg, 1.12 mmol) in dry THF (10 mL) was added 1M LiHMDS/THF solution (3.47 mL, 3.47 mmol) dropwise at −78° C. and stirred for 30 minutes. Then to the mixture was added NFSI (388 mg, 1.23 mmol)/THF solution (10 mL) dropwise at −78° C. and the reaction was stirred for 2 hours. After the reaction was completed, saturated $NH_4Cl$ aqueous solution was added to quench the reaction. The mixture was extracted with EtOAc. The organic layer was collected, condensed under reduce pressure and purified by flash column chromatography (eluting with PE/EA) to give compound B11 as yellow solid (230 mg, yield: 46%). MS (m/z): 446.2 $[M+H]^+$

(D) 3-(4-((3,3-Difluorocyclobutyl)amino)-6-(((R)-1,1,1-trifluoropropan-2-yl)amino)-1,3,5-triazin-2-yl)-2,6,6-trifluorocyclohex-2-en-1-ol Compound 259 was prepared according to the procedure of Compound 39, using compound B11 and corresponding reagents. MS (m/z): 448.0 $[M+H]^+$ $^1H$ NMR (400 MHz, $CD_3OD$): δ 4.91-4.81 (s, 1H), 4.26-4.09 (m, 2H), 2.92-2.76 (m, 2H), 2.72-2.33 (m, 4H), 2.18-1.96 (m, 2H), 1.30-1.22 (m, 3H).

The compounds in the below table were prepared according to the procedure of Compound 259 using the corresponding intermediates and reagents under appropriate conditions that will be recognized by POSITA:

| Comp. | Structure | MS (M + H)⁺ | ¹H NMR | Intermediate |
|---|---|---|---|---|
| 260 | 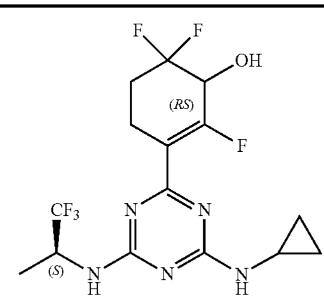 | 398.0 | ¹H NMR (400 MHz, CD₃OD): δ 4.99-4.83 (m, 1H), 4.26-4.09 (m, 1H), 2.76-2.53 (m, 2H), 2.51-2.34 (m, 1H), 2.17-1.95 (m, 2H), 1.31-1.23 (m, 3H), 0.69-0.59 (m, 2H), 0.48-0.38 (m, 2H). | I-85 |
| 261 | 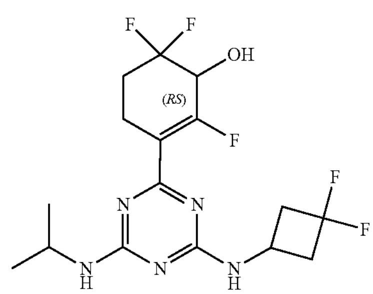 [SMILES: CC(C)Nc1nc(NC2CC(F)(F)C2)nc(C2=C(F)C(O)C(F)(F)CC2)n1] | 394.2 | ¹H NMR (400 MHz, CD₃OD): δ 4.36-4.09 (m, 3H), 3.02-2.87 (m, 2H), 2.79-2.43 (m, 4H), 2.26-2.04 (m, 2H), 1.28-1.15 (m, 6H). | I-37 |

-continued
| Comp. | Structure | MS (M + H)+ | 1H NMR | Intermediate |
|---|---|---|---|---|
| 270 | 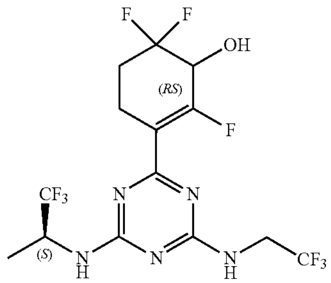 | 440.2 | 1H NMR (400 MHz, CD3OD): δ 4.92-4.82 (m, 1H), 4.28-3.90 (m, 3H), 2.72-2.38 (m, 2H), 2.20-1.96 (m, 2H), 1.33-1.21 (m, 3H). | I-86 |
| 271 | 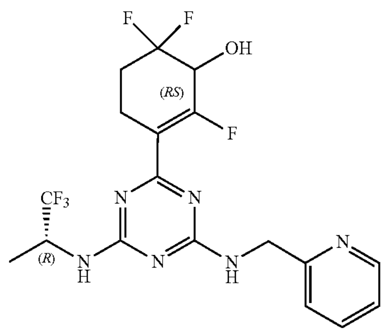 | 449.2 | 1H NMR (400 MHz, CD3OD): δ 8.31-8.20 (m, 1H), 7.63-7.50 (m, 1H), 7.25-7.14 (m, 1H), 7.13-7.01 (m, 1H), 4.83-4.68 (m, 1H), 4.52-4.39 (m, 2H), 4.13-3.98 (m, 1H), 2.57-2.18 (m, 2H), 2.08-1.78 (m, 2H), 1.18-1.00 (m, 3H). | I-87 |
Compound 274
3-(4-((3,3-difluorocyclobutyl)amino)-6-(isopropylamino)-1,3,5-triazin-2-yl)-2,6,6-trifluorocyclohex-2-en-1-D-1-ol
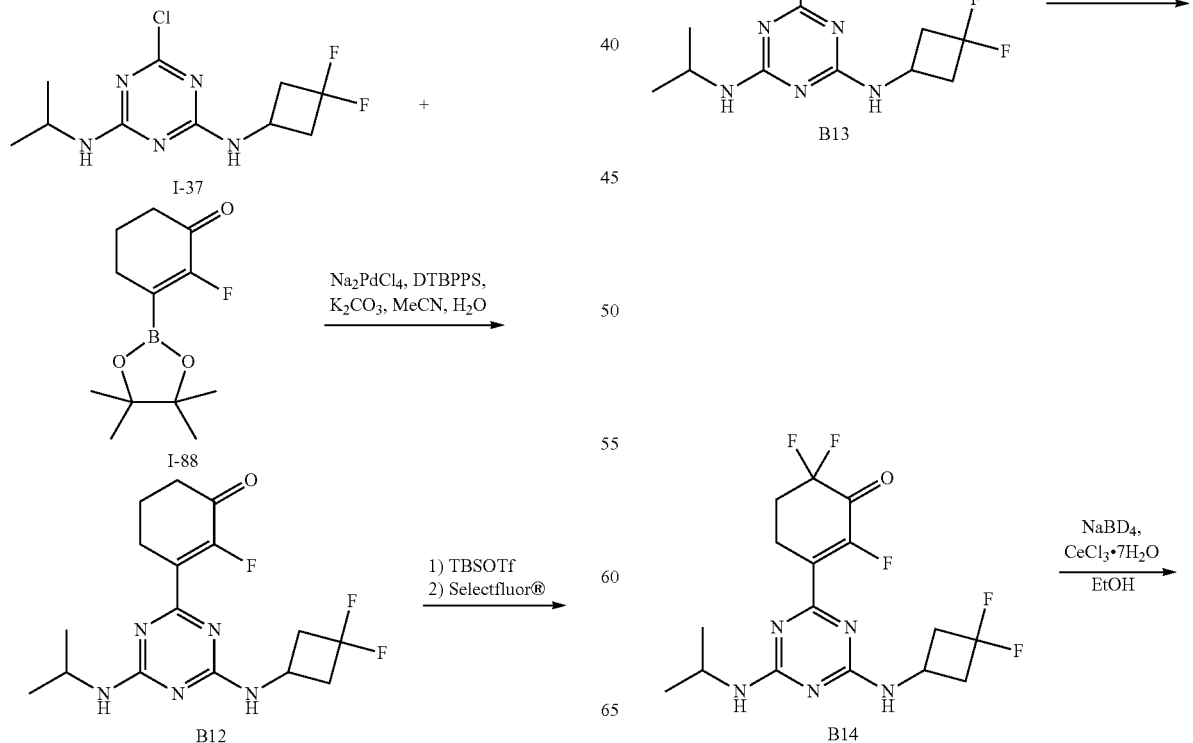

-continued

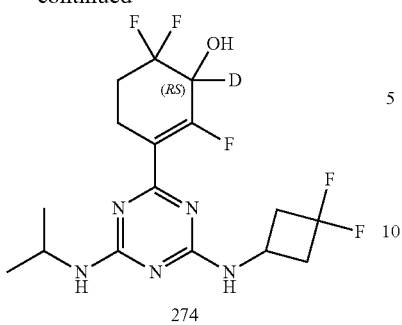

274

(A) 3-(4-((3,3-Difluorocyclobutyl)amino)-6-(isopropylamino)-1,3,5-triazin-2-yl)-2-fluoro-cyclohex-2-en-1-one (B12)

Under $N_2$, a mixture of Intermediate I-37 (4.17 g, 15.0 mmol), Intermediate I-88 (4.32 g, 18.0 mmol), $Na_2PdCl_4$ (221 mg, 0.75 mmol), DTBPPS (402 mg, 1.5 mmol), $K_2CO_3$ (5.18 g, 37.5 mmol), MeCN (40 mL) and $H_2O$ (10 mL) was stirred at 60° C. for 2 hours. After the reaction was completed, the mixture was poured into water and extracted with DCM. The organic layer was collected, condensed and purified by flash column chromatography (eluting with PE/EA) to give Compound B12 as yellow solid (4.98 g, yield: 93%). MS (m/z): 356.1 $[M+H]^+$ (B) 3-(4-((3,3-Difluorocyclobutyl)amino)-6-(isopropylamino)-1,3,5-triazin-2-yl)-2,6-difluorocyclohex-2-en-1-one (B13)

The title compound B13 was prepared according to the procedures of Steps A and B of Compound 259, using Compound B12 and corresponding reagents. MS (m/z): 374.1 $[M+H]^+$ (C) 3-(4-((3,3-Difluorocyclobutyl)amino)-6-(isopropylamino)-1,3,5-triazin-2-yl)-2,6,6-trifluorocyclohex-2-en-1-one (B14)

The title compound B14 was prepared according to the procedures of Steps A and B of Compound 259, using compound B13 and corresponding reagents. MS (m/z): 392.0 $[M+H]^+$ (D) 3-(4-((3,3-Difluorocyclobutyl)amino)-6-(isopropylamino)-1,3,5-triazin-2-yl)-2,6,6-trifluorocyclohex-2-en-1-D-1-ol Compound 274 was prepared according to the procedure of Step B of Compound 1, using Compound B14, $NaBD_4$ and corresponding reagents. MS (m/z): 395.1 $[M+H]^+$ $^1$H NMR (400 MHz, $CD_3OD$): δ 4.33-4.20 (m, 1H), 4.20-4.03 (m, 1H), 3.05-2.85 (m, 2H), 2.80-2.41 (m, 4H), 2.29-2.02 (m, 2H), 1.25-1.14 (m, 6H).

The compounds in the below table were prepared according to the procedure of Compound 274 using the corresponding intermediates and reagents under appropriate conditions that will be recognized by POSITA:

| Comp. | Structure | MS (M + H)+ | $^1$H NMR | Intermediate |
|---|---|---|---|---|
| 275 | 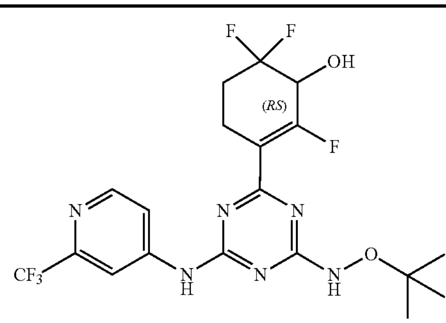 | 479.2 | $^1$H NMR (400 MHz, $CD_3OD$): δ 8.67-8.30 (m, 2H), 8.06-7.80 (m, 1H), 4.45-4.23 (m, 1H), 2.93-2.75 (m, 1H), 2.69-2.50 (m, 1H), 2.33-2.06 (m, 2H), 1.42-1.20 (m, 9H). | I-63 |
| 276 | 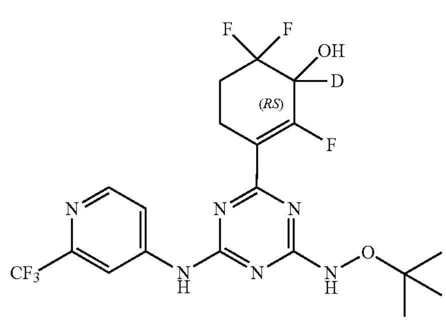 [SMILES: [2H]C1(O)C(F)=C(c2nc(NOC(C)(C)C)nc(Nc3ccnc(C(F)(F)F)c3)n2)CCC1(F)F] | 480.2 | $^1$H NMR (400 MHz, $CD_3OD$): δ 8.67-8.32 (m, 2H), 8.08-7.80 (m, 1H), 2.91-2.75 (m, 1H), 2.69-2.52 (m, 1H), 2.32-2.08 (m, 2H), 1.42-1.26 (m, 9H). | I-63 |

-continued

| Comp. | Structure | MS (M + H)+ | 1H NMR | Intermediate |
|---|---|---|---|---|
| 277 | 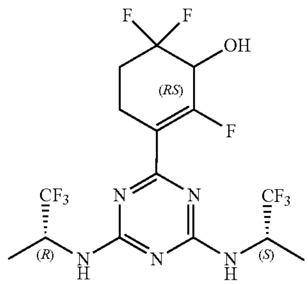 | 454.2 | 1H NMR (400 MHz, CD3OD): δ 5.05-4.91 (m, 2H), 4.38-4.16 (m, 1H), 2.83-2.66 (m, 1H), 2.62-2.45 (m, 1H), 2.29-2.03 (m, 2H), 1.44-1.26 (m, 6H). | I-89 |
| 278 | 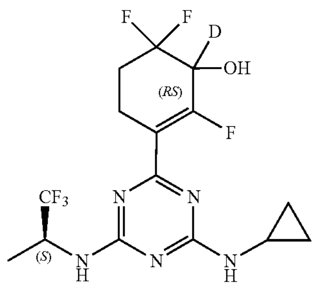 | 399.2 | 1H NMR (400 MHz, CD3OD): δ 5.14-4.92 (m, 1H), 2.88-2.64 (m, 2H), 2.59-2.43 (m, 1H), 2.32-1.99 (m, 2H), 1.45-1.28 (m, 3H), 0.82-0.66 (m, 2H), 0.58-0.45 (m, 2H). | I-85 |
| 279 | 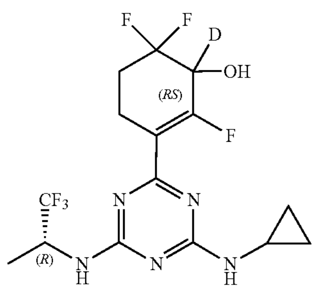 | 399.0 | 1H NMR (400 MHz, CD3OD): δ 5.13-4.93 (m, 1H), 2.90-2.64 (m, 2H), 2.61-2.41 (m, 1H), 2.33-1.99 (m, 2H), 1.49-1.24 (m, 3H), 0.86-0.67 (m, 2H), 0.62-0.46 (m, 2H). | I-16 |
| 281 | 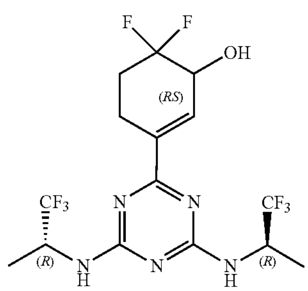 | 436.2 | 1H NMR (400 MHz, CD3OD): δ 7.22-6.87 (m, 1H), 5.10-4.91 (m, 2H), 4.49-4.21 (m, 1H), 2.90-2.54 (m, 2H), 2.34-1.98 (m, 2H), 1.50-1.20 (m, 6H). | I-3 |
| 282 | 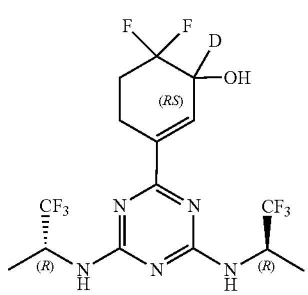 | 437.2 | 1H NMR (400 MHz, CD3OD): δ 7.22-6.87 (m, 1H), 5.10-4.91 (m, 2H), 2.90-2.54 (m, 2H), 2.34-1.98 (m, 2H), 1.50-1.20 (m, 6H). | I-3 |

-continued

| Comp. | Structure | MS (M + H)+ | 1H NMR | Intermediate |
|---|---|---|---|---|
| 283 | 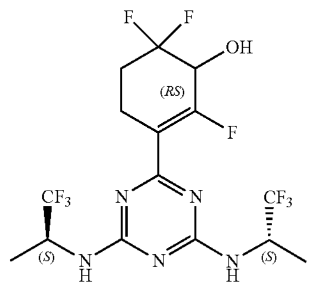 | 454.0 | 1H NMR (400 MHz, CD3OD): δ 5.05-4.90 (m, 2H), 4.40-4.19 (m, 1H), 2.84-2.66 (m, 1H), 2.62-2.45 (m, 1H), 2.30-2.03 (m, 2H), 1.42-1.27 (m, 6H). | I-32 |
| 293 | 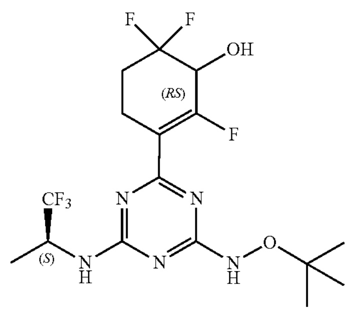 | 430.2 | 1H NMR (400 MHz, CD3OD): δ 5.09-4.91 (m, 1H), 4.34-4.21 (m, 1H), 2.82-2.68 (m, 1H), 2.61-2.46 (m, 1H), 2.28-2.03 (m, 2H), 1.39-1.34 (m, 3H), 1.29-1.26 (m, 9H). | I-90 |
| 294 | 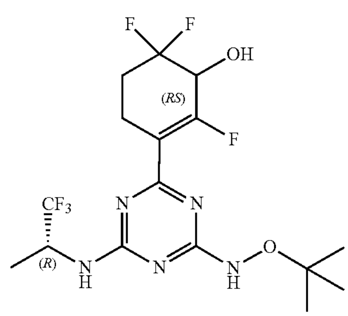 | 430.2 | 1H NMR (400 MHz, CD3OD): δ 5.09-4.91 (m, 1H), 4.34-4.21 (m, 1H), 2.82-2.68 (m, 1H), 2.61-2.46 (m, 1H), 2.28-2.03 (m, 2H), 1.39-1.34 (m, 3H), 1.29-1.26 (m, 9H). | I-91 |
| 296 | 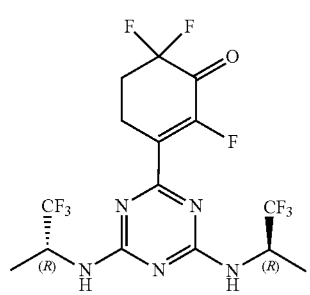 | 452.1 | 1H NMR (400 MHz, CD3OD): δ 5.01-4.88 (m, 2H), 3.07-2.09 (m, 4H), 1.39-1.31 (m, 6H). | I-3 |
| 298 | 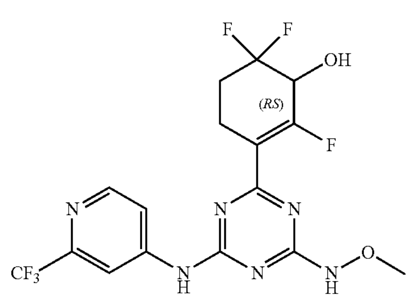 [SMILES: CONc1nc(Nc2ccnc(C(F)(F)F)c2)nc(C2=C(F)C(O)C(F)(F)CC2)n1] | 437.1 | 1H NMR (400 MHz, CD3OD): δ 8.77-8.34 (m, 2H), 8.01-7.69 (m, 1H), 4.47-4.17 (m, 1H), 3.81 (s, 3H), 2.89-2.73 (m, 1H), 2.67-2.52 (m, 1H), 2.30-2.06 (m, 2H). | I-92 |

135

Compound 297

2,6,6-Trifluoro-3-(4-(methoxyamino)-6-(((R)-1,1,1-trifluoropropan-2-yl)amino)-1,3,5-triazin-2-yl)cyclohex-2-en-1-ol

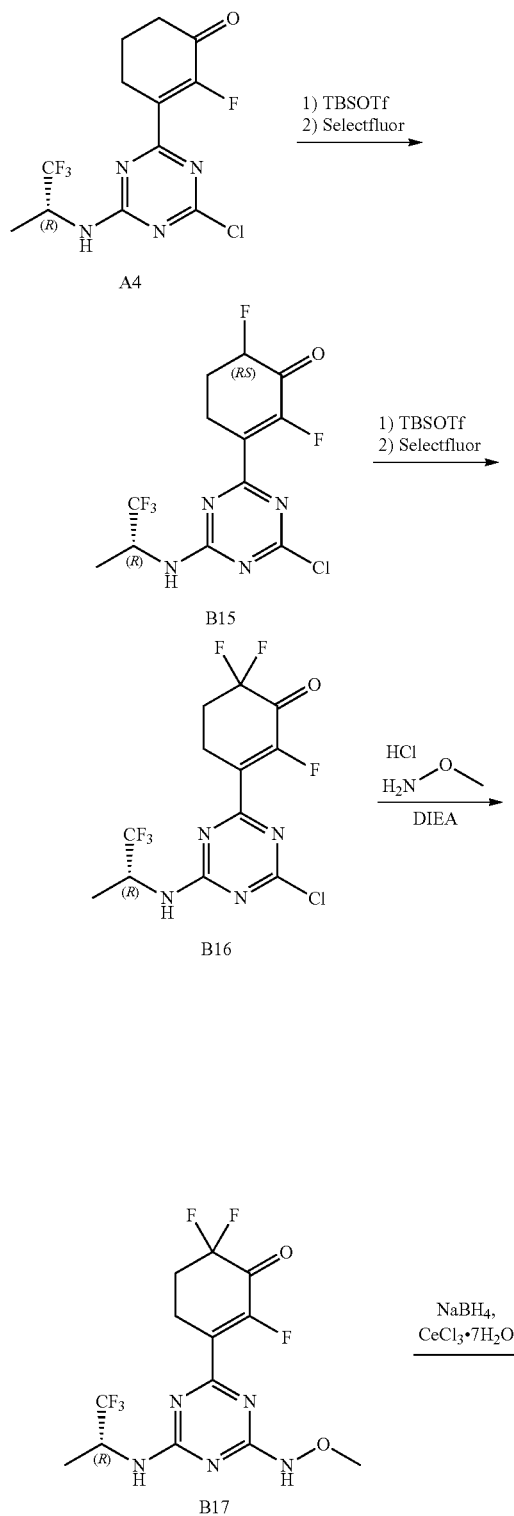

136
-continued

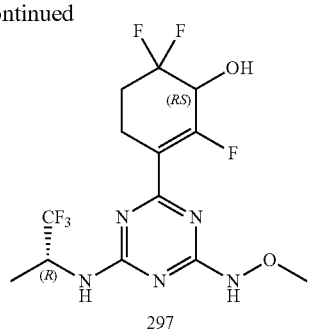

(A) (R)-3-(4-chloro-6-((1,1,1-trifluoropropan-2-yl)amino)-1,3,5-triazin-2-yl)-2,6,6-trifluoro-cyclohex-2-en-1-one (B16)

The title compound B16 was prepared according to the procedure of Steps B and C of Compound 274, using Intermediate A4 and corresponding reagents. MS (m/z): 375.1 [M+H]$^+$ (B) (R)-2,6,6-trifluoro-3-(4-(methoxyamino)-6-((1,1,1-trifluoropropan-2-yl)amino)-1,3,5-triazin-2-yl)cyclohex-2-en-1-one (B17)

The title compound B17 was prepared according to the procedure of Compound 190, using Compound B16 and corresponding reagents. MS (m/z): 386.1 [M+H]$^+$ (C) 2,6,6-Trifluoro-3-(4-(methoxyamino)-6-(((R)-1,1,1-trifluoropropan-2-yl)amino)-1,3,5-triazin-2-yl)cyclohex-2-en-1-ol Compound 297 was prepared according to the procedure of Step B of Compound 1, using compound B17 and corresponding reagents. MS (m/z): 388.2 [M+H]$^+$
$^1$H NMR (400 MHz, CD$_3$OD): δ 5.04-4.92 (m, 1H), 4.34-4.20 (m, 1H), 3.81-3.66 (m, 3H), 2.80-2.64 (m, 1H), 2.59-2.44 (m, 1H), 2.31-2.04 (m, 2H), 1.41-1.32 (m, 3H).

Compound 280

3-(4-Amino-6-(((R)-1,1,1-trifluoropropan-2-yl)amino)-1,3,5-triazin-2-yl)-2,6,6-trifluoro-cyclohex-2-en-1-ol

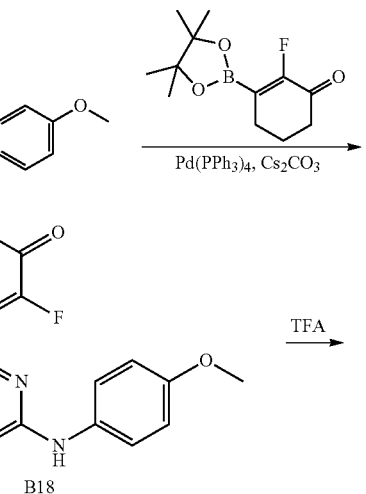

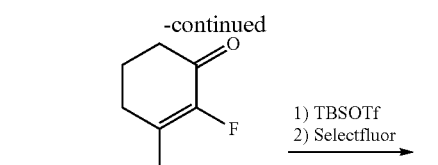

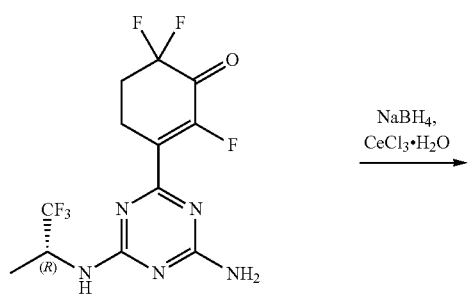

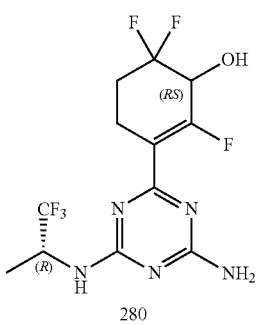

(A) (R)-2-fluoro-3-(4-((4-methoxyphenyl)amino)-6-((1,1,1-trifluoropropan-2-yl)amino)-1,3,5-triazin-2-yl)cyclohex-2-en-1-one (B18)

The title compound B18 was prepared according to the procedure of Compound 1, using Intermediate I-105 and corresponding reagents. MS (m/z): 440.2 [M+H]$^+$ (B) (R)-3-(4-amino-6-((1,1,1-trifluoropropan-2-yl)amino)-1,3,5-triazin-2-yl)-2-fluoro-cyclohex-2-en-1-one (B19)

A mixture of Compound B18 (1.4 g, 3.19 mmol) in TFA (10 mL) was stirred at reflux for 2 hours. The solvent was removed under vacuo. The residue was dissolved in EtOAc and washed with saturated NaHCO$_3$ aqueous solution. The organic layer was collected, condensed under reduced pressure to give title compound B19 as yellow solid (800 mg, yield 79%), which was used for the next step without purification.

(C) 3-(4-Amino-6-(((R)-1,1,1-trifluoropropan-2-yl)amino)-1,3,5-triazin-2-yl)-2,6,6-trifluorocyclohex-2-en-1-ol Compound 280 was prepared according to the procedure of Compound 274, using Compound B19 and corresponding reagents. MS (m/z): 358.1 [M+H]$^+$;

$^1$H NMR (400 MHz, CD$_3$OD): δ 5.00-4.92 (m, 1H), 4.38-4.18 (m, 1H), 2.80-2.61 (m, 1H), 2.61-2.44 (m, 1H), 2.31-2.10 (m, 2H), 1.50-1.23 (m, 3H).

Compound 284

3-(4,6-Diamino-1,3,5-triazin-2-yl)-2,6,6-trifluorocyclohex-2-en-1-ol

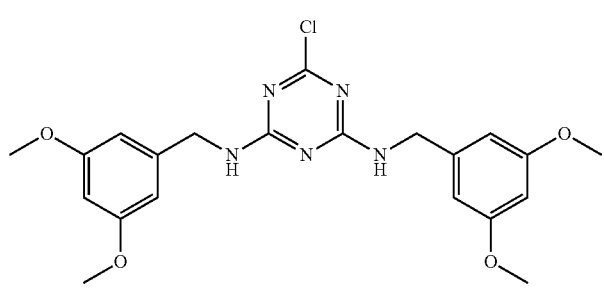 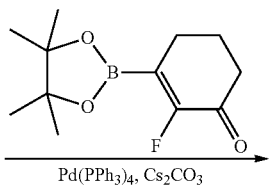

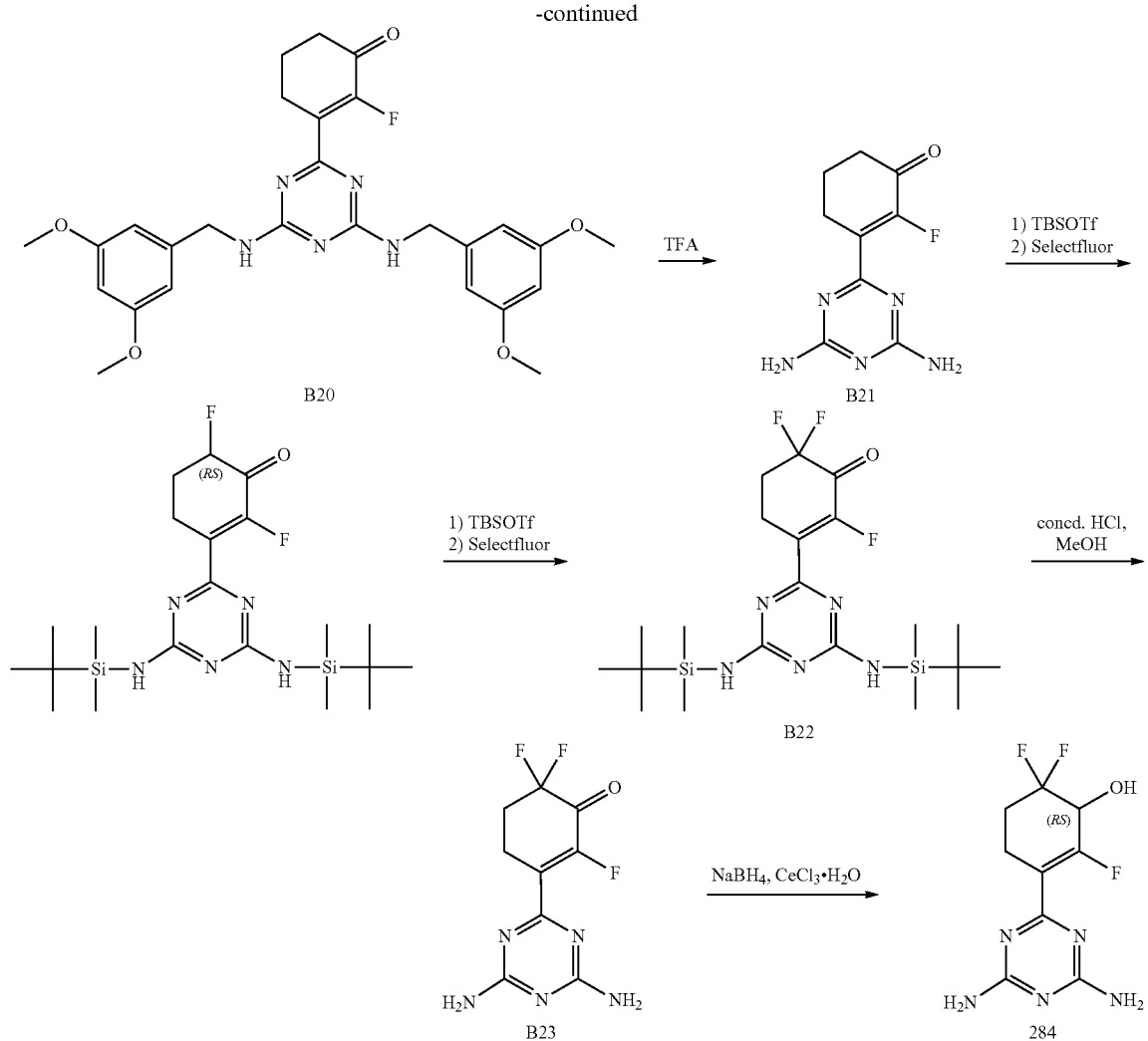

(A) 3-(4,6-Bis((3,5-dimethoxybenzyl)amino)-1,3,5-triazin-2-yl)-2-fluorocyclohex-2-en-1-one (B20)

The title compound B20 was prepared according to the procedure of Compound 1, using Intermediate I-106 and corresponding reagents. MS (m/z): 542.1 [M+H]+

(B) 3-(4,6-Diamino-1,3,5-triazin-2-yl)-2-fluorocyclohex-2-en-1-one (B21)

The title compound B21 was prepared according to the procedure of Step B of Compound 280, using compound B20 and corresponding reagents. MS (m/z): 224.0 [M+H]+

(C) 3-(4,6-Bis((tert-butyldimethylsilyl)amino)-1,3,5-triazin-2-yl)-2,6,6-trifluorocyclohex-2-en-1-one (B22)

The title compound B22 was prepared according to the procedure of Steps B and C of Compound 274, using compound B21 and corresponding reagents. MS (m/z): 488.1 [M+H]+

(D) 3-(4,6-Diamino-1,3,5-triazin-2-yl)-2,6,6-trifluorocyclohex-2-en-1-one (B23)

A solution of Compound B22 (410 mg, 0.84 mmol) in concentrated HCl aqueous solution (1 mL) and MeOH (5 mL) was stirred at room temperature for 30 minutes. The mixture was diluted with EtOAc and adjusted to pH=8 with saturated NaHCO$_3$ aqueous solution. The organic layer was collected, concentrated to dryness under vacuo and purified by flash column chromatography (eluting with MeOH and water) to give the title compound B23 as white solid (150 mg, yield: 69%). MS (m/z): 260.0 [M+H]+

(E) 3-(4,6-Diamino-1,3,5-triazin-2-yl)-2,6,6-trifluorocyclohex-2-en-1-ol

Compound 284 was prepared according to the procedure of Step B of Compound 1, using Compound B23 and corresponding reagents. MS (m/z): 262.0 [M+H]+

$^1$H NMR (400 MHz, CD$_3$OD): δ 4.33-4.20 (m, 1H), 2.73-2.60 (m, 1H), 2.56-2.43 (m, 1H), 2.29-2.04 (m, 2H).

Compound 99

3-(4,6-Bis(((R)-1,1,1-trifluoropropan-2-yl)amino)-1,3,5-triazin-2-yl)-6-chloro-2-fluoro-cyclohex-2-en-1-ol

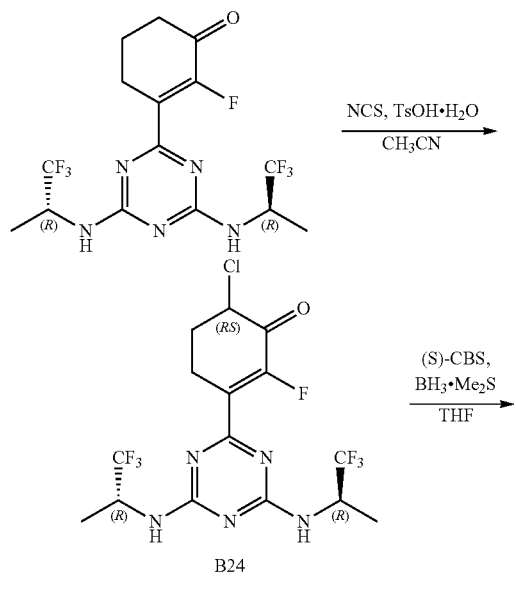

(A) 3-(4,6-Bis(((R)-1,1,1-trifluoropropan-2-yl)amino)-1,3,5-triazin-2-yl)-6-chloro-2-fluoro-cyclohex-2-en-1-one (B24)

To a sealed tube was added 3-(4,6-bis(((R)-1,1,1-trifluoropropan-2-yl)amino)-1,3,5-triazin-2-yl)-2-fluorocyclohex-2-en-1-one (prepared according to the procedure of Compound 1 using Intermediate I-3, 700 mg, 1.69 mmol), NCS (224 mg, 1.69 mmol), TsOH·H₂O (321 mg, 1.69 mmol) and MeCN (10 mL) in sequence. The mixture was heated to 80° C. and stirred for 16 hours. After the reaction was completed, the mixture was cooled to room temperature, condensed and purified by flash column chromatography (eluting with gradient PE/EA=100:0-0:100) to give the title compound B24 as white solid (320 mg, yield 42.2%). MS (m/z): 450.1, 452.1 [M+H]⁺

(B) 3-(4,6-Bis(((R)-1,1,1-trifluoropropan-2-yl)amino)-1,3,5-triazin-2-yl)-6-chloro-2-fluoro-cyclohex-2-en-1-ol Compound 99 was prepared according to the procedure of Compound 39 using Compound B24 and corresponding reagents. MS (m/z): 452.1 [M+H]⁺

¹H NMR (400 MHz, CD₃OD): δ 5.02-4.90 (m, 2H), 4.40-4.33 (m, 1H), 4.27-4.19 (m, 1H), 2.80-2.66 (m, 1H), 2.52-2.38 (m, 1H), 2.13-1.97 (m, 2H), 1.36-1.30 (m, 6H).

Compound 122

(R)-3-(4-(isopropylamino)-6-((1,1,1-trifluoropropan-2-yl)amino)-1,3,5-triazin-2-yl)cyclohex-2-en-1-one

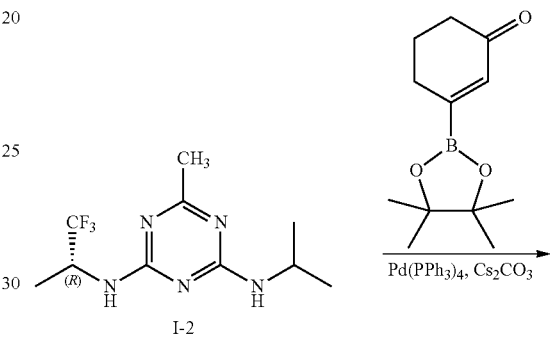

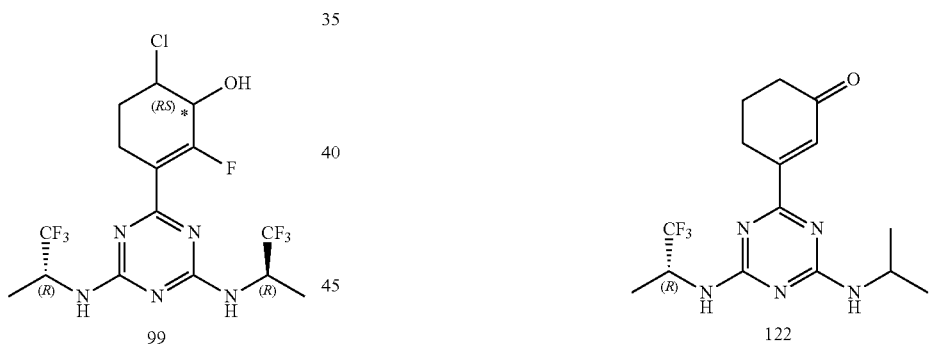

To a flask were added Intermediate I-2 (500 mg, 1.76 mmol), 3-(4,4,5,5-tetramethyl-1,3,2-dioxaborolan-2-yl)cyclohex-2-en-1-one (391 mg, 1.76 mmol), Cs₂CO₃ (1144 mg, 3.52 mmol), Pd(PPh₃)₄ (101 mg, 0.09 mmol), 1,4-dioxane (20 mL) and water (4 mL). The mixture was stirred at 80° C. for 2 hours under nitrogen atmosphere. After the reaction was completed, the mixture was cooled to room temperature, condensed and purified by flash column chromatography (eluting with PE/EA) to give the title compound as a white solid (350 mg, yield 57.9%). MS (m/z): 344.1 [M+H]⁺

¹H NMR (400 MHz, CD₃OD): δ 7.00 (s, 1H), 5.05-4.86 (m, 1H), 4.26-4.04 (m, 1H), 2.87-2.74 (m, 2H), 2.48-2.41 (m, 2H), 2.11-2.02 (m, 2H), 1.39-1.32 (m, 3H), 1.23-1.17 (m, 6H).

The compounds in the below table were prepared according to the procedure of Compound 122 using the corresponding intermediates and reagents under appropriate conditions that will be recognized by POSITA:

| Comp. | Structure | MS (M + H)+ | 1H NMR | Intermediate |
|---|---|---|---|---|
| 123 | 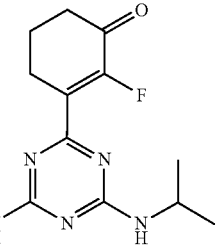 | 362.1 | 1H NMR (400 MHz, CD3OD): δ 5.01-4.90 (m, 1H), 4.22-4.10 (m, 1H), 2.89-2.77 (m, 2H), 2.64-2.55 (m, 2H), 2.12-2.02 (m, 2H), 1.39-1.32 (m, 3H), 1.23-1.17 (m, 6H). | I-2 |
| 295 | 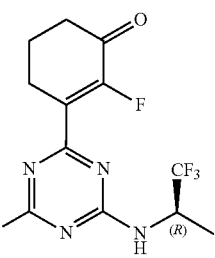 | 416.2 | 1H NMR (400 MHz, CD3OD): δ 5.00-4.88 (m, 2H), 2.91-2.78 (m, 2H), 2.62-2.53 (m, 2H), 2.11-2.00 (m, 2H), 1.40-1.30 (m, 6H). | I-3 |

Compound 124

3-(4-(Isopropylamino)-6-(((R)-1,1,1-trifluoropropan-2-yl)amino)-1,3,5-triazin-2-yl)cyclohex-2-en-1-ol

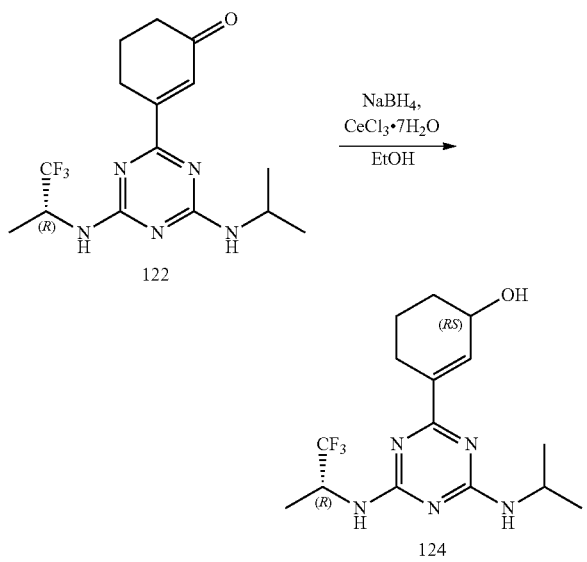

To a flask were added Compound 122 (250 mg, 0.73 mmol), CeCl3·7H2O (353 mg, 0.95 mmol) and EtOH (10 mL). The mixture was cooled to 0° C., NaBH4 (36 mg, 0.95 mmol) was added and the reaction was stirred at 0° C. for 2 hours. After the reaction was completed, the mixture was quenched by the addition of saturated NH4Cl aqueous solution (3 mL) and water (20 mL) and extracted with EtOAc. The organic layer was collected, condensed and purified by flash column chromatography (eluting with PE/EA) to give the title compound as a white solid (210 mg, yield: 83.3%). MS (m/z): 346.0 [M+H]+

1H NMR (400 MHz, CD3OD): δ 7.19-6.92 (m, 1H), 5.10-4.87 (m, 1H), 4.37-4.26 (m, 1H), 4.25-4.07 (m, 1H), 2.51-2.30 (m, 2H), 2.01-1.82 (m, 2H), 1.71-1.49 (m, 2H), 1.38-1.30 (m, 3H), 1.23-1.12 (m, 6H).

The compounds in the below table were prepared according to the procedure of Compound 124 using the corresponding intermediates and reagents under appropriate conditions that will be recognized by POSITA:

| Comp. | Structure | MS (M + H)+ | 1H NMR | Intermediate |
|---|---|---|---|---|
| 125 | 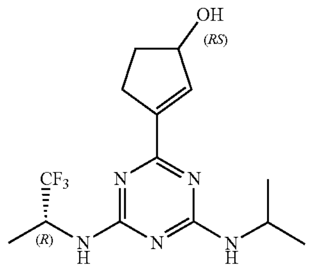 | 332.0 | 1H NMR (400 MHz, CD3OD): δ 6.88-6.70 (m, 1H), 5.07-4.87 (m, 2H), 4.23-4.08 (m, 1H), 2.90-2.77 (m, 1H), 2.63-2.49 (m, 1H), 2.43-2.30 (m, 1H), 1.85-1.69 (m, 1H), 1.39-1.31 (m, 3H), 1.22-1.17 (m, 6H). | I-2 |
| 126 | 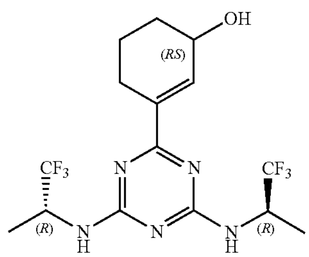 | 400.0 | 1H NMR (400 MHz, CD3OD): δ 7.23-7.01 (m, 1H), 5.08-4.87 (m, 2H), 4.37-4.27 (m, 1H), 2.49-2.35 (m, 2H), 1.98-1.82 (m, 2H), 1.68-1.53 (m, 2H), 1.39-1.32 (m, 6H). | I-3 |
| 127 | 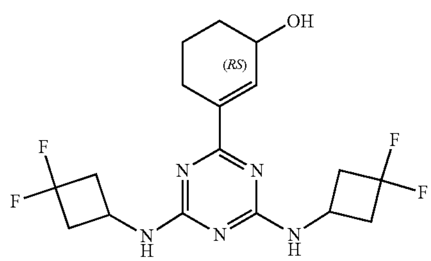 [SMILES: OC1C=C(c2nc(NC3CC(F)(F)C3)nc(NC3CC(F)(F)C3)n2)CCC1] | 388.1 | 1H NMR (400 MHz, CD3OD): δ 7.22-6.93 (m, 1H), 4.36-4.19 (m, 3H), 2.97-2.87 (m, 4H), 2.69-2.50 (m, 4H), 2.45-2.34 (m, 2H), 1.97-1.80 (m, 2H), 1.67-1.51 (m, 2H). | I-10 |
| 128 | 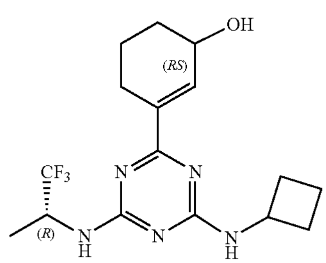 | 358.1 | 1H NMR (400 MHz, CD3OD): δ 7.26-6.90 (m, 1H), 5.10-4.92 (m, 1H), 4.60-4.26 (m, 2H), 2.56-2.23 (m, 4H), 2.11-1.81 (m, 4H), 1.79-1.49 (m, 4H), 1.42-1.28 (m, 3H). | I-15 |
| 129 | 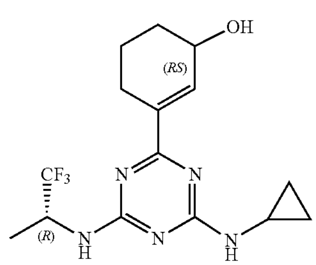 | 344.1 | 1H NMR (400 MHz, CD3OD): δ 7.27-6.85 (m, 1H), 5.17-4.95 (m, 1H), 4.45-4.20 (m, 1H), 2.84-2.63 (m, 1H), 2.53-2.27 (m, 2H), 2.00-1.82 (m, 2H), 1.74-1.51 (m, 2H), 1.43-1.29 (m, 3H), 0.84-0.67 (m, 2H), 0.58-0.46 (m, 2H). | I-16 |
| 130 | 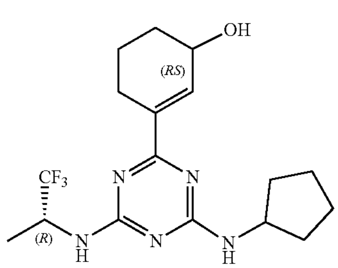 | 372.1 | 1H NMR (400 MHz, CD3OD): δ 7.22-6.89 (m, 1H), 5.09-4.92 (m, 1H), 4.41-4.18 (m, 2H), 2.54-2.31 (m, 2H), 2.09-1.82 (m, 4H), 1.80-1.69 (m, 2H), 1.67-1.44 (m, 6H), 1.40-1.31 (m, 3H). | I-12 |

-continued

| Comp. | Structure | MS (M + H)+ | ¹H NMR | Intermediate |
|---|---|---|---|---|
| 131 | 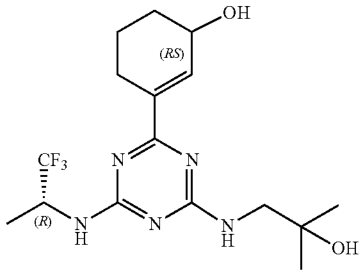 | 376.1 | ¹H NMR (400 MHz, CD₃OD): δ 7.24-6.95 (m, 1H), 5.12-4.90 (m, 1H), 4.43-4.25 (m, 1H), 3.53-3.37 (m, 2H), 2.47-2.33 (m, 2H), 2.01-1.81 (m, 2H), 1.69-1.52 (m, 2H), 1.38-1.33 (m, 3H), 1.19 (s, 6H). | I-7 |
| 132 | 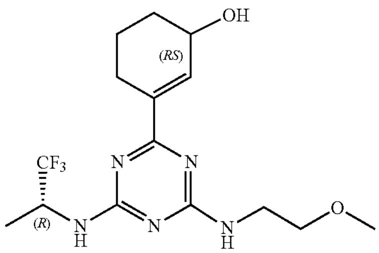 | 362.1 | ¹H NMR (400 MHz, CD₃OD): δ 7.23-6.91 (m, 1H), 5.12-4.91 (m, 1H), 4.43-4.25 (m, 1H), 3.65-3.46 (m, 4H), 3.36 (s, 3H), 2.53-2.32 (m, 2H), 2.01-1.83 (m, 2H), 1.69-1.52 (m, 2H), 1.40-1.31 (m, 3H). | I-17 |
| 133 | 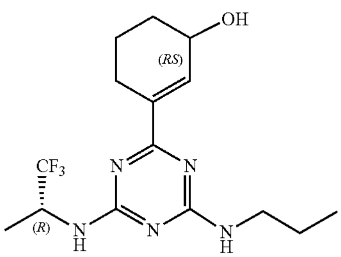 | 346.1 | ¹H NMR (400 MHz, CD₃OD): δ 7.02-6.87 (m, 1H), 5.11-4.90 (m, 1H), 4.40-4.23 (m, 1H), 3.40-3.30 (m, 2H), 2.55-2.28 (m, 2H), 1.98-1.81 (m, 2H), 1.68-1.53 (m, 4H), 1.39-1.31 (m, 3H), 0.97-0.89 (m, 3H). | I-18 |
| 134 | 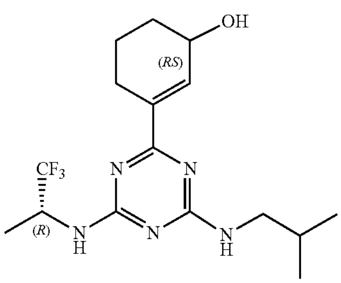 | 360.1 | ¹H NMR (400 MHz, CD₃OD): δ 7.23-6.90 (m, 1H), 5.14-4.89 (m, 1H), 4.45-4.21 (m, 1H), 3.25-3.07 (m, 2H), 2.50-2.33 (m, 2H), 1.97-1.80 (m, 3H), 1.74-1.51 (m, 2H), 1.38-1.31 (m, 3H), 0.95-0.89 (m, 6H). | I-13 |
| 135 | 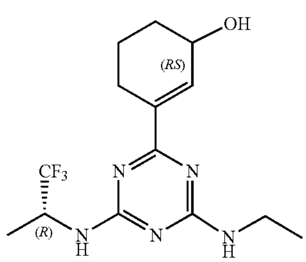 | 332.1 | ¹H NMR (400 MHz, CD₃OD): δ 7.28-6.88 (m, 1H), 5.14-4.93 (m, 1H), 4.40-4.22 (m, 1H), 3.48-3.35 (m, 2H), 2.57-2.27 (m, 2H), 1.98-1.83 (m, 2H), 1.70-1.52 (m, 2H), 1.40-1.31 (m, 3H), 1.20-1.13 (m, 3H). | I-19 |

-continued

| Comp. | Structure | MS (M + H)+ | 1H NMR | Intermediate |
|---|---|---|---|---|
| 136 | ![structure 136] | 386.1 | 1H NMR (400 MHz, CD3OD): δ 7.22-6.92 (m, 1H), 5.11-4.88 (m, 1H), 4.41-4.26 (m, 1H), 3.95-3.72 (m, 1H), 2.53-2.31 (m, 2H), 2.08-1.86 (m, 4H), 1.79-1.70 (m, 2H), 1.68-1.53 (m, 3H), 1.41-1.20 (m, 8H). | I-20 |
| 137 | ![structure 137] | 374.1 | 1H NMR (400 MHz, CD3OD): δ 7.31-7.215 (m, 1H), 5.09-4.95 (m, 1H), 4.39-4.30 (m, 1H), 3.16-2.81 (m, 1H), 2.51-2.37 (m, 2H), 2.01-1.84 (m, 2H), 1.71-1.51 (m, 2H), 1.40-1.34 (m, 3H), 1.22-1.11 (m, 6H). | I-4 |

Compound 138

(R)-6-(3,3-difluorocyclohex-1-en-1-yl)-$N^2$-isopropyl-$N^4$-(1,1,1-trifluoropropan-2-yl)-1,3,5-triazine-2,4-diamine

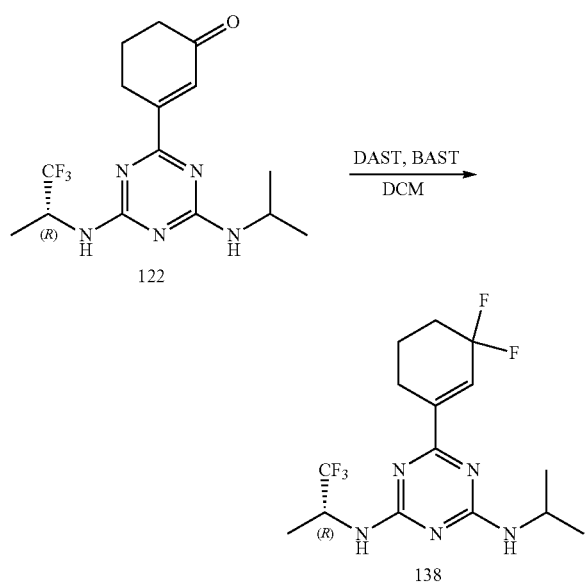

To a sealed tube were added Compound 122 (100 mg, 0.29 mmol), DAST (1 mL), BAST (1 mL) and DCM (10 mL). The mixture was stirred at 80° C. for 48 hours. After the reaction was completed, the mixture was cooled to room temperature, condensed and purified by flash column chromatography (eluting with PE/EA) to give the title compound as a white solid (40 mg, yield: 38.1%). MS (m/z): 366.1 [M+H]+

1H NMR (400 MHz, CD3OD): δ 7.00-6.82 (m, 1H), 5.05-4.88 (m, 1H), 4.27-4.05 (m, 1H), 2.59-2.47 (m, 2H), 2.14-2.00 (m, 2H), 1.91-1.83 (m, 2H), 1.39-1.32 (m, 3H), 1.22-1.17 (m, 6H).

Compound 139 in the below table was prepared according to the procedure of Compounds 138 using the corresponding intermediates and reagents under appropriate conditions that will be recognized by POSITA:

| Comp. | Structure | MS (M + H)+ | 1H NMR | Intermediate |
|---|---|---|---|---|
| 139 | 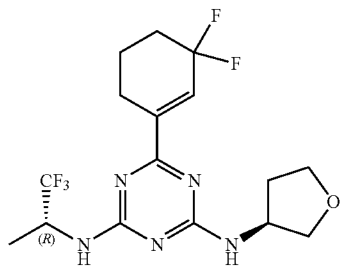 | 394.0 | 1H NMR (400 MHz, CD3OD): δ 7.12-6.83 (m, 1H), 5.07-4.92 (m, 1H), 4.64-4.41 (m, 1H), 4.03-3.88 (m, 2H), 3.87-3.76 (m, 1H), 3.72-3.60 (m, 1H), 2.64-2.46 (m, 2H), 2.34-2.18 (m, 1H), 2.13-2.00 (m, 2H), 1.95-1.82 (m, 3H), 1.42-1.30 (m, 3H). | I-8 |

Compound 140

6-(3-Methoxycyclohex-1-en-1-yl)-$N^2,N^4$-bis((R)-1,1,1-trifluoropropan-2-yl)-1,3,5-triazine-2,4-diamine Compound 141

6-(3-(Dimethylamino)cyclohex-1-en-1-yl)-$N^2,N^4$-bis((R)-1,1,1-trifluoropropan-2-yl)-1,3,5-triazine-2,4-diamine

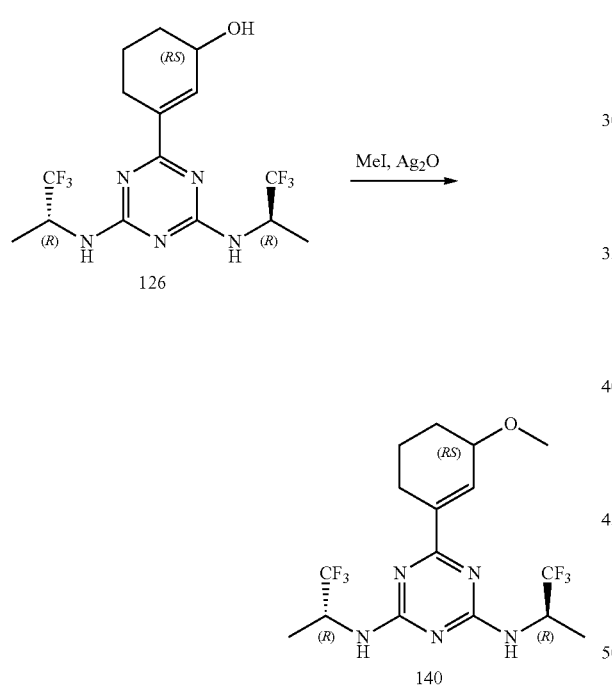

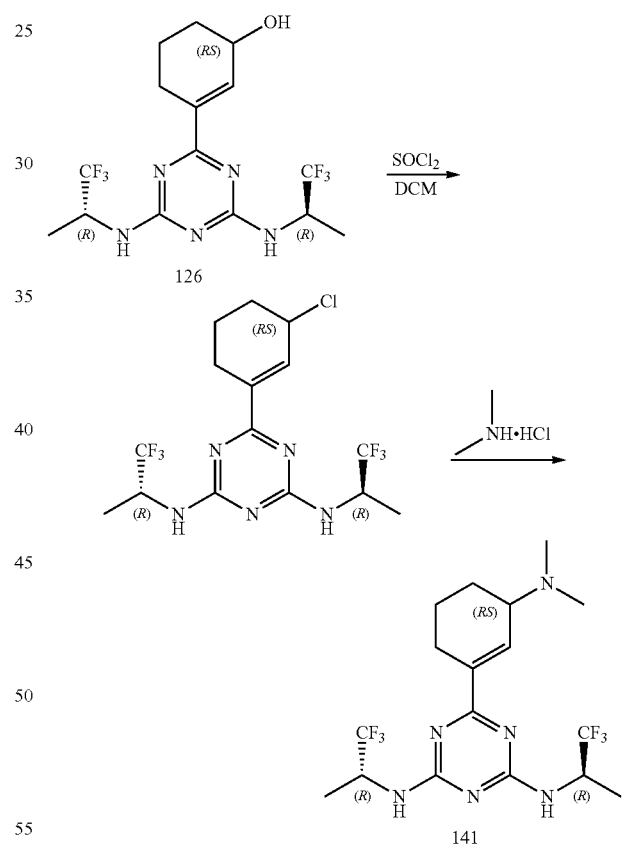

A mixture of Compound 126 (100 mg, 0.25 mmol) and Ag$_2$O (115 mg, 0.5 mmol) in CH$_3$I (4 mL) was stirred at reflux for 16 hours. After the reaction was completed, the mixture was cooled to room temperature, condensed and purified by flash column chromatography (eluting with PE/EA) to give the title compound as a white solid (60 mg, yield: 58.3%). MS (m/z): 414.0 [M+H]$^+$; $^1$H NMR (400 MHz, CD$_3$OD): δ 7.27-7.08 (m, 1H), 5.05-4.87 (m, 2H), 4.03-3.91 (m, 1H), 3.42 (s, 3H), 2.51-2.34 (m, 2H), 1.98-1.80 (m, 2H), 1.69-1.56 (m, 2H), 1.38-1.29 (m, 6H).

To a solution of Compound 126 (50 mg, 0.125 mmol) in dry DCM (3 mL) was added SOCl$_2$ (16 mg, 0.137 mmol) under ice bath cooling ° C., and the mixture was stirred in ice bath for 30 minutes. Then, the solution was charged into a sealed tube, dimethylamine hydrochloride (20 mg, 0.25 mmol) was added, and the mixture was stirred at reflux overnight. After the reaction was completed, the mixture was cooled to room temperature and partitioned between EtOAc and water. The organic layer was collected, condensed and purified by flash column chromatography (eluting with PE/EA) to give the title compound as a white solid (10 mg, yield: 18.9%). MS (m/z): 427.0 [M+H]+

$^1$H NMR (400 MHz, CD$_3$OD): δ 7.27-7.11 (m, 1H), 5.06-4.89 (m, 2H), 3.58-3.44 (m, 1H), 2.64-2.53 (m, 1H), 2.44-2.38 (m, 6H), 2.38-2.25 (m, 1H), 2.05-1.92 (m, 2H), 1.66-1.53 (m, 2H), 1.39-1.31 (m, 6H).

Compound 142 in the below table was prepared according to the procedure of Compound 141 using the corresponding intermediates and reagents under appropriate conditions that will be recognized by POSITA:

hours, quenched by the addition of saturated NH$_4$Cl aqueous solution and extracted with EtOAc. The organic layer was collected, condensed and purified by flash column chromatography (eluting with PE/EA) to give the title compound as a white solid (10 mg, yield: 8.6%). MS (m/z): 468.0 [M+H]+;

$^1$H NMR (400 MHz, CD$_3$OD): δ 7.10 (s, 1H), 5.05-4.88 (m, 2H), 2.81-2.63 (m, 1H), 2.35-2.21 (m, 1H), 1.92-1.77 (m, 4H), 1.39-1.31 (m, 6H).

| Comp. | Structure | MS (M + H)+ | $^1$H NMR | Intermediate |
|---|---|---|---|---|
| 142 | 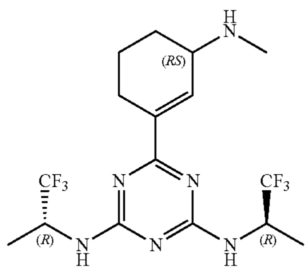 | 413.1 | $^1$H NMR (400 MHz, CD$_3$OD): δ 7.26-7.06 (m, 1H), 5.08-4.91 (m, 2H), 3.89-3.73 (m, 1H), 2.74-2.66 (m, 3H), 2.63-2.44 (m, 2H), 2.19-2.07(m, 1H), 2.02-1.92 (m, 1H), 1.76-1.57(m, 2H), 1.38-1.33 (m, 6H). | Comp. 126 |

Compound 143

3-(4,6-Bis(((R)-1,1,1-trifluoropropan-2-yl)amino)-1,3,5-triazin-2-yl)-1-(trifluoromethyl)-cyclohex-2-en-1-ol Compound 144

3-(4-(Isopropylamino)-6-(((R)-1,1,1-trifluoropropan-2-yl)amino)-1,3,5-triazin-2-yl)cyclohex-3-en-1-ol

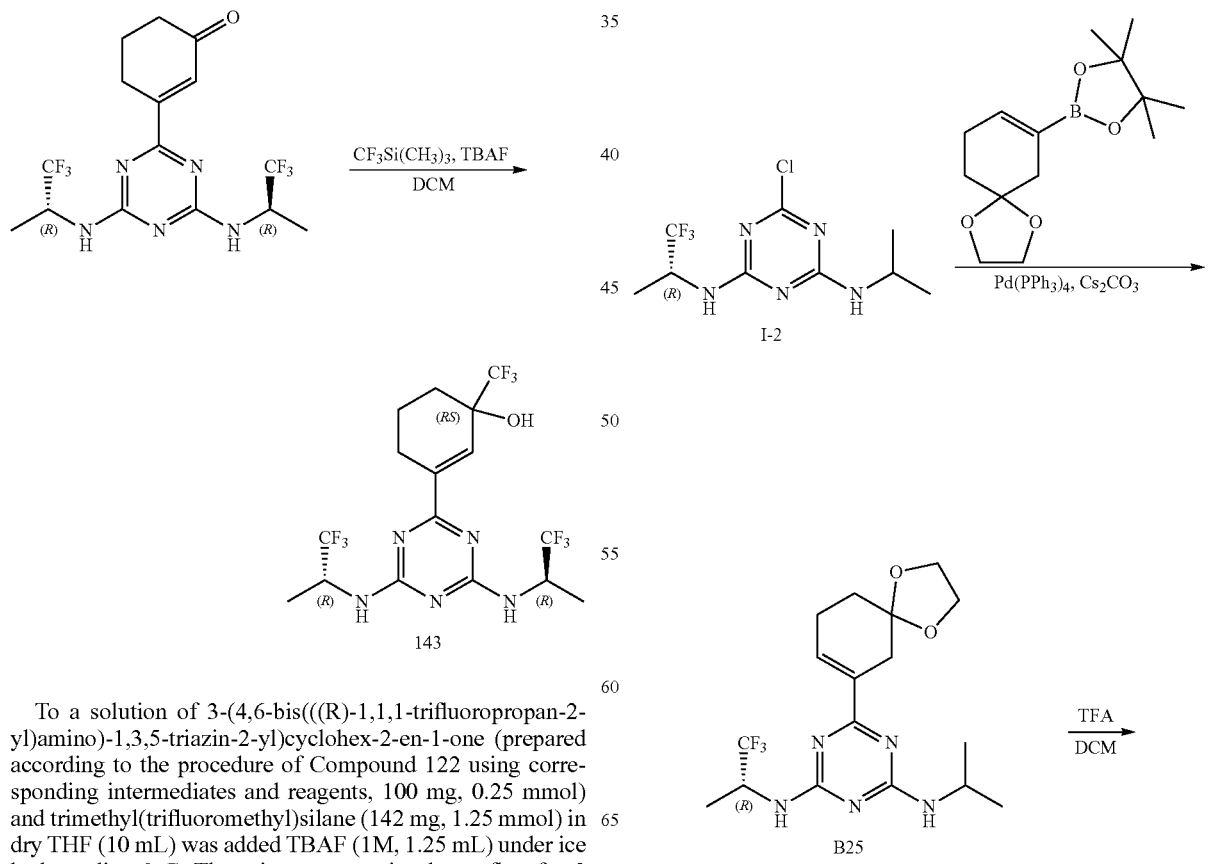

To a solution of 3-(4,6-bis(((R)-1,1,1-trifluoropropan-2-yl)amino)-1,3,5-triazin-2-yl)cyclohex-2-en-1-one (prepared according to the procedure of Compound 122 using corresponding intermediates and reagents, 100 mg, 0.25 mmol) and trimethyl(trifluoromethyl)silane (142 mg, 1.25 mmol) in dry THF (10 mL) was added TBAF (1M, 1.25 mL) under ice bath cooling ° C. The mixture was stirred at reflux for 2

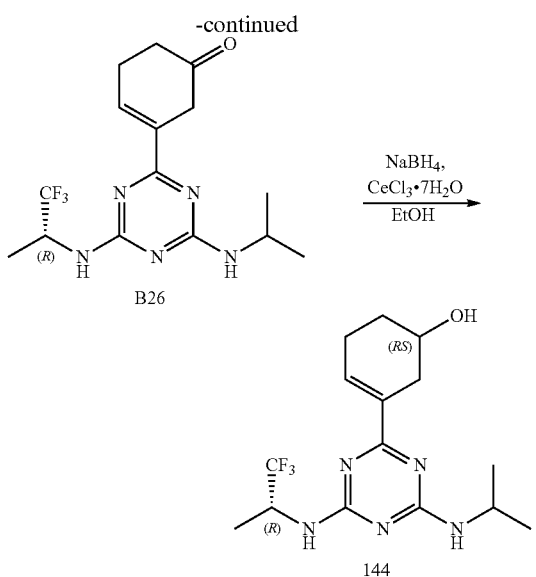

chromatography (eluting with PE/EA) to give the title compound B26 as yellow solid (200 mg, yield: 51.5%). MS (m/z): 344.3 [M+H]$^+$ (C) 3-(4-(Isopropylamino)-6-(((R)-1,1,1-trifluoropropan-2-yl)amino)-1,3,5-triazin-2-yl)cyclohex-3-en-1-ol Compound 144 was prepared according to the procedure of Compound 124 using Compound B26 and corresponding reagents. MS (m/z): 346.3 [M+H]$^+$ $^1$H NMR (400 MHz, CD$_3$OD): δ 7.27-6.96 (m, 1H), 5.08-4.89 (m, 1H), 4.28-4.07 (m, 1H), 4.02-3.83 (m, 1H), 2.91-2.72 (m, 1H), 2.47-2.20 (m, 3H), 1.93-1.80 (m, 1H), 1.65-1.53 (m, 1H), 1.38-1.28 (m, 3H), 1.24-1.13 (m, 6H).

Compound 145 in the below table was prepared according to the procedure of Compound 144 using the corresponding intermediates and reagents under appropriate conditions that will be recognized by POSITA:

| Comp. | Structure | MS (M + H)$^+$ | $^1$H NMR | Intermediate |
|---|---|---|---|---|
| 145 | OH (RS) ... CF$_3$ (R) | 346.3 | $^1$H NMR (400 MHz, CD$_3$OD): δ 7.1-6.90 (m, 1H), 5.04-4.88 (m, 1H), 4.25-4.07 (m, 1H), 3.97-3.85 (m, 1H), 2.74-2.60 (m, 1H), 2.57-2.48 (m, 1H), 2.46-2.33 (m, 1H), 2.21-2.09 (m, 1H), 1.97-1.87 (m, 1H), 1.70-1.58 (m, 1H), 1.36-1.29 (m, 3H), 1.21-1.14 (m, 6H). | I-2 |

(A) (R)—N$^2$-isopropyl-6-(1,4-dioxaspiro[4.5]dec-7-en-7-yl)-N$^4$-(1,1,1-trifluoropropan-2-yl)-1,3,5-triazine-2,4-diamine (B25)

Under nitrogen atmosphere, to a flask were added Intermediate I-2 (320 mg, 1.13 mmol), 4,4,5,5-tetramethyl-2-(1,4-dioxaspiro[4.5]dec-7-en-7-yl)-1,3,2-dioxaborolane (300 mg, 1.13 mmol), Cs$_2$CO$_3$ (734 mg, 2.26 mmol), Pd(PPh$_3$)$_4$ (69 mg, 0.06 mmol), 1,4-dioxane (10 mL) and water (2 mL). The mixture was stirred at 80° C. for 2 hours. After the reaction was completed, the mixture was cooled to room temperature, condensed and purified by flash column chromatography (eluting with PE/EA) to give the title compound B25 as white solid.

(B) (R)-3-(4-(Isopropylamino)-6-((1,1,1-trifluoropropan-2-yl)amino)-1,3,5-triazin-2-yl)cyclohex-3-en-1-one (B26)

To the solution of Compound B25 in dry DCM (3 mL) was added TFA (3 mL) and the mixture was stirred overnight at room temperature. After the reaction was completed, the reaction was quenched by the addition of saturated NaHCO$_3$ aqueous solution and extracted with EtOAc. The organic layer was collected, condensed and purified by flash column Compound 152

2-Fluoro-3-(4-(((R)-1-phenylethyl)amino)-6-(((R)-1,1,1-trifluoropropan-2-yl)amino)-1,3,5-triazin-2-yl)cyclohex-2-en-1-ol

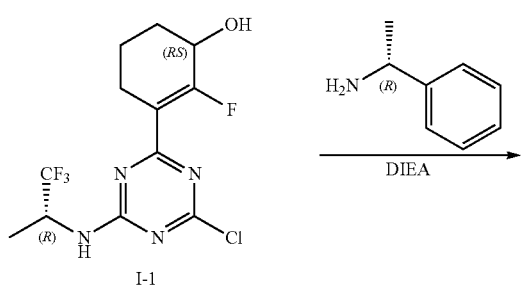

152

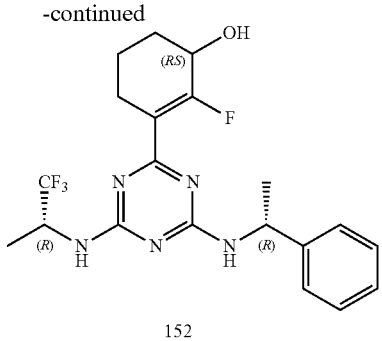

To a sealed tube was added Intermediate I-1 (50 mg, 0.15 mmol), (R)-1-phenylethan-1-amine (36 mg, 0.30 mmol), DIEA (77 mg, 0.60 mmol) and 1,4-dioxane (3 mL) in sequence. The mixture was stirred at 100° C. for 2 hours. After the reaction was completed, the mixture was cooled to room temperature, condensed and purified by flash column chromatography (eluting with PE/EA) to give the title compound as white solid (15 mg, yield: 23.4%). MS (m/z): 426.3 [M+H]$^+$ $^1$H NMR (400 MHz, CD$_3$OD): δ 7.35-7.15 (m, 5H), 5.22-4.60 (m, 2H), 4.33-4.21 (m, 1H), 2.62-2.23 (m, 2H), 1.89-1.73 (m, 3H), 1.67-1.58 (m, 1H), 1.50-1.44 (m, 3H), 1.34-1.28 (m, 2H), 1.16-1.07 (m, 1H).

The compounds in the below table were prepared according to the procedure of Compound 152 using the corresponding intermediates and reagents under appropriate conditions that will be recognized by POSITA:

| Comp. | Structure | MS (M + H)$^+$ | $^1$H NMR | Intermediate |
|---|---|---|---|---|
| 153 | 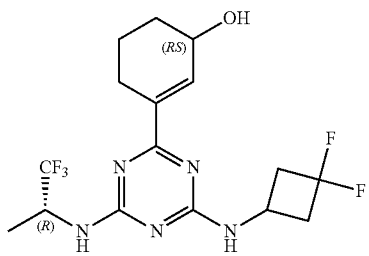 | 394.1 | $^1$H NMR (400 MHz, CD$_3$OD): δ 7.21-6.96 (m, 1H), 5.09-4.88 (m, 1H), 4.39-4.13 (m, 2H), 2.99-2.87 (m, 2H), 2.71-2.50 (m, 2H), 2.47-2.32 (m, 2H), 1.99-1.81 (m, 2H), 1.67-1.52 (m, 2H), 1.39-1.31 (m, 3H). | I-25 |
| 154 | 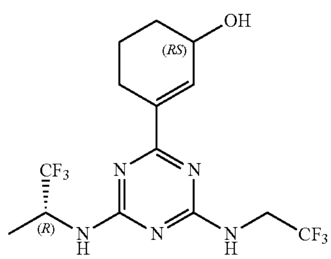 | 386.1 | $^1$H NMR (400 MHz, CD$_3$OD): δ 7.26-7.03 (m, 1H), 5.07-4.90 (m, 1H), 4.38-4.26 (m, 1H), 4.21-4.02 (m, 2H), 2.49-2.33 (m, 2H), 1.97-1.82 (m, 2H), 1.67-1.52 (m, 2H), 1.39-1.31 (m, 3H). | I-25 |
| 155 | 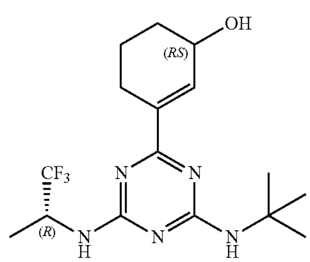 | 360.1 | $^1$H NMR (400 MHz, CD$_3$OD): δ 7.21-6.89 (m, 1H), 5.07-4.87 (m, 1H), 4.36-4.24 (m, 1H), 2.48-2.33 (m, 2H), 1.97-1.83 (m, 2H), 1.68-1.52 (m, 2H), 1.43 (s, 9H), 1.38-1.32 (m, 3H). | I-25 |
| 156 | 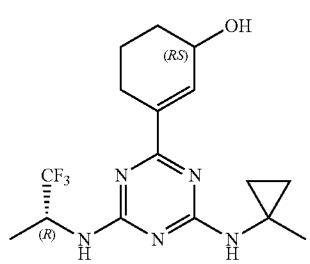 | 358.1 | $^1$H NMR (400 MHz, CD$_3$OD): δ 7.25-6.90 (m, 1H), 5.13-4.93 (m, 1H), 4.38-4.23 (m, 1H), 2.54-2.31 (m, 2H), 1.97-1.81 (m, 2H), 1.69-1.51 (m, 2H), 1.42-1.31 (m, 6H), 0.80-0.72 (m, 2H), 0.66-0.58 (m, 2H). | I-25 |

-continued

| Comp. | Structure | MS (M + H)⁺ | ¹H NMR | Intermediate |
|---|---|---|---|---|
| 157 | 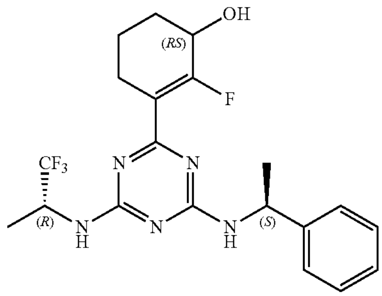 | 426.4 | ¹H NMR (400 MHz, CD₃OD): δ 7.40-7.15 (m, 5H), 5.23-4.62 (m, 2H), 4.34-4.18 (m, 1H), 2.62-2.24 (m, 2H), 1.88-1.60 (m, 4H), 1.53-1.44 (m, 3H), 1.35-1.29 (m, 2H), 1.18-1.07 (m, 1H). | I-1 |
| 158 | 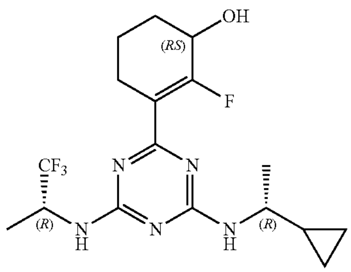 | 390.1 | ¹H NMR (400 MHz, CD₃OD): δ 4.99-4.88 (m, 1H), 4.33-4.22 (m, 1H), 3.61-3.40 (m, 1H), 2.65- 2.47 (m, 1H), 2.43-2.25 (m, 1H), 1.91-1.72 (m, 3H), 1.70-1.59 (m, 1H), 1.36-1.31 (m, 3H), 1.27-1.21 (m, 3H), 1.03-0.86 (m, 1H), 0.56-0.30 (m, 3H), 0.26-0.15 (m, 1H). | I-1 |
| 159 | 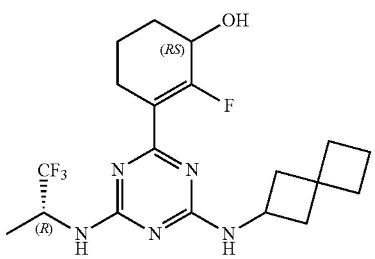 | 416.3 | ¹H NMR (400 MHz, CD₃OD): δ 4.97-4.88 (m, 1H), 4.35-4.13 (m, 2H), 2.60-2.47 (m, 1H), 2.44-2.26 (m, 3H), 2.10-2.02 (m, 2H), 1.97-1.76 (m, 9H), 1.70-1.60 (m, 1H), 1.38-1.29 (m, 3H). | I-1 |
| 160 | 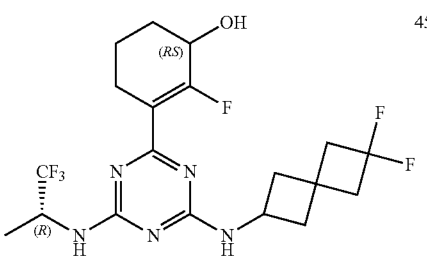 | 452.3 | ¹H NMR (400 MHz, CD₃OD): δ 4.97-4.89 (s, 1H), 4.43-4.22 (m, 2H), 2.68-2.43 (m, 7H), 2.37-2.25 (m, 1H), 2.121-2.06 (m, 2H), 1.91-1.73 (m, 3H), 1.73-1.58 (m, 1H), 1.37-1.29 (m, 3H). | I-1 |
| 161 | 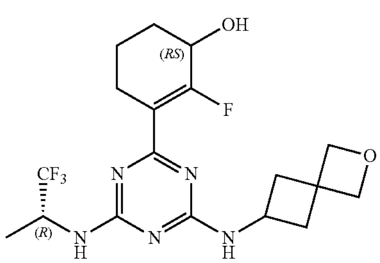 | 418.3 | ¹H NMR (400 MHz, CD₃OD): δ 4.97-4.88 (m, 1H), 4.78-4.71 (m, 2H), 4.64-4.55 (m, 2H), 4.37-4.14 (m, 2H), 2.70-2.48 (m, 3H), 2.38-2.12 (m, 3H), 1.90-1.61 (m, 4H), 1.38-1.29 (m, 3H). | I-1 |

| Comp. | Structure | MS (M + H)+ | 1H NMR | Intermediate |
|---|---|---|---|---|
| 162 | 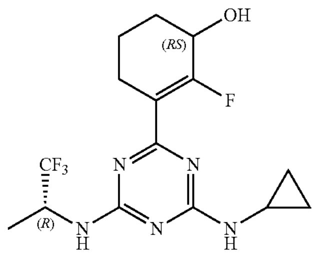 | 362.3 | 1H NMR (400 MHz, CD3OD): δ 5.10-4.89 (m, 1H), 4.33-4.20 (m, 1H), 2.79-2.67 (m, 1H), 2.64-2.48 (m, 1H), 2.40-2.22 (m, 1H), 1.89-1.72 (m, 3H), 1.70-1.59 (br, 1H), 1.40-1.31 (m, 3H), 0.77-0.67 (m, 2H), 0.55-0.48 (m, 2H). | I-1 |
| 163 | 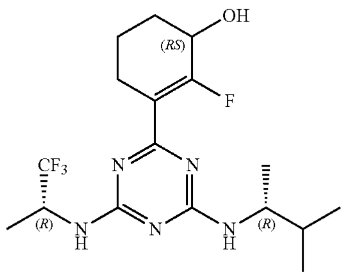 | 392.3 | 1H NMR (400 MHz, CD3OD): δ 4.98-4.89 (m, 1H), 4.33-4.22 (m, 1H), 4.00-3.86 (m, 1H), 2.62-2.47 (m, 1H), 2.41-2.23 (m, 1H), 1.89-1.72 (m, 4H), 1.71-1.60 (m, 1H), 1.38-1.30 (m, 3H), 1.15-1.07 (m, 3H), 0.96-0.88 (m, 6H). | I-1 |
| 164 | 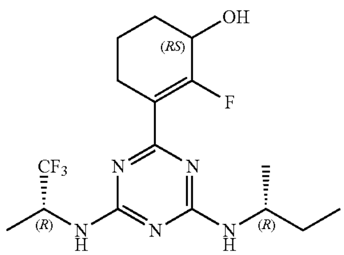 | 378.3 | 1H NMR (400 MHz, CD3OD): δ 4.97-4.90 (m, 1H), 4.34-4.22 (m, 1H), 4.03-3.91 (m, 1H), 2.63-2.48 (m, 1H), 2.40-2.24 (m, 1H), 1.90-1.73 (m, 3H), 1.69-1.61 (m, 1H), 1.58-1.47 (m, 2H), 1.39-1.30 (m, 3H), 1.19-1.11 (m, 3H), 0.97-0.88 (m, 3H). | I-1 |
| 165 | 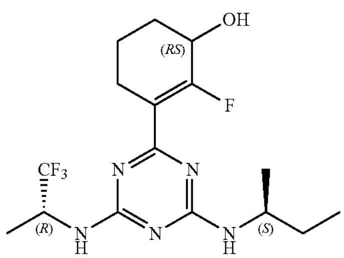 | 378.3 | 1H NMR (400 MHz, CD3OD): δ 4.97-4.90 (m, 1H), 4.34-4.22 (m, 1H), 4.03-3.91 (m, 1H), 2.63-2.48 (m, 1H), 2.40-2.24 (m, 1H), 1.90-1.73 (m, 3H), 1.69-1.61 (m, 1H), 1.58-1.47 (m, 2H), 1.39-1.30 (m, 3H), 1.19-1.11 (m, 3H), 0.97-0.88 (m, 3H). | I-1 |
| 166 | 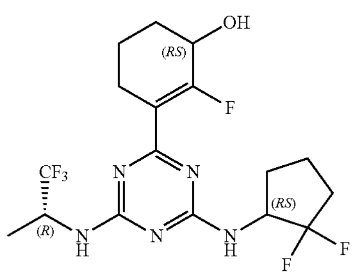 | 426.3 | 1H NMR (400 MHz, CD3OD): δ 5.02-4.95 (m, 1H), 4.78-4.57 (m, 1H), 4.41-4.22 (m, 1H), 2.57-2.52 (m, 1H), 2.43-2.31 (m, 1H), 2.27-2.05 (m, 3H), 1.95-1.62 (m, 7H), 1.43-1.31 (m, 3H). | I-1 |

-continued

| Comp. | Structure | MS (M + H)+ | 1H NMR | Intermediate |
|---|---|---|---|---|
| 167 | 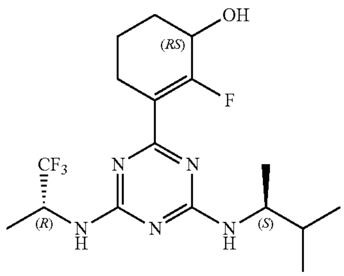 | 392.4 | 1H NMR (400 MHz, CD3OD): δ 5.00-4.93 (m, 1H), 4.36-4.23 (m, 1H), 4.04-3.90 (m, 1H), 2.64-2.50 (m, 1H), 2.40-2.27 (m, 1H), 1.90-1.63 (m, 5H), 1.40-1.32 (m, 3H), 1.18-1.09 (m, 3H), 0.98-0.88 (m, 6H). | I-1 |
| 168 | 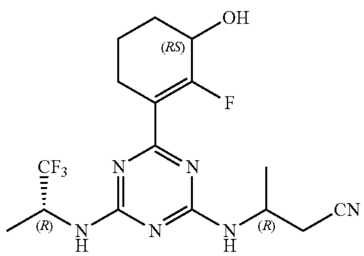 | 389.3 | 1H NMR (400 MHz, CD3OD): δ 4.99-4.93 (m, 1H), 4.42-4.25 (m, 2H), 2.88-2.71 (m, 2H), 2.66-2.52 (m, 1H), 2.44-2.28 (m, 1H), 1.92-1.83 (m, 2H), 1.82-1.73 (m, 1H), 1.71-1.63 (m, 1H), 1.42-1.31 (m, 6H). | I-1 |
| 169 | 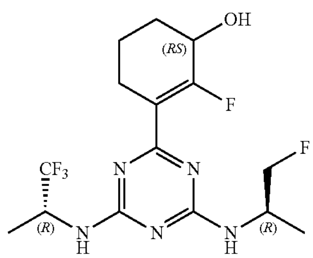 | 382.2 | 1H NMR (400 MHz, CD3OD): δ 5.01-4.92 (m, 1H), 4.51-4.26 (m, 4H), 2.64-2.49 (m, 1H), 2.39-2.25 (m, 1H), 1.90-1.61 (m, 4H), 1.40-1.31 (m, 3H), 1.27-1.19 (m, 3H). | I-1 |
| 170 | 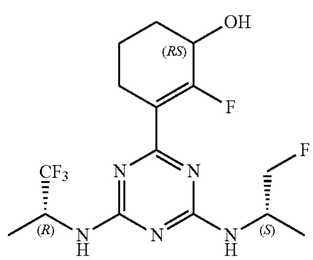 | 382.3 | 1H NMR (400 MHz, CD3OD): δ 5.01-4.92 (m, 1H), 4.51-4.26 (m, 4H), 2.64-2.49 (m, 1H), 2.39-2.25 (m, 1H), 1.90-1.61 (m, 4H), 1.40-1.31 (m, 3H), 1.27-1.19 (m, 3H). | I-1 |
| 171 | 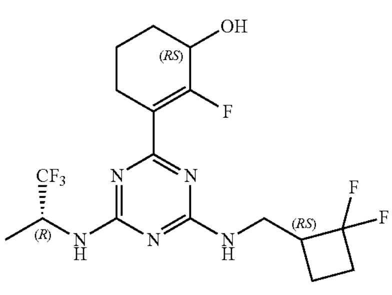 | 426.3 | 1H NMR (400 MHz, CD3OD): δ 4.99-4.91 (m, 1H), 4.34-4.24 (m, 1H), 3.67-3.44 (m, 2H), 3.19-3.03 (m, 1H), 2.60-2.30 (m, 4H), 1.95-1.74 (m, 4H), 1.70-1.62 (m, 1H), 1.58-1.49 (m, 1H), 1.39-1.33 (m, 3H). | I-1 |

| Comp. | Structure | MS (M + H)+ | ¹H NMR | Intermediate |
|---|---|---|---|---|
| 172 | 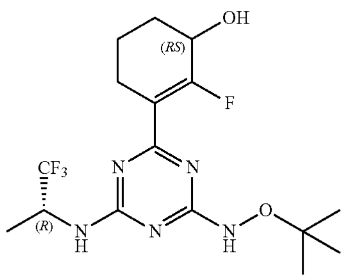 | 394.3 | ¹H NMR (400 MHz, CD₃OD): δ 5.02-4.93 (m, 1H), 4.33-4.26 (m, 1H), 2.63-2.55 (m, 1H), 2.34-2.28 (m, 1H), 1.90-1.76 (m, 3H), 1.71-1.62 (m, 1H), 1.38-1.35 (m, 3H), 1.28 (s, 9H). | I-1 |
| 173 | 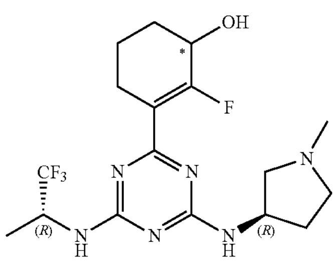 | 405.2 | ¹H NMR (400 MHz, CD₃OD): δ 5.01-4.90 (m, 1H), 4.58-4.43 (m, 1H), 4.35-4.25 (m, 1H), 3.00-2.84 (m, 1H), 2.71-2.42 (m, 4H), 2.40-2.21 (m, 5H), 1.89-1.58 (m, 5H), 1.40-1.28 (m, 3H). | I-61 |
| 174 | 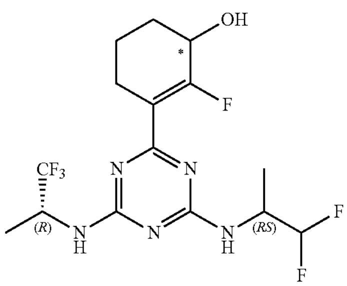 | 400.2 | ¹H NMR (400 MHz, CD₃OD): δ 6.07-5.70 (m, 1H), 5.01-4.88 (m, 1H), 4.52-4.35 (m, 1H), 4.33-4.23 (m, 1H), 2.65-2.51 (m, 1H), 2.44-2.25 (m, 1H), 1.89-1.61 (m, 4H), 1.38-1.30 (m, 3H), 1.28-1.21 (m, 3H). | I-61 |
| 175 | 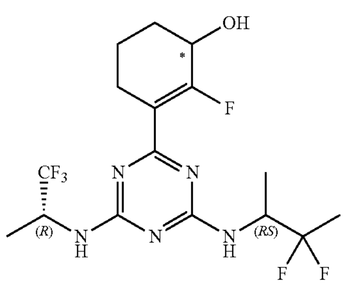 | 414.2 | ¹H NMR (400 MHz, CD₃OD): δ 5.03-4.89 (m, 1H), 4.69-4.51 (m, 1H), 4.35-4.22 (m, 1H), 2.68-2.50 (m, 1H), 2.41-2.25 (m, 1H), 1.90-1.73 (m, 3H), 1.68-1.50 (m, 4H), 1.38-1.31 (m, 3H), 1.28-1.22 (m, 3H). | I-61 |
| 176 | 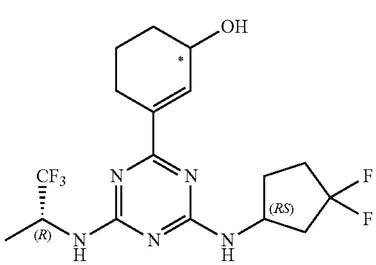 | 408.1 | ¹H NMR (400 MHz, CD₃OD): δ 7.27-6.94 (m, 1H), 5.10-4.87 (m, 1H), 4.57-4.38 (m, 1H), 4.36-4.25 (m, 1H), 2.62-2.48 (m, 1H), 2.47-2.32 (m, 2H), 2.28-2.15 (m, 2H), 2.13-1.97 (m, 2H), 1.96-1.72 (m, 3H), 1.66-1.50 (m, 2H), 1.39-1.31 (m, 3H). | I-26 |

-continued

| Comp. | Structure | MS (M + H)+ | 1H NMR | Intermediate |
|---|---|---|---|---|
| 177 | 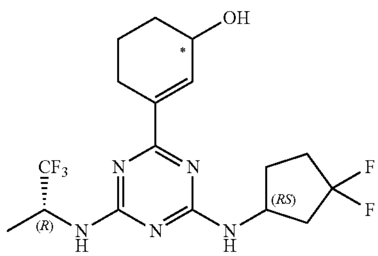 | 408.1 | 1H NMR (400 MHz, CD3OD): δ 7.27-6.94 (m, 1H), 5.10-4.87 (m, 1H), 4.57-4.38 (m, 1H), 4.36-4.25 (m, 1H), 2.62-2.48 (m, 1H), 2.47-2.32 (m, 2H), 2.28-2.15 (m, 2H), 2.13-1.97 (m, 2H), 1.96-1.72 (m, 3H), 1.66- 1.50 (m, 2H), 1.39-1.31 (m, 3H). | I-27 |
| 178 | 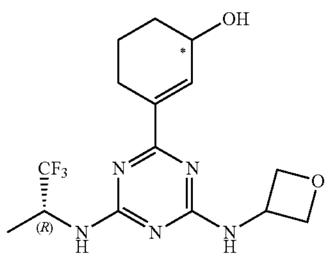 | 360.0 | 1H NMR (400MHz, CD3OD): δ 7.17-6.98 (m, 1H), 5.18-4.90 (m, 2H), 4.90-4.86 (m, 2H), 4.66-4.59 (m, 2H), 4.35-4.26 (m, 1H), 2.46-2.35 (m, 2H), 1.97-1.81 (m, 2H), 1.67-1.52 (m, 2H), 1.35-1.30 (m, 3H). | I-27 |
| 179 | 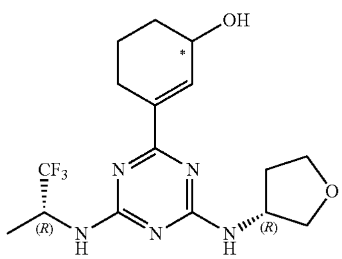 | 374 | 1H NMR (400 MHz, CD3OD): δ 7.23-6.95 (m, 1H), 5.08-4.90 (m, 1H), 4.61-4.44 (m, 1H), 4.35-4.25 (m, 1H), 4.00-3.89 (m, 2H), 3.85-3.76 (m, 1H), 3.70-3.59 (m, 1H), 2.48-2.35 (m, 2H), 2.29-2.18 (m, 1H), 1.96-1.83 (m, 3H), 1.68-1.52 (m, 2H), 1.37-1.31 (m, 3H). | I-27 |
| 180 | 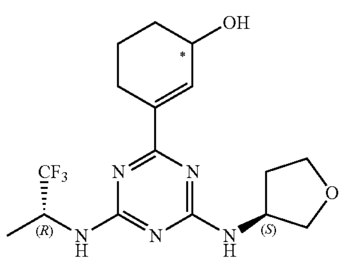 | 374 | 1H NMR (400 MHz, CD3OD): δ 7.23-6.95 (m, 1H), 5.08-4.90 (m, 1H), 4.61-4.44 (m, 1H), 4.35-4.25 (m, 1H), 4.00-3.89 (m, 2H), 3.85-3.76 (m, 1H), 3.70-3.59 (m, 1H), 2.48-2.35 (m, 2H), 2.29-2.18 (m, 1H), 1.96-1.83 (m, 3H), 1.68-1.52 (m, 2H), 1.37-1.31 (m, 3H). | I-27 |
| 181 | 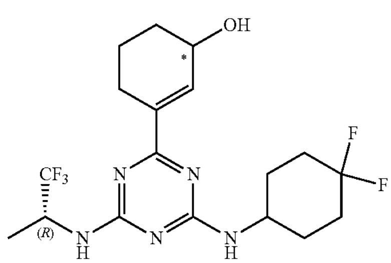 | 422.1 | 1H NMR (400 MHz, CD3OD): δ 7.23-6.93 (m, 1H), 5.13-4.88 (m, 1H), 4.39-4.27 (m, 1H), 4.14-3.91 (m, 1H), 2.53-2.35 (m, 2H), 2.14-1.81 (m, 8H), 1.73-1.51 (m, 4H), 1.40-1.30 (m, 3H). | I-27 |
| 182 | 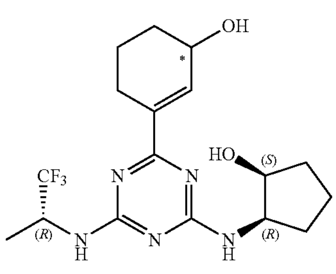 | 388.2 | 1H NMR (400 MHz, CD3OD): δ 7.24-6.90 (m, 1H), 5.10-4.88 (m, 1H), 4.39-4.27 (m, 1H), 4.23-4.08 (m, 2H), 2.46-2.35 (m, 2H), 2.07-1.97 (m, 1H), 1.95-1.80 (m, 4H), 1.70-1.52 (m, 5H), 1.37-1.31 (m, 3H). | I-27 |

-continued

| Comp. | Structure | MS (M + H)+ | 1H NMR | Intermediate |
|---|---|---|---|---|
| 183 | (structure: cyclohexenyl-OH substituted triazine with CF3/(R)-NH and (S)-NH-CH(CH3)-CH2-OMe) | 376.3 | 1H NMR (400 MHz, CD3OD): δ 7.20-6.93 (m, 1H), 5.07-4.89 (m, 1H), 4.37-4.19 (m, 2H), 3.48-3.41 (m, 1H), 3.38-3.32 (m, 4H), 2.45-2.34 (m, 2H), 1.96-1.81 (m, 2H), 1.67-1.53 (m, 2H), 1.37-1.31 (m, 3H), 1.20-1.15 (m, 3H). | I-27 |
| 184 | (structure: cyclohexenyl-OH substituted triazine with CF3/(R)-NH and (RS)-NH-CH(CH3)-CH2-OH) | 362.2 | 1H NMR (400 MHz, CD3OD): δ 7.19-6.91 (m, 1H), 5.06-4.90 (m, 1H), 4.35-4.07 (m, 2H), 3.63-3.48 (m, 2H), 2.47-2.33 (m, 2H), 1.96-1.81 (m, 2H), 1.67-1.52 (m, 2H), 1.36-1.31 (m, 3H), 1.22-1.16 (m, 3H). | I-27 |

Compound 186

6-(Cyclohex-1-en-1-yl)-N²,N⁴-bis((R)-1,1,1-trifluoropropan-2-yl)-1,3,5-triazine-2,4-diamine

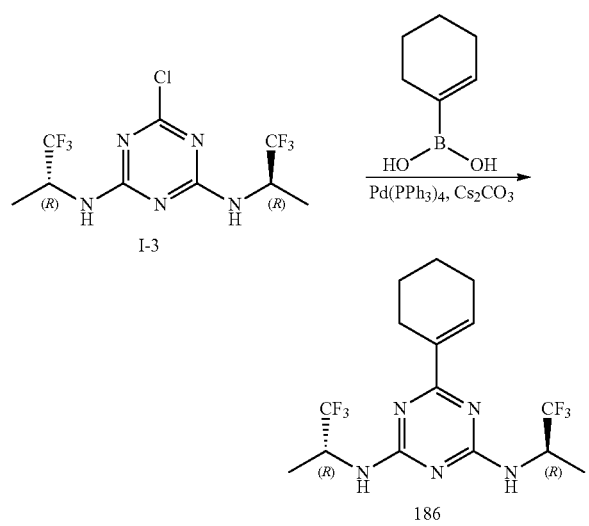

Under nitrogen atmosphere, to a flask was added Intermediate I-3 (150 mg, 0.44 mmol), cyclohex-1-en-1-ylboronic acid (85 mg, 0.66 mmol), Cs₂CO₃ (290 mg, 0.88 mmol), Pd(PPh₃)₄ (26 mg, 0.022 mmol), 1,4-dioxane (10 mL) and water (2 mL) in sequence. The mixture was stirred at 100° C. for 16 hours. After the reaction was completed, the mixture was cooled to room temperature, condensed and purified by flash column chromatography (eluting with PE/EA) to give the title compound as white solid (154 mg, yield: 90.4%). MS (m/z): 384.1 [M+H]⁺

1H NMR (400 MHz, DMSO-d₆): δ 7.84-7.60 (m, 2H), 7.18 (s, 1H), 5.07-4.76 (m, 2H), 2.40-2.28 (m, 2H), 2.25-2.16 (m, 2H), 1.68-1.52 (m, 4H), 1.34-1.25 (m, 6H).

The compounds in the below table were prepared according to the procedure of Compound 186 using the corresponding intermediates and reagents under appropriate conditions that will be recognized by POSITA:

| Comp. | Structure | MS (M + H)+ | 1H NMR | Intermediate |
|---|---|---|---|---|
| 187 | 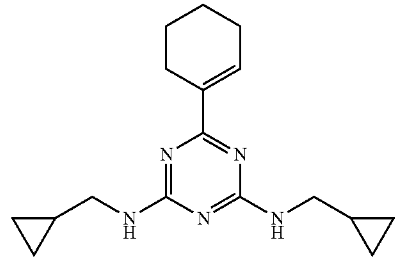 [SMILES: C1=C(c2nc(NCC3CC3)nc(NCC3CC3)n2)CCCC1] | 300.2 | 1H NMR (400 MHz, CD3OD): δ 7.20-6.87 (m, 1H), 3.27-3.16 (m, 4H), 2.45-2.34 (m, 2H), 2.26-2.18 (m, 2H), 1.74-1.60 (m, 4H), 1.12-1.00 (m, 2H), 0.53-0.39 (m, 4H), 0.29-0.16 (m, 4H). | I-6 |
| 188 | 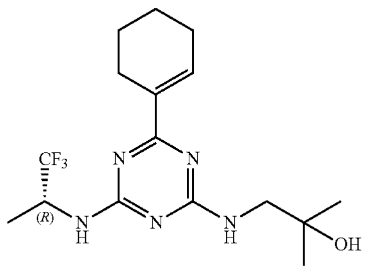 | 360.1 | 1H NMR (400 MHz, CD3OD): δ 7.41-6.99 (m, 1H), 5.11-4.88 (m, 1H), 3.60-3.34 (m, 2H), 2.55-2.35 (m, 2H), 2.29-2.15 (m, 2H), 1.81-1.57 (m, 4H), 1.40-1.30 (m, 3H), 1.19 (s, 6H). | I-7 |
| 189 | 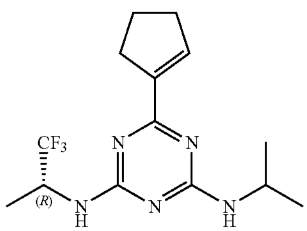 | 316.1 | 1H NMR (400 MHz, CD3OD): δ 6.96-6.78 (m, 1H), 5.06-4.87 (m, 1H), 4.25-4.07 (m, 1H), 2.72-2.62 (m, 2H), 2.56-2.49 (m, 2H), 2.03-1.93 (m, 2H), 1.38-1.30 (m, 3H), 1.22-1.15 (m, 6H). | I-2 |

Compound 190

(R)-6-(cyclohex-1-en-1-yl)-N²-isopropyl-N⁴-(1,1,1-trifluoropropan-2-yl)-1,3,5-triazine-2,4-diamine

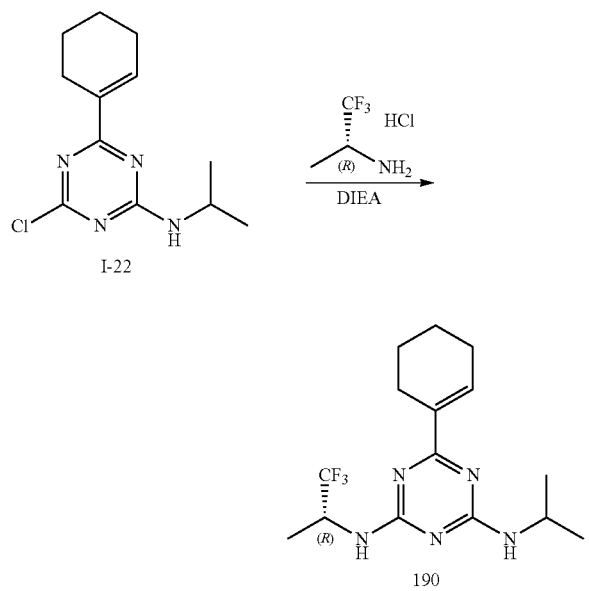

A mixture of Intermediate I-22 (85 mg, 0.33 mmol), (R)-1,1,1-trifluoropropan-2-amine hydrochloride (201 mg, 1.34 mmol) and DIEA (0.47 mL, 2.69 mmol) in 1,4-dioxane (3 mL) was stirred under microwave at 150° C. for 3 hours. After the reaction was completed, the mixture was cooled to room temperature, condensed and purified by flash column chromatography (eluting with PE/EA) to give the title compound as yellow solid (18 mg, yield 14%). MS (m/z): 330.1 [M+H]+

1H NMR (400 MHz, CD3OD): δ 7.32-6.94 (m, 1H), 4.66-4.52 (7, 1H), 4.32-4.02 (m, 1H), 2.52-2.33 (m, 2H), 2.29-2.16 (i, 2H), 1.79-1.60 (i, 4H), 1.40-1.29 (i, 3H), 1.24-1.14 (i, 6H).

The compounds in the below table were prepared according to the procedure of Compound 190 using the corresponding intermediates and reagents under appropriate conditions that will be recognized by POSITA:

| Comp. | Structure | MS (M + H)+ | 1H NMR | Intermediate |
|---|---|---|---|---|
| 191 | 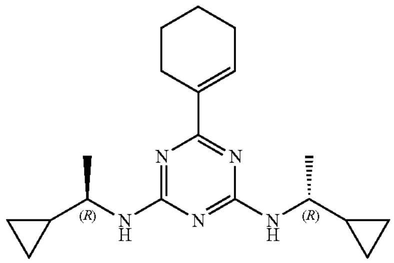 | 328.2 | 1H NMR (400 MHz, CD3OD): δ 7.19-6.85 (m, 1H), 3.60-3.40 (m, 2H), 2.46-2.29 (m, 2H), 2.25-2.16 (m, 2H), 1.73-1.60 (m, 4H), 1.23 (d, J = 6.6 Hz, 6H), 0.97-0.85 (m, 2H), 0.53-0.30 (m, 6H), 0.23-0.15 (m, 2H). | I-23 |
| 192 | 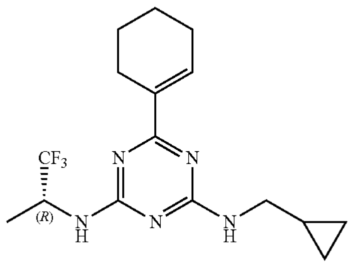 | 342.1 | 1H NMR (400 MHz, CD3OD): δ 7.30-7.02 (m, 1H), 5.08-4.90 (m, 1H), 3.28-3.16 (m, 2H), 2.50-2.34 (m, 2H), 2.28-2.18 (m, 2H), 1.79-1.59 (m, 4H), 1.40-1.31 (m, 3H), 1.15-1.01 (m, 1H), 0.56-0.44 (m, 2H), 0.30-0.19 (m, 2H). | I-24 |
| 193 | 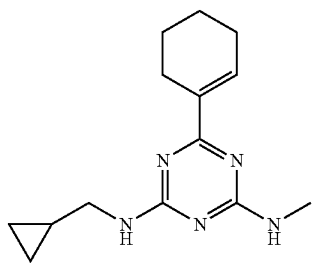 [SMILES: CNc1nc(NCC2CC2)nc(C2=CCCCC2)n1] | 260.1 | 1H NMR (400 MHz, CD3OD): δ 7.25-6.82 (m, 1H), 3.28-3.13 (m, 2H), 2.89 (s, 3H), 2.47-2.33 (m, 2H), 2.27-2.17 (m, 2H), 1.75-1.60 (m, 4H), 1.14-0.99 (m, 1H), 0.53-0.42 (m, 2H), 0.31-0.17 (m, 2H). | I-24 |
| 194 | 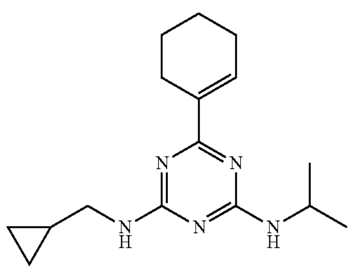 [SMILES: CC(C)Nc1nc(NCC2CC2)nc(C2=CCCCC2)n1] | 288.2 | 1H NMR (400 MHz, CD3OD): δ 7.24-6.85 (m, 1H), 4.27-4.06 (m, 1H), 3.28-3.17 (m, 2H), 2.45-2.35 (m, 2H), 2.26-2.19 (m, 2H), 1.75-1.61 (m, 4H), 1.19 (d, J = 6.5 Hz, 6H), 1.12-1.01 (m, 1H), 0.53-0.43 (m, 2H), 0.29-0.18 (m, 2H). | I-24 |
| 195 | 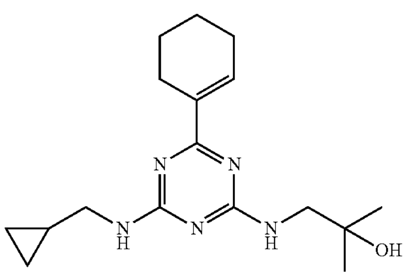 [SMILES: CC(C)(O)CNc1nc(NCC2CC2)nc(C2=CCCCC2)n1] | 318.2 | 1H NMR (400 MHz, CD3OD): δ 7.26-6.89 (m, 1H), 3.45-3.35 (m, 2H), 3.27-3.16 (m, 2H), 2.45-2.35 (m, 2H), 2.26-2.19 (m, 2H), 1.75-1.61 (m, 4H), 1.20 (s, 6H), 1.10-1.02 (m, 1H), 0.52-0.43 (m, 2H), 0.26-0.19 (m, 2H). | I-24 |

Compounds 206 and 207

3-(5-Fluoro-4,6-bis(((R)-1,1,1-trifluoropropan-2-yl)amino)pyrimidin-2-yl)cyclohex-2-en-1-ol and 3-(5-fluoro-2,6-bis(((R)-1,1,1-trifluoropropan-2-yl)amino)pyrimidin-4-yl)cyclohex-2-en-1-ol

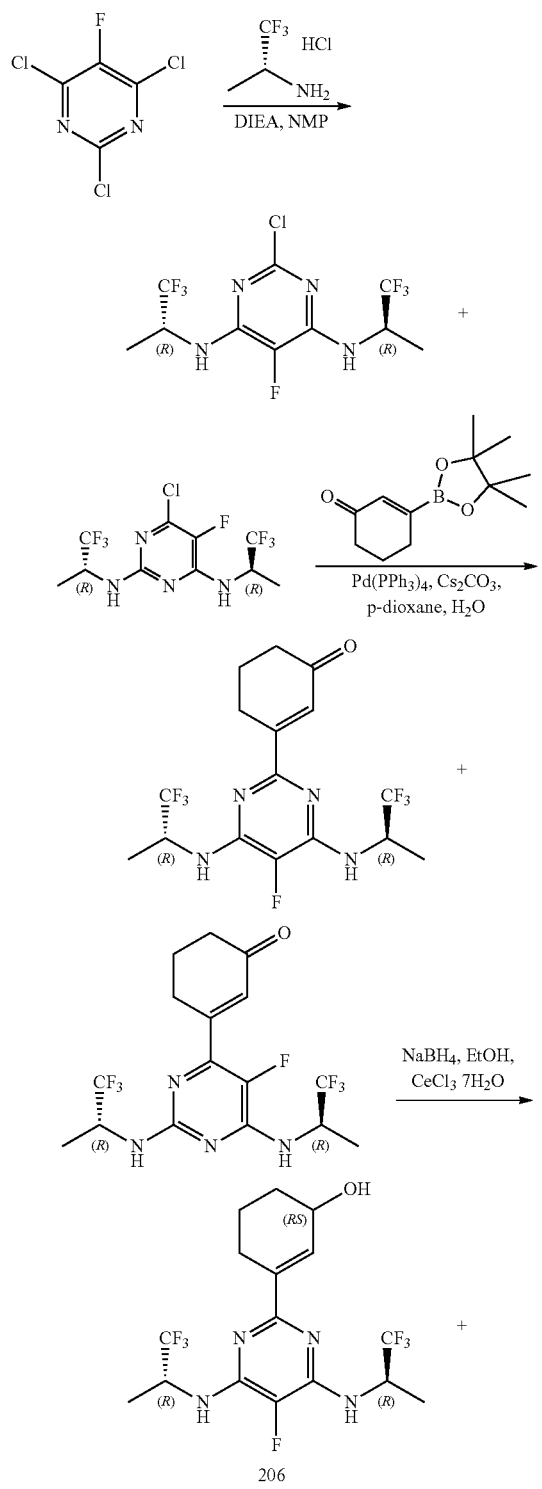

(A) A Mixture of 2-chloro-5-fluoro-$N^4$,$N^6$-bis((R)-1,1,1-trifluoropropan-2-yl)pyrimidine-4,6-diamine and 6-chloro-5-fluoro-$N^2$,$N^4$-bis((R)-1,1,1-trifluoropropan-2-yl)pyrimidine-2,4-diamine Under nitrogen atmosphere, a mixture of 2,4,6-trichloro-5-fluoropyrimidine (1.12 g, 5.6 mmol), (R)-1,1,1-trifluoropropan-2-amine hydrochloride (2.51 g, 16.8 mmol), DIEA (4.22 g, 56 mmol) and N-methylpyrrolidone (5 mL) was stirred under microwave at 200° C. for 1 hour. After cooled to room temperature, the mixture was directly injected into RP-C18 column and purified by flash column chromatography (eluting with gradient water/MeOH=100:0-0:100) to give the product as white solid (80 mg, yield 4.2%). MS (m/z): 354.9 [M+H]$^+$

(B) A mixture of 3-(5-fluoro-4,6-bis(((R)-1,1,1-trifluoropropan-2-yl)amino) pyrimidin-2-yl)cyclohex-2-en-1-one and 3-(5-fluoro-2,6-bis(((R)-1,1,1-trifluoropropan-2-yl)amino) pyrimidin-4-yl)cyclohex-2-en-1-one Under nitrogen atmosphere, a mixture of the product obtained in step (A) (80 mg, 0.23 mmol), 3-(4,4,5,5-tetramethyl-1,3,2-dioxaborolan-2-yl)cyclohex-2-en-1-one (50 mg, 0.23 mmol), Cs$_2$CO$_3$ (150 mg, 0.46 mmol), 1,4-dioxane (5 mL) and water (1.5 mL) was stirred under microwave at 130° C. for 40 minutes. After cooled to room temperature, the mixture was condensed and purified by flash column chromatography (eluting with gradient PE/EA=100:0-0:100) to give the product as white solid (60 mg, yield: 63.2%). MS (m/z): 415.0 [M+H]$^+$

(C) 3-(5-Fluoro-4,6-bis(((R)-1,1,1-trifluoropropan-2-yl)amino)pyrimidin-2-yl) cyclohex-2-en-1-ol and 3-(5-fluoro-2,6-bis(((R)-1,1,1-trifluoropropan-2-yl)amino)pyrimidin-4-yl) cyclohex-2-en-1-ol Compounds 206 and 207 were prepared according to the procedure of Compound 124 using the mixture of 3-(5-fluoro-4,6-bis(((R)-1,1,1-trifluoropropan-2-yl)amino) pyrimidin-2-yl)cyclohex-2-en-1-one and 3-(5-fluoro-2,6-bis (((R)-1,1,1-trifluoro propan-2-yl)amino)pyrimidin-4-yl) cyclohex-2-en-1-one obtained in step (B) and corresponding reagents, and purified by flash column chromatography (eluting with gradient PE/EA=100:0-0:100).

Compound 206, MS (m/z): 417.0 [M+H]$^+$. $^1$H NMR (400 MHz, CD$_3$OD): δ 6.97-6.89 (m, 1H), 5.21-5.03 (m, 2H), 4.38-4.26 (m, 1H), 2.55-2.34 (m, 2H), 1.96-1.82 (m, 2H), 1.68-1.52 (m, 2H), 1.42-1.32 (m, 6H).

Compound 207, MS (m/z): 417.0 [M+H]⁺. ¹H NMR (400 MHz, CD₃OD): δ 6.47-6.40 (m, 1H), 5.10-4.97 (m, 1H), 4.82-4.72 (m, 1H), 4.35-4.26 (m, 1H), 2.50-2.30 (m, 2H), 1.99-1.85 (m, 2H), 1.71-1.56 (m, 2H), 1.38 (d, J=7.1 Hz, 3H), 1.32 (d, J=7.0 Hz, 3H).

The compounds in the below table were prepared according to the procedure described above, using corresponding intermediates and reagents under appropriate conditions that will be recognized by POSITA:

| Comp. | Structure | MS (M + H)⁺ | ¹H NMR | Intermediate |
|---|---|---|---|---|
| 212 | 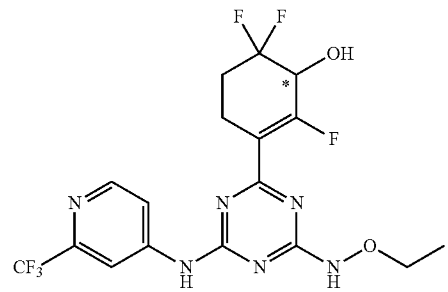 [SMILES: CCONc1nc(Nc2ccnc(C(F)(F)F)c2)nc(C2=C(F)C(O)C(F)(F)CC2)n1] | 451.2 | ¹H NMR (400 MHz, CD₃OD): δ 8.54-8.35 (m, 2H), 7.98-7.78 (m, 1H), 4.37-4.24 (m, 1H), 4.10-3.94 (m, 2H), 2.89-2.72 (m, 1H), 2.66-2.52 (m, 1H), 2.33-2.05 (m, 2H), 1.33-1.24 (m, 3H). | I-93 |
| 213 | 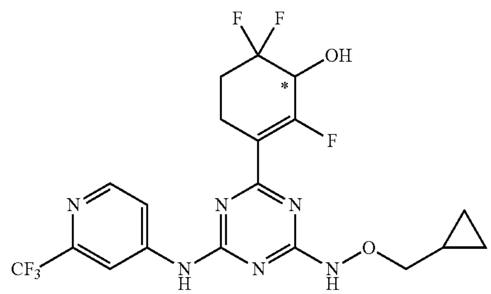 [SMILES: OC1C(F)=C(c2nc(NOCC3CC3)nc(Nc3ccnc(C(F)(F)F)c3)n2)CCC1(F)F] | 477.2 | ¹H NMR (400 MHz, CD₃OD): δ 8.50-8.31 (m, 2H), 8.00-7.88 (m, 1H), 4.41-4.24 (m, 1H), 3.78 (d, J = 7.2 Hz, 2H), 2.90-2.73 (m, 1H), 2.66-2.49 (m, 1H), 2.32-2.05 (m, 2H), 1.26-1.09 (m, 1H), 0.62-0.51 (m, 2H), 0.35-0.25 (m, 2H). | I-94 |
| 214 | 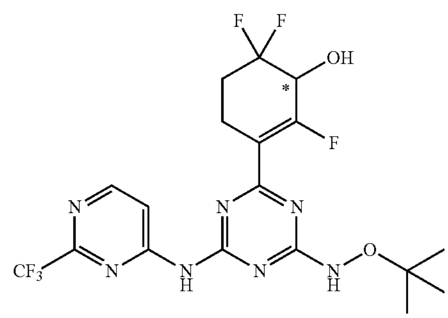 [SMILES: CC(C)(C)ONc1nc(Nc2ccnc(C(F)(F)F)n2)nc(C2=C(F)C(O)C(F)(F)CC2)n1] | 480.0 | ¹H NMR (400 MHz, CD₃OD): δ 8.92-8.76 (m, 1H), 8.73-8.64 (m, 1H), 4.40-4.26 (m, 1H), 2.93-2.77 (m, 1H), 2.71-2.55 (m, 1H), 2.34-2.07 (m, 2H), 1.31 (s, 9H). | I-95 |
| 215 | 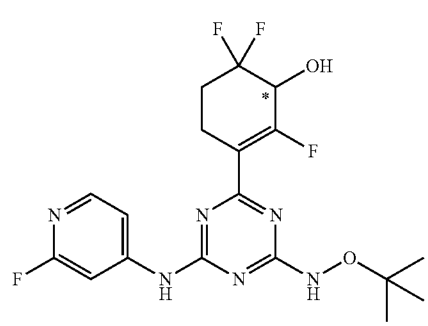 [SMILES: CC(C)(C)ONc1nc(Nc2ccnc(F)c2)nc(C2=C(F)C(O)C(F)(F)CC2)n1] | 429.2 | ¹H NMR (400 MHz, CD₃OD): δ 8.05-7.88 (m, 2H), 7.47-7.43 (m, 1H), 4.34-4.30 (m, 1H), 2.85-2.77 (m, 1H), 2.65-2.55 (m, 1H), 2.31-2.06 (m, 2H), 1.32 (s, 9H). | I-65 |

-continued

| Comp. | Structure | MS (M + H)+ | 1H NMR | Intermediate |
|---|---|---|---|---|
| 216 | 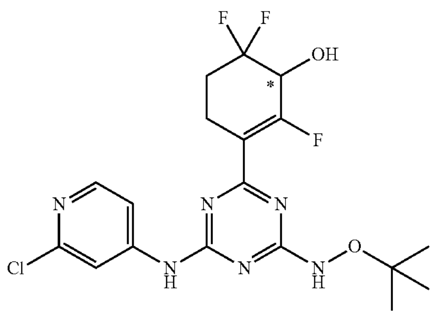 [SMILES: CC(C)(C)ONc1nc(Nc2ccnc(Cl)c2)nc(C2=C(F)C(O)C(F)(F)CC2)n1] | 445.0 | 1H NMR (400 MHz, CD3OD): δ 8.31 (s, 1H), 8.13-8.02 (m, 1H), 7.64-7.47 (m, 1H), 4.38-4.23 (m, 1H), 2.89-2.71 (m, 1H), 2.66-2.50 (m, 1H), 2.32-2.03 (m, 2H), 1.32 (s, 9H). | I-96 |
| 217 | 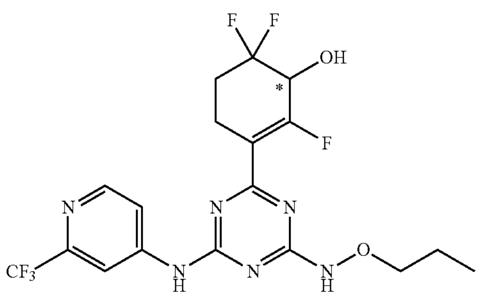 [SMILES: CCCONc1nc(Nc2ccnc(C(F)(F)F)c2)nc(C2=C(F)C(O)C(F)(F)CC2)n1] | 465.2 | 1H NMR (400 MHz, CD3OD): δ 8.61-8.28 (m, 2H), 8.07-7.76 (m, 1H), 4.42-4.16 (m, 1H), 4.03-3.82 (m, 2H), 2.88-2.72 (m, 1H), 2.67-2.50 (m, 1H), 2.31-2.06 (m, 2H), 1.80-1.63 (m, 2H), 1.10-0.90 (m, 3H). | I-97 |
| 218 | 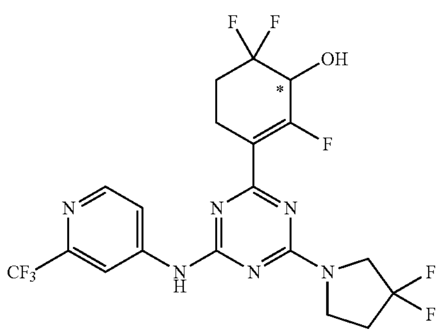 [SMILES: OC1C(F)=C(c2nc(Nc3ccnc(C(F)(F)F)c3)nc(N3CCC(F)(F)C3)n2)CCC1(F)F] | 497.2 | 1H NMR (400 MHz, CD3OD): δ 8.61-8.26 (m, 2H), 7.91-7.74 (m, 1H), 4.45-4.21 (m, 1H), 3.98-3.77 (m, 4H), 2.90-2.75 (m, 1H), 2.65-2.41 (m, 3H), 2.30-2.05 (m, 2H). | I-98 |
| 220 | 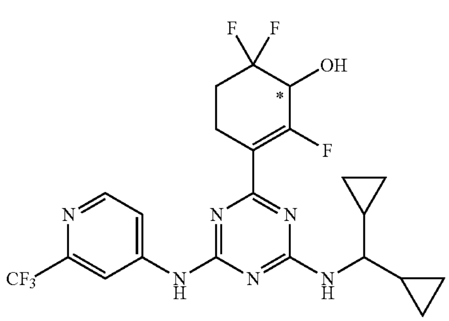 [SMILES: OC1C(F)=C(c2nc(Nc3ccnc(C(F)(F)F)c3)nc(NC(C3CC3)C3CC3)n2)CCC1(F)F] | 501.1 | 1H NMR (400 MHz, CD3OD): δ 8.77-7.63 (m, 2H), 7.68 (s, 1H), 4.39-4.18 (m, 1H), 3.27-3.16 (m, 1H), 2.89-2.45 (m, 2H), 2.33-2.02 (m, 2H), 1.17-0.98 (m, 2H), 0.60-0.47 (m, 2H), 0.44-0.27 (m, 6H). | I-99 |

-continued

| Comp. | Structure | MS (M + H)+ | ¹H NMR | Intermediate |
|---|---|---|---|---|
| 221 | 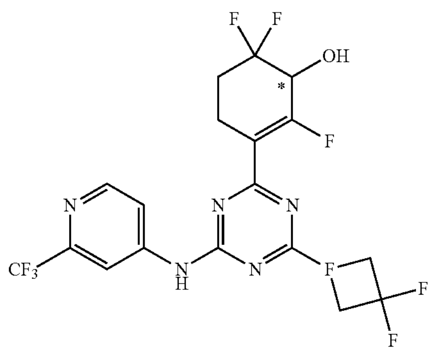 | 483.2 | ¹H NMR (400 MHz, CD₃OD): δ 8.50-8.37 (m, 2H), 7.88-7.80 (m, 1H), 4.60-4.40 (m, 4H), 4.34-4.27 (m, 1H), 2.85-2.75 (m, 1H), 2.65-2.55 (m, 1H), 2.31-2.05 (m, 2H). | I-100 |
| 243 | 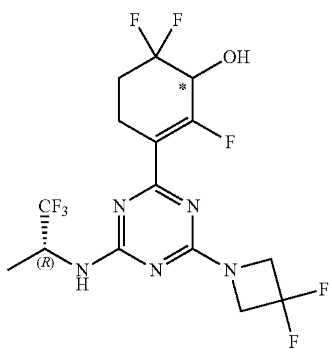 | 434.0 | ¹H NMR (400 MHz, CD₃OD): δ 5.03-4.86 (m, 1H), 4.49-4.34 (m, 4H), 4.30-4.20 (m, 1H), 2.75-2.65 (m, 1H), 2.55-2.45 (m, 1H), 2.27-2.02 (m, 2H), 1.45-1.33 (m, 3H). | I-101 |
| 244 | 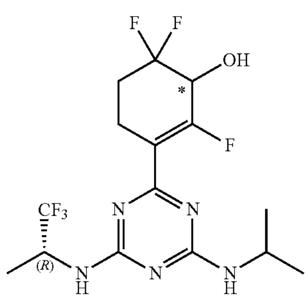 | 400.0 | ¹H NMR (400 MHz, CD₃OD): δ 5.01-4.90 (br, 1H), 4.37-4.20 (m, 1H), 4.19-4.03 (m, 1H), 2.85-2.39 (m, 2H), 2.32-2.02 (m, 2H), 1.43-1.29 (m, 3H), 1.23-1.09 (m, 6H). | I-2 |
| 299 | 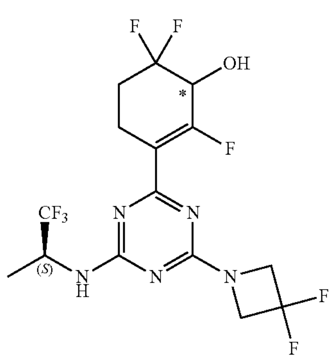 | 434.0 | ¹H NMR (400 MHz, CD₃OD): δ 5.04-4.86 (m, 1H), 4.50-4.34 (m, 4H), 4.31-4.20 (m, 1H), 2.78-2.65 (m, 1H), 2.59-2.44 (m, 1H), 2.29-1.98 (m, 2H), 1.41-1.31 (m, 3H). | I-102 |

-continued

| Comp. | Structure | MS (M + H)+ | 1H NMR | Intermediate |
|---|---|---|---|---|
| 300 | 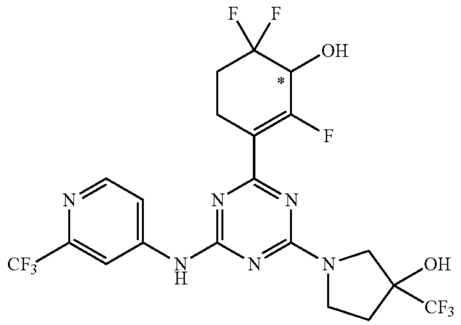 [SMILES: OC1C(F)=C(c2nc(Nc3ccnc(C(F)(F)F)c3)nc(N3CCC(O)(C(F)(F)F)C3)n2)CCC1(F)F] | 545.1 | 1H NMR (400 MHz, CD3OD): δ 8.60-8.47 (m, 1H), 8.43-8.38 (m, 1H), 7.86-7.70 (m, 1H), 4.38-4.23 (m, 1H), 4.01-3.66 (m, 4H), 2.89-2.73 (m, 1H), 2.69-2.51 (m, 1H), 2.41-2.06 (m, 4H). | I-103 |
| 301 | 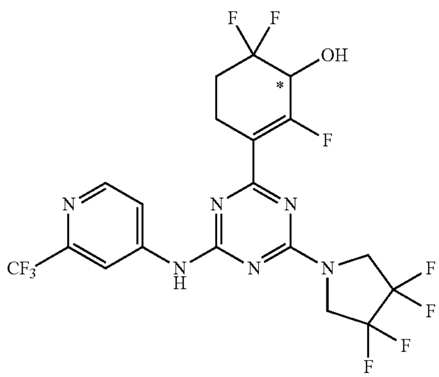 [SMILES: OC1C(F)=C(c2nc(Nc3ccnc(C(F)(F)F)c3)nc(N3CC(F)(F)C(F)(F)C3)n2)CCC1(F)F] | 533.1 | 1H NMR (400 MHz, CD3OD): δ 8.51-8.43 (m, 1H), 8.42-8.38 (m, 1H), 7.91-7.84 (m, 1H), 4.40-4.29 (m, 1H), 4.24-4.12 (m, 4H), 2.93-2.77 (m, 1H), 2.69-2.55 (m, 1H), 2.36-2.06 (m, 2H). | I-104 |

Compounds 197 and 198

3-(4,6-Bis(((R)-1,1,1-trifluoropropan-2-yl)amino)-1,3,5-triazin-2-yl)-2,6,6-trifluorocyclohex-2-en-1-ol, optically pure diastereoisomers

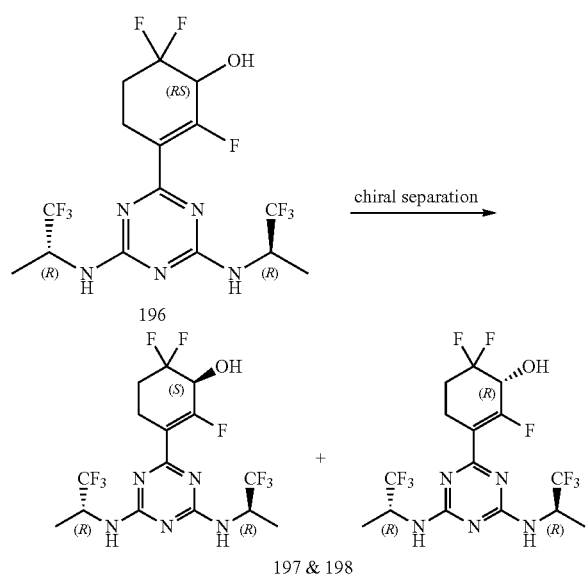

The Compound 196 was resolved by chiral HPLC to provide a pair of optically pure diastereoisomers, Compounds 197 and 198 (Chiral HPLC conditions: Preparation instrument: Shimadzu LC-10AD vp; Column: Daicel AD-H (250 mm*30 mm, 5um); mobile phase: n-heptane/isopropanol=90/10; flow rate: 40 mL/min; column temperature: 40° C.). The first eluent (RT=4.203 min) was concentrated and purified by flash column chromatography (eluting with gradient PE/EA=100:0-0:100) to give a compound named as Compound 197, de %=99.27%, MS (m/z): 454.1 [M+1]+. The second eluent (RT=5.906 min) was concentrated and purified by flash column chromatography (eluting with gradient PE/EA=100:0-0:100) to give a compound named as Compound 198, de %=97.82%, MS (m/z): 454.2 [M+1]+.

Compound 197: 1H NMR (400 MHz, CD3OD): δ 5.00-4.86 (m, 2H), 4.36-4.17 (m, 1H), 2.80-2.65 (m, 1H), 2.58-2.42 (m, 1H), 2.25-2.05 (m, 2H), 1.37-1.31 (m, 6H).

Compound 198: 1H NMR (400 MHz, CD3OD): δ 5.00-4.86 (m, 2H), 4.36-4.17 (m, 1H), 2.80-2.65 (m, 1H), 2.58-2.42 (m, 1H), 2.25-2.05 (m, 2H), 1.37-1.31 (m, 6H).

The compounds in the below table were prepared according to the procedure of Compounds 197 and 198 using the corresponding compounds and under appropriate HPLC conditions (flow rate: 0.5 mL/min; detection wavelength: UV 254 nm):

| Comp. | Structure | MS (M+H)+ | 1H NMR | RT (min) | Purity | Chiral HPLC Condition | Comp. for separation |
|---|---|---|---|---|---|---|---|
| 100 | (structure: (R)-OH cyclohexene with F, pyrimidine, isopropyl-NH, (R)-CF3-CH-NH) + (structure: (S)-OH analog); labeled 100 & 101 | 364.1 | 1H NMR (400 MHz, CD3OD): δ 5.00-4.89 (m, 1H), 4.33-4.24 (m, 1H), 4.21-4.06 (m, 1H), 2.63-2.47 (m, 1H), 2.47 (br, 1H), 1.93-1.71 (m, 3H), 1.70-1.61 (m, 1H), 1.40-1.30 (m, 3H), 1.21-1.15 (m, 6H). | 1.230 | ee% = 100% | Column: OJ-H (0.46 cm I.D. × 15 cm L); Mobile phase: n-heptane/isopropanol (0.1% Et2NH) = 90/10 | 1 |
| 101 | | 364.1 | 1H NMR (400 MHz, CD3OD): δ 5.01-4.90 (m, 1H), 4.34-4.24 (m, 1H), 4.20-4.06 (m, 1H), 2.65-2.48 (m, 1H), 2.23 (m, 1H), 1.92-1.72 (m, 3H), 1.68-1.59 (m, 1H), 1.40-1.31 (m, 3H), 1.14 (m, 6H). | 1.316 | ee% = 100% | | |
| 102 | (structure: (R)-OH cyclohexene with F, pyrimidine, two (R)-CF3-CH-NH groups) + diastereomer; labeled 102 & 103 | 418.0 | 1H NMR (400 MHz, CD3OD): δ 5.03-4.88 (m, 2H), 4.34-4.25 (m, 1H), 2.68-2.51 (m, 1H), 2.41-2.26 (m, 1H), 1.90-1.74 (m, 3H), 1.70-1.58 (m, 1H), 1.37-1.31 (m, 6H). | 1.899 | de% = 100% | Column: AD-H (0.46 cm I.D. × 15 cm L); Mobile phase: n-heptane/isopropanol (0.1% Et2NH) = 80/20 | 2 |
| 103 | | 418.1 | 1H NMR (400 MHz, CD3OD): δ 5.02-4.87 (m, 2H), 4.34-4.24 (m, 1H), 2.64-2.50 (m, 1H), 2.45-2.32 (m, 1H), 1.91-1.71 (m, 3H), 1.69-1.71 (m, 1H), 1.38-1.30 (m, 6H). | 2.263 | de% = 100% | | |

| Comp. | Structure | MS (M + H)⁺ | ¹H NMR | RT (min) | Purity | Chiral HPLC Condition | Comp. for separation |
|---|---|---|---|---|---|---|---|
| 104 | 104 & 105 | 406.3 | ¹H NMR (400 MHz, CD₃OD): δ 4.37-4.22 (m, 3H), 3.02-2.86 (m, 4H), 2.73-2.50 (m, 5H), 2.41-2.25 (m, 1H), 1.91-1.72 (m, 3H), 1.72-1.62 (m, 1H). | 3.608 | ee% = 100% | Column: AD-H (0.46 cm I.D. × 15 cm L); Mobile phase: n-heptane/isopropanol (0.1% EtNH) = 70/30 | 5 |
| 105 | | 406.3 | ¹H NMR (400 MHz, CD₃OD): δ 4.37-4.22 (m, 3H), 3.02-2.86 (m, 4H), 2.73-2.50 (m, 5H), 2.41-2.25 (m, 1H), 1.91-1.72 (m, 3H), 1.72-1.62 (m, 1H). | 3.871 | ee% = 100% | | |
| 106 | 106 & 107 | 432.1 | ¹H NMR (400 MHz, CD₃OD): δ 5.02-4.89 (m, 2H), 4.53-4.41 (m, 1H), 2.77-2.62 (m, 1H), 2.40-2.27 (m, 1H), 2.02-1.83 (m, 3H), 1.74-1.61 (m, 3H), 1.39-1.32 (m, 6H). | 10.540 | de% = 97.79% | Column: AS-H (0.46 cm I.D. × 15 cm L); Mobile phase: n-heptane/isopropanol = 90/10 | 19 |
| 107 | | 432.2 | ¹H NMR (400 MHz, CD₃OD): δ 5.02-4.89 (m, 2H), 4.53-4.41 (m, 1H), 2.77-2.62 (m, 1H), 2.40-2.27 (m, 1H), 2.02-1.83 (m, 3H), 1.74-1.61 (m, 3H), 1.39-1.32 (m, 6H). | 18.120 | de% = 97.84% | | |

| Comp. | Structure | MS (M + H)+ | 1H NMR | RT (min) | Purity | Chiral HPLC Condition | Comp. for separation |
|---|---|---|---|---|---|---|---|
| 108 | (structure, 108 & 109) | 407.1 | 1H NMR (400 MHz, CD3OD): δ 4.38-4.15 (m, 2H), 3.05-2.85 (m, 4H), 2.72-2.48 (m, 5H), 2.40-2.26 (m, 1H), 1.90-1.61 (m, 4H) | 4.596 | de% = 99.8% | Column: AD-H (0.46 cm I.D. × 15 cm L); Mobile phase: n-heptane/isopropanol = 70/30 | |
| 109 | | 407.1 | 1H NMR (400 MHz, CD3OD): δ 4.38-4.15 (m, 2H), 3.05-2.85 (m, 4H), 2.72-2.48 (m, 5H), 2.40-2.26 (m, 1H), 1.90-1.61 (m, 4H). | 4.897 | de% = 99.32% | | |
| 110 | (structure, 110 & 111) | 419.1 | 1H NMR (400 MHz, CD3OD): δ 5.02-4.87 (m, 2H), 2.68-2.51 (m, 1H), 2.44-2.28 (m, 1H), 1.92-1.63 (m, 4H), 1.42-1.30 (m, 6H) | 10.090 | de% = 100% | Column: AD-H (0.46 cm I.D. × 15 cm L); Mobile phase: n-heptane/isopropanol = 90/10 | 18 |
| 111 | | 419.1 | 1H NMR (400 MHz, CD3OD): δ 5.02-4.87 (m, 2H), 2.68-2.51 (m, 1H), 2.44-2.28 (m, 1H), 1.92-1.63 (m, 4H), 1.42-1.30 (m, 6H) | 16.800 | de% = 100% | | |

| Comp. | Structure | MS (M+H)⁺ | ¹H NMR | RT (min) | Purity | Chiral HPLC Condition | Comp. for separation |
|---|---|---|---|---|---|---|---|
| 112 | (structure, 112 & 113) | 421.1 | ¹H NMR (400 MHz, CD₃OD): δ 5.00-4.87 (m, 2H), 2.63-2.53 (m, 1H), 2.37-2.26 (m, 1H), 1.81-1.69 (m, 1H), 1.67-1.60 (m, 1H), 1.37-1.31 (m, 6H) | 5.500 | de% = 100% | Column: AD-H (0.46 cm I.D. × 15 cm L); Mobile phase: n-heptane/isopropanol = 80/20 | 83 |
| 113 | | 421.1 | ¹H NMR (400 MHz, CD₃OD): δ 5.00-4.87 (m, 2H), 2.63-2.53 (m, 1H), 2.37-2.26 (m, 1H), 1.81-1.69 (m, 1H), 1.67-1.60 (m, 1H), 1.37-1.31 (m, 6H) | 7.420 | de% = 97.54% | | |
| 114 | (structure, 114 & 115) | 415.1 | ¹H NMR (400 MHz, CD₃OD): δ 4.98-4.89 (m, 1H), 4.35-4.13 (m, 1H), 3.02-2.81 (m, 2H), 2.75-2.46 (m, 3H), 2.44-2.24 (m, 1H), 1.82-1.71 (m, 1H), 1.69-1.58 (m, 1H), 1.38-1.28 (m, 3H) | 5.960 | de% = 100% | Column: AD-H (0.46 cm I.D. × 15 cm L); Mobile phase: n-heptane/isopropanol = 80/20 | 90 |
| 115 | | 415.1 | ¹H NMR (400 MHz, CD₃OD): δ 4.98-4.89 (m, 1H), 4.35-4.13 (m, 1H), 3.02-2.81 (m, 2H), 2.75-2.46 (m, 3H), 2.44-2.24 (m, 1H), 1.82-1.71 (m, 1H), 1.58-1.28 (m, 3H) | 7.800 | de% = 98.30% | | |

| Comp. | Structure | MS (M + H)+ | 1H NMR | RT (min) | Purity | Chiral HPLC Condition | Comp. for separation |
|---|---|---|---|---|---|---|---|
| 116 | 116 & 117 | 409.1 | 1H NMR (400 MHz, CD3OD): δ 4.36-4.14 (m, 2H), 2.98-2.85 (m, 4H), 2.67-2.46 (m, 5H), 2.39-2.22 (m, 1H), 1.82-1.71 (m, 1H), 1.68-1.57 (m, 1H) | 10.170 | de% = 100% | Column: AD-H (0.46 cm I.D. × 15 cm L); Mobile phase: n-heptane/isopropanol = 80/20 | 91 |
| 117 | | 409.1 | 1H NMR (400 MHz, CD3OD): δ 4.36-4.14 (m, 2H), 2.98-2.85 (m, 4H), 2.67-2.46 (m, 5H), 2.39-2.22 (m, 1H), 1.82-1.71 (m, 1H), 1.68-1.57 (m, 1H) | 13.590 | de% = 99.16% | | |
| 118 | 118 & 119 | 364.1 | 1H NMR (400 MHz, CD3OD): δ 5.00-4.89 (m, 1H), 4.36-4.25 (m, 1H), 4.19-4.08 (m, 1H), 2.68-2.50 (m, 1H), 2.40-2.24 (m, 1H), 1.96-1.57 (m, 4H), 1.41-1.29 (m, 3H), 1.23-1.12 (m, 6H) | 1.334 | de% = 97.56% | Column: AS-H (0.46 cm I.D. × 15 cm L); Mobile phase: n-heptane/isopropanol = 90/10 | 33 |
| 119 | | 364.1 | 1H NMR (400 MHz, CD3OD): δ 5.01-4.89 (m, 1H), 4.32-4.25 (m, 1H), 4.20-4.07 (m, 1H), 2.64-2.48 (m, 1H), 2.42-2.26 (m, 1H), 1.93-1.59 (m, 4H), 1.38-1.31 (m, 3H), 1.22-1.15 (m, 6H) | 1.403 | de% = 100% | | |

| Comp. | Structure | MS (M + H)+ | 1H NMR | RT (min) | Purity | Chiral HPLC Condition | Comp. for separation |
|---|---|---|---|---|---|---|---|
| 120 | 120 & 121 | 412.0 | 1H NMR (400 MHz, CD3OD): δ 5.05-4.89 (m, 1H), 4.41-4.13 (m, 2H), 3.08-2.80 (m, 2H), 2.78-2.24 (m, 4H), 2.01-1.60 (m, 4H), 1.47-1.24 (m, 3H) | 2.589 | de% = 100% | Column: OJ-H (0.46 cm I.D. × 25 cm L); Mobile phase: n-heptane/isopropanol (0.1% Et2NH) = 90/10 | 31 |
| 121 | | 412.0 | 1H NMR (400 MHz, CD3OD): δ 5.07-4.88 (m, 1H), 4.39-4.13 (m, 2H), 3.06-2.83 (m, 2H), 2.77-2.23 (m, 4H), 1.95-1.60 (m, 4H), 1.45-1.28 (m, 3H) | 3.189 | de% = 100% | | |
| 146 | 146 & 147 | 346.1 | 1H NMR (400 MHz, CD3OD): δ 7.21-6.90 (m, 1H), 5.03-4.92 (m, 1H), 4.36-4.26 (m, 1H), 4.22-4.07 (m, 1H), 2.48-2.34 (m, 2H), 1.96-1.83 (m, 2H), 1.66-1.54 (m, 2H), 1.37-1.31 (m, 3H), 1.26-1.13 (m, 6H) | 1.526 | de% = 100% | Column: AS-H (0.46 cm I.D. × 15 cm L); Mobile phase: n-heptane/isopropanol = 80/20 | 124 |
| 147 | | 346.1 | 1H NMR (400 MHz, CD3OD): δ 7.18-6.93 (m, 1H), 5.06-4.91 (m, 1H), 4.37-4.25 (m, 1H), 4.24-4.06 (m, 1H), 2.51-2.28 (m, 2H), 1.98-1.79 (m, 2H), 1.69-1.49 (m, 2H), 1.38-1.30 (m, 3H), 1.22-1.15 (m, 6H) | 1.995 | de% = 99.774% | | |

| Comp. | Structure | MS (M + H)+ | 1H NMR | RT (min) | Purity | Chiral HPLC Condition | Comp. for separation |
|---|---|---|---|---|---|---|---|
| 148 | 148 & 149 | 400.1 | 1H NMR (400 MHz, CD3OD): δ 7.22-7.03 (m, 1H), 5.06-4.87 (m, 2H), 4.36-4.26 (m, 1H), 2.50-2.34 (m, 2H), 1.99-1.81 (m, 2H), 1.68-1.50 (m, 2H), 1.38-1.31 (m, 6H) | 1.169 | de% = 100% | Column: AS-H (0.46 cm I.D. × 15 cm L); Mobile phase: n-heptane/ isopropanol (0.1% Et2NH) = 80/20 | 126 |
| 149 | | 400.1 | 1H NMR (400 MHz, CD3OD): δ 7.22-7.03 (m, 1H), 5.06-4.87 (m, 2H), 4.36-4.26 (m, 1H), 2.50-2.34 (m, 2H), 1.99-1.81 (m, 2H), 1.68-1.50 (m, 2H), 1.38-1.31 (m, 6H) | 2.443 | de% = 100% | | |
| 150 | 150 & 151 | 388.1 | 1H NMR (400 MHz, CD3OD): δ 7.22-6.93 (m, 1H), 4.36-4.19 (m, 3H), 2.87-2.69-2.50 (m, 4H), 2.45-2.34 (m, 2H), 1.97-1.80 (m, 2H), 1.67-1.51 (m, 2H) | 2.492 | ee% = 100% | Column: AS-H (0.46 cm I.D. × 15 cm L); Mobile phase: n-heptane/ isopropanol = 70/30 | 127 |
| 151 | | 388.1 | 1H NMR (400 MHz, CD3OD): δ 7.22-6.93 (m, 1H), 4.36-4.19 (m, 3H), 2.87-2.69-2.50 (m, 4H), 2.45-2.34 (m, 2H), 1.97-1.80 (m, 2H), 1.67-1.51 (m, 2H) | 3.658 | ee% = 100% | | |

| Comp. | Structure | MS (M + H)+ | 1H NMR | RT (min) | Purity | Chiral HPLC Condition | Comp. for separation |
|---|---|---|---|---|---|---|---|
| 222 | 222 & 223 | 431.0 | 1H NMR (400 MHz, CD3OD): δ 8.93-8.78 (m, 2H), 7.98-7.93 (m, 1H), 7.84-7.77 (m, 1H), 4.37-4.30 (m, 1H), 2.70-2.61 (m, 1H), 2.48-2.36 (m, 1H), 1.92-1.86 (m, 2H), 1.85-1.76 (m, 1H), 1.73-1.65 (m, 1H), 1.33 (s, 9H) | 5.097 | ee% = 99.89% | Column: IC-H (0.46 cm I.D. x 15 cm L); Mobile phase: n-heptane/isopropanol = 60/40 | 34 |
| 223 | | 431.0 | 1H NMR (400 MHz, CD3OD): δ 8.93-8.75 (m, 2H), 7.98-7.93 (m, 1H), 7.83-7.77 (m, 1H), 4.37-4.30 (m, 1H), 2.71-2.61 (m, 1H), 2.48-2.36 (m, 1H), 1.92-1.86 (m, 2H), 1.85-1.77 (m, 1H), 1.73-1.66 (m, 1H), 1.33 (s, 9H) | 6.651 | ee% = 97.67% | | |
| 236 | 236 & 237 | 442.2 | 1H NMR (400 MHz, CD3OD): δ 4.41-4.08 (m, 3H), 3.01-2.82 (m, 4H), 2.74-2.43 (m, 6H), 2.25-2.02 (m, 2H) | 4.121 | ee% = 100% | Column: AD-H (0.46 cm I.D. x 15 cm L); Mobile phase: n-heptane/isopropanol (0.1% Et2NH) = 80/20 | 203 |
| 237 | | 442.2 | 1H NMR (400 MHz, CD3OD): δ 4.41-4.08 (m, 3H), 3.01-2.82 (m, 4H), 2.74-2.43 (m, 6H), 2.25-2.02 (m, 2H) | 4.453 | ee% = 100% | | |

| Comp. | Structure | MS (M+H)+ | 1H NMR | RT (min) | Purity | Chiral HPLC Condition | Comp. for separation |
|---|---|---|---|---|---|---|---|
| 249 | 249 & 250 | 455.2 | 1H NMR (400 MHz, CD3OD): δ 5.03-4.87 (m, 2H), 2.82-2.66 (m, 1H), 2.62-2.45 (m, 1H), 2.27-2.02 (m, 2H), 1.40-1.29 (m, 6H) | 2.293 | de% = 100% | Column: AD-H (0.46 cm I.D. × 15 cm L); Mobile phase: n-heptane/isopropanol (0.1% Et2NH) = 80/20 | 211 |
| 250 | | 455.2 | 1H NMR (400 MHz, CD3OD): δ 5.03-4.87 (m, 2H), 2.82-2.66 (m, 1H), 2.62-2.45 (m, 1H), 2.27-2.02 (m, 2H), 1.40-1.29 (m, 6H) | 2.898 | de% = 100% | | |
| 251 | 251 & 252 | 398.0 | 1H NMR (400 MHz, CD3OD): δ 5.14-4.92 (m, 1H), 4.33-4.19 (m, 1H), 2.81-2.60 (m, 1H), 2.60-2.41 (m, 1H), 2.25-2.05 (m, 2H), 1.38-1.32 (m, 3H), 0.77-0.69 (m, 2H), 0.55-0.48 (m, 2H) | 2.179 | de% = 100% | Column: OJ-H (0.46 cm I.D. × 15 cm L); Mobile phase: n-heptane/isopropanol = 90/10 | 238 |
| 252 | | 398.0 | 1H NMR (400 MHz, CD3OD): δ 5.04-4.94 (m, 1H), 4.32-4.19 (m, 1H), 2.83-2.61 (m, 2H), 2.58-2.42 (m, 1H), 2.23-2.05 (m, 2H), 1.39-1.32 (m, 3H), 0.77-0.69 (m, 2H), 0.57-0.47 (m, 2H) | 2.465 | de% = 99.76% | | |

| Comp. | Structure | MS (M + H)+ | 1H NMR | RT (min) | Purity | Chiral HPLC Condition | Comp. for separation |
|---|---|---|---|---|---|---|---|
| 253 | 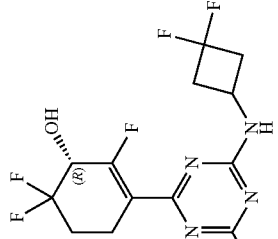 253 & 254 | 448.0 | 1H NMR (400 MHz, CD3OD): δ 5.04-4.89 (m, 1H), 4.38-4.16 (m, 2H), 3.05-2.85 (m, 2H), 2.81-2.43 (m, 4H), 2.31-1.96 (m, 2H), 1.42-1.30 (m, 3H) | 3.225 | de% = 100% | Column: OJ-H (0.46 cm I.D. × 15 cm L); Mobile phase: n-heptane/ethanol = 80/20 | 239 |
| 254 | | 448.0 | 1H NMR (400 MHz, CD3OD): δ 5.05-4.92 (m, 1H), 4.34-4.14 (m, 2H), 3.02-2.85 (m, 2H), 2.80-2.45 (m, 4H), 2.29-2.01 (m, 2H), 1.43-1.29 (m, 3H) | 3.790 | de% = 100% | | |
| 255 | 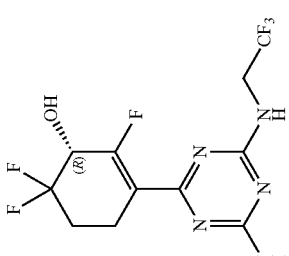 255 & 256 | 440.0 | 1H NMR (400 MHz, CD3OD): δ 4.97-4.83 (m, 1H), 4.29-3.90 (m, 3H), 2.58-2.51 (m, 1H), 2.37 (m, 1H), 1.93-1.37 (m, 3H) | 3.119 | de% = 100% | Column: OJ-H (0.46 cm I.D. × 15 cm L); Mobile phase: n-heptane/isopropanol = 80/20 | 245 |
| 256 | | 440.0 | 1H NMR (400 MHz, CD3OD): δ 5.03-4.82 (m, 1H), 4.27-3.84 (m, 3H), 2.75-2.58 (m, 1H), 2.52-2.35 (m, 1H), 2.21-1.95 (m, 2H), 1.39-1.23 (m, 3H) | 3.644 | de% = 100% | | |

| Comp. | Structure | MS (M + H)+ | 1H NMR | RT (min) | Purity | Chiral HPLC Condition | Comp. for separation |
|---|---|---|---|---|---|---|---|
| 257 | 257 & 258 | 400.0 | 1H NMR (400 MHz, CD3OD): δ 4.90-4.81 (m, 1H), 4.24-4.11 (m, 1H), 3.33-3.14 (m, 2H), 2.70-2.55 (m, 1H), 2.48-2.34 (m, 1H), 2.17-2.96 (m, 2H), 1.56-1.44 (m, 2H), 1.29-1.23 (m, 3H), 0.88-0.80 (m, 3H) | 3.436 | de% = 99.24% | Column: AD-H (0.46 cm I.D. × 15 cm L); Mobile phase: n-heptane/ isopropanol = 80/20 | 248 |
| 258 | | 400.0 | 1H NMR (400 MHz, CD3OD): δ 4.90-4.83 (m, 1H), 4.25-4.10 (m, 1H), 3.34-3.13 (m, 2H), 2.70-2.54 (m, 1H), 2.54-2.33 (m, 1H), 2.19-1.96 (m, 2H), 1.56-1.44 (m, 2H), 1.29-1.22 (m, 3H), 0.89-0.81 (m, 3H) | 4.005 | de% = 99.74% | | |
| 262 | 262 & 263 | 447.9 | 1H NMR (400 MHz, CD3OD): δ 5.04-4.95 (m, 1H), 4.42-4.14 (m, 2H), 2.87 (m, 2H), 2.84-2.45 (m, 4H), 2.31-2.06 (m, 2H), 1.45-1.33 (m, 3H) | 3.388 | de% = 100% | Column: AD-H (0.46 cm I.D. × 15 cm L); Mobile phase: n-heptane/ isopropanol = 80/20 | 259 |
| 263 | | 448.0 | 1H NMR (400 MHz, CD3OD): δ 4.92-4.83 (m, 1H), 4.31-4.04 (m, 2H), 2.94-2.73 (m, 2H), 2.72-2.34 (m, 4H), 2.18-1.91 (m, 2H), 1.32-1.21 (m, 3H) | 3.968 | de% = 99.48% | | |

| Comp. | Structure | MS (M+H)⁺ | ¹H NMR | RT (min) | Purity | Chiral HPLC Condition | Comp. for separation |
|---|---|---|---|---|---|---|---|
| 264 | (264 & 265) | 398.0 | ¹H NMR (400 MHz, CD₃OD): δ 5.00-4.83 (m, 1H), 4.26-4.09 (m, 1H), 2.73-2.53 (m, 2H), 2.53-2.34 (m, 1H), 2.17-1.94 (m, 2H), 1.31-1.22 (m, 3H), 0.70-0.58 (m, 2H), 0.47-0.39 (m, 2H) | 3.524 | de% = 99.56% | Column: AD-H (0.46 cm I.D. × 15 cm L); Mobile phase: n-heptane/isopropanol = 80/20 | 260 |
| 265 | | 398.0 | ¹H NMR (400 MHz, CD₃OD): δ 5.03-4.83 (m, 1H), 4.26-4.10 (m, 1H), 2.78-2.54 (m, 2H), 2.52-2.32 (m, 1H), 2.19-1.94 (m, 2H), 1.32-1.22 (m, 3H), 0.71-0.53 (m, 2H), 0.51-0.35 (m, 2H) | 3.737 | de% = 99.58% | | |
| 272 | (272 & 273) | 394.1 | ¹H NMR (400 MHz, CD₃OD): δ 4.36-4.09 (m, 3H), 3.02-2.87 (m, 2H), 2.79-2.43 (m, 4H), 2.26-2.04 (m, 2H), 1.28-1.15 (m, 6H) | 4.176 | ee% = 100% | Column: AD-H (0.46 cm I.D. × 15 cm L); Mobile phase: n-heptane/isopropanol = 70/30 | 261 |
| 273 | | 394.0 | ¹H NMR (400 MHz, CD₃OD): δ 4.36-4.09 (m, 3H), 3.02-2.87 (m, 2H), 2.79-2.43 (m, 4H), 2.26-2.04 (m, 2H), 1.15 (m, 6H) | 4.696 | ee% = 100% | | |

| Comp. | Structure | MS (M + H)+ | 1H NMR | RT (min) | Purity | Chiral HPLC Condition | Comp. for separation |
|---|---|---|---|---|---|---|---|
| 285 | 285 & 286 | 479.2 | 1H NMR (400 MHz, CD3OD): δ 8.67-8.30 (m, 2H), 8.06-7.80 (m, 1H), 4.45-4.23 (m, 1H), 2.93-2.75 (m, 1H), 2.69-2.50 (m, 1H), 2.33-2.06 (m, 2H), 1.20 (m, 9H) | 3.399 | ee% = 100% | Column: AD-H (0.46 cm I.D. × 15 cm L); Mobile phase: n-heptane/isopropanol = 70/30 | 275 |
| 286 | | 479.2 | 1H NMR (400 MHz, CD3OD): δ 8.67-8.30 (m, 2H), 8.06-7.80 (m, 1H), 4.45-4.23 (m, 1H), 2.93-2.75 (m, 1H), 2.69-2.50 (m, 1H), 2.33-2.06 (m, 2H), 1.20 (m, 9H) | 4.089 | ee% = 100% | | |
| 287 | 287 & 288 | 480.2 | 1H NMR (400 MHz, CD3OD): δ 8.67-8.32 (m, 2H), 8.08-7.80 (m, 1H), 2.91-2.75 (m, 1H), 2.69-2.52 (m, 1H), 2.32-2.08 (m, 2H), 1.42-1.26 (m, 9H) | 3.400 | ee% = 100% | Column: AD-H (0.46 cm I.D. × 15 cm L); Mobile phase: n-heptane/isopropanol = 70/30 | 276 |
| 288 | | 480.2 | 1H NMR (400 MHz, CD3OD): δ 8.67-8.32 (m, 2H), 8.08-7.80 (m, 1H), 2.69-2.52 (m, 1H), 2.32-2.08 (m, 2H), 1.42-1.26 (m, 9H) | 4.086 | ee% = 100% | | |

| Comp. | Structure | MS (M + H)+ | 1H NMR | RT (min) | Purity | Chiral HPLC Condition | Comp. for separation |
|---|---|---|---|---|---|---|---|
| 289 | 289 & 290 | 358.2 | 1H NMR (400 MHz, CD3OD): δ 5.00-4.92 (m, 1H), 4.38-4.18 (m, 1H), 2.80-2.61 (m, 1H), 2.61-2.44 (m, 1H), 2.31-2.10 (m, 2H), 1.50-1.23 (m, 3H) | 3.506 | de% = 100% | Column: AD-H (0.46 cm I.D. × 15 cm L); Mobile phase: n-heptane/isopropanol = 80/20 | 280 |
| 290 | | 358.1 | 1H NMR (400 MHz, CD3OD): δ 5.00-4.92 (m, 1H), 4.38-4.18 (m, 1H), 2.80-2.61 (m, 1H), 2.61-2.44 (m, 1H), 2.31-2.10 (m, 2H), 1.50-1.23 (m, 3H) | 3.754 | de% = 100% | | |
| 291 | 291 & 292 | 436.2 | 1H NMR (400 MHz, CD3OD): δ 7.22-6.87 (m, 1H), 5.10-4.91 (m, 2H), 4.49-4.21 (m, 1H), 2.90-2.54 (m, 2H), 2.34-1.98 (m, 2H), 1.50-1.20 (m, 6H) | 2.376 | de% = 100% | Column: AD-H (0.46 cm I.D. × 15 cm L); Mobile phase: n-heptane/isopropanol = 80/20 | 281 |
| 292 | | 436.2 | 1H NMR (400 MHz, CD3OD): δ 7.22-6.87 (m, 1H), 5.10-4.91 (m, 2H), 4.49-4.21 (m, 1H), 2.90-2.54 (m, 2H), 2.34-1.98 (m, 2H), 1.50-1.20 (m, 6H) | 3.321 | de% = 100% | | |

Example 3 Fluorescent Determination of IDH2-R140Q Cell Activity

Materials:

U87MGR140Q cells: U87MG cells were purchased from ATCC cell bank and then transfected with plasmid containing IDH2-R140Q mutation, and monoclonal cells stably expressing the R140Q mutation were isolated for experiments. The cells were cultured in MEM medium containing 10% FBS.

96-well plate a: Beckman Dickinson, Catalog No. 353072;

96-well plate b: Thermo, Catalog No. 249952;

96-well plate c: Greiner, Catalog No. 675076.

Solution Preparation:

Enzyme reaction solution: 1 mM nicotinamide adenine dinucleotide (NAD), 0.6 ng/μL D-2-hydroxyglutarate dehydrogenase (D2HGDH), 0.8 U/mL lipoamidase dehydrogenase (Diaphorase) and 60 μM Resazurin in 40 mM Tris.HCl pH 8.8 assay buffer.

Standard curve stock solution: The standard of 2-HG sodium salt was serially diluted in serum-free MEM medium to make a standard curve stock solution. The final gradient concentrations are: 500 μM, 167 μM, 56 μM, 18.5 μM, 6 μM, 2 μM, 0.7 μM, 0.2 μM.

Methods:

100 μL of U87MGR140Q cells were seeded at a density of 6×10$^4$/mL per well in a 96-well plate a. The plate was incubated at 37° C. with 5% $CO_2$ overnight, then 10 μL per well of test compound solution diluted in serum-free MEM (final concentration of test compound: 10 μM, 3.3 μM, 1.1 μM, 0.37 μM, 0.12 μM, 0.041 μM, 0.014 μM and 0.005 μM, final DMSO concentration is 0.5%) or 10 μL of control solution (serum-free MEM medium containing 0.5% DMSO in final concentration) was added and incubated for 72 hours.

From each well of 96-well plate a, 50 μL of the culture supernatant was transferred to the corresponding well of 96-well plate b; at the same time, 50 μL of standard curve stocking solution was added to other wells of 96-well plate b. Then 10 μl of 360 mM hydrochloric acid was added to all the wells. After shaking and mixing, the plate was placed on ice for 10 minutes, and then 10 μl of 420 mM Tris-base was added. After shaking and mixing, the plate was placed on ice for additional 5 minutes. Then the plate was centrifuged at 2500 rpm for 10 minutes.

After centrifuging, from each well of 96-well plate b, 20 μL of the supernatant was transferred to 96-well plate c. An additional 80 μL of the enzyme reaction solution was added to each well and incubated at 25° C. for 90 minutes.

Detection:

The plate c was measured on Tecan Infinite F500 Reader instrument at 544 nm excitation and 590 nm emission. A standard curve of the fluorescence value vs. the corresponding 2-HG concentration was made, and the 2-HG concentration corresponding to each concentration point of the compound was calculated, then the inhibition ratio was calculated, and the data was analyzed using XLfit5 (ID Business Solutions Limited) software to obtain the $IC_{50}$ value.

The inhibition ratio was calculated as follows:

Inhibition Ratio (IH %)=(1-2-HG concentration of test compound treated cells/2-HG concentration of control cells)×100%.

The followings are the activity values of some of the compounds of the invention determined in this example.

| Compound | $IC_{50}$ (μM) |
|---|---|
| 1 | 0.097 |
| 2 | 0.137 |
| 3 | 0.866 |
| 4 | 0.080 |
| 5 | 0.093 |
| 6 | 0.115 |
| 7 | 0.087 |
| 8 | 0.216 |
| 9 | 0.571 |
| 10 | 0.113 |
| 11 | 0.284 |
| 12 | 0.199 |
| 13 | 0.373 |
| 14 | 0.230 |
| 15 | 0.259 |
| 16 | 0.326 |
| 17 | 1.616 |
| 18 | 0.110 |
| 19 | 0.083 |
| 20 | 0.232 |
| 21 | 0.099 |
| 22 | 0.336 |
| 23 | 0.192 |
| 24 | 0.197 |
| 25 | 0.665 |
| 27 | 0.148 |
| 28 | 0.123 |
| 29 | 0.177 |
| 30 | 0.228 |
| 31 | 0.110 |
| 32 | 0.080 |
| 34 | 0.145 |
| 35 | 0.591 |
| 36 | 0.181 |
| 37 | 1.911 |
| 38 | 1.619 |
| 39 | 0.164 |
| 40 | 0.106 |
| 41 | 0.297 |
| 42 | 0.152 |
| 43 | 0.328 |
| 44 | 3.149 |
| 47 | 0.059 |
| 49 | 0.210 |
| 50 | 0.072 |
| 51 | 0.125 |
| 52 | 0.229 |
| 53 | 0.131 |
| 54 | 0.015 |
| 55 | 0.103 |
| 56 | 0.093 |
| 57 | 2.180 |
| 58 | 0.169 |
| 59 | 0.221 |
| 60 | 0.590 |
| 61 | 0.170 |
| 62 | 1.343 |
| 64 | 1.628 |
| 65 | 0.152 |
| 67 | 2.374 |
| 68 | 0.435 |
| 69 | 0.173 |
| 70 | 0.112 |
| 71 | 0.050 |
| 72 | 0.042 |
| 73 | 0.064 |
| 74 | 0.034 |
| 75 | 0.218 |
| 78 | 0.069 |
| 79 | 0.106 |
| 80 | 0.079 |
| 81 | 0.099 |
| 82 | 0.075 |
| 83 | 0.203 |
| 84 | 0.048 |
| 85 | 0.035 |
| 86 | 0.021 |
| 87 | 0.205 |
| 89 | 0.057 |

-continued

| Compound | IC$_{50}$ (μM) |
|---|---|
| 90 | 0.065 |
| 91 | 0.058 |
| 92 | 0.143 |
| 94 | 0.131 |
| 95 | 0.043 |
| 96 | 0.675 |
| 97 | 0.052 |
| 98 | 0.344 |
| 99 | 0.553 |
| 100 | 2.905 |
| 101 | 0.080 |
| 102 | 0.051 |
| 103 | 1.002 |
| 104 | 2.079 |
| 105 | 0.040 |
| 106 | 0.106 |
| 107 | 0.554 |
| 108 | 2.226 |
| 109 | 0.057 |
| 110 | 0.070 |
| 111 | 2.257 |
| 112 | 0.098 |
| 113 | 2.059 |
| 114 | 1.716 |
| 115 | 0.059 |
| 116 | 2.620 |
| 117 | 0.095 |
| 118 | 0.106 |
| 119 | 3.393 |
| 120 | 2.397 |
| 121 | 0.068 |
| 122 | 1.340 |
| 124 | 0.137 |
| 125 | 1.671 |
| 126 | 0.086 |
| 127 | 0.064 |
| 128 | 0.092 |
| 129 | 0.171 |
| 130 | 0.067 |
| 131 | 2.798 |
| 133 | 0.174 |
| 134 | 0.100 |
| 135 | 0.336 |
| 136 | 0.296 |
| 137 | 1.540 |
| 138 | 0.504 |
| 139 | 2.505 |
| 140 | 2.390 |
| 144 | 2.748 |
| 146 | 0.999 |
| 147 | 0.067 |
| 148 | 1.558 |
| 149 | 0.177 |
| 150 | 0.541 |
| 151 | 0.039 |
| 152 | 0.300 |
| 153 | 0.099 |
| 154 | 0.202 |
| 155 | 0.319 |
| 156 | 0.657 |
| 157 | 0.141 |
| 158 | 0.278 |
| 159 | 0.205 |
| 160 | 0.180 |
| 162 | 0.177 |
| 163 | 0.162 |
| 164 | 0.176 |
| 165 | 0.198 |
| 166 | 0.180 |
| 167 | 0.327 |
| 169 | 0.738 |
| 170 | 1.382 |
| 171 | 0.268 |
| 172 | 0.344 |
| 174 | 0.096 |
| 175 | 0.291 |
| 176 | 0.612 |

-continued

| Compound | IC$_{50}$ (μM) |
|---|---|
| 177 | 0.046 |
| 178 | 0.934 |
| 179 | 0.598 |
| 180 | 0.531 |
| 181 | 0.177 |
| 182 | 1.231 |
| 183 | 0.507 |
| 184 | 3.779 |
| 186 | 0.677 |
| 187 | 0.742 |
| 188 | 5.015 |
| 189 | 1.415 |
| 190 | 0.413 |
| 191 | 0.999 |
| 192 | 0.314 |
| 196 | 0.094 |
| 197 | 0.041 |
| 198 | 0.845 |
| 199 | 1.504 |
| 200 | 0.632 |
| 201 | 0.045 |
| 202 | 0.383 |
| 203 | 0.098 |
| 204 | 0.209 |
| 205 | 0.803 |
| 207 | 0.564 |
| 208 | 0.102 |
| 209 | 0.078 |
| 210 | 0.093 |
| 211 | 0.097 |
| 212 | 0.063 |
| 213 | 0.038 |
| 214 | 0.108 |
| 215 | 0.079 |
| 216 | 0.082 |
| 217 | 0.069 |
| 218 | 0.381 |
| 219 | 0.707 |
| 220 | 0.059 |
| 221 | 0.487 |
| 222 | 0.065 |
| 224 | 0.137 |
| 225 | 0.036 |
| 226 | 0.361 |
| 227 | 0.048 |
| 228 | 0.417 |
| 229 | 0.383 |
| 230 | 0.658 |
| 231 | 0.037 |
| 232 | 0.040 |
| 233 | 0.368 |
| 234 | 0.078 |
| 235 | 0.130 |
| 236 | 0.045 |
| 237 | 1.492 |
| 238 | 0.139 |
| 239 | 0.046 |
| 240 | 0.984 |
| 241 | 0.100 |
| 242 | 0.802 |
| 243 | 1.175 |
| 244 | 0.053 |
| 245 | 0.102 |
| 248 | 0.093 |
| 249 | 0.072 |
| 250 | 2.473 |
| 252 | 0.050 |
| 254 | 0.025 |
| 255 | 0.078 |
| 257 | 0.056 |
| 259 | 0.057 |
| 260 | 0.094 |
| 261 | 0.094 |
| 262 | 0.056 |
| 263 | 1.394 |
| 264 | 0.084 |
| 266 | 0.033 |

| Compound | IC₅₀ (μM) |
| --- | --- |
| 267 | 1.327 |
| 268 | 0.349 |
| 269 | 0.137 |
| 270 | 0.109 |
| 272 | 0.051 |
| 273 | 1.228 |
| 274 | 0.084 |
| 275 | 0.062 |
| 276 | 0.081 |
| 277 | 0.156 |
| 278 | 0.148 |
| 279 | 0.170 |
| 280 | >10 |
| 281 | 0.690 |
| 282 | 0.343 |
| 283 | 0.174 |
| 285 | 0.034 |
| 286 | 0.165 |
| 287 | 0.095 |
| 288 | 0.035 |
| 291 | 0.201 |
| 292 | 3.456 |
| 293 | 0.637 |
| 294 | 0.425 |
| 296 | 0.423 |
| 297 | 2.660 |
| 298 | 0.620 |

Example 4 Fluorescent Determination of IDH1-R132H Cell Activity

The 2-HG inhibitory activity of the compounds of the invention in U87MGR132H cells transfected with the IDH1-R132H mutant plasmid was determined according to the method of Example 3.

The followings are the activity values of some of the compounds of the invention determined in this example.

| Compound | IC₅₀ (μM) |
| --- | --- |
| 2 | 0.365 |
| 4 | 0.750 |
| 5 | 0.869 |
| 6 | 0.670 |
| 7 | 1.503 |
| 8 | 1.221 |
| 11 | 1.016 |
| 13 | 2.076 |
| 14 | 1.326 |
| 15 | 0.619 |
| 18 | 0.219 |
| 19 | 0.421 |
| 21 | 0.234 |
| 24 | 0.769 |
| 31 | 0.280 |
| 32 | 0.610 |
| 34 | >10 |
| 39 | 1.913 |
| 40 | 0.450 |
| 41 | 1.627 |
| 47 | 5.636 |
| 51 | 6.042 |
| 52 | 2.245 |
| 54 | 1.683 |
| 60 | >10 |
| 61 | >10 |
| 62 | 2.703 |
| 64 | >10 |
| 65 | >10 |
| 67 | >10 |
| 71 | 3.054 |
| 73 | >10 |
| 74 | 7.441 |
| 75 | >10 |
| 78 | 1.407 |
| 79 | 1.296 |
| 80 | 2.695 |
| 81 | 3.571 |
| 82 | 0.181 |
| 83 | 0.282 |
| 84 | 0.268 |
| 85 | 0.207 |
| 87 | 0.781 |
| 89 | 2.957 |
| 94 | 1.144 |
| 95 | 0.317 |
| 96 | 2.703 |
| 97 | 0.047 |
| 98 | 0.254 |
| 99 | 0.938 |
| 101 | 1.141 |
| 102 | 0.232 |
| 103 | 2.501 |
| 105 | 0.351 |
| 106 | 0.272 |
| 107 | 1.751 |
| 109 | 0.279 |
| 110 | 0.160 |
| 118 | 2.141 |
| 119 | >10 |
| 121 | 0.186 |
| 124 | 0.658 |
| 126 | 0.289 |
| 127 | 0.203 |
| 130 | 0.733 |
| 134 | 2.472 |
| 136 | 1.342 |
| 147 | 0.372 |
| 149 | 0.693 |
| 151 | 0.256 |
| 152 | 2.008 |
| 153 | 0.447 |
| 155 | 2.245 |
| 157 | 4.350 |
| 158 | 1.520 |
| 159 | 2.717 |
| 163 | 0.809 |
| 166 | 1.347 |
| 167 | 3.171 |
| 169 | 9.464 |
| 170 | 6.933 |
| 171 | 1.575 |
| 174 | 0.343 |
| 175 | 0.495 |
| 177 | 0.094 |
| 181 | 0.476 |
| 196 | 0.210 |
| 197 | 0.120 |
| 198 | 1.893 |
| 199 | >10 |
| 200 | >10 |
| 201 | 0.109 |
| 202 | 1.101 |
| 203 | 0.733 |
| 204 | >10 |
| 205 | >10 |
| 207 | 1.510 |
| 208 | 1.499 |
| 209 | 1.763 |
| 210 | 4.338 |
| 211 | 0.175 |
| 212 | >10 |
| 213 | >10 |
| 214 | >10 |
| 215 | >10 |
| 216 | 8.519 |
| 217 | >10 |
| 218 | >10 |
| 219 | 3.232 |

-continued

| Compound | IC$_{50}$ (μM) |
|---|---|
| 220 | 2.878 |
| 221 | >10 |
| 222 | >10 |
| 224 | 4.650 |
| 225 | 0.917 |
| 226 | 5.123 |
| 227 | 0.081 |
| 228 | 0.705 |
| 229 | >10 |
| 230 | >10 |
| 231 | 1.528 |
| 232 | 0.070 |
| 233 | 0.628 |
| 234 | 1.763 |
| 235 | 0.246 |
| 236 | 0.252 |
| 238 | 7.355 |
| 239 | 0.344 |
| 240 | >10 |
| 241 | 2.060 |
| 242 | 3.523 |
| 243 | >10 |
| 244 | 1.082 |
| 245 | 1.499 |
| 248 | 4.338 |
| 249 | 0.134 |
| 250 | 2.480 |
| 252 | 2.621 |
| 254 | 0.262 |
| 255 | 0.715 |
| 257 | 1.380 |
| 259 | 0.213 |
| 260 | >10 |
| 261 | 2.231 |
| 262 | 0.182 |
| 263 | 3.513 |
| 264 | >10 |
| 266 | 0.043 |
| 267 | 3.566 |
| 268 | 0.939 |
| 269 | 0.296 |
| 270 | 2.853 |
| 272 | 2.086 |
| 273 | >10 |
| 274 | 3.284 |
| 275 | 8.017 |
| 276 | 8.367 |
| 277 | 1.030 |
| 278 | >10 |
| 279 | 9.426 |
| 280 | >10 |
| 281 | 0.455 |
| 282 | 0.444 |
| 283 | 1.319 |
| 285 | 3.587 |
| 286 | >10 |
| 287 | >10 |
| 288 | 2.695 |
| 291 | 0.179 |
| 292 | 3.639 |
| 293 | >10 |
| 294 | 9.184 |
| 296 | 1.135 |
| 297 | >10 |
| 298 | >10 |

Example 5 Metabolic Stability Test in Liver Microsomes

Materials:

Male CD1 mouse liver microsomes was supplied by Research Institute for Liver Diseases (Shanghai) Co., Ltd. Male SD rat liver microsomes was supplied by BioreclamationIVT in US.

Phenacetin, glucose-6-phosphate (G-6-P), glucose-6-phosphate dehydrogenase (G-6-PD), and nicotinamide adenine dinucleotide phosphate (NADP) were supplied by Sigma-Aldrich (Missouri, USA).

Solution Preparation:

10 mM stock solution of test compound: Certain amount of test compound was weighed and dissolved in certain volume of dimethylsulfoxide (DMSO) to get the stock solution of test compound at 10 mM.

Reaction termination solution: Certain amount of phenacetin as internal standard was weighed and dissolved in acetonitrile to get the reaction termination solution at 1000 ng/mL, and stored at room temperature for use.

Experimental Method:

The stock solution of test compound was diluted to the designated concentration with organic solution (usually the mixtures of acetonitrile, methanol and water with different portions depending on the compound solution) to make the final concentration to be 1 μM and the contents of organic solvents no more than 1% (For DMSO, the controlled margin was 0.1%) in the final incubation system. 100 mM NADP, 500 mM G-6-P and 100 U/mL G-6-PDH were mixed and diluted with ultrapure water to provide the NADPH regenerating system containing 1 mM NADP, 5 mM G-6-P and 1 U/mL G-6-PD, which was pre-incubated at 37° C. water-bath for 10 min and then cooled on ice until being added into the reaction system. 20 mg/mL liver microsomes was mixed with 200 mM PBS and diluted with ultrapure water to make the concentrations of liver microsomes and PBS to be 0.5 mg/mL and 50 mM in the final incubation system, respectively. After the diluted liver microsomes was mixed with the NADPH regenerating solution, certain volumes of 100 mM EDTA and 300 mM MgCl$_2$ (concentration of EDTA and MgCl$_2$ in the final incubation system is 1 mM and 3 mM, respectively) were added, and the incubation system was put into 37° C. water bath. The incubation was commenced by adding the stock solution of test compound and maintained for 30 min. The incubation was terminated by adding the reaction termination solution. The 0 min sample was prepared by adding the reaction termination solution to the incubation system immediately prior to putting the system into the water bath with the addition of the stock solution of test compound. The terminated incubation mixtures were vortexed and centrifuged at 4400 rpm for 10 min, and the supernatant was collected for LC-MS/MS analysis.

Analytical Method:

The concentration of test compound was determined using LC-MS/MS method. Using the peak area ratio of the compound and the internal standard as an index, the percentage of remaining compound after incubation for 30 minutes as compared with the 0 minute sample was calculated, and the metabolic stability of the compound was evaluated.

According to the above tests, the compounds of the invention showed good metabolic stability. The metabolic stability of some exemplary compounds of the invention is as follows:

| Compound | Rat liver microsome stability | Mouse liver microsome stability |
|---|---|---|
| 1 | 73.8% | 83.5% |
| 2 | 99.0% | 83.8% |
| 4 | 62.9% | 82.1% |

-continued

| Compound | Rat liver microsome stability | Mouse liver microsome stability |
|---|---|---|
| 5 | 76.8% | 58.6% |
| 6 | 70.0% | 76.3% |
| 7 | 50.3% | 49.8% |
| 11 | 87.6% | 80.3% |
| 18 | 91.5% | 82.7% |
| 19 | 83.8% | 66.2% |
| 82 | 92.9% | 93.1% |
| 83 | 96.6% | 83.7% |
| 84 | 67.8% | 78.9% |
| 85 | 78.1% | 64.0% |
| 87 | 97.9% | 88.5% |
| 90 | 82.4% | 80.9% |
| 91 | 86.6% | 70.5% |
| 94 | 82.6% | 65.4% |
| 95 | 74.8% | 80.1% |
| 97 | 98.5% | 89.5% |
| 98 | 99.2% | 83.7% |
| 101 | 88.0% | 84.6% |
| 102 | 92.7% | 86.2% |
| 103 | 89.7% | 78.5% |
| 105 | 84.0% | 67.3% |
| 109 | 85.4% | 58.8% |
| 124 | 74.1% | 44.1% |
| 126 | 79.8% | 58.2% |
| 127 | 49.8% | 28.7% |
| 128 | 34.0% | 15.9% |
| 147 | 65.0% | 48.1% |
| 149 | 66.8% | 59.7% |
| 153 | 41.7% | 46.9% |
| 177 | 45.9% | 31.0% |
| 196 | 100.0% | 95.2% |
| 197 | 99.5% | 98.4% |
| 201 | 91.6% | 79.3% |
| 202 | 94.2% | 96.4% |
| 203 | 92.1% | 91.3% |
| 211 | 98.8% | 99.7% |
| 227 | 88.8% | 81.4% |
| 232 | 86.6% | 76.3% |
| 235 | 89.0% | 75.5% |
| 236 | 91.3% | 83.9% |
| 239 | 93.0% | 91.8% |
| 249 | 98.0% | 100.0% |
| 254 | 100.0% | 90.9% |
| 259 | 95.1% | 86.9% |
| 262 | 98.3% | 92.2% |
| 266 | 98.2% | 91.5% |
| 291 | 100.0% | 98.9% |

Example 6 Determination of Solubility

1. Preparation of Sample Solution

Sample standard solution: About 3-5 mg test compound was accurately weighed and added into a 5 mL sample tube, 5 mL DMSO was added. Shaking and sonicating for 1 hour.

pH 2.1 sample solution: About 1 mg test compound was accurately weighed and added into a 1 mL sample tube, 1 mL pH 2.1 sodium phosphate buffer was added. Shaking. Adding test compound to the solution, if the solution is visually clear, till there is obvious insoluble in the solution. Sonicating for 1 hour.

pH 7.4 sample solution: About 1 mg test compound was accurately weighed and added into a 1 mL sample tube, 1 mL pH 7.4 sodium phosphate buffer was added. Shaking. Adding test compound to the solution, if the solution is visually clear, till there is obvious insoluble in the solution. Sonicating for 1 hour.

2. Determination 1 mL sample standard solution was accurately pipetted into a HPLC tube. The peak area was determined by HPLC.

0.5 mL pH 2.1 sample solution was filtered by syringe filter and was accurately pipetted into a HPLC tube, and 0.5 mL pH 2.1 sodium phosphate buffer was accurately added. Shaking. The peak area was determined by HPLC.

0.5 mL pH 7.4 sample solution was filtered by syringe filter and was accurately pipetted into a HPLC tube, and 0.5 mL pH 7.4 sodium phosphate buffer was accurately added. Shaking. The peak area was determined by HPLC.

HPLC condition:
Instrument: Agilent 1200
Column: Agilent SB-C18 5 u 4.6*150 mm
Mobile phase:
  Phase A: Water (containing 0.1% formic acid)
  Phase B: MeOH (containing 0.1% formic acid)

| Gradient table | | |
|---|---|---|
| Time (min) | % A | % B |
| 0 | 95 | 5 |
| 10 | 5 | 95 |
| 13 | 5 | 95 |
| 14 | 95 | 5 |
| 16 | 95 | 5 |

3. Calculation

The solubility of the test compound in pH 2.1 and pH 7.4 sodium phosphate buffers were calculated by the following formulae:

$$\text{Sample solubility at pH 2.1 (mg/mL)} = 2 \times A \times Y \div X$$

$$\text{Sample solubility at pH 7.4 (mg/mL)} = 2 \times A \times Z \div X$$

wherein:
  A: The concentration of the test compound in sample standard solution, mg/mL;
  X: The peak area of sample standard solution;
  Y: The peak area of pH 2.1 sample solution;
  Z: The peak area of pH 7.4 sample solution.

The solubilities of some exemplary compounds of the invention are as follows:

| | Solubility (mg/mL) | |
|---|---|---|
| Compound | pH 2.1 | pH 7.4 |
| 3 | >1.000 | 0.716 |
| 9 | >1.000 | 0.085 |
| 20 | 0.570 | 0.062 |
| 68 | 0.141 | <0.005 |
| 71 | 0.064 | 0.055 |
| 82 | 0.146 | 0.037 |
| 97 | 0.077 | 0.021 |
| 102 | 0.729 | <0.005 |
| 125 | 0.448 | 0.019 |
| 219 | 0.190 | 0.060 |
| 223 | 0.060 | 0.016 |
| 243 | 0.055 | <0.005 |
| 249 | 0.036 | 0.011 |
| 262 | 0.237 | 0.013 |
| 271 | 0.974 | 0.124 |
| 284 | 0.789 | 0.818 |

The invention claimed is:
1. A compound of formula (I-1):

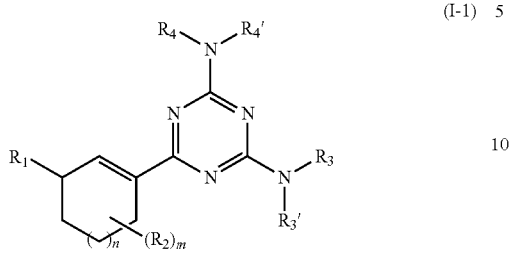

or a pharmaceutically acceptable salt, solvate, racemic mixture, enantiomer, diastereomer, or tautomer thereof, wherein $R_1$ is chosen from H, —OH, halo, $C_{1-6}$ alkyl, $C_{1-6}$ alkoxyl, —$NH_2$, —NH ($C_{1-4}$ alkyl), —N($C_{1-4}$ alkyl)$_2$, oxo, or $C_{3-8}$ cycloalkyl;

each of $R_2$ is independently chosen from H, deuterium, halo, —OH, —$NH_2$, —CN, —SH, $C_{1-6}$ alkyl, $C_{2-6}$ alkenyl, $C_{2-6}$ alkynyl, $C_{1-6}$ haloalkyl, $C_{3-8}$ cycloalkyl, oxo, —$OR_5$, —$OCOR_5$, —$NHR_5$, —$N(R_5)$ ($C_{1-4}$ alkyl), —$COR_5$, —$NHCOR_5$, or 3-8 membered heterocyclyl containing one or more heteroatoms independently chosen from N, O, and S; in which each of said $C_{1-6}$ alkyl, $C_{2-6}$ alkenyl, $C_{2-6}$ alkynyl, $C_{3-8}$ cycloalkyl or 3-8 membered heterocyclyl containing one or more heteroatoms independently chosen from N, O, and S is optionally substituted with one or more groups chosen from deuterium, halo, —CN, —OH, —SH, —$NH_2$, —NH ($C_{1-4}$ alkyl), —N($C_{1-4}$ alkyl)$_2$, or $C_{1-6}$ alkoxyl; or two $R_2$, which attach to the same carbon atom, together with the carbon atom they are attached to form a 3-5 membered cycloalkyl which is optionally substituted with one or more halo or deuterium;

$R_3'$ and $R_4'$ are both H;

$R_3$ and $R_4$ are independently chosen from H, $C_{1-6}$ alkyl, $C_{2-6}$ alkenyl, $C_{2-6}$ alkynyl, $C_{3-12}$ cycloalkyl, 3-12 membered heterocyclyl containing one or more heteroatoms independently chosen from N, O, and S, phenyl, 5-12 membered heteroaryl containing one or more heteroatoms independently chosen from N, O, and S, —C(O)$R_5$, —$OR_5$, or —$NHR_5$, in which each of said $C_{1-6}$ alkyl, $C_{2-6}$ alkenyl, $C_{2-6}$ alkynyl, $C_{3-12}$ cycloalkyl, 3-12 membered heterocyclyl containing one or more heteroatoms independently chosen from N, O, and S, phenyl, or 5-12 membered heteroaryl containing one or more heteroatoms independently chosen from N, O, and S is optionally substituted with one or more $R_{66}$; provided that $R_3$ and $R_4$ are not H simultaneously; provided that when one of $R_3$ and $R_4$ is optionally substituted phenyl or optionally substituted 5-6 membered heteroaryl containing one or more heteroatoms independently chosen from N, O, and S, the other one is —$OR_5$ or —$NHR_5$;

or $R_3$ and $R_3'$ are independently chosen from H, $C_{1-6}$ alkyl, $C_{2-6}$ alkenyl, $C_{2-6}$ alkynyl, $C_{3-12}$ cycloalkyl, 3-12 membered heterocyclyl containing one or more heteroatoms independently chosen from N, O, and S, phenyl, 5-12 membered heteroaryl containing one or more heteroatoms independently chosen from N, O, and S, —C(O)$R_5$, —$OR_5$, or —$NHR_5$, in which each of said $C_{1-6}$ alkyl, $C_{2-6}$ alkenyl, $C_{2-6}$ alkynyl, $C_{3-12}$ cycloalkyl, 3-12 membered heterocyclyl containing one or more heteroatoms independently chosen from N, O, and S, phenyl, or 5-12 membered heteroaryl containing one or more heteroatoms independently chosen from N, O, and S is optionally substituted with one or more $R_6$; $R_4$ and $R_4'$ together with the N atom they are attached to form a 3-8 membered heterocyclic ring containing one or more heteroatoms independently chosen from N, O, and S which is optionally substituted by one or more $R_6$;

$R_5$ is chosen from $C_{1-6}$ alkyl or $C_{3-8}$ cycloalkyl, each of which is optionally substituted with one or more groups independently chosen from halo, —CN, —OH, —SH, —$NH_2$, or $C_{1-6}$ alkoxyl;

each of $R_6$ is independently chosen from deuterium, halo, —CN, —OH, —SH, —$NH_2$, $C_{1-6}$ alkoxyl, $C_{1-6}$ alkyl, $C_{1-6}$ haloalkyl, $C_{3-8}$ cycloalkyl, 3-8 membered heterocyclyl containing one or more heteroatoms independently chosen from N, O, and S, phenyl, or 5-6 membered heteroaryl containing one or more heteroatoms independently chosen from N, O, and S, in which each of said $C_{1-6}$ alkoxyl, $C_{1-6}$ alkyl, $C_{3-8}$ cycloalkyl, 3-8 membered heterocyclyl containing one or more heteroatoms independently chosen from N, O, and S, phenyl, or 5-6 membered heteroaryl containing one or more heteroatoms independently chosen from N, O, and S is optionally substituted with one or more groups independently chosen from halo, —CN, —OH, —SH, —$NH_2$, $C_{1-6}$ alkoxyl, $C_{2-6}$ alkynyl, or $C_{1-6}$ alkyl;

m is 0, 1, 2, 3, 4, 5, or 6;
n is 0, 1, or 2.

2. The compound of formula (I-1) according to claim 1, or a pharmaceutically acceptable salt, solvate, racemic mixture, enantiomer, diastereomer, or tautomer thereof, wherein $R_1$ is chosen from H, —OH or halo.

3. The compound of formula (1-1) according to claim 2, or a pharmaceutically acceptable salt, solvate, racemic mixture, enantiomer, diastereomer, or tautomer thereof, wherein $R_1$ is —OH.

4. The compound of formula (I-1) according to claim 1, or a pharmaceutically acceptable salt, solvate, racemic mixture, enantiomer, diastereomer, or tautomer thereof, wherein, each of $R_2$ is independently chosen from H, deuterium, halo, —OH, —$NH_2$, —CN, —SH, $C_{1-6}$ alkyl, $C_{2-6}$ alkenyl, $C_{2-6}$ alkynyl, $C_{1-6}$ haloalkyl, $C_{3-8}$ cycloalkyl, oxo, —$OR_5$, —$OCOR_5$, —$NHR_5$, —$N(R_5)$ ($C_{1-4}$ alkyl), —$NHCOR_5$, or 3-8 membered heterocyclyl containing one or more heteroatoms independently chosen from N, O, and S.

5. The compound of formula (I-1) according to claim 4, or a pharmaceutically acceptable salt, solvate, racemic mixture, enantiomer, diastereomer, or tautomer thereof, wherein each of $R_2$ is independently chosen from H, deuterium, halo, $C_{1-6}$ alkyl, or $C_{1-6}$ haloalkyl.

6. The compound of formula (I-1) according to claim 1, or a pharmaceutically acceptable salt, solvate, racemic mixture, enantiomer, diastereomer, or tautomer thereof, wherein $R_3$ and $R_4$ are independently chosen from $C_{1-6}$ alkyl, $C_{3-12}$ cycloalkyl, 3-12 membered heterocyclyl containing one or more heteroatoms independently chosen from N, O, and S, phenyl, 5-12 membered heteroaryl containing one or more heteroatoms independently chosen from N, O, and S, —C(O)$R_5$, —$OR_5$, or —$NHR_5$, in which each of said $C_{1-6}$ alkyl, $C_{3-12}$ cycloalkyl, 3-12 membered heterocyclyl containing one or more heteroatoms independently chosen from N, O, and S, phenyl, or 5-12 membered heteroaryl containing one or more heteroatoms independently chosen from N, O, and S is optionally substituted with one or more $R_6$.

7. The compound of formula (I-1) according to claim 6, or a pharmaceutically acceptable salt, solvate, racemic mixture, enantiomer, diastereomer, or tautomer thereof, wherein $R_3$ and $R_4$ are independently chosen from $C_{1-6}$ alkyl substituted with one or more halo, 5-12 membered heteroaryl containing one or more heteroatoms independently chosen from N, O, and S substituted with $C_{1-6}$ haloalkyl, or —$OR_5$.

8. The compound of formula (I-1) according to claim 1, or a pharmaceutically acceptable salt, solvate, racemic mixture, enantiomer, diastereomer, or tautomer thereof, wherein $R_5$ is $C_{1-6}$ alkyl optionally substituted with one or more halo.

9. The compound of formula (I-1) according to claim 1, or a pharmaceutically acceptable salt, solvate, racemic mixture, enantiomer, diastereomer, or tautomer thereof, wherein each of $R_6$ is independently chosen from deuterium, halo, —CN, —OH, —$NH_2$, $C_{1-6}$ alkoxyl, $C_{1-6}$ alkyl, $C_{1-6}$ haloalkyl, $C_{3-8}$ cycloalkyl, 3-8 membered heterocyclyl containing one or more heteroatoms independently chosen from N, O, and S, phenyl, or 5-6 membered heteroaryl containing one or more heteroatoms independently chosen from N, O, and S, in which each of said $C_{1-6}$ alkoxyl, $C_{1-6}$ alkyl, $C_{3-8}$ cycloalkyl, 3-8 membered heterocyclyl containing one or more heteroatoms independently chosen from N, O, and S, phenyl, or 5-6 membered heteroaryl containing one or more heteroatoms independently chosen from N, O, and S is optionally substituted with one or more halo.

10. The compound of formula (I-1) according to claim 1, or a pharmaceutically acceptable salt, solvate, racemic mixture, enantiomer, diastereomer, or tautomer thereof, wherein n is 1.

11. The compound of formula (I-1) according to claim 1, or a pharmaceutically acceptable salt, solvate, racemic mixture, enantiomer, diastereomer, or tautomer thereof, wherein $R_3$ is chosen from H, $C_{1-6}$ alkyl optionally substituted by $C_{1-6}$ haloalkyl, or 5-12 membered heteroaryl containing one or more heteroatoms independently chosen from N, O, and S optionally substituted by $C_{1-6}$ haloalkyl;

$R_3'$ is H; $R_4$ and $R_4'$ together with the N atom they are attached to form a 3-8 membered heterocyclic ring containing one or more heteroatoms independently chosen from N, O, and S optionally substituted by one or more groups chosen from halo, —OH, or $C_{1-6}$ haloalkyl.

12. The compound of formula (I-1) according to claim 1, or a pharmaceutically acceptable salt, solvate, racemic mixture, enantiomer, diastereomer, or tautomer thereof, wherein the compound of formula (I-1) has the structure of formula (II-1); wherein X is halo; p is 0, 1, or 2; m is 0, 1, or 2;

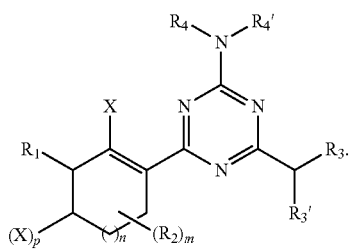

(II-1)

13. A compound selected from:

| Compound | Structure |
|---|---|
| 1 | 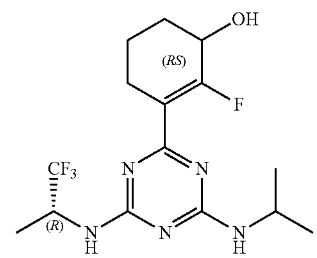 |
| 2 | 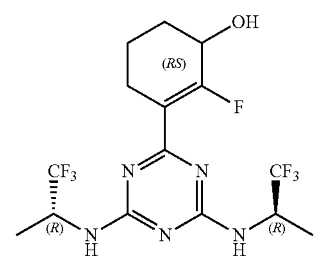 |
| 3 | 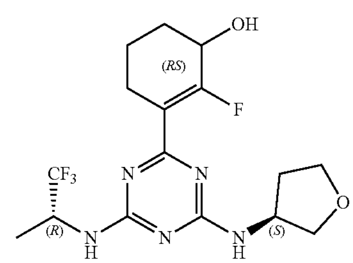 |
| 4 | 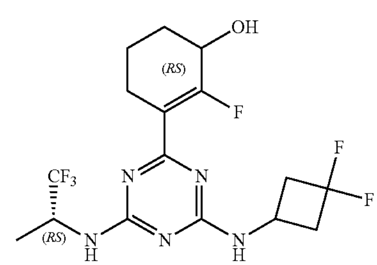 |
| 5 | 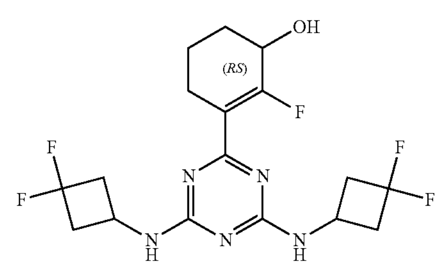 [SMILES: OC1CCCC(c2nc(NC3CC(F)(F)C3)nc(NC3CC(F)(F)C3)n2)=C1F] |
| 6 | 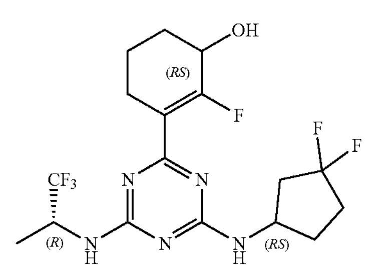 |

| Compound | Structure |
|---|---|
| 7 | 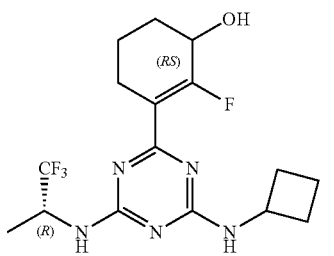 |
| 8 | 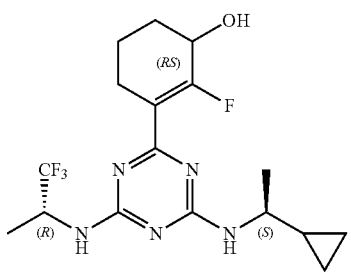 |
| 9 | 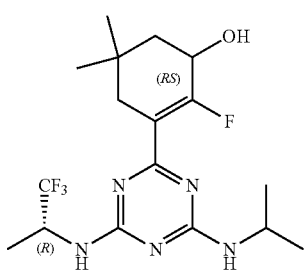 |
| 10 | 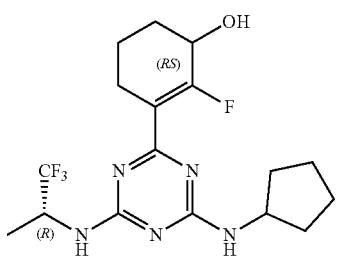 |
| 11 | 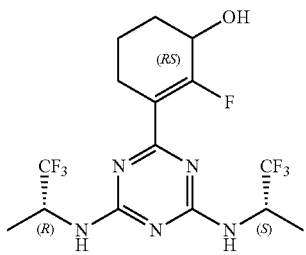 |
| 12 | 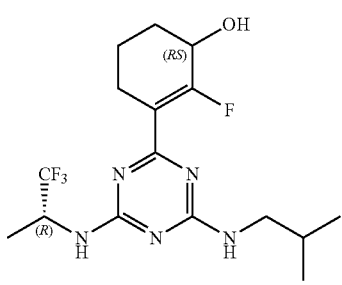 |
| Compound | Structure |
|---|---|
| 13 | 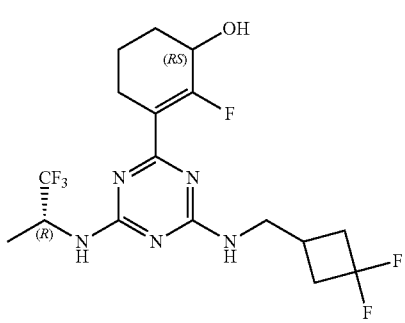 |
| 14 | 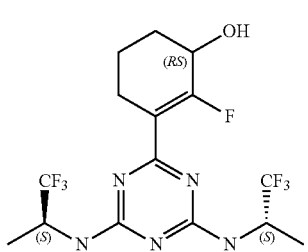 |
| 15 | 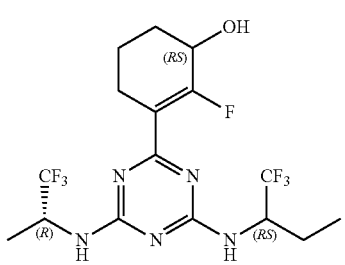 |
| 16 | 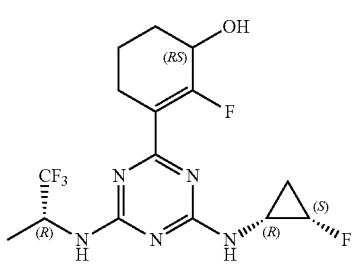 |
| 17 | 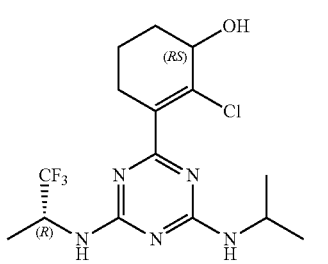 |

-continued
| Compound | Structure |
|---|---|
| 18 | 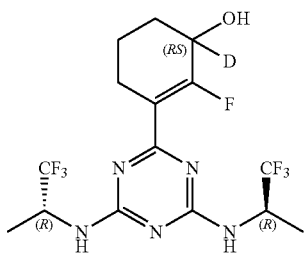 |
| 19 | 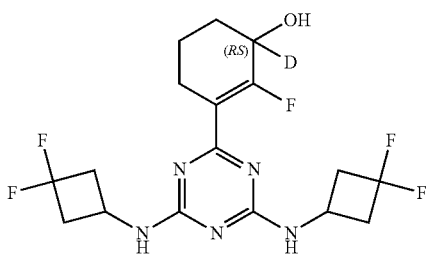 |
| 20 | 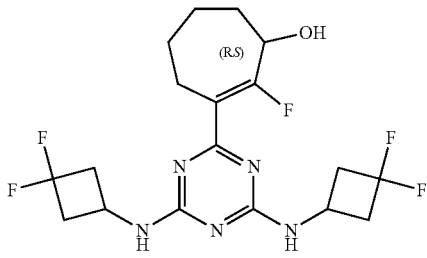 |
| 21 | 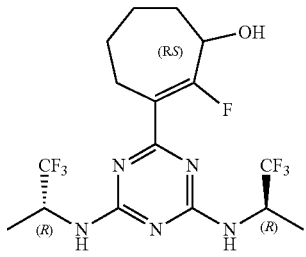 |
| 22 | 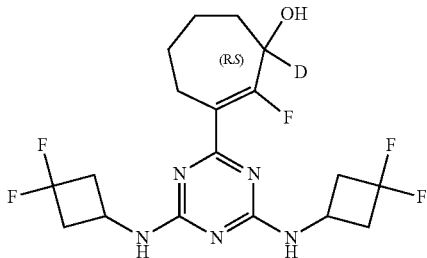 |
| 23 | 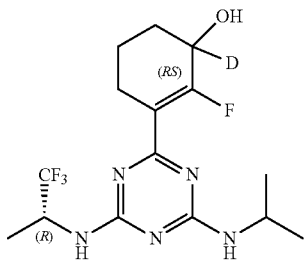 |
-continued
| Compound | Structure |
|---|---|
| 24 | 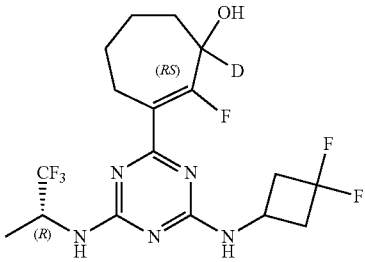 |
| 25 | 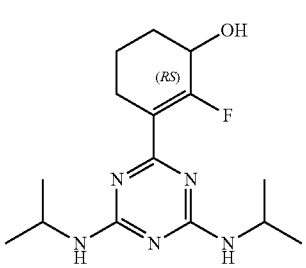 [SMILES: CC(C)Nc1nc(NC(C)C)nc(C2=C(F)C(O)CCC2)n1] |
| 26 | 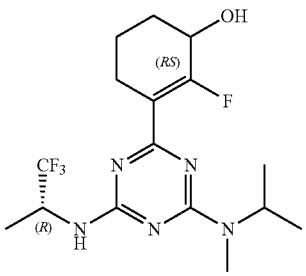 |
| 27 | 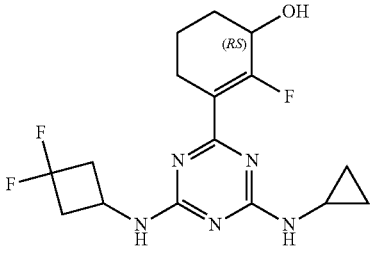 [SMILES: OC1CCCC(c2nc(NC3CC3)nc(NC3CC(F)(F)C3)n2)=C1F] |
| 28 | 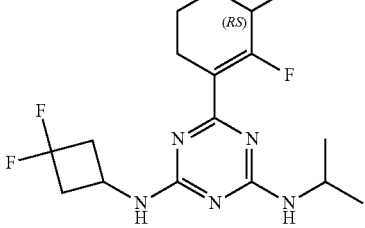 |
| 29 | 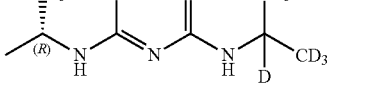 |

231
-continued
| Compound | Structure |
|---|---|
| 30 | 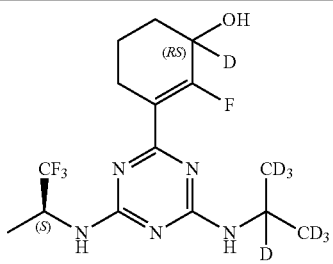 |
| 31 | 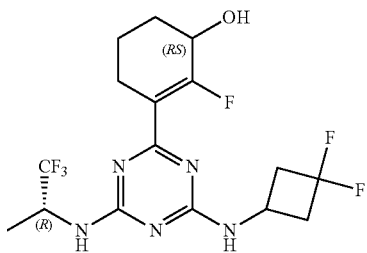 |
| 32 | 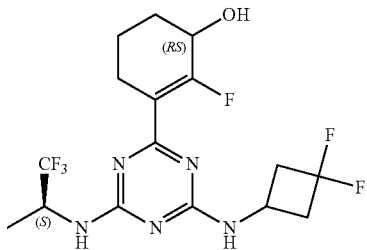 |
| 33 | 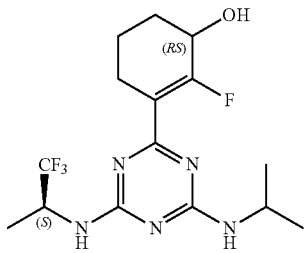 |
| 34 | 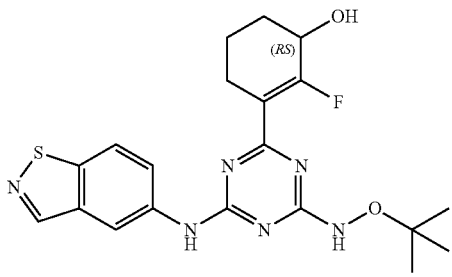 |
| 35 | 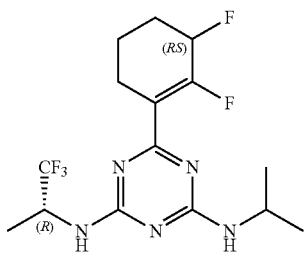 |
232
-continued
| Compound | Structure |
|---|---|
| 36 | 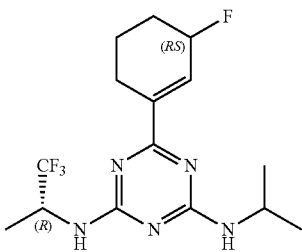 |
| 37 | 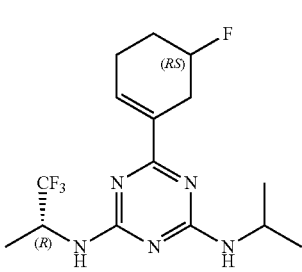 |
| 38 | 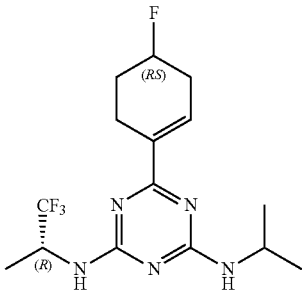 |
| 39 | 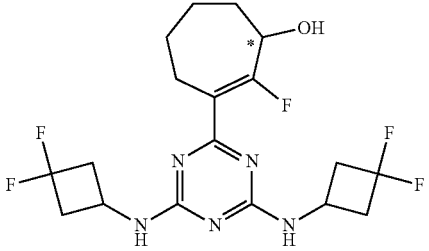 [SMILES: OC1CCCCC(c2nc(NC3CC(F)(F)C3)nc(NC3CC(F)(F)C3)n2)=C1F] |
| 40 | 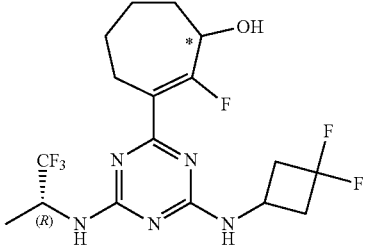 |
| 41 | 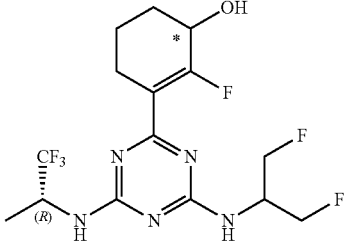 |

-continued
| Compound | Structure |
|---|---|
| 42 | 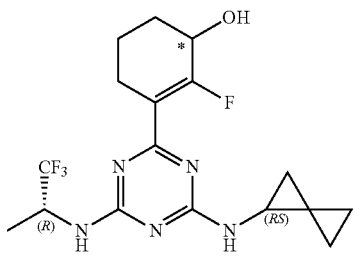 |
| 43 | 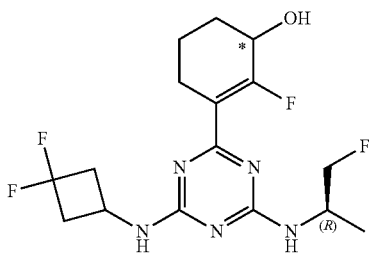 |
| 44 | 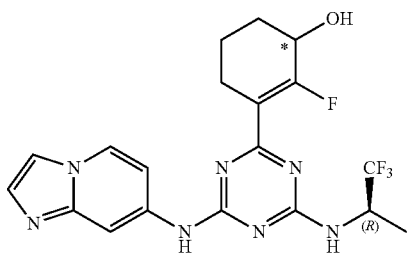 |
| 45 | 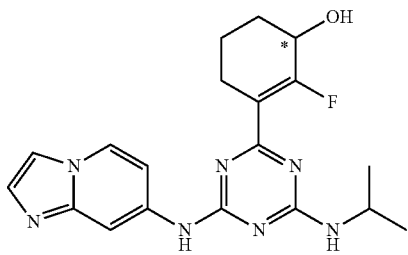 [SMILES: CC(C)Nc1nc(Nc2ccn3ccnc3c2)nc(C2=C(F)C(O)CCC2)n1] |
| 46 | 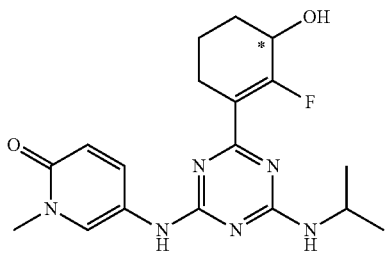 [SMILES: CC(C)Nc1nc(Nc2ccc(=O)n(C)c2)nc(C2=C(F)C(O)CCC2)n1] |
| 47 | 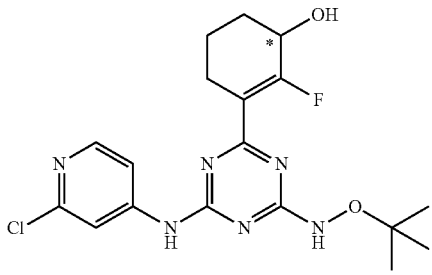 [SMILES: CC(C)(C)ONc1nc(Nc2ccnc(Cl)c2)nc(C2=C(F)C(O)CCC2)n1] |
-continued
| Compound | Structure |
|---|---|
| 48 | 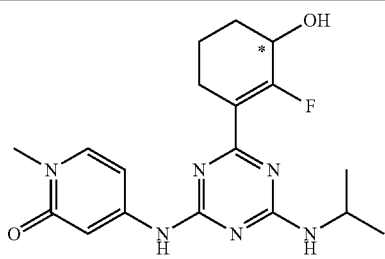 |
| 49 | 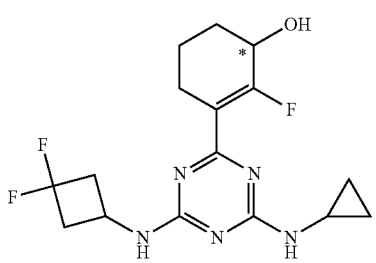 [SMILES: OC1CCCC(c2nc(NC3CC3)nc(NC3CC(F)(F)C3)n2)=C1F] |
| 50 | 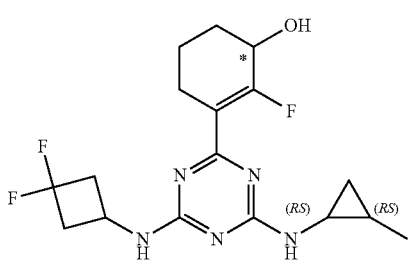 [SMILES: CC1CC1Nc1nc(NC2CC(F)(F)C2)nc(C2=C(F)C(O)CCC2)n1] |
| 51 | 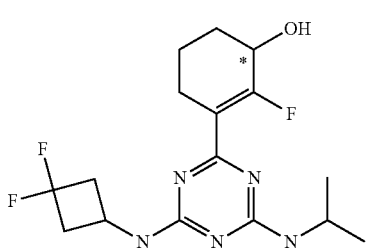 |
| 52 | 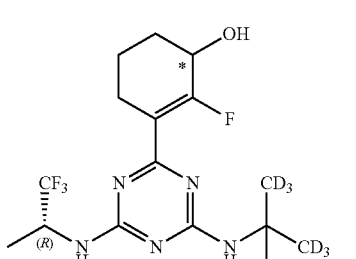 |
| 53 | 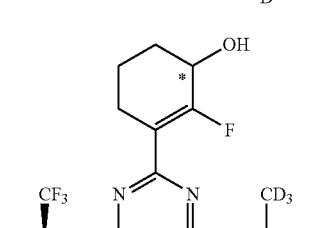 |

| Compound | Structure |
|---|---|
| 55 | 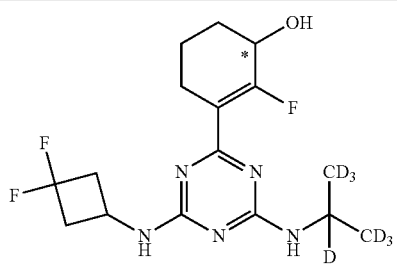 [SMILES: [2H]C([2H])([2H])C([2H])(Nc1nc(NC2CC(F)(F)C2)nc(C2=C(F)C(O)CCC2)n1)C([2H])([2H])[2H]] |
| 56 | 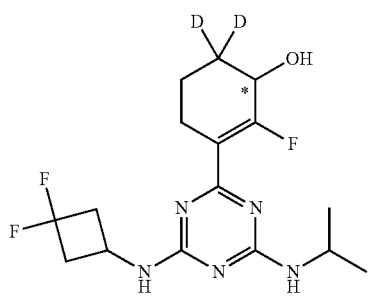 [SMILES: [2H]C1([2H])CCC(c2nc(NC(C)C)nc(NC3CC(F)(F)C3)n2)=C(F)C1O] |
| 57 | 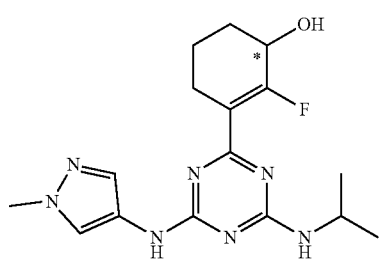 [SMILES: CC(C)Nc1nc(Nc2cnn(C)c2)nc(C2=C(F)C(O)CCC2)n1] |
| 59 | 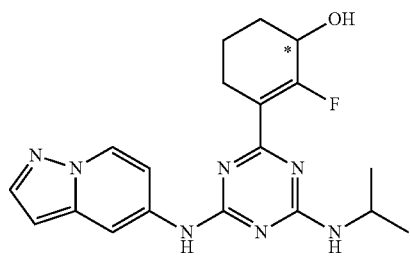 [SMILES: CC(C)Nc1nc(Nc2ccn3nccc3c2)nc(C2=C(F)C(O)CCC2)n1] |
| 60 | 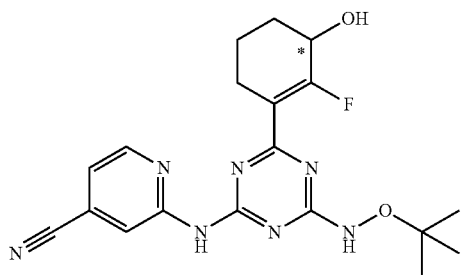 [SMILES: CC(C)(C)ONc1nc(Nc2cc(C#N)ccn2)nc(C2=C(F)C(O)CCC2)n1] |
| 61 | 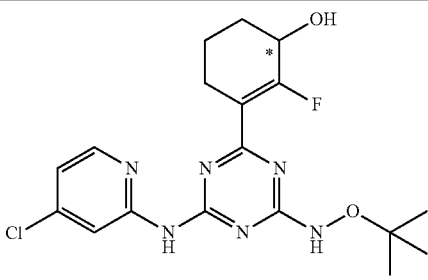 [SMILES: CC(C)(C)ONc1nc(Nc2cc(Cl)ccn2)nc(C2=C(F)C(O)CCC2)n1] |
| 62 | 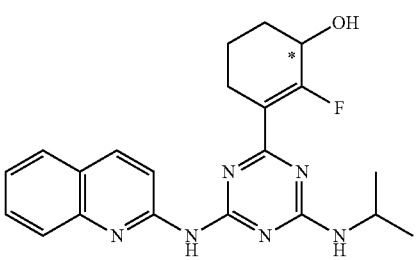 [SMILES: CC(C)Nc1nc(Nc2ccc3ccccc3n2)nc(C2=C(F)C(O)CCC2)n1] |
| 63 | 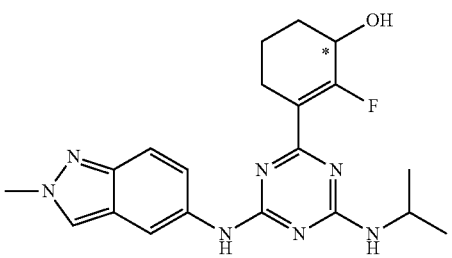 [SMILES: CC(C)Nc1nc(Nc2ccc3nn(C)cc3c2)nc(C2=C(F)C(O)CCC2)n1] |
| 64 | 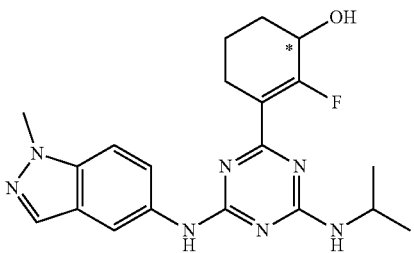 |
| 65 | 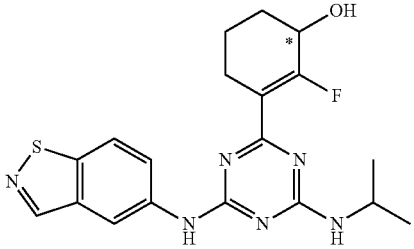 |
| 66 | 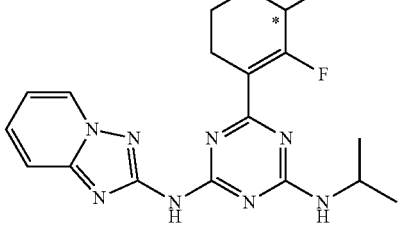 |

237
-continued
| Compound | Structure |
|---|---|
| 67 | 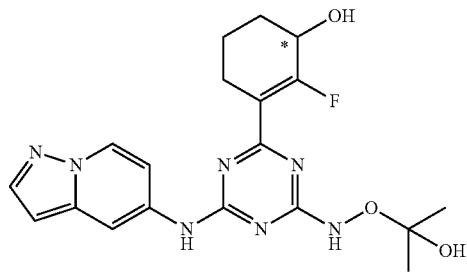 [SMILES: CC(C)(O)ONc1nc(Nc2ccn3nccc3c2)nc(C2=C(F)C(O)CCC2)n1] |
| 68 | 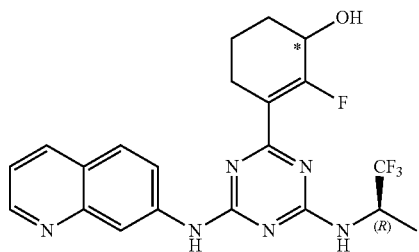 |
| 69 | 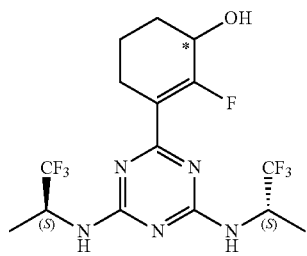 |
| 71 | 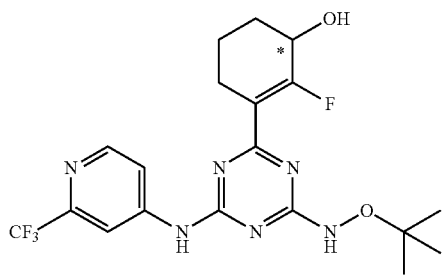 [SMILES: CC(C)(C)ONc1nc(Nc2ccnc(C(F)(F)F)c2)nc(C2=C(F)C(O)CCC2)n1] |
| 72 | 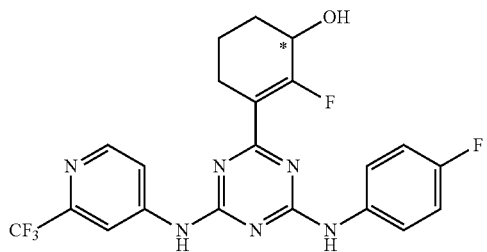 [SMILES: OC1CCCC(c2nc(Nc3ccc(F)cc3)nc(Nc3ccnc(C(F)(F)F)c3)n2)=C1F] |
| 73 | 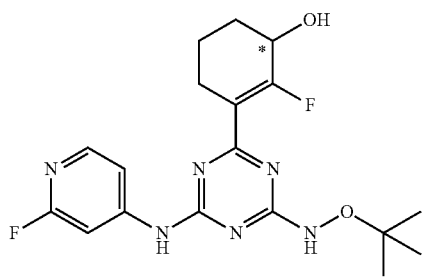 [SMILES: CC(C)(C)ONc1nc(Nc2ccnc(F)c2)nc(C2=C(F)C(O)CCC2)n1] |
238
-continued
| Compound | Structure |
|---|---|
| 74 | 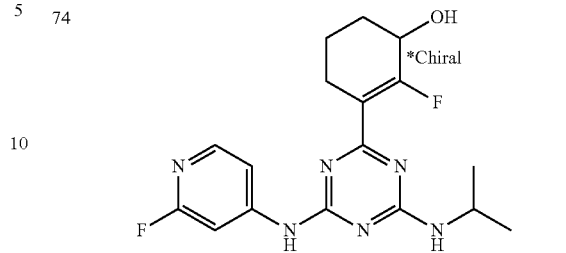 |
| 75 | 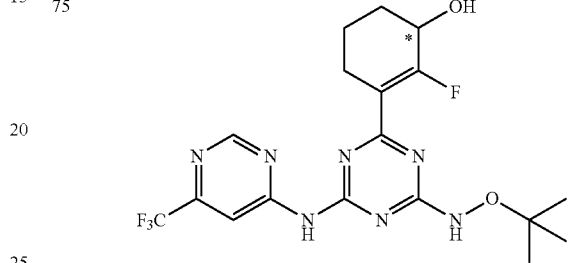 |
| 76 | 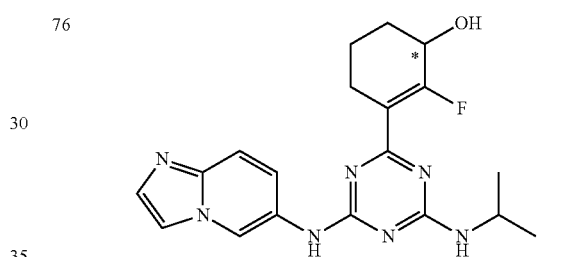 |
| 77 | 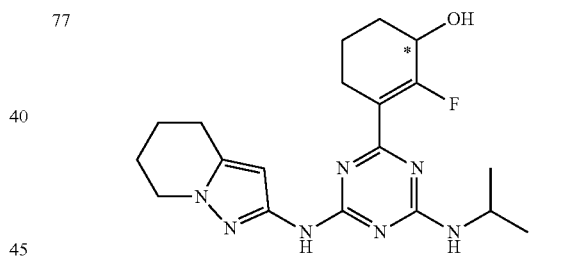 |
| 78 | 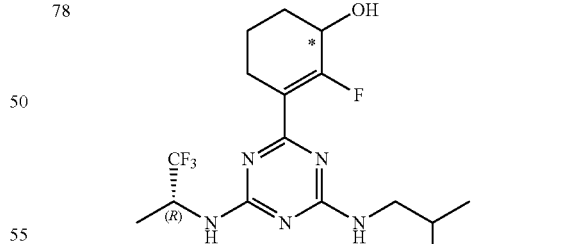 |
| 79 | 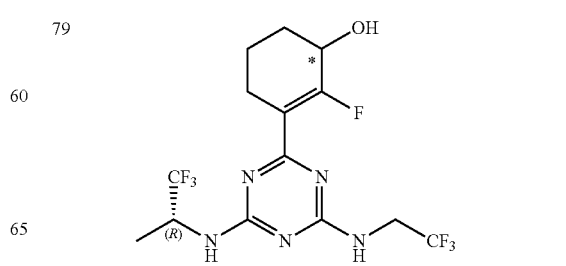 |

| Compound | Structure |
|---|---|
| 80 | 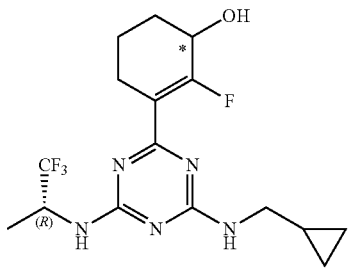 |
| 81 | 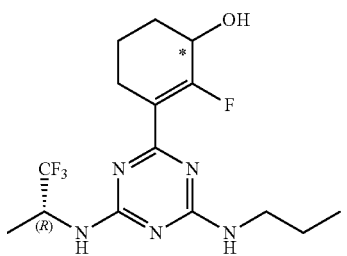 |
| 82 | 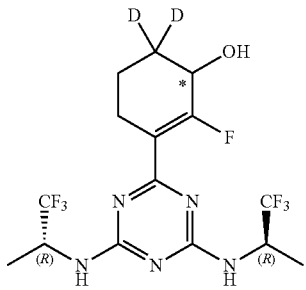 |
| 83 | 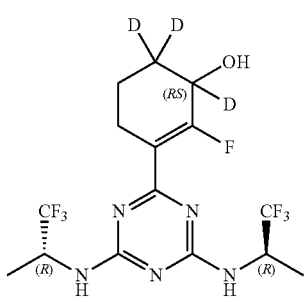 |
| 84 | 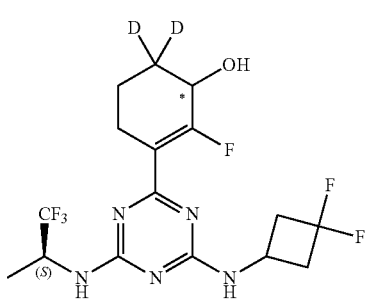 |
| Compound | Structure |
|---|---|
| 85 | 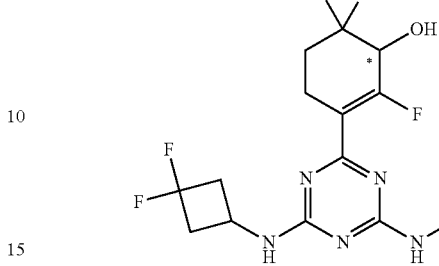 |
| 87 | 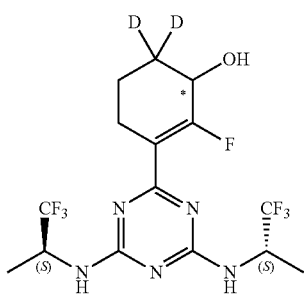 |
| 89 | 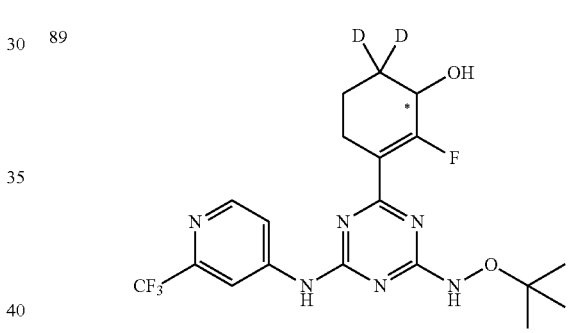 |
| 90 | 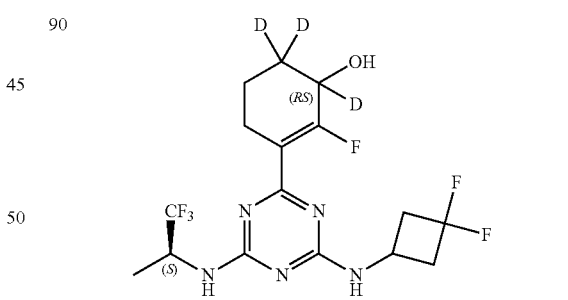 |
| 91 | 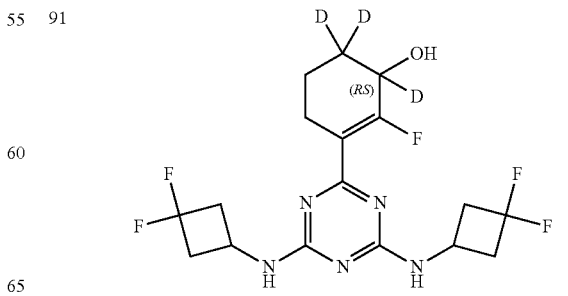 |

| Compound | Structure |
|---|---|
| 92 | 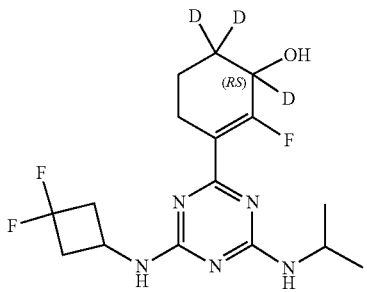 [SMILES: [2H]C1([2H])CCC(c2nc(NC(C)C)nc(NC3CC(F)(F)C3)n2)=C(F)C1([2H])O] |
| 93 | 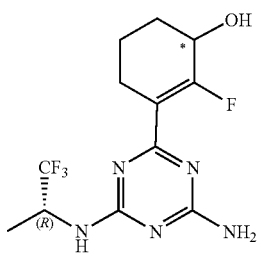 |
| 95 & 96 | 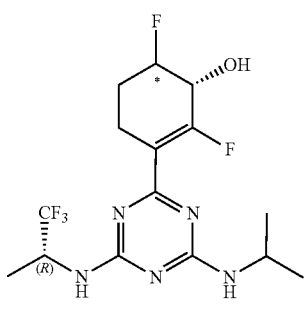 |
| 97 & 98 | 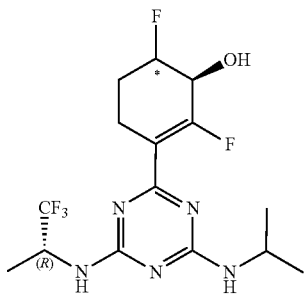 |
| Compound | Structure |
|---|---|
| | 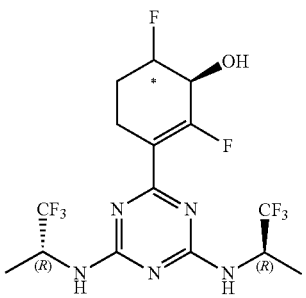 |
| 99 | 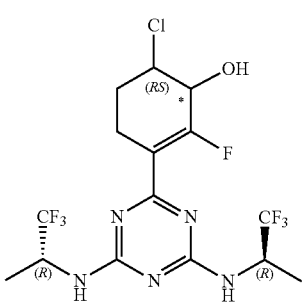 |
| 100 & 101 | 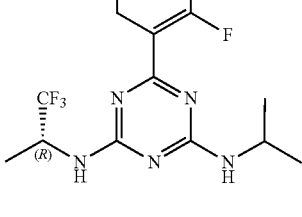 |
| | 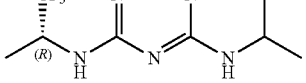 |
| 102 & 103 | 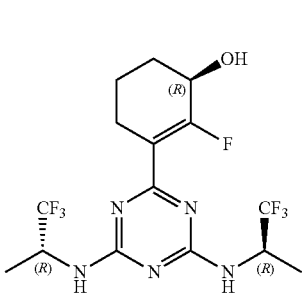 |

| Compound | Structure |
|---|---|
| 104 & 105 | 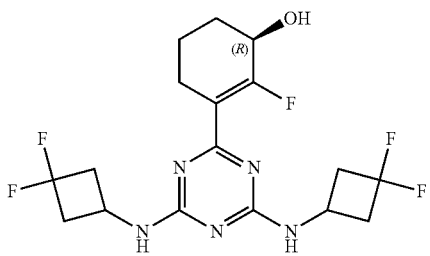 |
| 106 & 107 | 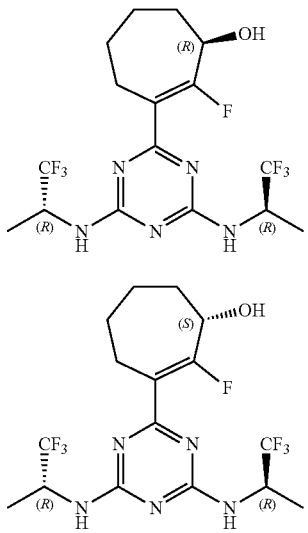 |
| 108 & 109 | 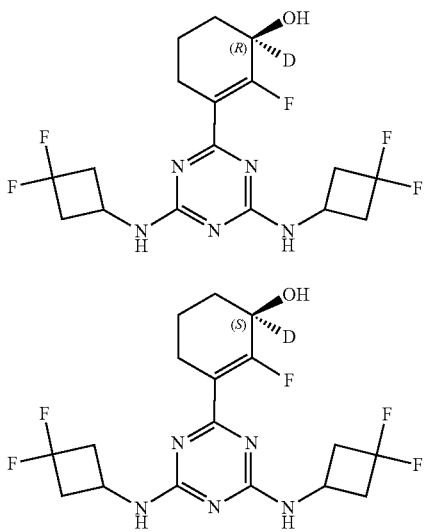 |
| Compound | Structure |
|---|---|
| 110 & 111 | 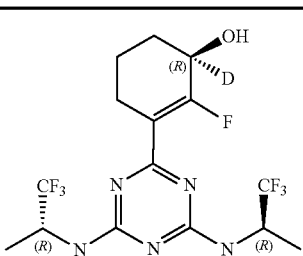 |
| 112 & 113 | 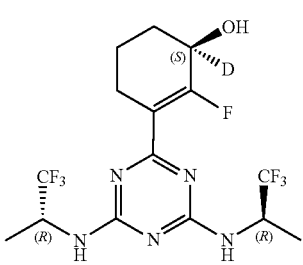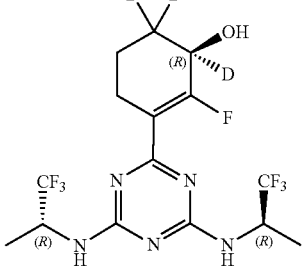 |
| 114 & 115 | 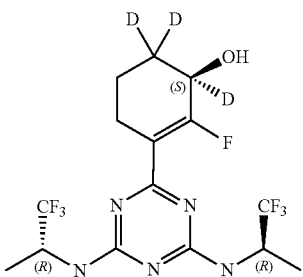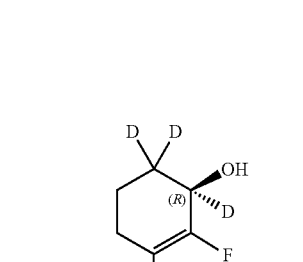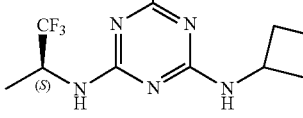 |

-continued
| Compound | Structure |
|---|---|
| | 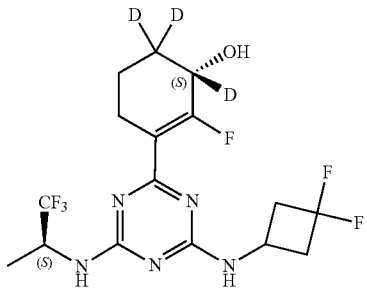 |
| 116 & 117 | 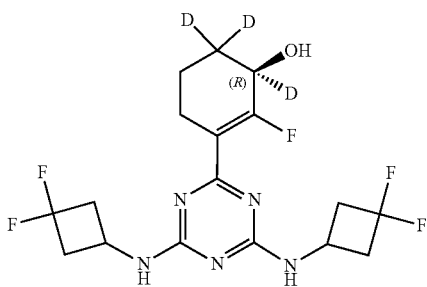 |
| | 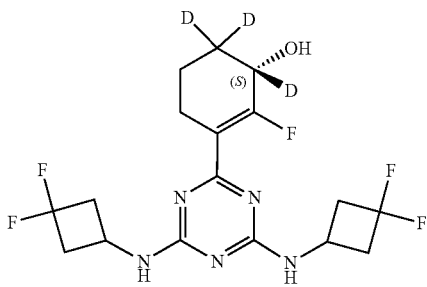 |
| 118 & 119 | 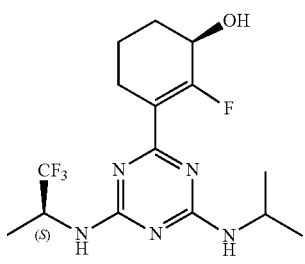 |
| | 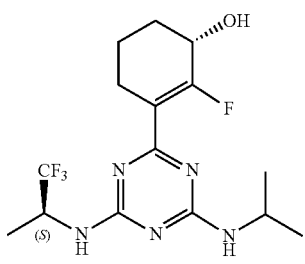 |
-continued
| Compound | Structure |
|---|---|
| 120 & 121 | 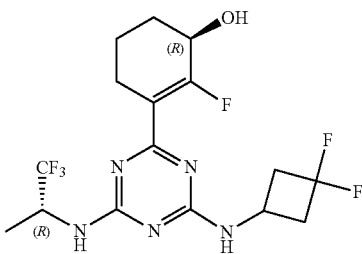 |
| | 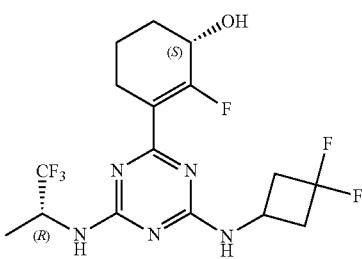 |
| 122 | 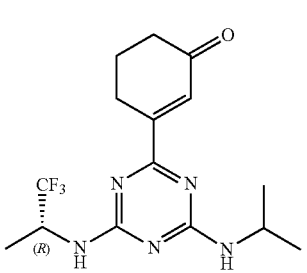 |
| 123 | 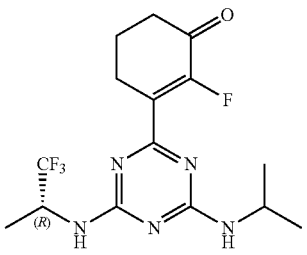 |
| 124 | 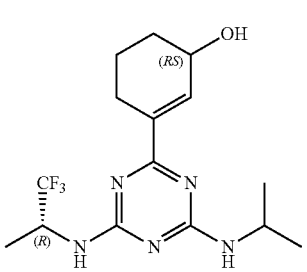 |
| 125 | 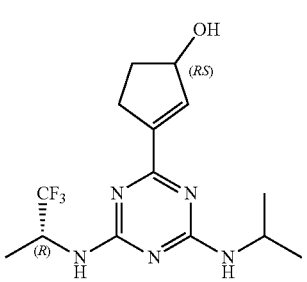 |

| Compound | Structure |
|---|---|
| 126 | 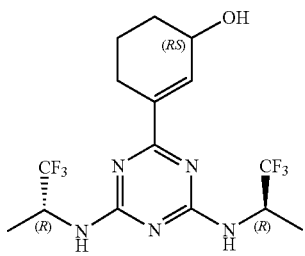 |
| 127 | 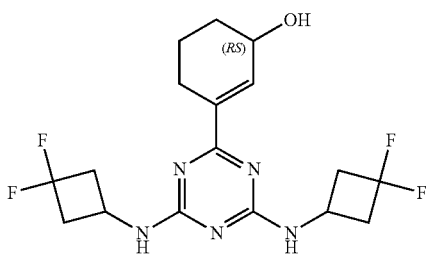 [SMILES: OC1C=C(c2nc(NC3CC(F)(F)C3)nc(NC3CC(F)(F)C3)n2)CCC1] |
| 128 | 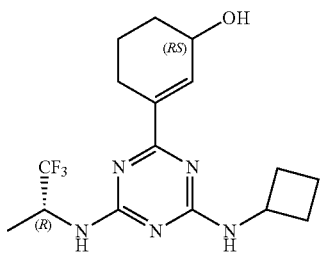 |
| 129 | 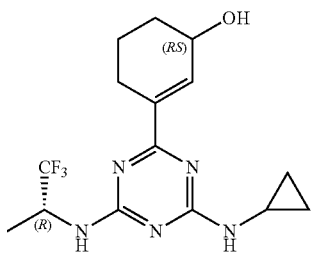 |
| 130 | 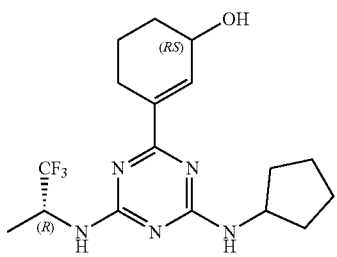 |
| 131 | 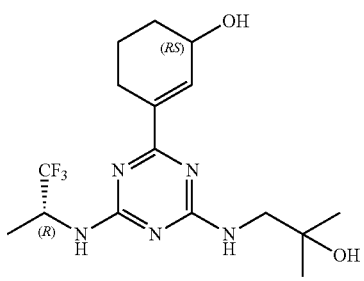 |
| Compound | Structure |
|---|---|
| 132 | 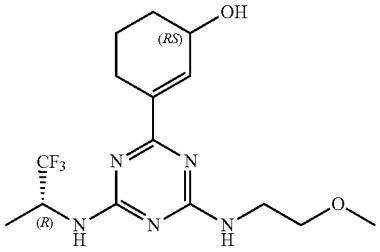 |
| 133 | 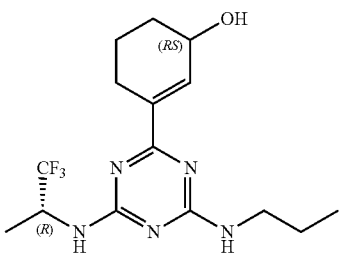 |
| 134 | 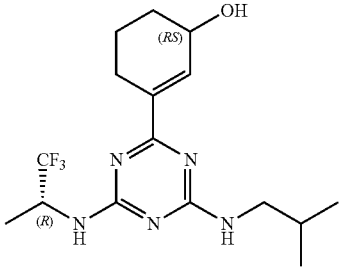 |
| 135 | 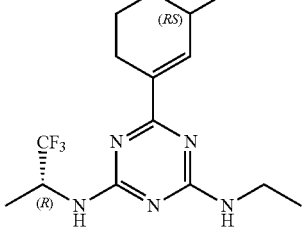 |
| 136 | 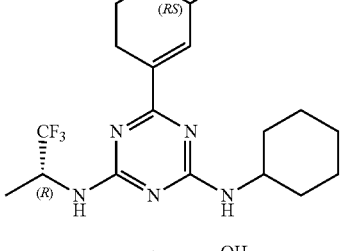 |
| 137 | 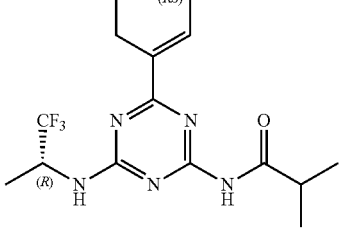 |

| Compound | Structure |
|---|---|
| 138 | 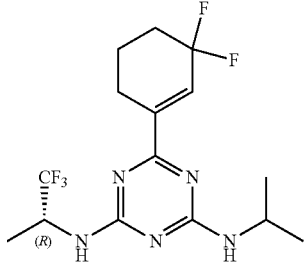 |
| 139 | 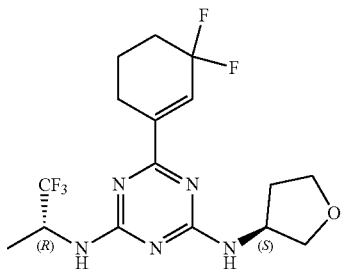 |
| 140 | 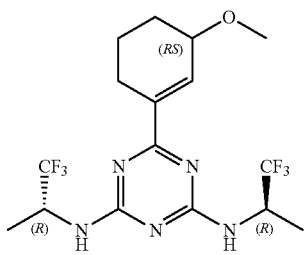 |
| 141 | 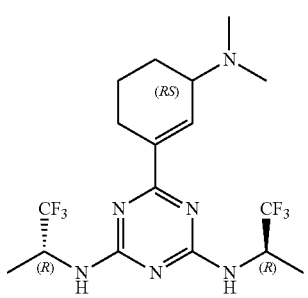 |
| 142 | 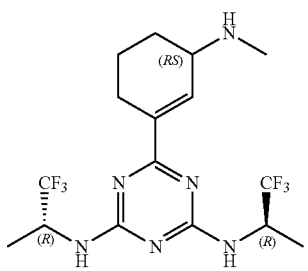 |
| Compound | Structure |
|---|---|
| 143 | 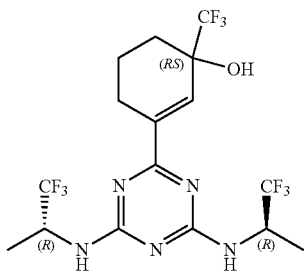 |
| 144 | 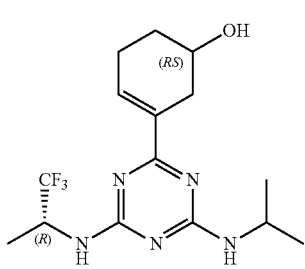 |
| 145 | 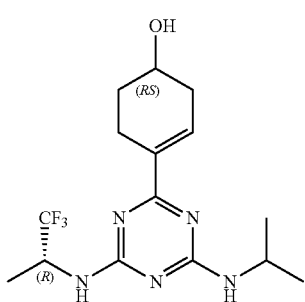 |
| 146 & 147 | 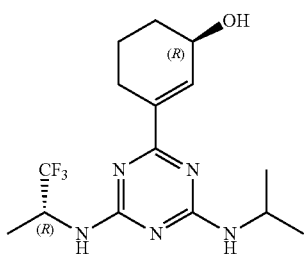 |
| | 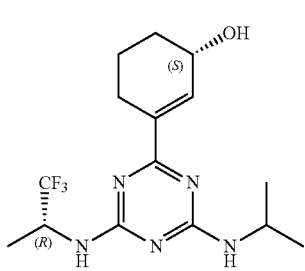 |

251
-continued
| Compound | Structure |
|---|---|
| 148 & 149 | 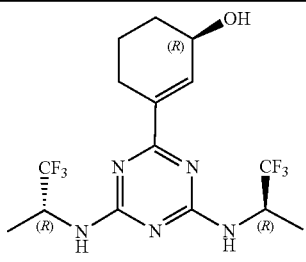 |
| 150 & 151 | 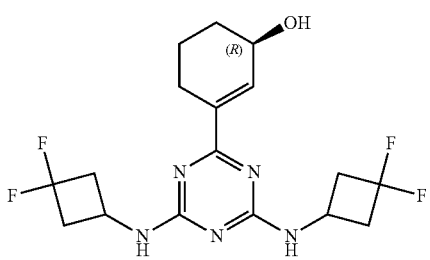 |
| 152 | 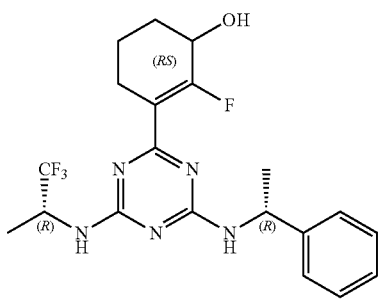 |
| 153 | 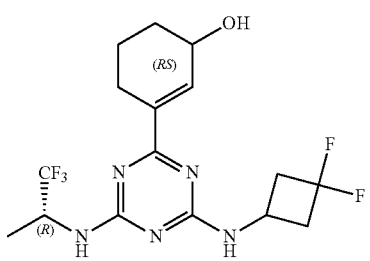 |
252
-continued
| Compound | Structure |
|---|---|
| 154 | 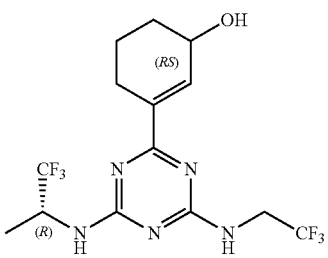 |
| 155 | 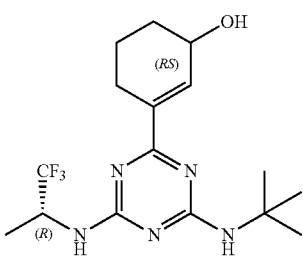 |
| 156 | 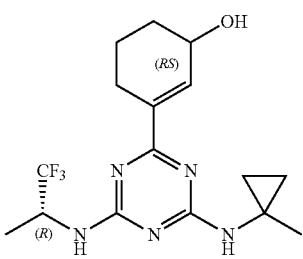 |
| 157 | 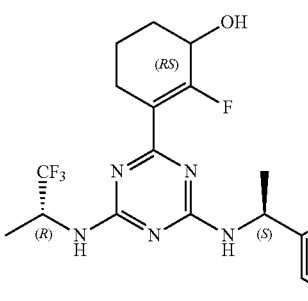 |
| 158 | 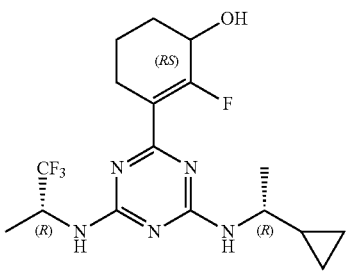 |

| Compound | Structure |
|---|---|
| 159 | 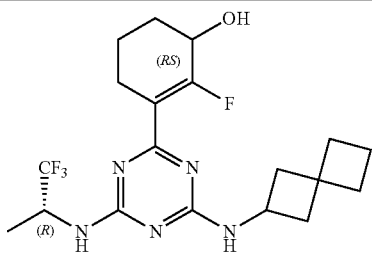 |
| 160 | 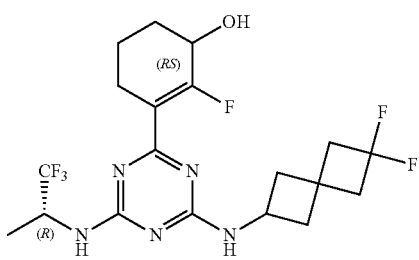 |
| 161 | 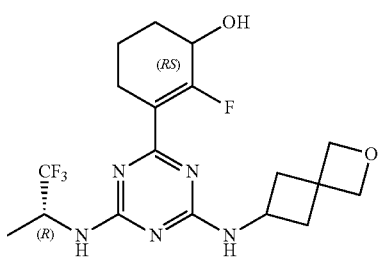 |
| 162 | 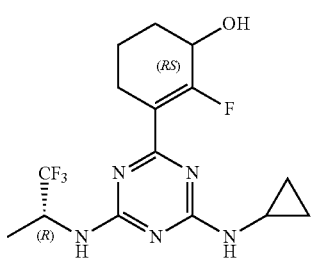 |
| 163 | 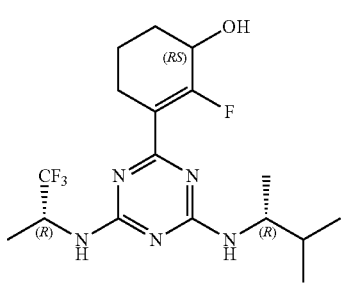 |
| 164 | 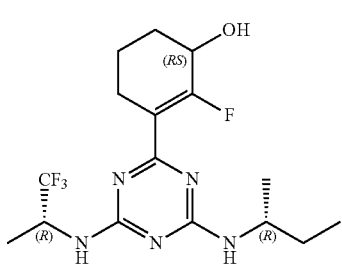 |
| 165 | 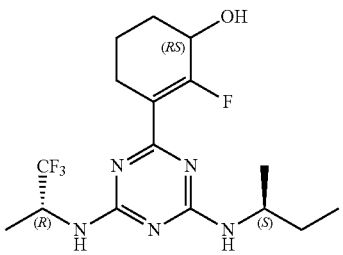 |
| 166 | 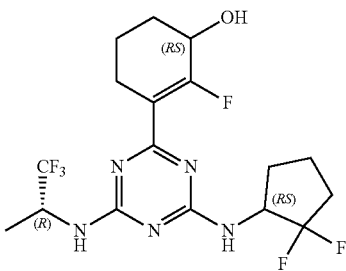 |
| 167 | 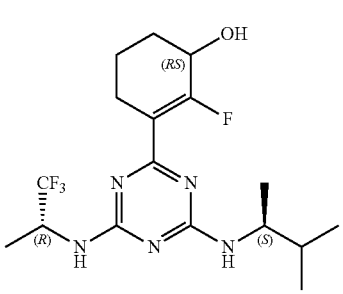 |
| 168 | 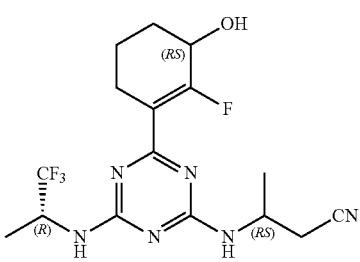 |
| 169 | 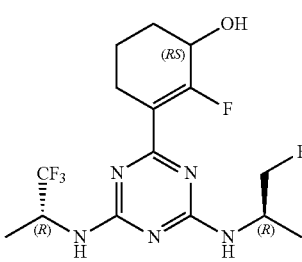 |
| 170 | 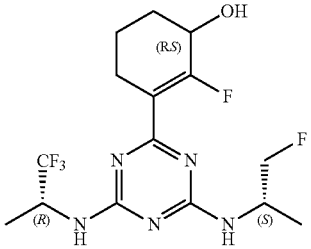 |

-continued
| Compound | Structure |
|---|---|
| 171 | 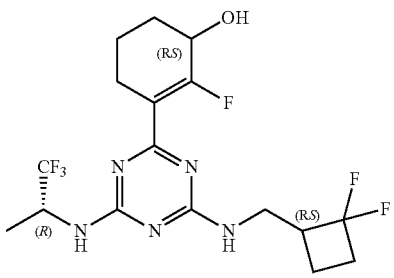 |
| 172 | 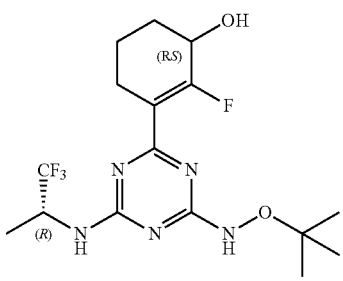 |
| 173 | 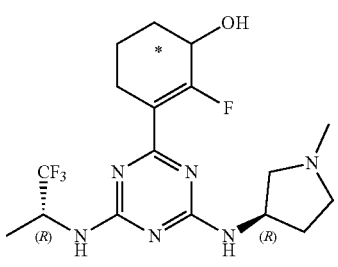 |
| 174 | 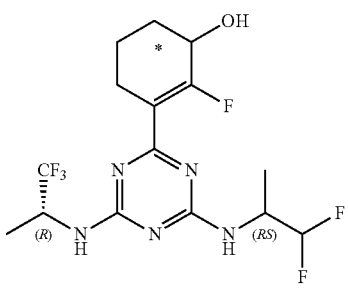 |
| 175 | 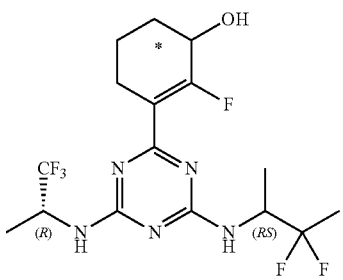 |
-continued
| Compound | Structure |
|---|---|
| 175 & 177 | 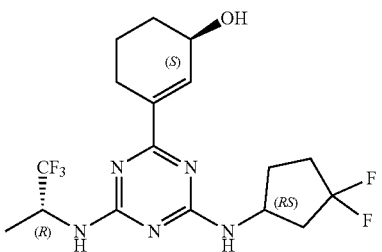 |
| | 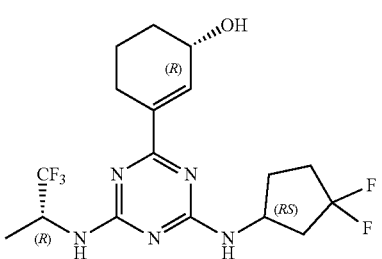 |
| 178 | 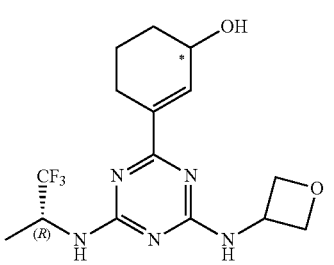 |
| 179 | 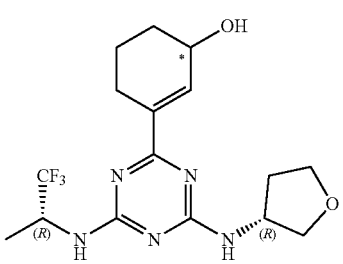 |
| 180 | 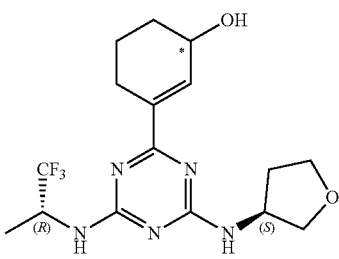 |
| 181 | 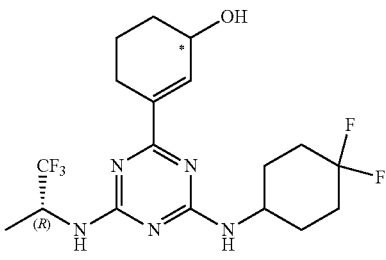 |

| Compound | Structure |
|---|---|
| 182 | 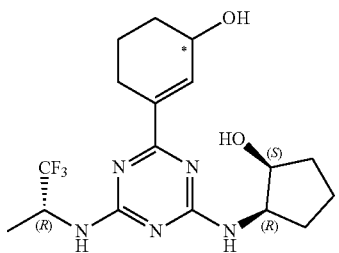 |
| 183 | 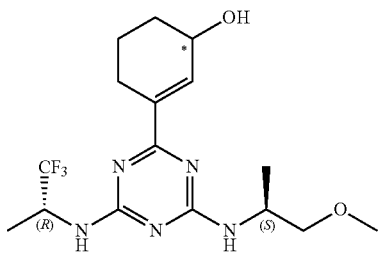 |
| 184 | 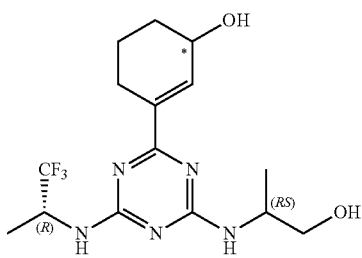 |
| 186 | 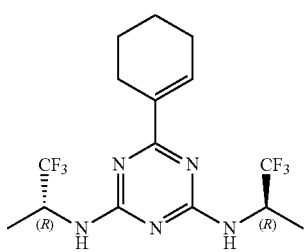 |
| 187 | 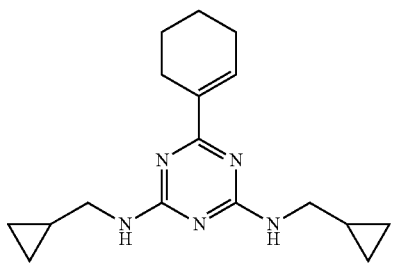 [SMILES: C1=C(c2nc(NCC3CC3)nc(NCC3CC3)n2)CCCC1] |
| 188 | 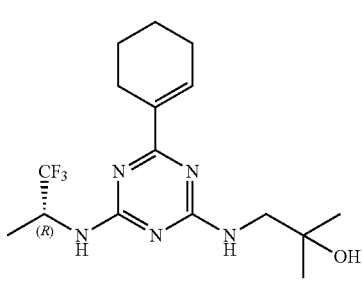 |
| Compound | Structure |
|---|---|
| 189 | 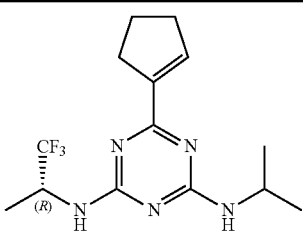 |
| 190 | 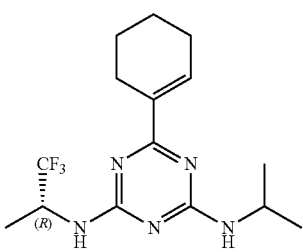 |
| 191 | 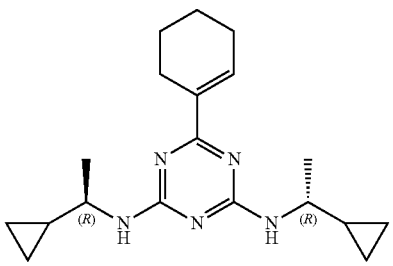 |
| 192 | 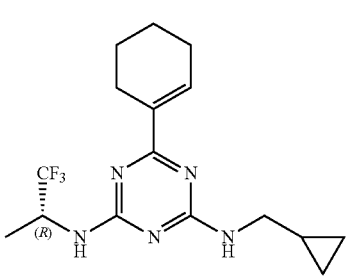 |
| 193 | 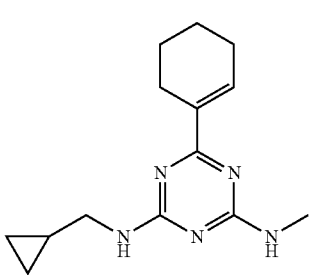 [SMILES: CNc1nc(NCC2CC2)nc(C2=CCCCC2)n1] |
| 194 | 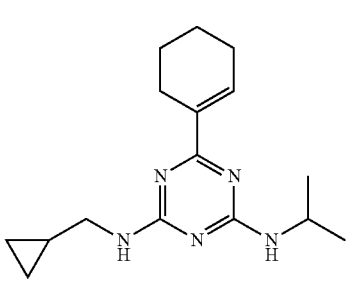 [SMILES: CC(C)Nc1nc(NCC2CC2)nc(C2=CCCCC2)n1] |

259
-continued
| Compound | Structure |
|---|---|
| 195 | 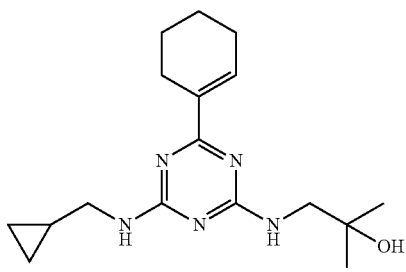 [SMILES: CC(C)(O)CNc1nc(NCC2CC2)nc(C2=CCCCC2)n1] |
| 199 | 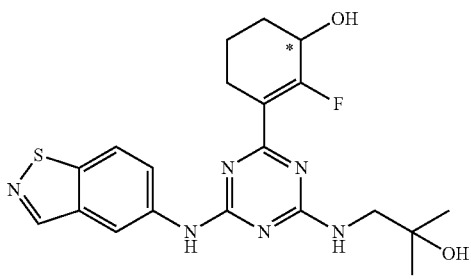 [SMILES: CC(C)(O)CNc1nc(Nc2ccc3sncc3c2)nc(C2=C(F)C(O)CCC2)n1] |
| 200 | 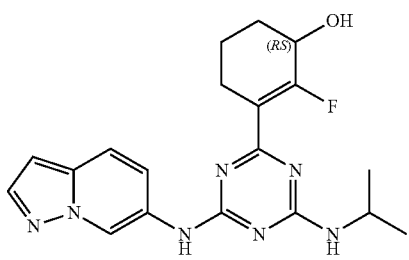 |
| 201 & 202 | 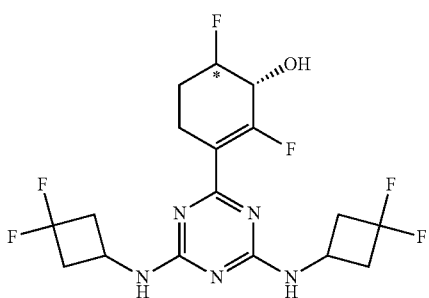 [SMILES: O[C@@H]1C(F)=C(c2nc(NC3CC(F)(F)C3)nc(NC3CC(F)(F)C3)n2)CCC1F] 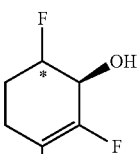   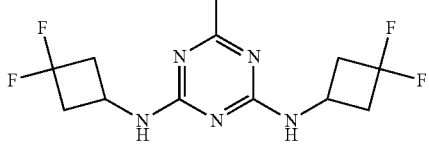 |
260
-continued
| Compound | Structure |
|---|---|
| 203 | 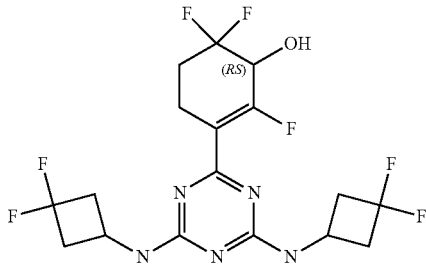 |
| 204 | 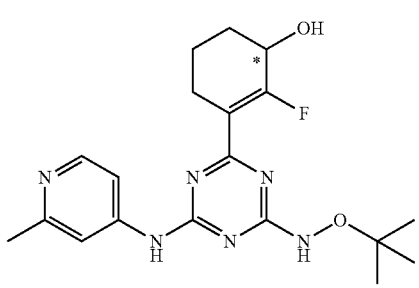 [SMILES: Cc1cc(Nc2nc(NOC(C)(C)C)nc(C3=C(F)C(O)CCC3)n2)ccn1] |
| 205 | 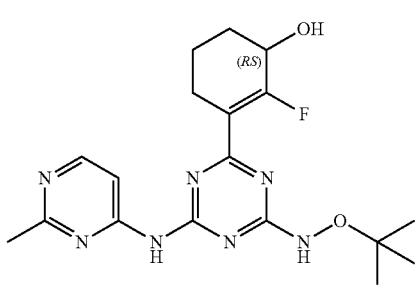 [SMILES: Cc1nccc(Nc2nc(NOC(C)(C)C)nc(C3=C(F)C(O)CCC3)n2)n1] |
| 206 | 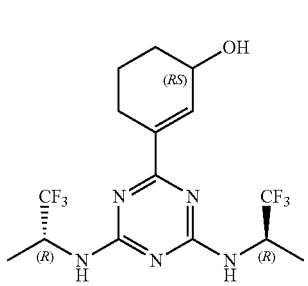 |
| 207 | 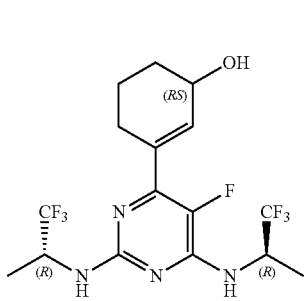 |

-continued
| Compound | Structure |
|---|---|
| 209 | 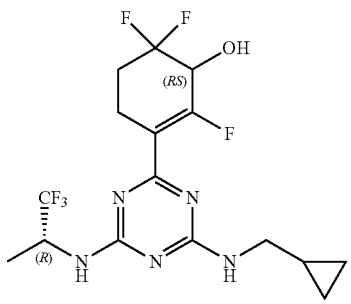 |
| 212 | 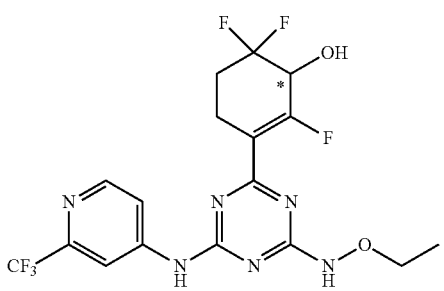 [SMILES: CCONc1nc(Nc2ccnc(C(F)(F)F)c2)nc(C2=C(F)C(O)C(F)(F)CC2)n1] |
| 213 | 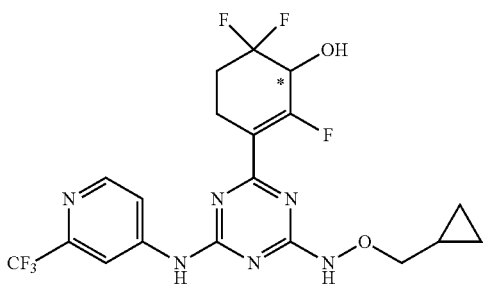 [SMILES: OC1C(F)=C(c2nc(NOCC3CC3)nc(Nc3ccnc(C(F)(F)F)c3)n2)CCC1(F)F] |
| 214 | 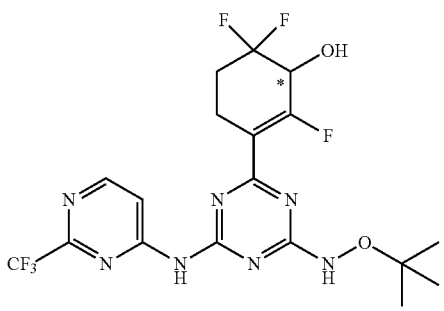 [SMILES: CC(C)(C)ONc1nc(Nc2ccnc(C(F)(F)F)n2)nc(C2=C(F)C(O)C(F)(F)CC2)n1] |
| 215 | 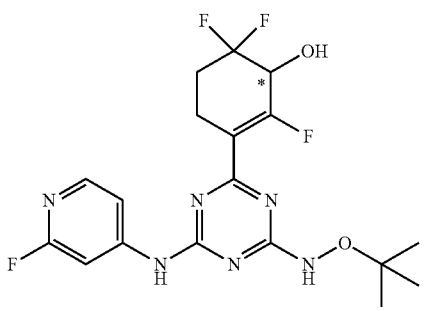 [SMILES: CC(C)(C)ONc1nc(Nc2ccnc(F)c2)nc(C2=C(F)C(O)C(F)(F)CC2)n1] |
| 216 | 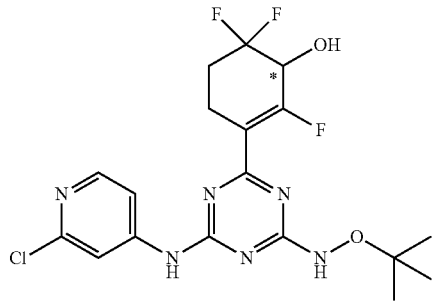 [SMILES: CC(C)(C)ONc1nc(Nc2ccnc(Cl)c2)nc(C2=C(F)C(O)C(F)(F)CC2)n1] |
| 217 | 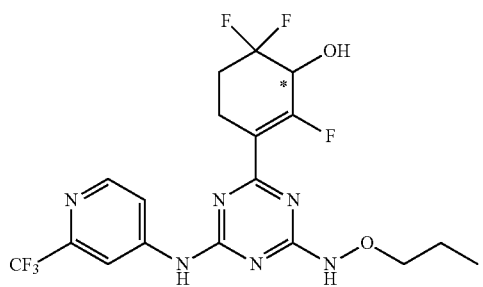 [SMILES: CCCONc1nc(Nc2ccnc(C(F)(F)F)c2)nc(C2=C(F)C(O)C(F)(F)CC2)n1] |
| 218 | 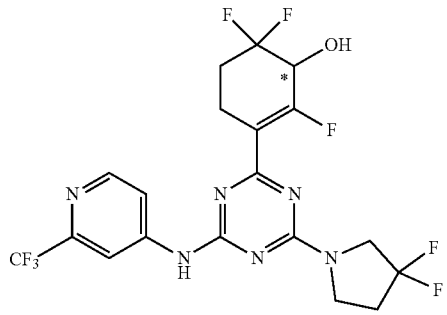 [SMILES: OC1C(F)=C(c2nc(Nc3ccnc(C(F)(F)F)c3)nc(N3CCC(F)(F)C3)n2)CCC1(F)F] |
| 219 | 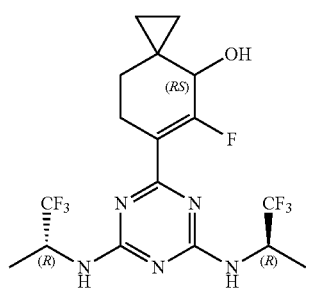 |
| 220 | 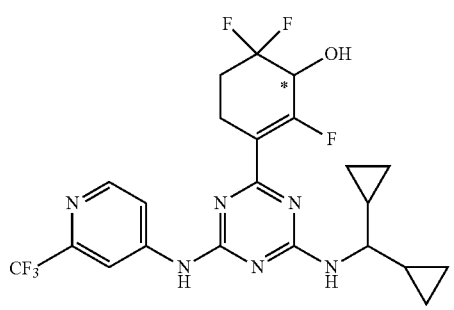 [SMILES: OC1C(F)=C(c2nc(Nc3ccnc(C(F)(F)F)c3)nc(NC(C3CC3)C3CC3)n2)CCC1(F)F] |

-continued
| Compound | Structure |
|---|---|
| 221 | 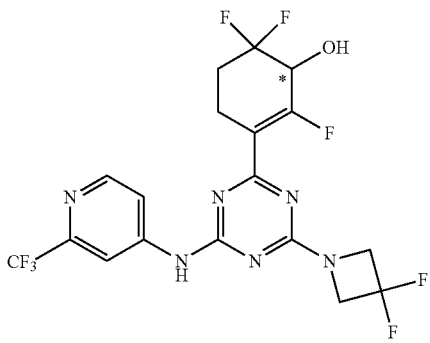 [SMILES: OC1C(F)=C(c2nc(Nc3ccnc(C(F)(F)F)c3)nc(N3CC(F)(F)C3)n2)CCC1(F)F] |
| 222 & 223 | 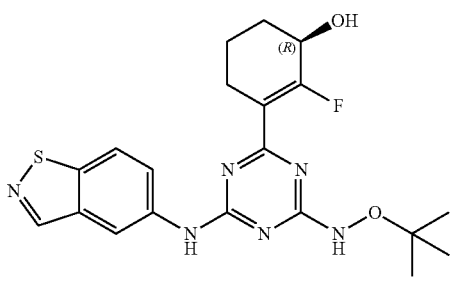 |
| 224 | 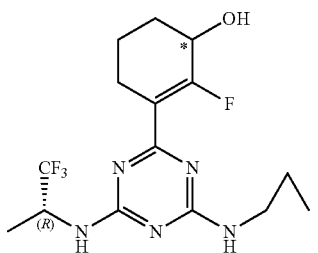 |
| 225 & 226 | 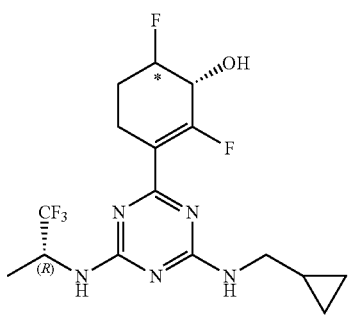 |
-continued
| Compound | Structure |
|---|---|
| | 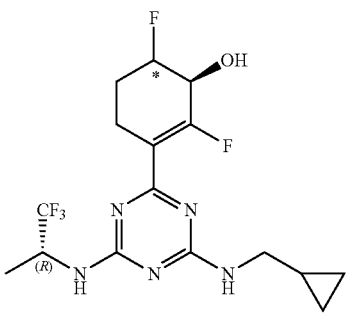 |
| 227 & 228 | 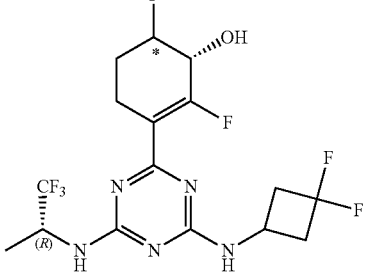 |
| | 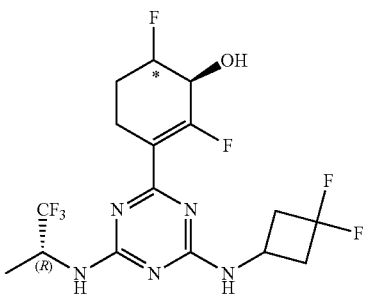 |
| 229 | 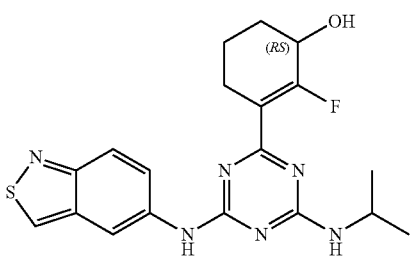 [SMILES: CC(C)Nc1nc(Nc2ccc3nscc3c2)nc(C2=C(F)C(O)CCC2)n1] |
| 230 & 231 | 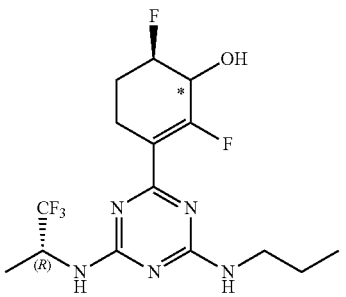 |

265
-continued
| Compound | Structure |
|---|---|
| | 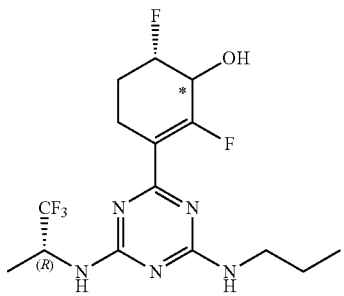 |
| 232 & 233 | 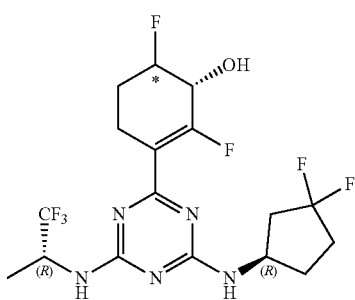 |
| | 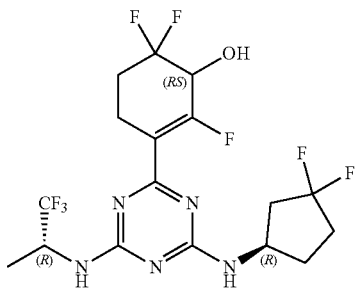 |
| 235 | 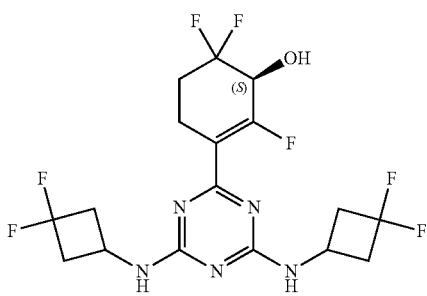 |
| 236 & 237 | 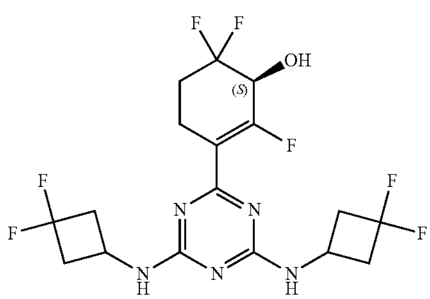 |
266
-continued
| Compound | Structure |
|---|---|
| | 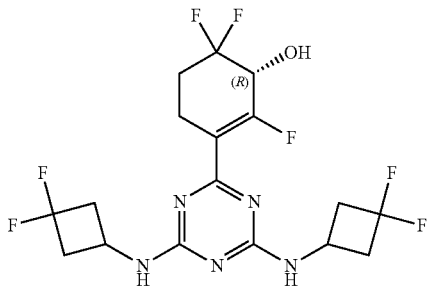 |
| 238 | 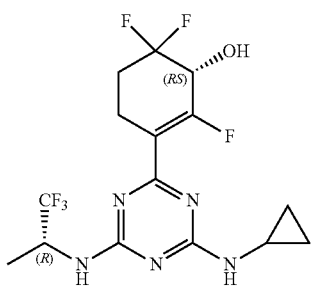 |
| 239 | 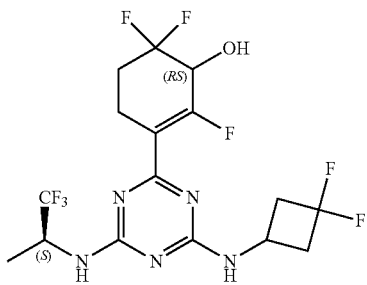 |
| 240 | 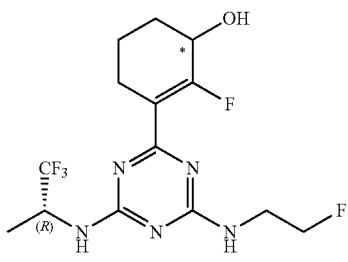 |
| 241 | 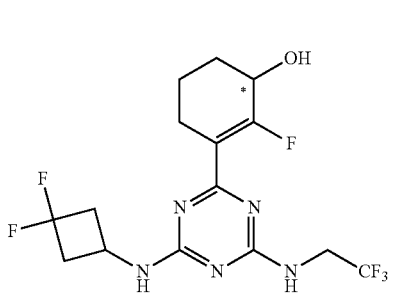 |

| Compound | Structure |
|---|---|
| 242 | 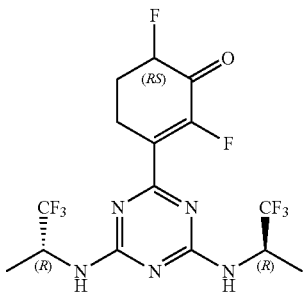 |
| 243 | 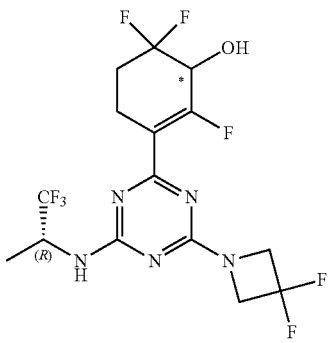 |
| 246 & 247 | 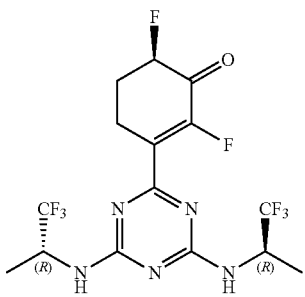 |
| | 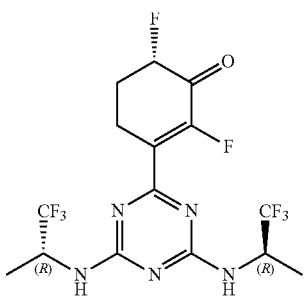 |
| 251 & 252 | 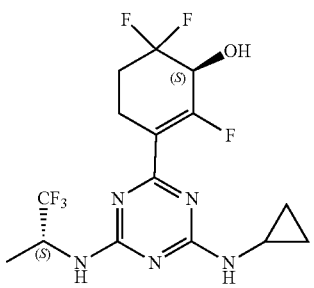 |
| Compound | Structure |
|---|---|
| | 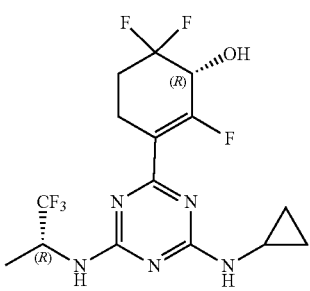 |
| 253 & 254 | 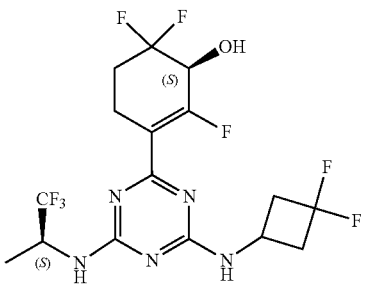 |
| | 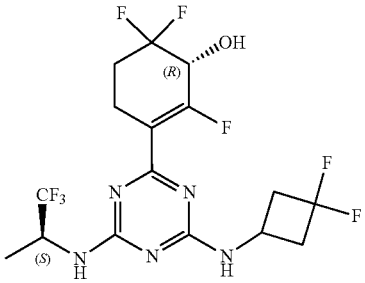 |
| 259 | 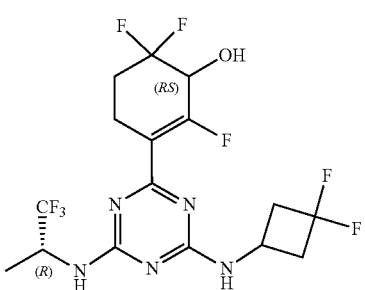 |
| 260 | 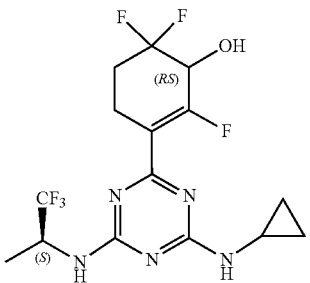 |

269
-continued
| Compound | Structure |
|---|---|
| 261 | 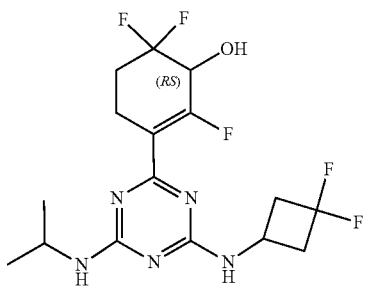 [SMILES: CC(C)Nc1nc(NC2CC(F)(F)C2)nc(C2=C(F)C(O)C(F)(F)CC2)n1] |
| 262 & 263 | 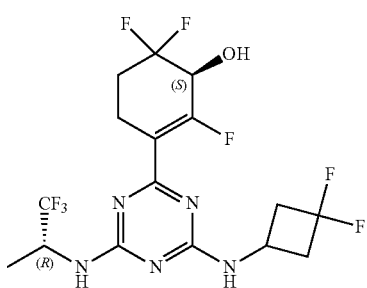 |
| 264 & 265 | 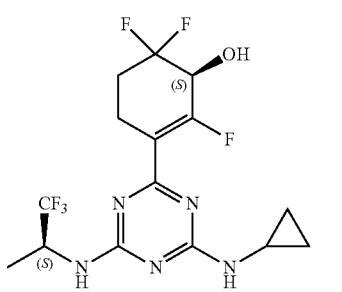 |
| | 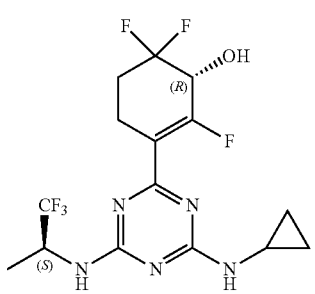 |
270
-continued
| Compound | Structure |
|---|---|
| 266, 267, 268, & 269 | 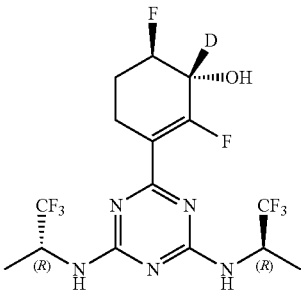 |
| | 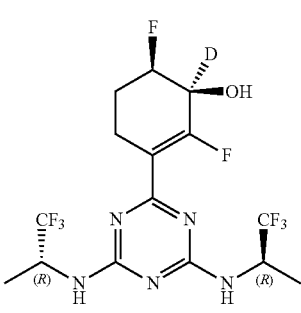 |
| | 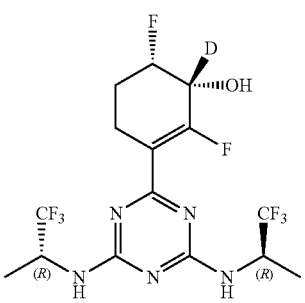 |
| | 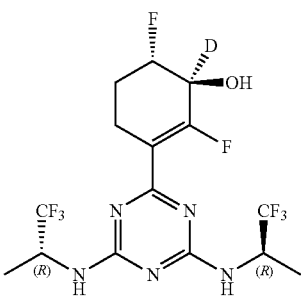 |
| 270 | 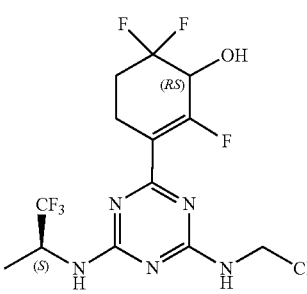 |

| Compound | Structure |
|---|---|
| 271 | 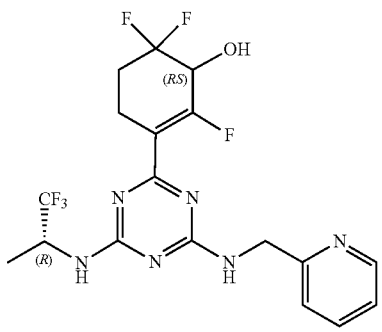 |
| 272 & 273 | 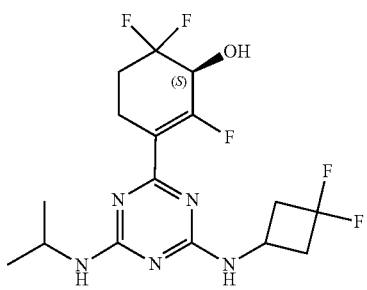 |
| 274 | 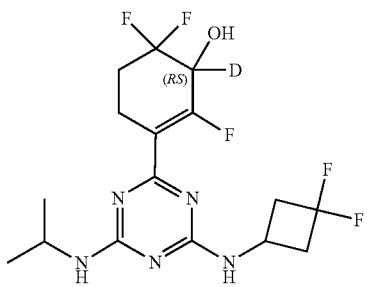 |
| 275 | 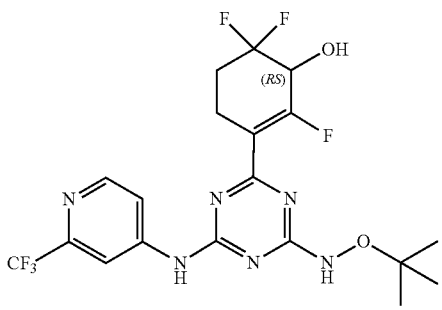 |
| Compound | Structure |
|---|---|
| 277 | 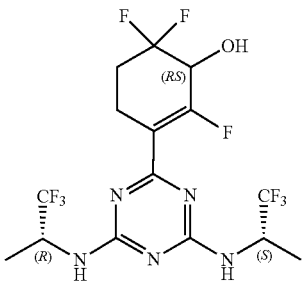 |
| 278 | 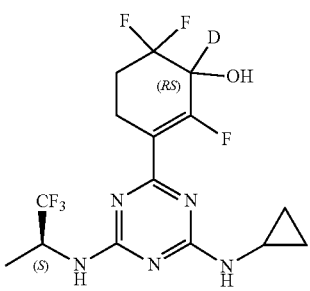 |
| 279 | 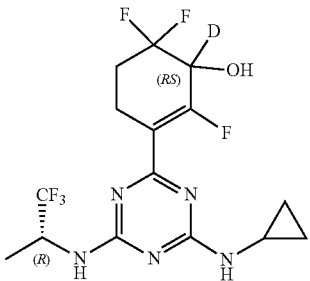 |
| 280 | 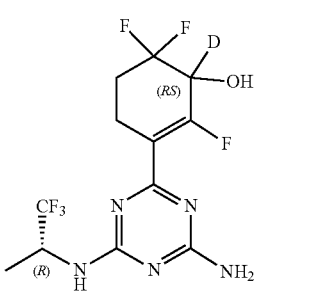 |
| 281 | 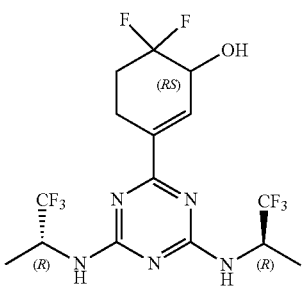 |

273
-continued
| Compound | Structure |
|---|---|
| 282 | 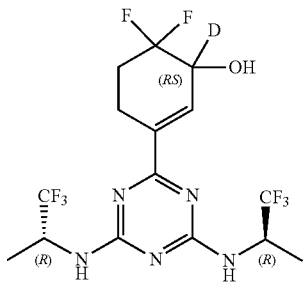 |
| 283 | 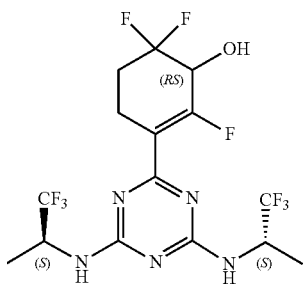 |
| 285 & 286 | 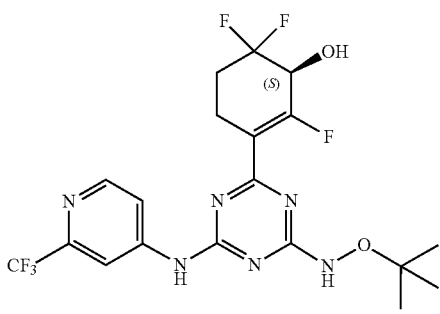 |
| 287 & 288 | 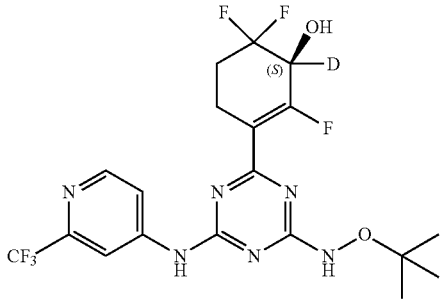 |
274
-continued
| Compound | Structure |
|---|---|
| | 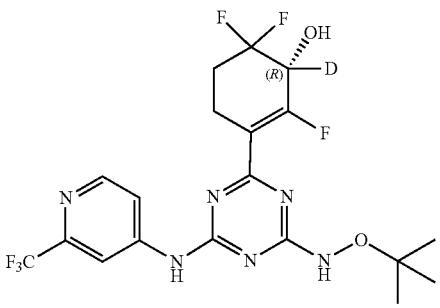 |
| 289 & 290 | 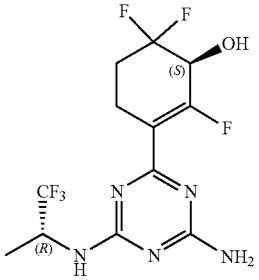 |
| | 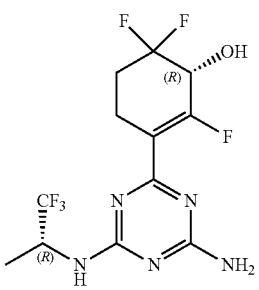 |
| 291 & 292 | 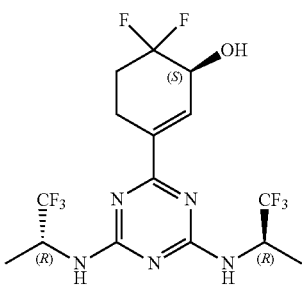 |
| | 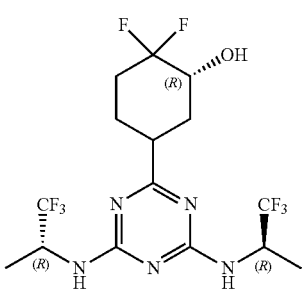 |

| Compound | Structure |
|---|---|
| 293 | 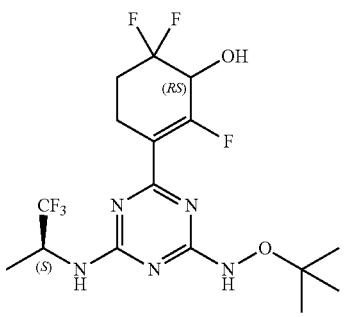 |
| 294 | 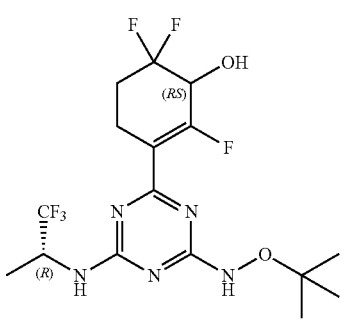 |
| 295 | 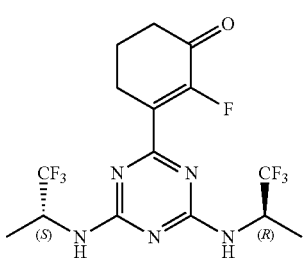 |
| 296 | 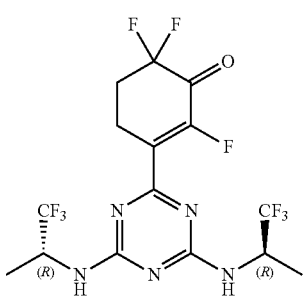 |
| 297 | 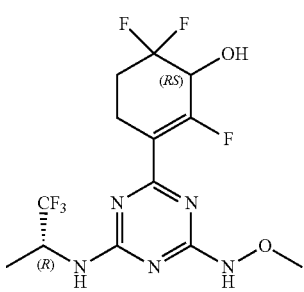 |
| 298 | 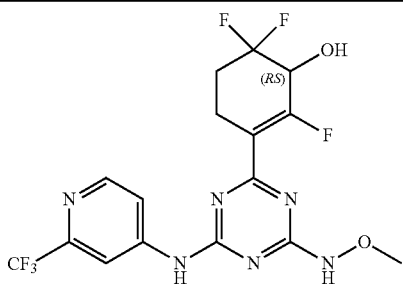 |
| 299 | 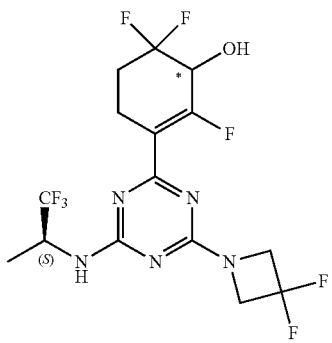 |
| 300 | 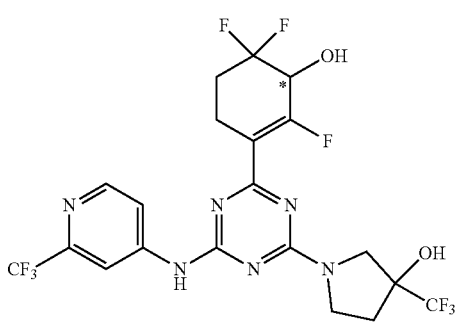 [SMILES: OC1C(F)=C(c2nc(Nc3ccnc(C(F)(F)F)c3)nc(N3CCC(O)(C(F)(F)F)C3)n2)CCC1(F)F] |
| 301 | 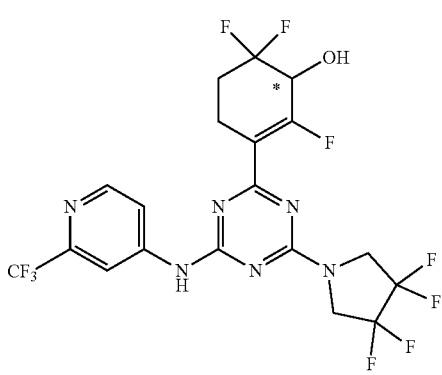 [SMILES: OC1C(F)=C(c2nc(Nc3ccnc(C(F)(F)F)c3)nc(N3CC(F)(F)C(F)(F)C3)n2)CCC1(F)F] | or a pharmaceutically acceptable salt thereof.

14. A pharmaceutical composition comprising the compound of claim 1, or a pharmaceutically acceptable salt thereof, and optionally comprising at least one pharmaceutically acceptable excipient.

15. The compound of formula (1-1) according to claim 1, or a pharmaceutically acceptable salt, solvate, racemic mixture, enantiomer, diastereomer, or tautomer thereof, wherein $R_3$ and $R_4$ are independently chosen from $C_{1-6}$ alkyl substituted with one or more halo.

* * * * *